United States Patent
Kaieda et al.

(10) Patent No.: US 10,081,624 B2
(45) Date of Patent: Sep. 25, 2018

(54) HETEROCYCLIC COMPOUND

(71) Applicant: Takeda Pharmaceutical Company Limited, Chuo-ku, Osaka-shi, Osaka (JP)

(72) Inventors: Akira Kaieda, Kanagawa (JP); Naoki Ishii, Kanagawa (JP); Hiroshi Nara, Kanagawa (JP); Masato Yoshikawa, Kanagawa (JP); Masaki Daini, Kanagawa (JP); Masashi Toyofuku, Kanagawa (JP); Kousuke Hidaka, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 37 days.

(21) Appl. No.: 15/506,380

(22) PCT Filed: Aug. 25, 2015

(86) PCT No.: PCT/JP2015/073858
§ 371 (c)(1),
(2) Date: Feb. 24, 2017

(87) PCT Pub. No.: WO2016/031815
PCT Pub. Date: Mar. 3, 2016

(65) Prior Publication Data
US 2018/0222896 A1    Aug. 9, 2018

(30) Foreign Application Priority Data

Aug. 26, 2014 (JP) .................................. 2014-172058

(51) Int. Cl.
| | |
|---|---|
| C07D 413/12 | (2006.01) |
| C07D 413/14 | (2006.01) |
| C07D 417/14 | (2006.01) |
| C07D 471/04 | (2006.01) |
| C07D 487/04 | (2006.01) |
| C07D 491/08 | (2006.01) |
| C07D 513/04 | (2006.01) |

(52) U.S. Cl.
CPC ......... C07D 413/12 (2013.01); C07D 413/14 (2013.01); C07D 417/14 (2013.01); C07D 471/04 (2013.01); C07D 487/04 (2013.01); C07D 491/08 (2013.01); C07D 513/04 (2013.01)

(58) Field of Classification Search
CPC ... C07C 413/12; C07C 413/14; C07C 417/14; C07C 471/04; C07C 487/04; C07C 491/08; C07C 513/04
USPC .................................................... 514/232.2
See application file for complete search history.

(56) References Cited

U.S. PATENT DOCUMENTS

| | | |
|---|---|---|
| 2012/0289495 A1 | 11/2012 | Baloglu et al. |
| 2013/0059883 A1 | 3/2013 | Baloglu et al. |
| 2014/0142105 A1 | 5/2014 | Hebach et al. |
| 2014/0329825 A1 | 11/2014 | Hebach et al. |
| 2014/0378385 A1 | 12/2014 | Raje et al. |
| 2015/0038534 A1 | 2/2015 | Baloglu et al. |
| 2017/0015655 A1 | 1/2017 | Kaieda et al. |
| 2017/0305866 A1 | 10/2017 | Raje et al. |

FOREIGN PATENT DOCUMENTS

| | | |
|---|---|---|
| JP | 2009-514858 A | 4/2009 |
| JP | 2010-531359 A | 9/2010 |
| JP | 2014-523857 A | 9/2014 |
| WO | WO 2011/088181 A1 | 7/2011 |
| WO | WO 2011/088192 A1 | 7/2011 |
| WO | WO 2013/006408 A1 | 1/2013 |
| WO | WO 2013/008162 A1 | 1/2013 |
| WO | WO 2013/009810 A1 | 1/2013 |
| WO | WO 2013/009827 A1 | 1/2013 |
| WO | WO 2013/009830 A1 | 1/2013 |
| WO | WO 2013/066831 A1 | 5/2013 |

(Continued)

OTHER PUBLICATIONS

Azad et al., "The future of epigenetic therapy in solid tumours—lessons from the past," Nature Review Clinical Oncology, 2013, 10:256-266.

(Continued)

*Primary Examiner* — Yevgeny Valenrod
(74) *Attorney, Agent, or Firm* — Foley & Lardner LLP

(57) ABSTRACT

The present invention provides a heterocyclic compound having a HDAC inhibitory action, and useful for the treatment of autoimmune diseases and/or inflammatory diseases, graft versus host disease, cancers, central nervous diseases including neurodegenerative diseases and the like, and a medicament comprising the compound.

The present invention relates to a compound represented by the formula (I):

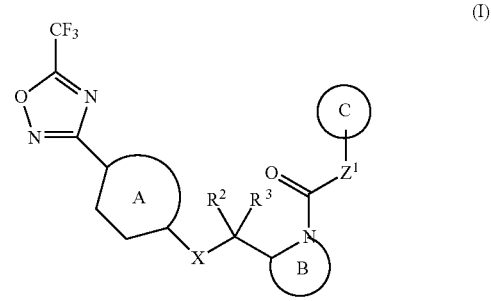

wherein each symbol is as defined in the specification, or a salt thereof.

14 Claims, 1 Drawing Sheet

(56) References Cited

FOREIGN PATENT DOCUMENTS

| WO | WO 2013/066833 A1 | 5/2013 |
|---|---|---|
| WO | WO 2013/066835 A1 | 5/2013 |
| WO | WO 2013/066838 A1 | 5/2013 |
| WO | WO 2013/066839 A1 | 5/2013 |
| WO | WO 2013/080120 A1 | 6/2013 |
| WO | WO 2016/039398 A1 | 3/2016 |
| WO | WO 2017/014170 A1 | 1/2017 |
| WO | WO 2017/014321 A1 | 1/2017 |
| WO | WO 2017/033946 A1 | 3/2017 |

OTHER PUBLICATIONS

Chuang et al., "Multiple roles of HDAC inhibition in neurodegenerative conditions," Trends in Neuroscience, 2009, 32:591-601.

Chung et al., "A Therapeutic Strategy Uses Histone Deacetylase Inhibitors to Modulate the Expression of Genes Involved in the Pathogenesis of Rheumatoid Arthritis," Mol. Ther., 2003, 8:707-717.

de Zoeten et al., "Histone Deacetylase 6 and Heat Shock Protein 90 Control the Functions of Foxp3+T-Regulatory Cells," Molecular and Cellular Biology, May 2011, 31(10):2066-2078.

Glauben et al., "Histone Hyperacetylation is Associated with Amelioration of Experimental Colitis in Mice," The Journal of Immunology, 2006, 176:5015-5022.

Gouindarajan et al., "Reducing HDAC6 ameliorates cognitive deficits in a mouse model for Alzheimer's disease," EMBO Mol. Med., 2013, 5:52-63.

Haberland et al., "The many roles of histone deacetylases in development and physiology: implications for disease and therapy," Nature Reviews Genetics, Jan. 2009, 10:32-42.

Hancock et al., "HDAC inhibitor therapy in autoimmunity and transplantation," Ann. Rheum. Dis., 2011, 71:i46-i54.

Jochems et al., "Antidepressant-Like Properties of Novel HDAC6-Selective Inhibitors with Improved Brain Bioavailability," Neuropsychopharmacology, 2014, 39:389-400.

Kalin et al., "Development and Therapeutic Implications of Selective Histone Deactylase 6 Inhibitors," Journal of Medicinal Chemistry, 2013, 56:6297-6313.

Li et al., "HDAC inhibitor reduces cytokine storm and facilitates induction of chimerism that reverses lupus in anti-CD3 conditioning regimen," Proc. Natl. Acad. Sci. USA, 2008, 104:4796-4801.

Lin et al., "Anti-rheumatic activities of histone deacetylase (HDAC) inhibitors in vivo in collagen-induced arthritis in rodents," British Journal of Pharmacology, 2007, 150:862-872.

Santo et al., "Preclinical activity, pharmacodynamics, and pharmacokinetic properties of a selective HDAC6 inhibitor, ACY-1215, in combination with bortezomib in multiple myeloma," Blood, Mar. 15, 2012, 119(11):2579-2589.

Shakespear et al., "Histone deacetylases as regulators of inflammation and immunity," Trends in Immunology, Jul. 2011, 32(7):335-353.

West et al., "New and emerging HDAC ihibitors for cancer treatment," The Journal of Clinical Investigation, Jan. 2014, 124(1):30-39.

International Search Report dated Oct. 20, 2016, in PCT/JP2016/071655.

Jin et al., "Design, synthesis and preliminary biological evaluation of indoline-2,3-dione derivatives as novel HDAC inhibitors," Bioorganic & Medicinal Chemistry, 2015, 23:4728-4736.

Kubinyi, H., Ed., 3D QSAR in Drug Design, Theory Methods and Applications: Ligand-Protein Interactions and Molecular Similarity, Springer, 1998, vol. 2-3, 800 pages, pp. 243-244 provided.

Terfloth et al., "Electronic Screening: Lead Finding From Database Mining," The Practice of Medicinal Chemistry, 2d. Ed., 2003, 768 pages, chs. 9-10 provided.

International Search Report dated Nov. 1, 2016, in PCT/JP2016/074573.

International Search Report dated Oct. 18, 2016, in PCT/JP2016/070936.

U.S. Appl. No. 15/745,290, filed Jan. 18, 2018, Kaieda.
U.S. Appl. No. 15/754,934, filed Feb. 23, 2018, Kaieda.

HETEROCYCLIC COMPOUND

CROSS-REFERENCE TO RELATED APPLICATIONS

This application is a National Stage application of PCT/JP2015/073858, filed Aug. 25, 2015, which claims priority from Japanese application JP 2014-172058, filed Aug. 26, 2014.

TECHNICAL FIELD

The present invention relates to a heterocyclic compound having a histone deacetylase (in the present specification, sometimes to be referred to as "HDAC") inhibitory action, preferably a class II HDAC inhibitory action, more preferably a HDAC6 inhibitory action, which is useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, Parkinson's disease, Huntington's disease, etc.) and the like, and a pharmaceutical composition comprising the compound and the like.

BACKGROUND OF THE INVENTION

HDAC is a generic term for proteins deacetylating histone, and mainly controls gene expression in the nucleus of cells. HDAC has various types, and is reported to be deeply related to pathological conditions such as immune, inflammation, cancer, nervous disease and the like. The gene expression regulation by HDAC is dependent on kinds of cell, target protein to be acted on, or cellular environment (Non-Patent Document 1).

Acetylation of histone is one of important determinants for gene expression. It is known that acetylation of histone generally acts in the direction of acceleration of transcription, and deacetylation of histone generally acts in the direction of suppression of gene expression. HDAC is a generic term for enzymes removing an acetyl group from lysine residue of target protein including histone. HDAC family is classified into four kinds of HDACs (class I HDACs (HDAC1, 2, 3, 8), class II HDACs (HDAC4, 5, 6, 7, 9, 10), class III HDACs (SIRT1-7), class IV HDAC (HDAC11)). Among them, class I HDACs is ubiquitously expressed, and mainly localized in the nucleus. It shows high enzyme activity against histone, and its role as modification of histone and transcription repressor is widely studied. Class II HDAC is classified into IIa (HDAC4, 5, 7, 9) and IIb (HDAC6, 10) based on the domain structure. Class IIa HDACs have an N-terminal domain bonded to transcription factor and a C-terminal domain having a nuclear transport signal, and can move between nucleus and cytoplasm. Unlike the other HDACs, its expression pattern is comparatively localized. For example, HDAC5 and HDAC9 are expressed in muscle, heart and brain. On the other hand, class IIb HDACs has a tandem structure of deacetylating domain, unlike class IIa HDACs, and HDAC6 is mainly expressed in cytoplasm. As the target molecule of HDAC6, α-tubulin and cortactin and the like, which are cytoskeleton proteins, are reported. It is known that low molecular HDAC inhibitors cause various cellular reactions such as cell-growth inhibition, cellular differentiation and cellular apoptosis, and HDAC inhibitors such as SAHA (vorinostat) and FK228 (romidepsin) are presently clinically used for T-cell malignant lymphoma as indication. In addition, effects of HDAC inhibitor on animal models of some inflammatory diseases, for example, models of arthritis, inflammatory bowel disease, GvHD, sepsis and the like are also reported (Non-Patent Documents 1, 2 and 3).

It is reported that vorinostat and trichostatin, which are HDAC inhibitors, show symptom improvement of pathological condition and actions such as protection action and the like in various animal models of autoimmune disease or inflammatory disease including arthritis model, enteritis model, GvHD model and the like (see Non-Patent Documents 4 to 7). In addition, it is reported that tubacin, which is a HDAC6 inhibitor, enhances regulatory T cell inhibitory action, and suppresses T-cell-dependent immune response in experimental enteritis model (Non-Patent Document 8). Therefore, HDAC inhibitor and/or HDAC6 inhibitor can be therapeutic drugs for various autoimmune diseases and/or inflammatory diseases such as inflammatory bowel disease, rheumatoid arthritis, psoriasis, Sjogren's syndrome, Behcet's disease, multiple sclerosis, systemic lupus erythematosus and the like, GvHD and the like (Non-Patent Documents 2 and 9).

In addition, HDAC has an important role in tumor formation because it regulates activities of tumor suppressor gene and oncogene. For example, it is reported that overexpression of HDAC in prostate cancer, colorectal cancer, breast cancer, lung cancer, liver cancer, stomach cancer and the like correlates with decrease in disease-free survival and overall survival (Non-Patent Document 3). Therefore, HDAC inhibitor targeting solid cancer and blood tumor is developed. Vorinostat and romidepsin, which are HDAC inhibitors, have been approved by FDA as a therapeutic drug for T-cell malignant lymphoma, and plural HDAC inhibitors are preclinical or in clinical trials (Non-Patent Document 10). In addition, it is reported that ACY-1215, which is a HDAC6 inhibitor, has a tumor growth inhibitory action or an extended survival action in multiple myeloma model, when used in combination with bortezomib (Non-Patent Document 11). Therefore, HDAC inhibitor and/or HDAC6 inhibitor can be therapeutic drugs for cancers such as multiple myeloma, leukemia, uterine leiomyosarcoma, prostate cancer, cachexia, myelofibrosis and the like.

On the other hand, it is reported that vorinostat and valproic acid, which are HDAC inhibitors, show actions such as improvement of spatial memory, increased motor function and the like in animal models such as Alzheimer's disease model, Huntington's disease model and the like (Non-Patent Document 12). In addition, it is reported that ACY-738 and ACY-775, which are HDAC6 inhibitors, show a significant antidepressant action in ethopharmacological experiments such as tail suspension test and the like (Non-Patent Document 13). Moreover, it is reported that HDAC6 also has an important role in regulation of amyloid β involved in maintenance of homeostasis of tau and stability of microtubule which are deeply related to Alzheimer's disease, and that inhibition of HDAC6 improves memory in neurodegeneration mouse model in water maze test using HDAC6 knockout mouse and APPPS1-21 mouse which is a Alzheimer's disease mouse model (Non-Patent Documents 14 and 15). Therefore, HDAC inhibitor and/or HDAC6 inhibitor can be therapeutic drugs for central nervous system diseases including neurodegenerative diseases.

The compounds having a structure similar to that of the compound described in the present specification are, for example, the following compounds.

(1) Patent Document 1 discloses a compound represented by the following formula:

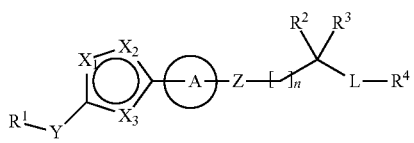

wherein each symbol is as defined in the document, which is a HDAC inhibitor, and is effective against autoimmune disease, immune disease, inflammatory disease and the like. However, the compound does not have a structure corresponding to "—CO—$Z^1$-Ring C" in the following compound (I) of the present invention.

(2) Patent Document 2 discloses a compound represented by the following formula:

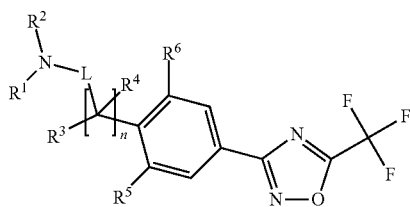

wherein each symbol is as defined in the document, which is a HDAC4 inhibitor, and is effective against neurodegenerative disease accompanied by cerebral ischemia and the like. However, the compound does not have a structure corresponding to "—CO—$Z^1$-Ring C" in the following compound (I) of the present invention.

(3) Patent Document 3 discloses a compound represented by the following formula:

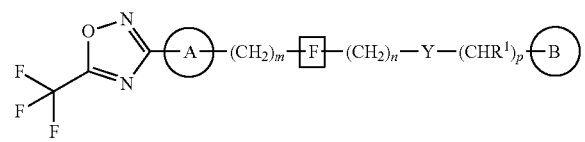

wherein each symbol is as defined in the document, which has a Class II HDAC (HDAC4, HDAC5, HDAC6, HDAC7, HDAC9) inhibitory action, and is useful for the prophylaxis and treatment of autoimmune disease, immune disease, inflammatory disease and the like. However, the compound does not have a structure corresponding to "—CO—$Z^1$-Ring C" in the following compound (I) of the present invention.

(4) Patent Document 4 discloses a compound represented by the following formula:

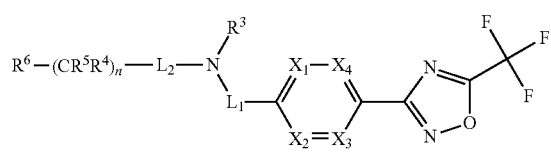

wherein each symbol is as defined in the document, which is a HDAC4 inhibitor, and is effective against neurodegenerative disease accompanied by cerebral ischemia and the like. However, the compound does not have a structure corresponding to w-CO—$Z^1$-Ring C" in the following compound (I) of the present invention.

DOCUMENT LIST

Patent Document

Patent Document 1 WO 2011/088181
Patent Document 2 WO 2013/008162
Patent Document 3 WO 2013/066835
Patent Document 4 WO 2013/080120

Non-Patent Document

Non-Patent Document 1 Nature Reviews Genetics 10, 32-42 (2009).
Non-Patent Document 2 Trend in Immunology 32, 335-343 (2011).
Non-Patent Document 3 J Clin Invest 124, 30-39 (2014).
Non-Patent Document 4 Mol Ther 8, 707-717 (2003).
Non-Patent Document 5 J Immunol 176, 5015-5022 (2006).
Non-Patent Document 6 Br J Pharmacol 150, 862-872 (2007).
Non-Patent Document 7 Proc Natl Acad Sci USA 105, 4796-4801 (2008).
Non-Patent Document 8 Mol Cell Biol 31, 2066-2078 (2011).
Non-Patent Document 9 Ann Rheum Dis 71, i46-i54 (2011).
Non-Patent Document 10 Nature Review Clinical Oncology 10, 256-266 (2013).
Non-Patent Document 11 Blood 119, 2579-2589 (2012).
Non-Patent Document 12 Trend in Neuroscience 32, 591-601 (2009).
Non-Patent Document 13 Neuropsychopharmacology 39, 389-400 (2014).
Non-Patent Document 14 EMBO Mol Med 5, 52-63 (2013).
Non-Patent Document 15 Journal of Medicinal Chemistry 56, 6297-6313 (2013).

SUMMARY OF THE INVENTION

Problems to be Solved by the Invention

The present invention aims to provide a heterocyclic compound having a HDAC inhibitory action, and useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, Parkinson's disease, Huntington's disease, etc.) and the like, and a pharmaceutical composition comprising the compound.

Means of Solving the Problems

The present inventors have conducted intensive studies to solve the above-mentioned problems, and have found that a compound represented by the following formula (I) has a superior HDAC inhibitory action, and completed the present invention based on these findings.

Accordingly, the present invention provides the following.

[1]

A compound represented by the formula (I):

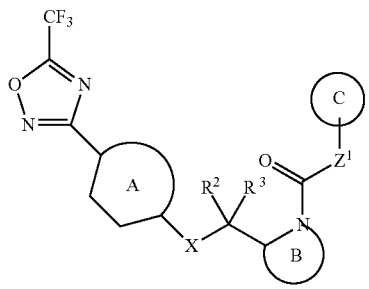

wherein
Ring A is an optionally further substituted 5- or 6-membered ring,
X is —CONR¹— or —NR¹CO—,
R¹ is a hydrogen atom or a substituent,
R² and R³ are the same or different and each is a hydrogen atom or a substituent,
Ring B is an optionally further substituted nitrogen-containing heterocycle,
Z¹ is a bond, or a spacer in which the number of atoms in the main chain is 1 to 3, and
Ring C is an optionally further substituted ring,
or a salt thereof (hereinafter sometimes to be referred to as compound (I)).

[2]

The compound or salt of the above-mentioned [1], wherein Ring A is a 5- or 6-membered ring optionally further substituted by 1 to 3 substituents selected from
    (1) a halogen atom, and
    (2) a $C_1$-$C_6$ alkyl group;
X is —CONR¹— or —NR¹CO—, and R¹ is a hydrogen atom or a $C_{1-6}$ alkyl group;
R² and R³ are hydrogen atoms;
Ring B is a nitrogen-containing heterocycle optionally further substituted by 1 to 3 $C_{6-14}$ aryl-carbonyl groups;
Z¹ is a bond, —NR$^a$—, —CR$^b_2$—, —CR$^b_2$—CR$^b_2$— or —CR$^b_2$—O—;
    wherein
    R$^a$ is a hydrogen atom or a $C_{1-6}$ alkyl group; and
    R$^b$ are each independently a hydrogen atom, a halogen atom, a
$C_{1-6}$ alkyl group or a $C_{6-14}$ aryl group; and
Ring C is a ring optionally further substituted by 1 to 3 substituents selected from
    (a) a halogen atom,
    (b) a $C_{1-6}$ alkyl group optionally substituted by 1 to 3 substituents selected from
        (i) a halogen atom,
        (ii) a hydroxy group, and
        (iii) a $C_{1-6}$ alkoxy group,
    (c) a $C_{6-14}$ aryl group,
    (d) a cyano group,
    (e) a $C_{1-6}$ alkoxy group optionally substituted by 1 to 3 substituents selected from
        (i) a halogen atom, and
        (ii) a hydroxy group,
    (f) a 3- to 14-membered non-aromatic heterocyclic group,
    (g) a 5- to 14-membered aromatic heterocyclic group,
    (h) a $C_{3-10}$ cycloalkyl group,
    (i) a hydroxy group,
    (j) an oxo group,
    (k) a carboxy group,
    (l) a $C_{1-6}$ alkoxy-carbonyl group,
    (m) a carbamoyl group, and
    (n) a mono- or di-$C_{1-6}$ alkyl-carbamoyl group optionally substituted by 1 to 3 hydroxy groups.

[3]

The compound or salt of the above-mentioned [1], wherein Ring A is
(1) a benzene ring optionally further substituted by 1 to 3 substituents selected from
    (a) a halogen atom, and
    (b) a $C_{1-6}$ alkyl group, or
(2) a 5- or 6-membered monocyclic aromatic heterocycle;
X is —CONR¹— or —NR¹CO—, and R¹ is a hydrogen atom or a $C_{1-6}$ alkyl group;
R² and R³ are hydrogen atoms;
Ring B is a 4- to 10-membered nitrogen-containing heterocycle optionally further substituted by 1 to 3 $C_{6-14}$ aryl-carbonyl groups;
Z¹ is a bond, —NR$^a$—, —CR$^b_2$—, —CR$^b_2$—CR$^b_2$— or —CR$^b_2$—O—;
    wherein
    R$^a$ is a hydrogen atom or a $C_{1-6}$ alkyl group; and
    R$^b$ are each independently a hydrogen atom, a halogen atom, a $C_{1-6}$ alkyl group or a $C_{6-14}$ aryl group; and
Ring C is
(1) a $C_{6-14}$ aromatic hydrocarbon ring optionally further substituted by 1 to 3 substituents selected from
    (a) a halogen atom,
    (b) a $C_{1-6}$ alkyl group optionally substituted by 1 to 3 halogen atoms,
    (c) a $C_{6-14}$ aryl group,
    (d) a cyano group,
    (e) a $C_{1-6}$ alkoxy group optionally substituted by 1 to 3 hydroxy groups,
    (f) a 3- to 8-membered monocyclic non-aromatic heterocyclic group,
    (g) a carboxy group,
    (h) a $C_{1-6}$ alkoxy-carbonyl group, and
    (i) a mono- or di-$C_{1-6}$ alkyl-carbamoyl group optionally substituted by 1 to 3 hydroxy groups,
(2) a $C_{3-10}$ cycloalkane ring optionally further substituted by 1 to 3 substituents selected from
    (a) a $C_{6-14}$ aryl group, and
    (b) a cyano group,
(3) a 5- to 14-membered aromatic heterocycle optionally further substituted by 1 to 3 substituents selected from
    (a) a $C_{1-6}$ alkyl group optionally substituted by 1 to 3 substituents selected from a halogen atom and a hydroxy group,
    (b) a $C_{3-10}$ cycloalkyl group,
    (c) a $C_{1-6}$ alkoxy group optionally substituted by 1 to 3 halogen atoms, and
    (d) a hydroxy group, or
(4) a 3- to 14-membered non-aromatic heterocycle optionally further substituted by 1 to 3 substituents selected from
    (a) a $C_{1-6}$ alkyl group optionally substituted by 1 to 3 substituents selected from a hydroxy group, a halogen atom and a $C_{1-6}$ alkoxy group,
    (b) a $C_{6-14}$ aryl group,
    (c) an oxo group,
    (d) a halogen atom,
    (e) a hydroxy group,
    (f) a cyano group, (g) a 5- or 6-membered monocyclic aromatic heterocyclic group, and
(h) a carbamoyl group.

[4]

The compound or salt of the above-mentioned [1], wherein
Ring A is
(1) a benzene ring optionally further substituted by 1 to 3 substituents selected from
  (a) a halogen atom, and
  (b) a $C_{1-6}$ alkyl group,
(2) a pyridine ring, or
(3) a thiophene ring;
X is —$CONR^1$— or —$NR^1CO$—, and $R^1$ is a hydrogen atom or a $C_{1-6}$ alkyl group;
$R^2$ and $R^3$ are hydrogen atoms;
Ring B is
(1) a morpholine ring,
(2) a piperidine ring,
(3) a piperazine ring optionally further substituted by one benzoyl group,
(4) a pyrrolidine ring,
(5) an indoline ring,
(6) an isoindoline ring,
(7) a tetrahydroquinoline ring, or
(8) a tetrahydroisoquinoline ring;
$Z^1$ is a bond, —$NR^a$—, —$CR^b{}_2$—, —$CR^b{}_2$—$CR^b{}_2$— or —$CR^b{}_2$—O—,
  wherein
  $R^a$ is a hydrogen atom or a $C_{1-6}$ alkyl group, and
  $R^b$ are each independently a hydrogen atom, a halogen atom, a $C_{1-6}$ alkyl group or a phenyl group; and
Ring C is
(1) a benzene ring optionally further substituted by 1 to 3 substituents selected from
  (a) a halogen atom,
  (b) a $C_{1-6}$ alkyl group optionally substituted by 1 to 3 halogen atoms,
  (c) a phenyl group,
  (d) a cyano group,
  (e) a $C_{1-6}$ alkoxy group optionally substituted by 1 to 3 hydroxy groups,
  (f) a morpholinyl group,
  (g) a carboxy group,
  (h) a $C_{1-6}$ alkoxy-carbonyl group, and
  (i) a mono- or di-$C_{1-5}$ alkyl-carbamoyl group optionally substituted by 1 to 3 hydroxy groups,
(2) a $C_{3-10}$ cycloalkane ring optionally further substituted by 1 to 3 substituents selected from
  (a) a phenyl group, and
  (b) a cyano group,
(3) an adamantane ring,
(4) a pyridine ring optionally further substituted by 1 to 3 substituents selected from
  (a) a $C_{1-6}$ alkyl group,
  (b) a $C_{3-10}$ cycloalkyl group,
  (c) a $C_{1-6}$ alkoxy group optionally substituted by 1 to 3 halogen atoms, and
  (d) a hydroxy group,
(5) a thiophene ring optionally further substituted by 1 to 3 $C_{1-6}$ alkyl groups,
(6) a pyrazole ring optionally further substituted by 1 to 3 $C_{1-6}$ alkyl groups optionally substituted by 1 to 3 substituents selected from a halogen atom and a hydroxy group,
(7) an imidazole ring optionally further substituted by 1 to 3 $C_{1-6}$ alkyl groups,
(8) an oxadiazole ring optionally further substituted by 1 to 3 $C_{1-6}$ alkyl groups,
(9) an isoxazole ring optionally further substituted by 1 to 3 $C_{1-6}$ alkyl groups,
(10) a thiadiazole ring optionally further substituted by 1 to 3 $C_{1-6}$ alkyl groups,
(11) a thiazole ring optionally further substituted by 1 to 3 $C_{1-6}$ alkyl groups,
(12) an indazole ring optionally further substituted by 1 to 3 $C_{1-6}$ alkyl groups,
(13) a benzofuran ring optionally further substituted by 1 to 3 $C_{1-6}$ alkyl groups,
(14) an imidazopyridine ring optionally further substituted by 1 to 3 $C_{1-6}$ alkyl groups,
(15) a pyrazolopyrimidine ring,
(16) an imidazothiazole ring optionally further substituted by 1 to 3 $C_{1-6}$ alkyl groups,
(17) an oxetane ring optionally further substituted by 1 to 3 phenyl groups,
(18) a pyrrolidine ring optionally further substituted by 1 to 3 substituents selected from
  (a) a $C_{1-6}$ alkyl group optionally substituted by 1 to 3 substituents selected from a hydroxy group, a halogen atom and a $C_{1-6}$ alkoxy group,
  (b) an oxo group,
  (c) a phenyl group,
  (d) a hydroxy group,
  (e) a cyano group,
  (f) a pyridyl group, and
  (g) a carbamoyl group,
(19) a piperidine ring optionally further substituted by 1 to 3 substituents selected from
  (a) a halogen atom, and
  (b) a $C_{1-6}$ alkyl group optionally substituted by 1 to 3 hydroxy groups,
(20) a morpholine ring optionally further substituted by 1 to 3 $C_{1-6}$ alkyl groups optionally substituted by 1 to 3 hydroxy groups,
(21) a tetrahydropyran ring,
(22) a tetrahydrofuran ring,
(23) a dihydropyrimidine ring optionally further substituted by 1 to 3 oxo groups,
(24) a dihydrobenzofuran ring,
(25) a dihydrochromene ring,
(26) a tetrahydroindazole ring optionally further substituted by 1 to 3 $C_{1-6}$ alkyl groups,
(27) a 8-oxa-3-azabicyclo[3.2.1]octane ring,
(28) a 3-oxa-8-azabicyclo[3.2.1]octane ring,
(29) a 3-azabicyclo[3.1.0]hexane ring optionally further substituted by 1 to 3 halogen atoms,
(30) a 2-oxa-6-azaspiro[3.5]nonane ring,
(31) a 2-oxa-7-azaspiro[3.5]nonane ring, or
(32) an oxazepane ring optionally further substituted by 1 to 3 $C_{1-6}$ alkyl groups optionally substituted by 1 to 3 hydroxy groups.

[4A]

The compound or salt of the above-mentioned [1], wherein Ring A is a 5- or 6-membered ring optionally further substituted by 1 to 3 substituents selected from
(1) a halogen atom, and
(2) a $C_{1-6}$ alkyl group;
X is —$CONR^1$— or —$NR^1CO$—, and $R^1$ is a hydrogen atom or a $C_{1-6}$ alkyl group;
$R^2$ and $R^3$ are hydrogen atoms;
Ring B is a nitrogen-containing heterocycle optionally further substituted by 1 to 3 $C_{6-14}$ aryl-carbonyl groups;

9

$Z^1$ is a bond, —NR$^a$—, —CR$^b_2$—, —CR$^b_2$—CR$^b_2$— or —CR$^b_2$—O—;
wherein
R$^a$ is a hydrogen atom or a $C_{1-6}$ alkyl group; and
R$^b$ are each independently a hydrogen atom, a halogen atom, a $C_{1-6}$ alkyl group or a $C_{6-14}$ aryl group; and
Ring C is a ring optionally further substituted by 1 to 3 substituents selected from
  (a) a halogen atom,
  (b) a $C_{1-6}$ alkyl group optionally substituted by 1 to 3 substituents selected from
    (i) a halogen atom, and
    (ii) a hydroxy group,
  (c) a $C_{6-14}$ aryl group,
  (d) a cyano group,
  (e) a $C_{1-6}$ alkoxy group optionally substituted by 1 to 3 halogen atoms,
  (f) a 3- to 14-membered non-aromatic heterocyclic group,
  (g) a $C_{3-10}$ cycloalkyl group,
  (h) a hydroxy group, and
  (i) an oxo group.

[4B]
The compound or salt of the above-mentioned [1], wherein Ring A is a benzene ring, a pyridine ring or a thiophene ring, each of which is optionally further substituted by 1 to 3 substituents selected from
  (1) a halogen atom, and
  (2) a $C_{1-6}$ alkyl group;
X is —CONR$^1$— or —NR$^1$CO—, and R$^1$ is a hydrogen atom or a $C_{1-6}$ alkyl group;
R$^2$ and R$^3$ are hydrogen atoms;
Ring B is
(1) a morpholine ring,
(2) a piperidine ring,
(3) a piperazine ring optionally further substituted by one benzoyl group,
(4) a pyrrolidine ring,
(5) an indoline ring,
(6) an isoindoline ring,
(7) a tetrahydroquinoline ring, or
(8) a tetrahydroisoquinoline ring;
$Z^1$ is a bond, —NR$^a$—, —CR$^b_2$—, or —CR$^b_2$—O—;
wherein
R$^a$ is a hydrogen atom or a $C_{1-6}$ alkyl group; and
R$^b$ are each independently a hydrogen atom, a halogen atom, a $C_{1-6}$ alkyl group or a phenyl group; and
Ring C is
(1) a benzene ring optionally further substituted by 1 to 3 substituents selected from
  (a) a halogen atom,
  (b) a $C_{1-6}$ alkyl group optionally substituted by 1 to 3 halogen atoms,
  (c) a phenyl group,
  (d) a cyano group,
  (e) a $C_{1-6}$ alkoxy group, and
  (f) a morpholinyl group,
(2) a $C_{3-10}$ cycloalkane ring optionally further substituted by 1 to 3 substituents selected from
  (a) a phenyl group, and
  (b) a cyano group,
(3) an adamantane ring,
(4) a pyridine ring optionally further substituted by 1 to 3 substituents selected from
  (a) a $C_{1-6}$ alkyl group,
  (b) a $C_{3-10}$ cycloalkyl group,
  (c) a $C_{1-6}$ alkoxy group optionally substituted by 1 to 3 halogen atoms, and
  (d) a hydroxy group,

10

(5) a thiophene ring optionally further substituted by 1 to 3 $C_{1-6}$ alkyl groups,
(6) a pyrazole ring optionally further substituted by 1 to 3 $C_{1-6}$ alkyl groups optionally substituted by 1 to 3 halogen atoms,
(7) an imidazole ring optionally further substituted by 1 to 3 $C_{1-6}$ alkyl groups,
(8) an oxadiazole ring optionally further substituted by 1 to 3 $C_{1-6}$ alkyl groups,
(9) an isoxazole ring optionally further substituted by 1 to 3 $C_{1-6}$ alkyl groups,
(10) a thiadiazole ring optionally further substituted by 1 to 3 $C_{1-6}$ alkyl groups,
(11) a thiazole ring optionally further substituted by 1 to 3 $C_{1-5}$ alkyl groups,
(12) an indazole ring optionally further substituted by 1 to 3 $C_{1-6}$ alkyl groups,
(13) a benzofuran ring,
(14) an imidazopyridine ring optionally further substituted by 1 to 3 $C_{1-6}$ alkyl groups,
(15) a pyrazolopyrimidine ring,
(16) an imidazothiazole ring optionally further substituted by 1 to 3 $C_{1-6}$ alkyl groups,
(17) an oxetane ring optionally further substituted by 1 to 3 phenyl groups,
(18) a pyrrolidine ring optionally further substituted by 1 to 3 substituents selected from
  (a) a $C_{1-6}$ alkyl group optionally substituted by 1 to 3 hydroxy groups, and
  (b) an oxo group,
(19) a piperidine ring,
(20) a morpholine ring,
(21) a tetrahydropyran ring,
(22) a tetrahydrofuran ring,
(23) a dihydropyrimidine ring optionally further substituted by 1 to 3 oxo groups,
(24) a dihydrobenzofuran ring,
(25) a dihydrochromene ring,
(26) a tetrahydroindazole ring optionally further substituted by 1 to 3 $C_{1-6}$ alkyl groups,
(27) a 8-oxa-3-azabicyclo[3.2.1]octane ring, or
(28) a 3-oxa-8-azabicyclo[3.2.1]octane ring.

[5]
The compound or salt of any of the above-mentioned [1] to [4], wherein $Z^1$ is a bond.

[6]
The compound or salt of any of the above-mentioned [1] to [4], wherein Ring B is a morpholine ring having no additional substituent.

[7]
The compound or salt of any of the above-mentioned [1] to [4], wherein
Ring A is a benzene ring;
X is —CONH—;
R$^2$ and R$^3$ are hydrogen atoms;
Ring B is a morpholine ring;
$Z^1$ is a bond; and
Ring C is a benzene ring, a pyrazole ring, an isoxazole ring or an indazole ring, each of which is optionally further substituted by 1 to 3 substituents selected from
  (a) a halogen atom, and
  (b) a $C_{1-6}$ alkyl group.

[7A]
The compound or salt of any of the above-mentioned [1] to [4], wherein
Ring A is a benzene ring;
X is —CONH—;

R² and R³ are hydrogen atoms;
Ring B is a morpholine ring;
Z¹ is a bond; and
Ring C is
(1) a benzene ring optionally further substituted by 1 to 3 halogen atoms,
(2) a pyrazole ring further substituted by 1 to 3 $C_{1-6}$ alkyl groups,
(3) an isoxazole ring further substituted by 1 to 3 $C_{1-6}$ alkyl groups, or
(4) an indazole ring further substituted by 1 to 3 $C_{1-6}$ alkyl groups.

[7B]

The compound or salt of any of the above-mentioned [1] to [4], wherein
Ring A is a benzene ring;
X is —CONH—;
R² and R³ are hydrogen atoms;
Ring B is a morpholine ring;
Z¹ is a bond; and
Ring C is a benzene ring optionally further substituted by 1 to 3 halogen atoms.

[8]

N-(((3S)-4-Benzoylmorpholin-3-yl)methyl)-4-(5-(trifluoromethyl)-1,2,4-oxadiazol-3-yl)benzamide, or a salt thereof.

[9]

N-(((3S)-4-(3,5-Dichlorobenzoyl)morpholin-3-yl)methyl)-4-(5-(trifluoromethyl)-1,2,4-oxadiazol-3-yl)benzamide, or a salt thereof.

[10]

N-(((3S)-4-((1-Methyl-1H-pyrazol-5-yl)carbonyl)morpholin-3-yl)methyl)-4-(5-(trifluoromethyl)-1,2,4-oxadiazol-3-yl)benzamide, or a salt thereof.

[11]

N-(((3S)-4-((2-Methyl-2H-indazol-3-yl)carbonyl)morpholin-3-yl)methyl)-4-(5-(trifluoromethyl)-1,2,4-oxadiazol-3-yl)benzamide, or a salt thereof.

[12]

A medicament comprising the compound or salt of any of the above-mentioned [1] to [11].

[13]

The medicament of the above-mentioned [12], which is a histone deacetylase inhibitor.

[14]

The medicament of the above-mentioned [12], which is an agent for the prophylaxis or treatment of autoimmune diseases and/or inflammatory diseases.

[15]

The compound or salt of the above-mentioned [1] for use in the prophylaxis or treatment of autoimmune diseases and/or inflammatory diseases.

[16]

A method of inhibiting histone deacetylase in a mammal, which comprises administering an effective amount of the compound or salt of the above-mentioned [1] to the mammal.

[17]

A method for the prophylaxis or treatment of autoimmune diseases and/or inflammatory diseases in a mammal, which comprises administering an effective amount of the compound or salt of the above-mentioned [1] to the mammal.

[18]

Use of the compound or salt of the above-mentioned [1] for the production of an agent for the prophylaxis or treatment of autoimmune diseases and/or inflammatory diseases.

Effect of the Invention

Compound (I) has a HDAC inhibitory action, and is useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, Parkinson's disease, Huntington's disease, etc.) and the like.

DETAILED DESCRIPTION OF THE INVENTION

Figure 1:
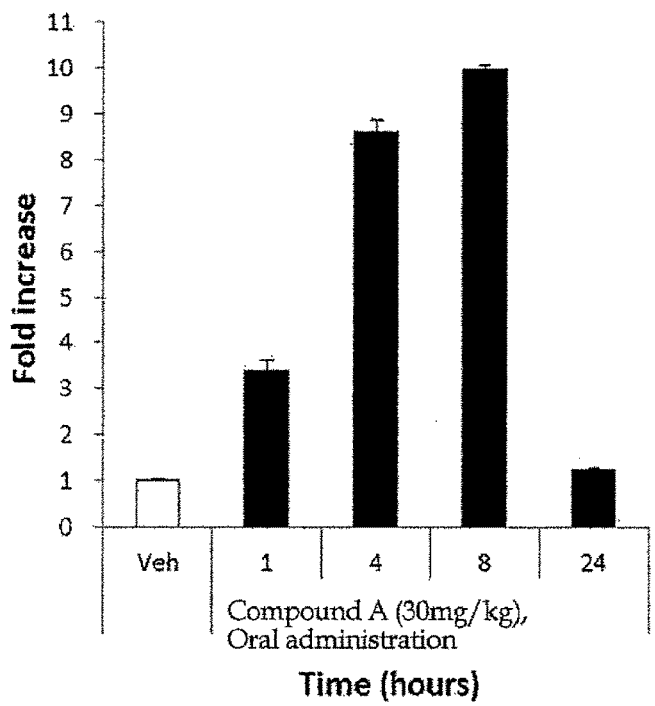
FIG. 1 shows increase in acetylated tubulin by compound A (compound of Example 36).

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluotocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-40}$ cycloalkenyl group" include cyclopropenyl, cyclobutenyl, cyclopentenyl, cyclohexenyl, cycloheptenyl and cyclooctenyl.

In the present specification, examples of the "$C_{5-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),

(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-5}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-4}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, O-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydropyranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tettahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_1$-$€$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5-10 to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ arylcarbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group. (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkyl-sulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamcylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a 07-16 aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{2-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-34}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(C$_2$H$_5$)—, —CH(C$_3$H—)—, —CH(CH(CH$_3$)$_2$)—, —(CH(CH))$_2$—, —CH$_2$—CH(CH$_3$)—, —CH(CH$_3$)—CH$_2$—, —CH$_2$—CH$_2$—C(CH$_3$)$_2$—, —C(CH$_3$)$_2$—CH$_2$—CH$_2$—, —CH$_2$—CH$_2$—CH$_2$—C(CH$_3$)$_2$— and —C(CH$_3$)$_2$—CH$_2$—CH$_2$—CH$_2$—.

In the present specification, examples of the "$C_{2-6}$ alkenylene group" include —CH=CH—, —CH$_2$—CH=CH—, —CH=CH—CH$_2$—, —C(CH$_3$)$_2$—CH=CH—, —CH=CH—C(CH$_3$)$_2$—, —CH$_2$—CH=CH—CH$_2$—, —CH$_2$—CH$_2$—CH=CH—, —CH=CH—CH$_2$—CH$_2$—, —CH=CH—CH$_2$—CH$_2$—CH$_2$— and —CH$_2$—CH$_2$—CH$_2$—CH=CH—.

In the present specification, examples of the "$C_{2-6}$ alkynylene group" include —C≡C—, —CH$_2$—C≡C—, —C≡C—CH$_2$—, —C(CH$_3$)$_2$—C≡C—, —C≡C—C(CH$_3$)$_2$—, —CH$_2$—C≡C—CH$_2$—, —CH$_2$—CH$_2$—C≡C—, —C≡C—CH$_2$—CH$_2$—, —C≡C—C≡C—, —C≡C—CH$_2$—CH$_2$—CH$_2$— and —CH$_2$—CH$_2$—CH$_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in the formula (I) is explained in detail in the following.

Ring A is an optionally further substituted 5- or 6-membered ring.

In Ring A, the atom that the oxadiazole is bonded to, and the atom that $X^1$ is bonded to, i.e., $A^1$ and $A^4$ in the following partial structure:

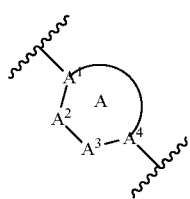

are each a carbon atom or a nitrogen atom, preferably both carbon atoms.

$A^2$ and $A^3$ in the above-mentioned partial structure are each a carbon atom, a nitrogen atom, an oxygen atom or a sulfur atom, preferably each a carbon atom or a sulfur atom, particularly preferably both carbon atoms.

The bond $A^1$-$A^2$, bond $A^2$-$A^3$ and bond $A^3$-$A^4$ are each a single bond or a double bond.

Examples of the "5- or 6-membered ring" of the "optionally further substituted 5- or 6-membered ring" for Ring A include
a benzene ring;
a cyclopentane ring, a cyclohexane ring;
5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, 1,2,4-triazole, 1,2,4-triazine and the like; and
5- or 6-membered monocyclic non-aromatic heterocycles such as tetrahydrothiophene, tetrahydrofuran, pyrroline, pyrrolidine, imidazoline, imidazolidine, oxazoline, oxazolidine, pyrazoline, pyrazolidine, thiazoline, thiazolidine, isothiazolidine, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine and the like.

The "5- or 6-membered ring" of the "optionally further substituted 5- or 6-membered ring" for Ring A is preferably a 5- or 6-membered aromatic ring (i.e., a benzene ring or a 5- or 6-membered monocyclic aromatic heterocycle), more preferably a benzene ring, a pyridine ring or a thiophene ring.

The "5- or 6-membered ring" of the "optionally further substituted 5- or 6-membered ring" for Ring A is optionally further substituted, for example, by substituent(s) selected from the above-mentioned Substituent Group A. The number of the substituents is, for example, 1 to 3. When the number of the substituents is 2 or more, the respective substituents may be the same or different.

Ring A is preferably a 5- or 6-membered ring (e.g., benzene, pyridine, thiophene) optionally further substituted by 1 to 3 substituents selected from
  (1) a halogen atom (e.g., a fluorine atom), and
  (2) a $C_{1-6}$ alkyl group (e.g., methyl).

Ring A is more preferably a benzene ring, a pyridine ring or a thiophene ring, each of which is optionally further substituted by 1 to 3 substituents selected from
  (1) a halogen atom (e.g., a fluorine atom), and
  (2) a $C_{1-6}$ alkyl group (e.g., methyl).

Ring A is further more preferably
(1) a benzene ring optionally further substituted by 1 to 3 substituents selected from
  (a) a halogen atom (e.g., a fluorine atom), and
  (b) a $C_{1-6}$ alkyl group (e.g., methyl), or (2) a 5- or 6-membered monocyclic aromatic heterocycle (e.g., pyridine, thiophene).

Ring A is still more preferably
(1) a benzene ring optionally further substituted by 1 to 3 substituents selected from
  (a) a halogen atom (e.g., a fluorine atom), and
  (b) a $C_{1-6}$ alkyl group (e.g., methyl),
(2) a pyridine ring, or
(3) a thiophene ring.

Ring A is particularly preferably a benzene ring.

X is —CONR$^1$— or —NR$^1$CO—, and R$^1$ is a hydrogen atom or a substituent. The left bond is bonded to Ring A, and the right bond is bonded to C(R$^2$) (R$^3$).

The "substituent" for R$^1$ is preferably an optionally substituted hydrocarbon group, more preferably an optionally substituted $C_{1-6}$ alkyl group, further more preferably a $C_{1-6}$ alkyl group (e.g., methyl).

Preferably, X is —CONR$^1$— or —NR$^1$CO—, and R$^1$ is a hydrogen atom or a $C_{1-6}$ alkyl group (e.g., methyl).

More preferably, X is —CONH—.

R$^2$ and R$^3$ are the same or different and each is a hydrogen atom or a substituent.

R$^2$ and R$^3$ are preferably both hydrogen atoms.

Ring B is an optionally further substituted nitrogen-containing heterocycle.

In Ring B, the atom that —C(R$^2$) (R$^3$) is bonded to, i.e., B$^1$ in the following partial structure:

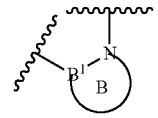

is a carbon atom.

The "nitrogen-containing heterocycle" of the "optionally further substituted nitrogen-containing heterocycle" for Ring B is optionally further substituted, for example, by substituent(s) selected from the above-mentioned Substituent Group A. The number of the substituents is, for example, 1 to 3. When the number of the substituents is 2 or more, the respective substituents may be the same or different.

Ring B is preferably a nitrogen-containing heterocycle (preferably a 4- to 10-membered nitrogen-containing heterocycle) (e.g., morpholine, piperidine, piperazine, pyrrolidine, indoline, isoindoline, tetrahydroquinoline, tetrahydroisoquinoline) optionally further substituted by 1 to 3 $C_{6-14}$ aryl-carbonyl groups (e.g., benzoyl).

Ring B is more preferably a 4- to 10-membered nitrogen-containing heterocycle (e.g., morpholine, piperidine, piperazine, pyrrolidine, indoline, isoindoline, tetrahydroquinoline, tetrahydroisoquinoline) optionally further substituted by 1 to 3 $C_{6-14}$ aryl-carbonyl groups (e.g., benzoyl).

Ring B is further more preferably
(1) a morpholine ring,
(2) a piperidine ring,
(3) a piperazine ring optionally further substituted by one benzoyl group,
(4) a pyrrolidine ring,
(5) an indoline ring,
(6) an isoindoline ring,
(7) a tetrahydroquinoline ring, or
(8) a tetrahydroisoquinoline ring.

In another embodiment, Ring B is more preferably a nitrogen-containing heterocycle (preferably a 3- to 8-membered monocyclic non-aromatic nitrogen-containing heterocycle) (e.g., morpholine).

In this embodiment, Ring B is further more preferably a 3- to 8-membered monocyclic non-aromatic nitrogen-containing heterocycle (e.g., morpholine).

Ring B is particularly preferably a morpholine ring having no additional substituent.

$Z^1$ is a bond, or a spacer in which the number of atoms in the main chain is 1 to 3.

Examples of the "spacer in which the number of atoms in the main chain is 1 to 3" for $Z^1$ include a spacer wherein the main chain consists of 1 to 3 atoms selected from a carbon atom, a nitrogen atom, a sulfur atom and an oxygen atom, and the atoms are optionally substituted by substituent(s) selected from Substituent Group A at substitutable position(s). Specific examples thereof include —O—, —NR$^a$—, —S—, —S(O)—, —S(O)$_2$—, —CR$^b_2$—, —C(O)—, —O—CR$^b_2$—, —CR$^b_2$—O—, —NR$^a$—CR$^b_2$—, —CR$^b_2$—NR$^a$—, —S—CR$^b_2$—, —CR$^b_2$—S—, —S(O)—CR$^b_2$—, —CR$^b_2$—S(O)—, —S(O)$_2$—CR$^b_2$—, —CR$^b_2$—S(O)$_2$—, —CR$^b_2$—CR$^b_2$—, —CR$^c$=CR$^c$—, —O—C(O)—, —C(O)—O—, —NR$^a$—C(O), —C(O)—NR$^a$—, —S—C(O)—, —C(O)—S—, —S(O)$_2$—O—, —O—S(O)$_2$—, —S(O)$_2$—NR$^a$—, —NR$^a$—S(O)$_2$—, —CR$^b_2$—C(O)—, —C(O)—CR$^b_2$—, —O—CR$^b_2$—CR$^b_2$—, —CR$^b_2$—O—CR$^b_2$—, —CR$^b_2$—CR$^b_2$—O—, —O—CR$^b_2$—O—, —NR$^a$—CR$^b_2$—CR$^b_2$—, —CR$^b_2$—NR$^a$—CR$^b_2$—, —CR$^b_2$—CR$^b_2$—NR$^a$—, —NR$^a$—CR$^b_2$—NR$^a$—, —S—CR$^b_2$—CR$^b_2$—, —CR$^b_2$—CR$^b_2$—S—, —S(O)—CR$^b_2$—CR$^b_2$—, —CR$^b_2$—CR$^b_2$—S(O)—, —S(O)$_2$—CR$^b_2$—CR$^b_2$—, —CR$^b_2$—CR$^b_2$—S(O)$_2$—, —CR$^b_2$—CR$^b_2$—CR$^b_2$—, —CR$^b_2$—CR$^c$=CR$^c$—, —CR$^c$=CR$^c$—CR$^b_2$—, —C(O)—CR$^b$CR$^b_2$—, —CR$^b_2$—CR$^b_2$—C(O)— (wherein each R$^a$, R$^b$ and R$^c$ in the formulas are each independently a hydrogen atom or a substituent selected from Substituent Group A) and the like. The left bond is bonded to C(O), and the right bond is bonded to Ring C.

Preferably, $Z^1$ is a bond, —NR$^a$—, —CR$^b_2$—, —CR$^b_2$—CR$^b_2$— or —CR$^b_2$—O—,
  wherein
  R$^a$ is a hydrogen atom or a $C_{1-6}$ alkyl group (e.g., methyl), and
  R$^b$ are each independently a hydrogen atom, a halogen atom (e.g., a fluorine atom), a $C_{1-6}$ alkyl group (e.g., methyl) or a $C_{6-14}$ aryl group (e.g., phenyl).

More preferably, $Z^1$ is a bond, —NR$^a$—, —CR$^b_2$—, —CR$^b_2$—CR$^b_2$— or —CR$^b_2$—O—,
  wherein
  R$^a$ is a hydrogen atom or a $C_{1-6}$ alkyl group (e.g., methyl), and
  R$^b$ are each independently a hydrogen atom, a halogen atom (e.g., a fluorine atom), a $C_{1-6}$ alkyl group (e.g., methyl) or a phenyl group
(specifically, $Z^1$ is a bond, —NH—, —N(CH$_3$)—, —CH$_2$—, —CH$_2$CH$_2$—, —CH(C$_6$H$_5$)—, —C(CH$_3$)$_2$—, —C(F)$_2$— or —CH$_2$O—).

Further more preferably, $Z^1$ is a bond.

Ring C is an optionally further substituted ring.

Examples of the "ring" of the "optionally further substituted ring" for Ring C include a hydrocarbon ring (e.g., a $C_{6-14}$ aromatic hydrocarbon ring, a $C_{3-10}$ cycloalkane ring, a $C_{3-10}$ cycloalkene ring) and a heterocycle (e.g., an aromatic heterocycle (e.g., a 5- to 14-membered (preferably 5- to 10-membered) aromatic heterocycle) and a non-aromatic heterocycle (e.g., a 3- to 14-membered (preferably 4- to 10-membered) non-aromatic heterocycle)).

The "ring" of the "optionally further substituted ring" for Ring C is optionally further substituted, for example, by substituent(s) selected from the following Substituent Group B. The number of the substituents is, for example, 1 to 3. When the number of the substituents is 2 or more, the respective substituents may be the same or different.

[Substituent Group B]
Substituent Group A wherein
"(57) an optionally halogenated $C_{1-6}$ alkyl group" is replaced by "(57) a $C_{1-6}$ alkyl group optionally substituted by substituent(s) selected from a halogen atom, a hydroxy group and a $C_{1-6}$ alkoxy group",
"(6) an optionally halogenated $C_{1-6}$ alkoxy group" is replaced by "(6) a $C_{1-6}$ alkoxy group optionally substituted by substituent(s) selected from a halogen atom and a hydroxy group", and
"(34) a mono- or di-$C_{1-6}$ alkyl-carbamoyl group" is replaced by "(34) a mono- or di-$C_{1-6}$ alkyl-carbamoyl group optionally substituted by 1 to 3 hydroxy groups".

Ring C is preferably a ring (e.g., a $C_{6-14}$ aromatic hydrocarbon ring (e.g., benzene), a $C_{3-10}$ cycloalkane ring (e.g., cyclopropane, cyclopentane, cyclohexane, adamantane), a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)), a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3-azabicyclo[3.2.1]octane, 3-oxa-8-azabicyclo[3.2.1]octane, 3-azabicyclo[3.1.0]hexane, 2-oxa-6-azaspiro[3.5]nonane, 2-oxa-7-azaspiro[3.5]nonane, oxazepane (e.g., 1,4-oxazepane)) optionally further substituted by 1 to 3 substituents selected from
  (a) a halogen atom (e.g., a fluorine atom, a chlorine atom),
  (b) a $C_{1-5}$ alkyl group (e.g., methyl, ethyl, isopropyl) optionally substituted by 1 to 3 substituents selected from
    (i) a halogen atom (e.g., a fluorine atom),
    (ii) a hydroxy group, and
    (iii) a $C_{1-6}$ alkoxy group (e.g., methoxy),
  (c) a $C_{6-14}$ aryl group (e.g., phenyl),
  (d) a cyano group,
  (e) a $C_{1-6}$ alkoxy group (e.g., methoxy, ethoxy) optionally substituted by 1 to 3 substituents selected from
    (i) a halogen atom (e.g., a fluorine atom), and
    (ii) a hydroxy group,
  (f) a 3- to 14-membered non-aromatic heterocyclic group (preferably a 3- to 8-membered monocyclic non-aromatic heterocyclic group) (e.g., morpholinyl),
  (g) a 5- to 14-membered aromatic heterocyclic group (preferably a 5- or 6-membered monocyclic aromatic heterocyclic group) (e.g., pyridyl),
  (h) a $C_{3-10}$ cycloalkyl group (e.g., cyclopropyl),
  (i) a hydroxy group,
  (j) an oxo group,
  (k) a carboxy group,
  (l) a $C_{1-6}$ alkoxy-carbonyl group (e.g., methoxycarbonyl),
  (m) a carbamoyl group, and
  (n) a mono- or di-$C_{1-6}$ alkyl-carbamoyl group (e.g.,ethylcarbamoyl) optionally substituted by 1 to 3 hydroxy groups.

Ring C is more preferably (1) a $C_{6-14}$ aromatic hydrocarbon ring (e.g., benzene) optionally further substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a $C_{6-14}$ aryl group (e.g., phenyl),
  (d) a cyano group,
  (e) a $C_{1-6}$ alkoxy group (e.g., methoxy, ethoxy) optionally substituted by 1 to 3 hydroxy groups,
  (f) a 3- to 8-membered monocyclic non-aromatic heterocyclic group (e.g., morpholinyl),
  (g) a carboxy group,
  (h) a $C_{1-6}$ alkoxy-carbonyl group (e.g., methoxycarbonyl), and
  (i) a mono- or di-$C_{1-6}$ alkyl-carbamoyl group (e.g., ethylcarbamoyl) optionally substituted by 1 to 3 hydroxy groups,
(2) a $C_{3-10}$ cycloalkane ring (e.g., cyclopropane, cyclopentane, cyclohexane, adamantane) optionally further substituted by 1 to 3 substituents selected from
  (a) a $C_{6-14}$ aryl group (e.g., phenyl), and
  (b) a cyano group,
(3) a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)) optionally further substituted by 1 to 3 substituents selected from
  (a) a $C_{1-6}$ alkyl group (e.g., methyl, ethyl, isopropyl) optionally substituted by 1 to 3 substituents selected from a halogen atom (e.g., a fluorine atom) and a hydroxy group,
  (b) a $C_{3-10}$ cycloalkyl group (e.g., cyclopropyl),
  (c) a $C_{1-6}$ alkoxy group (e.g., ethoxy) optionally substituted by 1 to 3 halogen atoms (e.g., a fluorine atom), and
  (d) a hydroxy group, or
(4) a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3-azabicyclo[3.2.1]octane, 3-oxa-8-azabicyclo[3.2.1]octane, 3-azabicyclo[3.1.0]hexane, 2-oxa-6-azaspiro[3.5]nonane, 2-oxa-7-azaspiro[3.5]nonane, oxazepane (e.g., 1,4-oxazepane)) optionally further substituted by 1 to 3 substituents selected from
  (a) a $C_{1-6}$ alkyl group (e.g., methyl; ethyl) optionally substituted by 1 to 3 substituents selected from a hydroxy group, a halogen atom (e.g., a fluorine atom) and a $C_{1-6}$ alkoxy group (e.g., methoxy),
  (b) a $C_{6-14}$ aryl group (e.g., phenyl),
  (c) an oxo group,
  (d) a halogen atom (e.g., a fluorine atom),
  (e) a hydroxy group,
  (f) a cyano group,
  (g) a 5- or 6-membered monocyclic aromatic heterocyclic group (e.g., pyridyl), and
  (h) a carbamoyl group.

Ring C is further more preferably
(1) a benzene ring optionally further substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a phenyl group,
  (d) a cyano group,
  (e) a $C_{1-6}$ alkoxy group (e.g., methoxy, ethoxy) optionally substituted by 1 to 3 hydroxy groups,
  (f) a morpholinyl group,
  (g) a carboxy group,
  (h) a $C_{1-6}$ alkoxy-carbonyl group (e.g., methoxycarbonyl), and
  (i) a mono- or di-$C_{1-6}$ alkyl-carbamoyl group (e.g., ethylcarbamoyl) optionally substituted by 1 to 3 hydroxy groups,
(2) a $C_{3-10}$ cycloalkane ring (e.g., cyclopropane, cyclopentane, cyclohexane) optionally further substituted by 1 to 3 substituents selected from
  (a) a phenyl group, and
  (b) a cyano group,
(3) an adamantane ring,
(4) a pyridine ring optionally further substituted by 1 to 3 substituents selected from
  (a) a $C_{1-6}$ alkyl group (e.g., methyl),
  (b) a $C_{3-10}$ cycloalkyl group (e.g., cyclopropyl),
  (c) a $C_{1-6}$ alkoxy group (e.g., ethoxy) optionally substituted by 1 to 3 halogen atoms (e.g., a fluorine atom), and
  (d) a hydroxy group,
(5) a thiophene ring optionally further substituted by 1 to 3 $C_{1-6}$ alkyl groups (e.g., methyl),
(6) a pyrazole ring optionally further substituted by 1 to 3 $C_{1-6}$ alkyl groups (e.g., methyl, ethyl, isopropyl) optionally substituted by 1 to 3 substituents selected from a halogen atom (e.g., a fluorine atom) and a hydroxy group,
(7) an imidazole ring optionally further substituted by 1 to 3 $C_{1-6}$ alkyl groups (e.g., methyl),
(8) an oxadiazole ring (e.g., a 1,2,5-oxadiazole ring) optionally further substituted by 1 to 3 $C_{1-6}$ alkyl groups (e.g., methyl),
(9) an isoxazole ring optionally further substituted by 1 to 3 $C_{1-6}$ alkyl groups (e.g., methyl, ethyl),
(10) a thiadiazole ring (e.g., a 1,2,3-thiadiazole ring) optionally further substituted by 1 to 3 $C_{1-6}$ alkyl groups (e.g., methyl),
(11) a thiazole ring optionally further substituted by 1 to 3 $C_{1-6}$ alkyl groups (e.g., methyl),
(12) an indazole ring (e.g., a 1H-indazole ring, a 2H-indazole ring) optionally further substituted by 1 to 3 $C_{1-6}$ alkyl groups (e.g., methyl),
(13) a benzofuran ring (e.g., a 1-benzofuran ring) optionally further substituted by 1 to 3 $C_{1-6}$ alkyl groups (e.g., methyl),
(14) an imidazopyridine ring (e.g., an imidazo[1,2-a]pyridine ring) optionally further substituted by 1 to 3 $C_{1-6}$ alkyl groups (e.g., methyl),
(15) a pyrazolopyrimidine ring (e.g., a pyrazolo[1,5-a]pyrimidine ring),
(16) an imidazothiazole ring (e.g., an imidazo[2,1-b]thiazole ring) optionally further substituted by 1 to 3 $C_{1-6}$ alkyl groups (e.g., methyl),
(17) an oxetane ring optionally further substituted by 1 to 3 phenyl groups,
(18) a pyrrolidine ring optionally further substituted by 1 to 3 substituents selected from
  (a) a $C_{1-6}$ alkyl group (e.g., methyl, ethyl) optionally substituted by 1 to 3 substituents selected from a hydroxy group, a halogen atom (e.g., a fluorine atom) and a $C_{1-6}$ alkoxy group (e.g., methoxy),
  (b) an oxo group, (c) a phenyl group,
(d) a hydroxy group,
(e) a cyano group,
(f) a pyridyl group, and
(g) a carbamoyl group,
(19) a piperidine ring optionally further substituted by 1 to 3 substituents selected from
  (a) a halogen atom (e.g., a fluorine atom), and
  (b) a $C_{1-5}$ alkyl group (e.g., methyl, ethyl) optionally substituted by 1 to 3 hydroxy groups,
(20) a morpholine ring optionally further substituted by 1 to 3 $C_{1-6}$ alkyl groups (e.g., methyl) optionally substituted by 1 to 3 hydroxy groups,
(21) a tetrahydropyran ring,
(22) a tetrahydrofuran ring,
(23) a dihydropyrimidine ring (e.g., a 1,6-dihydropyrimidine ring) optionally further substituted by 1 to 3 oxo groups,
(24) a dihydrobenzofuran ring (e.g., a 2,3-dihydro-1-benzofuran ring),
(25) a dihydrochromene ring (e.g., a 3,4-dihydro-2H-chromene ring),
(26) a tetrahydroindazole ring (e.g., a 4,5,6,7-tetrahydro-2H-indazole ring) optionally further substituted by 1 to 3 $C_{1-6}$ alkyl groups (e.g., methyl),
(27) a 8-oxa-3-azabicyclo[3.2.1]octane ring,
(28) a 3-oxa-8-azabicyclo[3.2.1]octane ring,
(29) a 3-azabicyclo[3.1.0]hexane ring optionally further substituted by 1 to 3 halogen atoms (e.g., a fluorine atom),
(30) a 2-oxa-6-azaspiro[3.5]nonane ring,
(31) a 2-oxa-7-azaspiro[3.5]nonane ring, or
(32) an oxazepane ring (e.g., a 1,4-oxazepane ring) optionally further substituted by 1 to 3 $C_{1-6}$ alkyl groups (e.g., methyl) optionally substituted by 1 to 3 hydroxy groups.

In another embodiment, Ring C is preferably a ring (e.g., a $C_{6-14}$ aromatic hydrocarbon ring (e.g., benzene), a $C_{3-10}$ cycloalkane ring (e.g., cyclopropane, cyclopentane, cyclohexane, adamantane), a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)), a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3-azabicyclo[3.2.1]octane, 3-oxa-8-azabicyclo[3.2.1]octane)) optionally further substituted by 1 to 3 substituents selected from
  (a) a halogen atom (e.g., a fluorine atom, a chlorine atom),
  (b) a $C_{1-6}$ alkyl group (e.g., methyl, ethyl, isopropyl) optionally substituted by 1 to 3 substituents selected from
    (i) a halogen atom (e.g., a fluorine atom), and
    (ii) a hydroxy group,
  (c) a $C_{6-14}$ aryl group (e.g., phenyl),
  (d) a cyano group,
  (e) a $C_{1-6}$ alkoxy group (e.g., methoxy, ethoxy) optionally substituted by 1 to 3 halogen atoms (e.g., a fluorine atom),
  (f) a 3- to 14-membered non-aromatic heterocyclic group (preferably a 3- to 8-membered monocyclic non-aromatic heterocyclic group) (e.g., morpholinyl),
  (g) a $C_{3-10}$ cycloalkyl group (e.g., cyclopropyl),
  (h) a hydroxy group, and
  (i) an oxo group.

In this embodiment, Ring C is more preferably
(1) a $C_{6-14}$ aromatic hydrocarbon ring (e.g., benzene) optionally further substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a $C_{6-14}$ aryl group (e.g., phenyl),
  (d) a cyano group,
  (e) a $C_{1-6}$ alkoxy group (e.g., methoxy), and
  (f) a 3- to 14-membered non-aromatic heterocyclic group (preferably a 3- to 8-membered monocyclic non-aromatic heterocyclic group) (e.g., morpholinyl),
(2) a $C_{3-10}$ cycloalkane ring (e.g., cyclopropane, cyclopentane, cyclohexane, adamantane) optionally further substituted by 1 to 3 substituents selected from
  (a) a $C_{6-14}$ aryl group (e.g., phenyl), and
  (b) a cyano group,
(3) a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)) optionally further substituted by 1 to 3 substituents selected from
  (a) a $C_{1-6}$ alkyl group (e.g., methyl, ethyl, isopropyl) optionally substituted by 1 to 3 halogen atoms (e.g., a fluorine atom),
  (b) a $C_{3-10}$ cycloalkyl group (e.g., cyclopropyl),
  (c) a $C_{1-6}$ alkoxy group (e.g., ethoxy) optionally substituted by 1 to 3 halogen atoms (e.g., a fluorine atom), and
  (d) a hydroxy group, or
(4) a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3-azabicyclo[3.2.1]octane, 3-oxa-8-azabicyclo[3.2.1]octane) optionally further substituted by 1 to 3 substituents selected from
  (a) a $C_{1-6}$ alkyl group (e.g., methyl) optionally substituted by 1 to 3 hydroxy groups,
  (b) a $C_{5-14}$ aryl group (e.g., phenyl), and
  (c) an oxo group.

In this embodiment, Ring C is further more preferably
(1) a benzene ring optionally further substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a phenyl group,
  (d) a cyano group,
  (e) a $C_{1-6}$ alkoxy group (e.g., methoxy), and
  (f) a morpholinyl group,
(2) a $C_{3-10}$ cycloalkane ring (e.g., cyclopropane, cyclopentane, cyclohexane) optionally further substituted by 1 to 3 substituents selected from
  (a) a phenyl group, and
  (b) a cyano group,
(3) an adamantane ring,
(4) a pyridine ring optionally further substituted by 1 to 3 substituents selected from (a) a $C_{1-6}$ alkyl group (e.g., methyl),
(b) a $C_{3-10}$ cycloalkyl group (e.g., cyclopropyl),
(c) a $C_{1-6}$ alkoxy group (e.g., ethoxy) optionally substituted by 1 to 3 halogen atoms (e.g., a fluorine atom), and
(d) a hydroxy group,
(5) a thiophene ring optionally further substituted by 1 to 3 $C_{1-6}$ alkyl groups (e.g., methyl),
(6) a pyrazole ring optionally further substituted by 1 to 3 $C_{1-6}$ alkyl groups (e.g., methyl, ethyl, isopropyl) optionally substituted by 1 to 3 halogen atoms (e.g., a fluorine atom),
(7) an imidazole ring optionally further substituted by 1 to 3 $C_{1-6}$ alkyl groups (e.g., methyl),
(8) an oxadiazole ring (e.g., a 1,2,5-oxadiazole ring) optionally further substituted by 1 to 3 $C_{1-6}$ alkyl groups (e.g., methyl),
(9) an isoxazole ring optionally further substituted by 1 to 3 $C_{1-5}$ alkyl groups (e.g., methyl, ethyl),
(10) a thiadiazole ring (e.g., a 1,2,3-thiadiazole ring) optionally further substituted by 1 to 3 $C_{1-6}$ alkyl groups (e.g., methyl),
(11) a thiazole ring optionally further substituted by 1 to 3 $C_{1-6}$ alkyl groups (e.g., methyl),
(12) an indazole ring (e.g., a 1H-indazole ring, a 2H-indazole ring) optionally further substituted by 1 to 3 $C_{1-6}$ alkyl groups (e.g., methyl),
(13) a benzofuran ring (e.g., a 1-benzofuran ring),
(14) an imidazopyridine ring (e.g., an imidazo[1,2-a]pyridine ring) optionally further substituted by 1 to 3 $C_{1-6}$ alkyl groups (e.g., methyl),
(15) a pyrazolopyrimidine ring (e.g., a pyrazolo[1,5-a]pyrimidine ring),
(16) an imidazothiazole ring (e.g., an imidazo[2,1-b]thiazole ring) optionally further substituted by 1 to 3 $C_{1-6}$ alkyl groups (e.g., methyl),
(17) an oxetane ring optionally further substituted by 1 to 3 phenyl groups,
(18) a pyrrolidine ring optionally further substituted by 1 to 3 substituents selected from
    (a) a $C_{1-6}$ alkyl group (e.g., methyl) optionally substituted by 1 to 3 hydroxy groups, and
    (b) an oxo group,
(19) a piperidine ring,
(20) a morpholine ring,
(21) a tetrahydropyran ring,
(22) a tetrahydrofuran ring,
(23) a dihydropyrimidine ring (e.g., a 1,6-dihydropyrimidine ring) optionally further substituted by 1 to 3 oxo groups,
(24) a dihydrobenzofuran ring (e.g., a 2,3-dihydro-1-benzofuran ring),
(25) a dihydrochromene ring (e.g., a 3,4-dihydro-2H-chromene ring),
(26) a tetrahydroindazole ring (e.g., a 4,5,6,7-tetrahydro-2H-indazole ring) optionally further substituted by 1 to 3 $C_{1-6}$ alkyl groups (e.g., methyl),
(27) a 8-oxa-3-azabicyclo[3.2.1]octane ring, or
(28) a 3-oxa-8-azabicyclo[3.2.1]octane ring.

In another embodiment, Ring C is more preferably a benzene ring, a pyrazole ring, an isoxazole ring or an indazole ring, each of which is optionally further substituted by 1 to 3 substituents selected from
    (a) a halogen atom (e.g., a chlorine atom), and
    (b) a $C_{1-6}$ alkyl group (e.g., methyl, ethyl).

In this embodiment, Ring C is further more preferably
(1) a $C_{6-14}$ aromatic hydrocarbon ring (e.g., benzene) optionally further substituted by 1 to 3 halogen atoms (e.g., a chlorine atom), or
(2) a 5- to 14-membered aromatic heterocycle (e.g., pyrazole, isoxazole, indazole (e.g., 2H-indazole)) optionally further substituted by 1 to 3 $C_{1-6}$ alkyl groups (e.g., methyl, ethyl).

Ring C is still more preferably
(1) a benzene ring optionally further substituted by 1 to 3 halogen atoms (e.g., a chlorine atom),
(2) a pyrazole ring optionally further substituted by 1 to 3 $C_{1-6}$ alkyl groups (e.g., methyl),
(3) an isoxazole ring optionally further substituted by 1 to 3 $C_{1-6}$ alkyl groups (e.g., methyl, ethyl), or
(4) an indazole ring (e.g., a 2H-indazole ring) optionally further substituted by 1 to 3 $C_{1-6}$ alkyl groups (e.g., methyl).

Ring C is still further more preferably
(1) a benzene ring optionally further substituted by 1 to 3 halogen atoms (e.g., a chlorine atom),
(2) a pyrazole ring further substituted by 1 to 3 $C_{1-6}$ alkyl groups (e.g., methyl),
(3) an isoxazole ring further substituted by 1 to 3 $C_{1-6}$ alkyl groups (e.g., methyl, ethyl), or
(4) an indazole ring (e.g., a 2H-indazole ring) further substituted by 1 to 3 $C_{1-6}$ alkyl groups (e.g., methyl).

Ring C is particularly preferably a benzene ring optionally further substituted by 1 to 3 halogen atoms (e.g., a chlorine atom).

Preferable specific examples of compound (I) include the following compounds:
[Compound A-1]
Compound (I) wherein
Ring A is a 5- or 6-membered ring (e.g., benzene, pyridine, thiophene) optionally further substituted by 1 to 3 substituents selected from
    (1) a halogen atom (e.g., a fluorine atom), and
    (2) a $C_{1-6}$ alkyl group (e.g., methyl);
X is —CONR$^1$— or —NR$^1$CO—, and R$^1$ is a hydrogen atom or a $C_{1-6}$ alkyl group (e.g., methyl);
R$^2$ and R$^3$ are hydrogen atoms;
Ring B is a nitrogen-containing heterocycle (preferably a 4- to 10-membered nitrogen-containing heterocycle) (e.g., morpholine, piperidine, piperazine, pyrrolidine, indoline, isoindoline, tetrahydroquinoline, tetrahydroisoquinoline) optionally further substituted by 1 to 3 $C_{6-14}$ aryl-carbonyl groups (e.g., benzoyl);
Z$^1$ is a bond, —NR$^a$—, —CR$^b_2$—, —CR$^b_2$—CR$^b_2$— or —CR$^b_2$—O—;
    wherein
    R$^a$ is a hydrogen atom or a $C_{1-6}$ alkyl group (e.g., methyl); and
    R$^b$ are each independently a hydrogen atom, a halogen atom (e.g., a fluorine atom), a $C_{1-6}$ alkyl group (e.g., methyl) or a $C_{6-14}$ aryl group (e.g., phenyl); and
Ring C is a ring (e.g., a $C_{6-14}$ aromatic hydrocarbon ring (e.g., benzene), a $C_{3-10}$ cycloalkane ring (e.g., cyclopropane, cyclopentane, cyclohexane, adamantane), a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)), a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3- azabicyclo[3.2.1]octane, 3-oxa-8-azabicyclo[3.2.1]octane), 3-azabicyclo[3.1.0]hexane, 2-oxa-6-azaspiro[3.5]nonane, 2-oxa-7-azaspiro[3.5]nonane, oxazepane (e.g., 1,4-oxazepane)) optionally further substituted by 1 to 3 substituents selected from
    (a) a halogen atom (e.g., a fluorine atom, a chlorine atom),
    (b) a $C_{1-6}$ alkyl group (e.g., methyl, ethyl, isopropyl) optionally substituted by 1 to 3 substituents selected from
        (i) a halogen atom (e.g., a fluorine atom),
        (ii) a hydroxy group, and
        (iii) a $C_{1-6}$ alkoxy group (e.g., methoxy),
    (c) a $C_{6-14}$ aryl group (e.g., phenyl),
    (d) a cyano group,
    (e) a $C_{1-6}$ alkoxy group (e.g., methoxy, ethoxy) optionally substituted by 1 to 3 substituents selected from
        (i) a halogen atom (e.g., a fluorine atom), and
        (ii) a hydroxy group,
    (f) a 3- to 14-membered non-aromatic heterocyclic group (preferably a 3- to 8-membered monocyclic non-aromatic heterocyclic group) (e.g., morpholinyl),
    (g) a 5- to 14-membered aromatic heterocyclic group (preferably a 5- or 6-membered monocyclic aromatic heterocyclic group) (e.g., pyridyl),
    (h) a $C_{3-10}$ cycloalkyl group (e.g., cyclopropyl),
    (i) a hydroxy group,
    (j) an oxo group,
    (k) a carboxy group,
    (l) a $C_{1-6}$ alkoxy-carbonyl group (e.g., methoxycarbonyl),
    (m) a carbamoyl group, and
    (n) a mono- or di-$C_{1-6}$ alkyl-carbamoyl group (e.g., ethylcarbamoyl) optionally substituted by 1 to 3 hydroxy groups.

[Compound A-2]
Compound (I) wherein
Ring A is
(1) a benzene ring optionally further substituted by 1 to 3 substituents selected from
    (a) a halogen atom (e.g., a fluorine atom), and
    (b) a $C_{1-6}$ alkyl group (e.g., methyl), or
(2) a 5- or 6-membered monocyclic aromatic heterocycle (e.g., pyridine, thiophene);
X is —CONR$^1$— or —NR$^1$CO—, and R$^1$ is a hydrogen atom or a $C_{1-6}$ alkyl group (e.g., methyl);
R$^2$ and R$^3$ are hydrogen atoms;
Ring B is a 4- to 10-membered nitrogen-containing heterocycle (e.g., morpholine, piperidine, piperazine, pyrrolidine, indoline, isoindoline, tetrahydroquinoline, tetrahydroisoquinoline) optionally further substituted by 1 to 3 $C_{6-14}$ arylcarbonyl groups (e.g., benzoyl);
$Z^1$ is a bond, —NR$^a$—, —CR$^b_2$—CR$^b_2$— or —CR$^b_2$—O—;
    wherein
    R$^a$ is a hydrogen atom or a $C_{1-6}$ alkyl group (e.g., methyl); and
    R$^b$ are each independently a hydrogen atom, a halogen atom (e.g., a fluorine atom), a $C_{1-6}$ alkyl group (e.g., methyl) or a $C_6$-14 aryl group (e.g., phenyl); and
Ring C is
(1) a $C_{6-14}$ aromatic hydrocarbon ring (e.g., benzene) optionally further substituted by 1 to 3 substituents selected from
    (a) a halogen atom (e.g., a fluorine atom, a chlorine atom),
    (b) a $C_{1-6}$ alkyl group (e.g., methyl) optionally substituted by 1 to 3 halogen atoms (e.g., a fluorine atom),
    (c) a $C_{6-14}$ aryl group (e.g., phenyl),
    (d) a cyano group,
    (e) a $C_{1-6}$ alkoxy group (e.g., methoxy, ethoxy) optionally substituted by 1 to 3 hydroxy groups,
    (f) a 3- to 8-membered monocyclic non-aromatic heterocyclic group (e.g., morpholinyl),
    (g) a carboxy group,
    (h) a $C_{1-6}$ alkoxy-carbonyl group (e.g., methoxycarbonyl), and
    (i) a mono- or di-$C_{1-6}$ alkyl-carbamoyl group (e.g., ethylcarbamoyl) optionally substituted by 1 to 3 hydroxy groups,
(2) a $C_{3-10}$ cycloalkane ring (e.g., cyclopropane, cyclopentane, cyclohexane, adamantane) optionally further substituted by 1 to 3 substituents selected from
    (a) a $C_{6-14}$ aryl group (e.g., phenyl), and
    (b) a cyano group,
(3) a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)) optionally further substituted by 1 to 3 substituents selected from
    (a) a $C_{1-6}$ alkyl group (e.g., methyl, ethyl, isopropyl) optionally substituted by 1 to 3 substituents selected from a halogen atom (e.g., a fluorine atom) and a hydroxy group,
    (b) a $C_{3-10}$ cycloalkyl group (e.g., cyclopropyl),
    (c) a $C_{1-6}$ alkoxy group (e.g., ethoxy) optionally substituted by 1 to 3 halogen atoms (e.g., a fluorine atom), and
    (d) a hydroxy group, or
(4) a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3-azabicyclo[3.2.1]octane, 3-oxa-8-azabicyclo[3.2.1]octane, 3-azabicyclo[3.1.0]hexane, 2-oxa-6-azaspiro[3.5]nonane, 2-oxa-7-azaspiro[3.5]nonane, oxazepane (e.g., 1,4-oxazepane)) optionally further substituted by 1 to 3 substituents selected from
    (a) a $C_{1-6}$ alkyl group (e.g., methyl, ethyl) optionally substituted by 1 to 3 substituents selected from a hydroxy group, a halogen atom (e.g., a fluorine atom) and a $C_{1-6}$ alkoxy group (e.g., methoxy),
    (b) a $C_{6-14}$ aryl group (e.g., phenyl),
    (c) an oxo group,
    (d) a halogen atom (e.g., a fluorine atom),
    (e) a hydroxy group,
    (f) a cyano group,
    (g) a 5- or 6-membered monocyclic aromatic heterocyclic group (e.g., pyridyl), and
    (h) a carbamoyl group.

[Compound A-3]
Compound (I) wherein
Ring A is
(1) a benzene ring optionally further substituted by 1 to 3 substituents selected from
    (a) a halogen atom (e.g., a fluorine atom), and
    (b) a $C_{1-6}$ alkyl group (e.g., methyl),
(2) a pyridine ring, or
(3) a thiophene ring;
X is —CONR$^1$— or —NR$^1$CO—, and R$^1$ is a hydrogen atom or a $C_{1-6}$ alkyl group (e.g., methyl);
R$^2$ and R$^3$ are hydrogen atoms;

Ring B is
(1) a morpholine ring,
(2) a piperidine ring,
(3) a piperazine ring optionally further substituted by one benzoyl group,
(4) a pyrrolidine ring,
(5) an indoline ring,
(6) an isoindoline ring,
(7) a tetrahydroquinoline ring, or
(8) a tetrahydroisoquinoline ring;
$Z^1$ is a bond, —$NR^a$—, —$CR^b_2$—, —$CR^b_2$—$CR^b_2$— or —$CR^b_2$—O—,
  wherein
    $R^a$ is a hydrogen atom or a $C_{1-6}$ alkyl group (e.g., methyl), and
    $R^b$ are each independently a hydrogen atom, a halogen atom (e.g., a fluorine atom), a $C_{1-6}$ alkyl group (e.g., methyl) or a phenyl group
(specifically, $Z^1$ is a bond, —NH—, —N($CH_3$)—, —$CH_2$—, —$CH_2CH_2$—, —CH($C_6H_5$)—, —C($CH_3$)$_2$—, —C(F)$_2$— or —$CH_2$O—); and
Ring C is
(1) a benzene ring optionally further substituted by 1 to 3 substituents selected from
    (a) a halogen atom (e.g., a fluorine atom, a chlorine atom),
    (b) a $C_{1-6}$ alkyl group (e.g., methyl) optionally substituted by 1 to 3 halogen atoms (e.g., a fluorine atom),
    (c) a phenyl group,
    (d) a cyano group,
    (e) a $C_{1-6}$ alkoxy group (e.g., methoxy, ethoxy) optionally substituted by 1 to 3 hydroxy groups,
    (f) a morpholinyl group,
    (g) a carboxy group,
    (h) a $C_{1-6}$ alkoxy-carbonyl group (e.g., methoxycarbonyl), and
    (i) a mono- or di-$C_{1-6}$ alkyl-carbamoyl group (e.g., ethylcarbamoyl) optionally substituted by 1 to 3 hydroxy groups,
(2) a $C_{3-10}$ cycloalkane ring (e.g., cyclopropane, cyclopentane, cyclohexane) optionally further substituted by 1 to 3 substituents selected from
    (a) a phenyl group, and
    (b) a cyano group,
(3) an adamantane ring,
(4) a pyridine ring optionally further substituted by 1 to 3 substituents selected from
    (a) a $C_{1-6}$ alkyl group (e.g., methyl),
    (b) a $C_{3-10}$ cycloalkyl group (e.g., cyclopropyl),
    (c) a $C_{1-6}$ alkoxy group (e.g., ethoxy) optionally substituted by 1 to 3 halogen atoms (e.g., a fluorine atom), and
    (d) a hydroxy group,
(5) a thiophene ring optionally further substituted by 1 to 3 $C_{1-6}$ alkyl groups (e.g., methyl),
(6) a pyrazole ring optionally further substituted by 1 to 3 $C_{1-6}$ alkyl groups (e.g., methyl, ethyl, isopropyl) optionally substituted by 1 to 3 substituents selected from a halogen atom (e.g., a fluorine atom) and a hydroxy group,
(7) an imidazole ring optionally further substituted by 1 to 3 $C_{1-6}$ alkyl groups (e.g., methyl),
(8) an oxadiazole ring (e.g., a 1,2,5-oxadiazole ring) optionally further substituted by 1 to 3 $C_{1-6}$ alkyl groups (e.g., methyl),
(9) an isoxazole ring optionally further substituted by 1 to 3 $C_{1-6}$ alkyl groups (e.g., methyl, ethyl),
(10) a thiadiazole ring (e.g., a 1,2,3-thiadiazole ring) optionally further substituted by 1 to 3 $C_{1-6}$ alkyl groups (e.g., methyl),
(11) a thiazole ring optionally further substituted by 1 to 3 $C_{1-6}$ alkyl groups (e.g., methyl),
(12) an indazole ring (e.g., a 1H-indazole ring, a 2H-indazole ring) optionally further substituted by 1 to 3 $C_{1-6}$ alkyl groups (e.g., methyl),
(13) a benzofuran ring (e.g., a 1-benzofuran ring) optionally further substituted by 1 to 3 $C_{1-6}$ alkyl groups (e.g., methyl),
(14) an imidazopyridine ring (e.g., an imidazo[1,2-a]pyridine ring) optionally further substituted by 1 to 3 $C_{1-6}$ alkyl groups (e.g., methyl),
(15) a pyrazolopyrimidine ring (e.g., a pyrazolo[1,5-a]pyrimidine ring),
(16) an imidazothiazole ring (e.g., an imidazo[2,1-b]thiazole ring) optionally further substituted by 1 to 3 $C_{1-6}$ alkyl groups (e.g., methyl),
(17) an oxetane ring optionally further substituted by 1 to 3 phenyl groups,
(18) a pyrrolidine ring optionally further substituted by 1 to 3 substituents selected from
    (a) a $C_{1-6}$ alkyl group (e.g., methyl, ethyl) optionally substituted by 1 to 3 substituents selected from a hydroxy group, a halogen atom (e.g., a fluorine atom) and a $C_{1-6}$ alkoxy group (e.g., methoxy),
    (b) an oxo group,
    (c) a phenyl group,
    (d) a hydroxy group,
    (e) a cyano group,
    (f) a pyridyl group, and
    (g) a carbamoyl group,
(19) a piperidine ring optionally further substituted by 1 to 3 substituents selected from
    (a) a halogen atom (e.g., a fluorine atom), and
    (b) a $C_{1-6}$ alkyl group (e.g., methyl, ethyl) optionally substituted by 1 to 3 hydroxy groups,
(20) a morpholine ring optionally further substituted by 1 to 3 $C_{1-6}$ alkyl groups (e.g., methyl) optionally substituted by 1 to 3 hydroxy groups,
(21) a tetrahydropyran ring,
(22) a tetrahydrofuran ring,
(23) a dihydropyrimidine ring (e.g., a 1,6-dihydropyrimidine ring) optionally further substituted by 1 to 3 oxo groups,
(24) a dihydrobenzofuran ring (e.g., a 2,3-dihydro-1-benzofuran ring),
(25) a dihydrochromene ring (e.g., a 3,4-dihydro-2H-chromene ring),
(26) a tetrahydroindazole ring (e.g., a 4,5,6,7-tetrahydro-2H-indazole ring) optionally further substituted by 1 to 3 $C_{1-6}$ alkyl groups (e.g., methyl),
(27) a 8-oxa-3-azabicyclo[3.2.1]octane ring,
(28) a 3-oxa-8-azabicyclo[3.2.1]octane ring,
(29) a 3-azabicyclo[3.1.0]hexane ring optionally further substituted by 1 to 3 halogen atoms (e.g., a fluorine atom),
(30) a 2-oxa-6-azaspiro[3.5]nonane ring,
(31) a 2-oxa-7-azaspiro[3.5]nonane ring, or
(32) an oxazepane ring (e.g., a 1,4-oxazepane ring) optionally further substituted by 1 to 3 $C_{1-6}$ alkyl groups (e.g., methyl) optionally substituted by 1 to 3 hydroxy groups.

[Compound B-1]
  Compound (I) wherein
Ring A is a 5- or 6-membered ring (e.g., benzene, pyridine, thiophene) optionally further substituted by 1 to 3 substituents selected from
    (1) a halogen atom (e.g., a fluorine atom), and
    (2) a $C_{1-6}$ alkyl group (e.g., methyl);
X is —$CONR^1$— or —$NR^1CO$—, and $R^1$ is a hydrogen atom or a $C_{1-6}$ alkyl group (e.g., methyl);
$R^2$ and $R^3$ are hydrogen atoms;

Ring B is a nitrogen-containing heterocycle (preferably a 4- to 10-membered nitrogen-containing heterocycle) (e.g., morpholine, piperidine, piperazine, pyrrolidine, indoline, isoindoline, tetrahydroquinoline, tetrahydroisoquinoline) optionally further substituted by 1 to 3 $C_{6-14}$ aryl-carbonyl groups (e.g., benzoyl);

$Z^1$ is a bond, —$NR^a$—, —$CR^b{}_2$—, —$CR^b{}_2$—$CR^b{}_2$— or —$CR^b{}_2$—O—;

wherein
$R^a$ is a hydrogen atom or a $C_{1-6}$ alkyl group (e.g., methyl); and $R^b$ are each independently a hydrogen atom, a halogen atom (e.g., a fluorine atom), a $C_{1-6}$ alkyl group (e.g., methyl) or a $C_{6-14}$ aryl group (e.g., phenyl); and Ring C is a ring (e.g., a $C_{6-14}$ aromatic hydrocarbon ring (e.g., benzene), a $C_{3-10}$ cycloalkane ring (e.g., cyclopropane, cyclopentane, cyclohexane, adamantane), a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)), a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3-azabicyclo[3.2.1]octane, 3-oxa-8-azabicyclo[3.2.1]octane)) optionally further substituted by 1 to 3 substituents selected from
  (a) a halogen atom (e.g., a fluorine atom, a chlorine atom),
  (b) a $C_{1-6}$ alkyl group (e.g., methyl, ethyl, isopropyl) optionally substituted by 1 to 3 substituents selected from
    (i) a halogen atom (e.g., a fluorine atom), and
    (ii) a hydroxy group,
  (c) a $C_{6-14}$ aryl group (e.g., phenyl),
  (d) a cyano group,
  (e) a $C_{1-6}$ alkoxy group (e.g., methoxy, ethoxy) optionally substituted by 1 to 3 halogen atoms (e.g., a fluorine atom),
  (f) a 3- to 14-membered non-aromatic heterocyclic group (preferably a 3- to 8-membered monocyclic non-aromatic heterocyclic group) (e.g., morpholinyl),
  (g) a $C_{3-10}$ cycloalkyl group (e.g., cyclopropyl),
  (h) a hydroxy group, and
  (i) an oxo group.

[Compound B-2]
Compound (I) wherein
Ring A is
(1) a benzene ring optionally further substituted by 1 to 3 substituents selected from
  (a) a halogen atom (e.g., a fluorine atom), and
  (b) a $C_{1-6}$ alkyl group (e.g., methyl), or
(2) a 5- or 6-membered monocyclic aromatic heterocycle (e.g., pyridine, thiophene);
X is —$CONR^1$— or —$NR^1CO$—, and $R^1$ is a hydrogen atom or a $C_{1-6}$ alkyl group (e.g., methyl);
$R^2$ and $R^3$ are hydrogen atoms;
Ring B is a nitrogen-containing heterocycle (preferably a 4- to 10-membered nitrogen-containing heterocycle) (e.g., morpholine, piperidine, piperazine, pyrrolidine, indoline, isoindoline, tetrahydroquinoline, tetrahydroisoquinoline) optionally further substituted by 1 to 3 $C_{6-14}$ aryl-carbonyl groups (e.g., benzoyl);

$Z^1$ is a bond, —$NR^a$—, —$CR^b{}_2$—, —$CR^b{}_2$—$CR^b{}_2$— or —$CR^b{}_2$—O—;

wherein
$R^a$ is a hydrogen atom or a $C_{1-6}$ alkyl group (e.g., methyl); and $R^b$ are each independently a hydrogen atom, a halogen atom (e.g., a fluorine atom), a $C_{1-6}$ alkyl group (e.g., methyl) or a $C_{6-14}$ aryl group (e.g., phenyl); and Ring C is
(1) a $C_{6-14}$ aromatic hydrocarbon ring (e.g., benzene) optionally further substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a $C_{6-14}$ aryl group (e.g., phenyl),
  (d) a cyano group,
  (e) a $C_{1-6}$ alkoxy group (e.g., methoxy), and
  (f) a 3- to 14-membered non-aromatic heterocyclic group (preferably a 3- to 8-membered monocyclic non-aromatic heterocyclic group) (e.g., morpholinyl),
(2) a $C_{3-10}$ cycloalkane ring (e.g., cyclopropane, cyclopentane, cyclohexane, adamantane) optionally further substituted by 1 to 3 substituents selected from
  (a) a $C_{6-14}$ aryl group (e.g., phenyl), and
  (b) a cyano group,
(3) a 5- to 14-membered aromatic heterocycle (e.g., pyridine, thiophene, pyrazole, imidazole, oxadiazole (e.g., 1,2,5-oxadiazole), isoxazole, thiadiazole (e.g., 1,2,3-thiadiazole), thiazole, indazole (e.g., 1H-indazole, 2H-indazole), benzofuran (e.g., 1-benzofuran), imidazopyridine (e.g., imidazo[1,2-a]pyridine), pyrazolopyrimidine (e.g., pyrazolo[1,5-a]pyrimidine), imidazothiazole (e.g., imidazo[2,1-b]thiazole)) optionally further substituted by 1 to 3 substituents selected from
  (a) a $C_{1-6}$ alkyl group (e.g., methyl, ethyl, isopropyl) optionally substituted by 1 to 3 halogen atoms (e.g., a fluorine atom),
  (b) a $C_{3-10}$ cycloalkyl group (e.g., cyclopropyl),
  (c) a $C_{1-6}$ alkoxy group (e.g., ethoxy) optionally substituted by 1 to 3 halogen atoms (e.g., a fluorine atom), and
  (d) a hydroxy group, or
(4) a 3- to 14-membered non-aromatic heterocycle (e.g., oxetane, pyrrolidine, piperidine, morpholine, tetrahydropyran, tetrahydrofuran, dihydropyrimidine (e.g., 1,6-dihydropyrimidine), dihydrobenzofuran (e.g., 2,3-dihydro-1-benzofuran), dihydrochromene (e.g., 3,4-dihydro-2H-chromene), tetrahydroindazole (e.g., 4,5,6,7-tetrahydro-2H-indazole), 8-oxa-3-azabicyclo[3.2.1]octane, 3-oxa-8-azabicyclo[3.2.1]octane) optionally further substituted by 1 to 3 substituents selected from
  (a) a $C_{1-6}$ alkyl group (e.g., methyl) optionally substituted by 1 to 3 hydroxy groups,
  (b) a $C_{6-14}$ aryl group (e.g., phenyl), and
  (c) an oxo group.

[Compound B-3a]
Compound (I) wherein
Ring A is a benzene ring, a pyridine ring or a thiophene ring, each of which is optionally further substituted by 1 to 3 substituents selected from
(1) a halogen atom (e.g., a fluorine atom), and
(2) a $C_{1-6}$ alkyl group (e.g., methyl);
X is —$CONR^1$— or —$NR^1CO$—, and $R^1$ is a hydrogen atom or a $C_{1-6}$ alkyl group (e.g., methyl);

$R^2$ and $R^3$ are hydrogen atoms;
Ring B is
(1) a morpholine ring,
(2) a piperidine ring,
(3) a piperazine ring optionally further substituted by one benzoyl group,
(4) a pyrrolidine ring,
(5) an indoline ring,
(6) an isoindoline ring,
(7) a tetrahydroquinoline ring, or
(8) a tetrahydroisoquinoline ring;
$Z^1$ is a bond, —NR$^a$—, —CR$^b_2$—CR$^b_2$— or —CR$^b_2$—O—,
  wherein
    R$^a$ is a hydrogen atom or a $C_{1-6}$ alkyl group (e.g., methyl), and
    R$^b$ are each independently a hydrogen atom, a halogen atom (e.g., a fluorine atom), a $C_{1-6}$ alkyl group (e.g., methyl) or a phenyl group
(specifically, $Z^1$ is a bond, —NH—, —N(CH$_3$)—, —CH$_2$—, —CH$_2$CH$_2$—, CH(C$_6$H$_5$)—, —C(CH$_3$)$_2$—, —C(F)$_2$— or —CH$_2$O—); and
Ring C is
(1) a benzene ring optionally further substituted by 1 to 3 substituents selected from
  (a) a halogen atom (e.g., a fluorine atom, a chlorine atom),
  (b) a $C_{1-6}$ alkyl group (e.g., methyl) optionally substituted by 1 to 3 halogen atoms (e.g., a fluorine atom),
  (c) a phenyl group,
  (d) a cyano group,
  (e) a $C_{1-6}$ alkoxy group (e.g., methoxy), and
  (f) a morpholinyl group,
(2) a $C_{3-10}$ cycloalkane ring (e.g., cyclopropane, cyclopentane, cyclohexane) optionally further substituted by 1 to 3 substituents selected from
  (a) a phenyl group, and
  (b) a cyano group,
(3) an adamantane ring,
(4) a pyridine ring optionally further substituted by 1 to 3 substituents selected from
  (a) a $C_{1-6}$ alkyl group (e.g., methyl),
  (b) a $C_{3-10}$ cycloalkyl group (e.g., cyclopropyl),
  (c) a $C_{1-6}$ alkoxy group (e.g., ethoxy) optionally substituted by 1 to 3 halogen atoms (e.g., a fluorine atom), and
  (d) a hydroxy group,
(5) a thiophene ring optionally further substituted by 1 to 3 $C_{1-6}$ alkyl groups (e.g., methyl),
(6) a pyrazole ring optionally further substituted by 1 to 3 $C_{1-6}$ alkyl groups (e.g., methyl, ethyl, isopropyl) optionally substituted by 1 to 3 halogen atoms (e.g., a fluorine atom),
(7) an imidazole ring optionally further substituted by 1 to 3 $C_{1-6}$ alkyl groups (e.g., methyl),
(8) an oxadiazole ring (e.g., a 1,2,5-oxadiazole ring) optionally further substituted by 1 to 3 $C_{1-6}$ alkyl groups (e.g., methyl),
(9) an isoxazole ring optionally further substituted by 1 to 3 $C_{1-6}$ alkyl groups (e.g., methyl, ethyl),
(10) a thiadiazole ring (e.g., a 1,2,3-thiadiazole ring) optionally further substituted by 1 to 3 $C_{1-6}$ alkyl groups (e.g., methyl),
(11) a thiazole ring optionally further substituted by 1 to 3 $C_{1-6}$ alkyl groups (e.g., methyl),
(12) an indazole ring (e.g., a 1H-indazole ring, a 2H-indazole ring) optionally further substituted by 1 to 3 $C_{1-6}$ alkyl groups (e.g., methyl),
(13) a benzofuran ring (e.g., a 1-benzofuran ring),
(14) an imidazopyridine ring (e.g., an imidazo[1,2-a]pyridine ring) optionally further substituted by 1 to 3 $C_{1-6}$ alkyl groups (e.g., methyl),
(15) a pyrazolopyrimidine ring (e.g., a pyrazolo[1,5-a]pyrimidine ring),
(16) an imidazothiazole ring (e.g., an imidazo[2,1-b]thiazole ring) optionally further substituted by 1 to 3 $C_{1-6}$ alkyl groups (e.g., methyl),
(17) an oxetane ring optionally further substituted by 1 to 3 phenyl groups,
(18) a pyrrolidine ring optionally further substituted by 1 to 3 substituents selected from
  (a) a $C_{1-6}$ alkyl group (e.g., methyl) optionally substituted by 1 to 3 hydroxy groups, and
  (b) an oxo group,
(19) a piperidine ring,
(20) a morpholine ring,
(21) a tetrahydropyran ring,
(22) a tetrahydrofuran ring,
(23) a dihydropyrimidine ring (e.g., a 1,6-dihydropyrimidine ring) optionally further substituted by 1 to 3 oxo groups,
(24) a dihydrobenzofuran ring (e.g., a 2,3-dihydro-1-benzofuran ring),
(25) a dihydrochromene ring (e.g., a 3,4-dihydro-2H-chromene ring),
(26) a tetrahydroindazole ring (e.g., a 4,5,6,7-tetrahydro-2H-indazole ring) optionally further substituted by 1 to 3 $C_{1-6}$ alkyl groups (e.g., methyl),
(27) a 8-oxa-3-azabicyclo[3.2.1]octane ring, or
(28) a 3-oxa-8-azabicyclo[3.2.1]octane ring.
[Compound B-3]
Compound (I) wherein
Ring A is
(1) a benzene ring optionally further substituted by 1 to 3 substituents selected from
  (a) a halogen atom (e.g., a fluorine atom), and
  (b) a $C_{1-6}$ alkyl group (e.g., methyl),
(2) a pyridine ring, or
(3) a thiophene ring;
X is —CONR$^1$— or —NR$^1$CO—, and $R^1$ is a hydrogen atom or a $C_{1-6}$ alkyl group (e.g., methyl);
$R^2$ and $R^3$ are hydrogen atoms;
Ring B is
(1) a morpholine ring,
(2) a piperidine ring,
(3) a piperazine ring optionally further substituted by one benzoyl group,
(4) a pyrrolidine ring,
(5) an indoline ring,
(6) an isoindoline ring,
(7) a tetrahydroquinoline ring, or
(8) a tetrahydroisoquinoline ring;
$Z^1$ is a bond, —NR$^a$—, —CR$^b_2$—, —CR$^b_2$— or —CR$^b_2$—O—,
  wherein
    R$^a$ is a hydrogen atom or a $C_{1-6}$ alkyl group (e.g., methyl), and
    R$^b$ are each independently a hydrogen atom, a halogen atom (e.g., a fluorine atom), a $C_{1-6}$ alkyl group (e.g., methyl) or a phenyl group
(specifically, $Z^1$ is a bond, —NH—, —N(CH$_3$)—, —CH$_2$—, —CH$_2$CH$_2$—, —CH(C$_6$H$_5$)—, —C(CH$_3$)$_2$—, —C(F)$_2$— or —CH$_2$O—); and
Ring C is
(1) a benzene ring optionally further substituted by 1 to 3 substituents selected from (a) a halogen atom (e.g., a fluorine atom, a chlorine atom),
(b) a $C_{1-6}$ alkyl group (e.g., methyl) optionally substituted by 1 to 3 halogen atoms (e.g., a fluorine atom),
(c) a phenyl group,
(d) a cyano group,
(e) a $C_{1-6}$ alkoxy group (e.g., methoxy), and
(f) a morpholinyl group,
(2) a $C_{3-10}$ cycloalkane ring (e.g., cyclopropane, cyclopentane, cyclohexane) optionally further substituted by 1 to 3 substituents selected from
  (a) a phenyl group, and
  (b) a cyano group,
(3) an adamantane ring,
(4) a pyridine ring optionally further substituted by 1 to 3 substituents selected from
  (a) a $C_{1-6}$ alkyl group (e.g., methyl),
  (b) a $C_{3-10}$ cycloalkyl group (e.g., cyclopropyl),
  (c) a $C_{1-6}$ alkoxy group (e.g., ethoxy) optionally substituted by 1 to 3 halogen atoms (e.g., a fluorine atom), and
  (d) a hydroxy group,
(5) a thiophene ring optionally further substituted by 1 to 3 $C_{1-6}$ alkyl groups (e.g., methyl),
(6) a pyrazole ring optionally further substituted by 1 to 3 $C_{1-6}$ alkyl groups (e.g., methyl, ethyl, isopropyl) optionally substituted by 1 to 3 halogen atoms (e.g., a fluorine atom),
(7) an imidazole ring optionally further substituted by 1 to 3 $C_{1-6}$ alkyl groups (e.g., methyl),
(8) an oxadiazole ring (e.g., a 1,2,5-oxadiazole ring) optionally further substituted by 1 to 3 $C_{1-6}$ alkyl groups (e.g., methyl),
(9) an isoxazole ring optionally further substituted by 1 to 3 $C_{1-6}$ alkyl groups (e.g., methyl, ethyl),
(10) a thiadiazole ring (e.g., a 1,2,3-thiadiazole ring) optionally further substituted by 1 to 3 $C_{1-6}$ alkyl groups (e.g., methyl),
(11) a thiazole ring optionally further substituted by 1 to 3 $C_{1-6}$ alkyl groups (e.g., methyl),
(12) an indazole ring (e.g., a 1H-indazole ring, a 2H-indazole ring) optionally further substituted by 1 to 3 $C_{1-6}$ alkyl groups (e.g., methyl),
(13) a benzofuran ring (e.g., a 1-benzofuran ring),
(14) an imidazopyridine ring (e.g., an imidazo[1,2-a]pyridine ring) optionally further substituted by 1 to 3 $C_{1-6}$ alkyl groups (e.g., methyl),
(15) a pyrazolopyrimidine ring (e.g., a pyrazolo[1,5-a]pyrimidine ring),
(16) an imidazothiazole ring (e.g., an imidazo[2,1-b]thiazole ring) optionally further substituted by 1 to 3 $C_{1-6}$ alkyl groups (e.g., methyl),
(17) an oxetane ring optionally further substituted by 1 to 3 phenyl groups,
(18) a pyrrolidine ring optionally further substituted by 1 to 3 substituents selected from
  (a) a $C_{1-6}$ alkyl group (e.g., methyl) optionally substituted by 1 to 3 hydroxy groups, and
  (b) an oxo group,
(19) a piperidine ring,
(20) a morpholine ring,
(21) a tetrahydropyran ring,
(22) a tetrahydrofuran ring,
(23) a dihydropyrimidine ring (e.g., a 1,6-dihydropyrimidine ring) optionally further substituted by 1 to 3 oxo groups,
(24) a dihydrobenzofuran ring (e.g., a 2,3-dihydro-1-benzofuran ring),
(25) a dihydrochromene ring (e.g., a 3,4-dihydro-2H-chromene ring),
(26) a tetrahydroindazole ring (e.g., a 4,5,6,7-tetrahydro-2H-indazole ring) optionally further substituted by 1 to 3 $C_{1-6}$ alkyl groups (e.g., methyl),
(27) a 8-oxa-3-azabicyclo[3.2.1]octane ring, or
(28) a 3-oxa-8-azabicyclo[3.2.1]octane ring.
[Compound C-1]
  Compound (I) wherein
Ring A is a benzene ring;
X is —CONH—;
$R^2$ and $R^3$ are hydrogen atoms;
Ring B is a nitrogen-containing heterocycle (preferably a 3- to 8-membered monocyclic non-aromatic nitrogen-containing heterocycle) (e.g., morpholine);
$Z^1$ is a bond; and
Ring C is
(1) a $C_{6-14}$ aromatic hydrocarbon ring (e.g., benzene) optionally further substituted by 1 to 3 halogen atoms (e.g., a chlorine atom), or
(2) a 5- to 14-membered aromatic heterocycle (e.g., pyrazole, isoxazole, indazole (e.g., 2H-indazole)) optionally further substituted by 1 to 3 $C_{1-6}$ alkyl groups (e.g., methyl, ethyl).
[Compound C-2]
  Compound (I) wherein
Ring A is a benzene ring;
X is —CONH—;
$R^2$ and $R^3$ are hydrogen atoms;
Ring B is a 3- to 8-membered monocyclic non-aromatic nitrogen-containing heterocycle (e.g., morpholine);
$Z^1$ is a bond; and
Ring C is
(1) a benzene ring optionally further substituted by 1 to 3 halogen atoms (e.g., a chlorine atom),
(2) a pyrazole ring optionally further substituted by 1 to 3 $C_{1-6}$ alkyl groups (e.g., methyl),
(3) an isoxazole ring optionally further substituted by 1 to 3 $C_{1-6}$ alkyl groups (e.g., methyl, ethyl), or
(4) an indazole ring (e.g., a 2H-indazole ring) optionally further substituted by 1 to 3 $C_{1-6}$ alkyl groups (e.g., methyl).
[Compound C-3a]
  Compound (I) wherein
Ring A is a benzene ring;
X is —CONH—;
$R^2$ and $R^3$ are hydrogen atoms;
Ring B is a morpholine ring;
$Z^1$ is a bond; and
Ring C is a benzene ring, a pyrazole ring, an isoxazole ring or an indazole ring, each of which is optionally further substituted by 1 to 3 substituents selected from
  (a) a halogen atom (e.g., a chlorine atom), and
  (b) a $C_{1-6}$ alkyl group (e.g., methyl, ethyl).
[Compound C-3]
  Compound (I) wherein
Ring A is a benzene ring;
X is —CONH—;
$R^2$ and $R^3$ are hydrogen atoms;
Ring B is a morpholine ring;
$Z^1$ is a bond; and
Ring C is
(1) a benzene ring optionally further substituted by 1 to 3 halogen atoms (e.g., a chlorine atom),
(2) a pyrazole ring further substituted by 1 to 3 $C_{1-6}$ alkyl groups (e.g., methyl),
(3) an isoxazole ring further substituted by 1 to 3 $C_{1-6}$ alkyl groups (e.g., methyl, ethyl), or
(4) an indazole ring (e.g., a 2H-indazole ring) further substituted by 1 to 3 $C_{1-6}$ alkyl groups (e.g., methyl).

[Compound D]
Compound (I) wherein
Ring A is a benzene ring;
X is —CONH—;
$R^2$ and $R^3$ are hydrogen atoms;
Ring B is a morpholine ring;
$Z^1$ is a bond; and
Ring C is a benzene ring optionally further substituted by 1 to 3 halogen atoms (e.g., a chlorine atom).

[Compound E]
N-(((3S)-4-benzoylmorpholin-3-yl)methyl)-4-(5-(trifluoromethyl)-1,2,4-oxadiazol-3-yl)benzamide, or a salt thereof,
N-(((3S)-4-(3,5-dichlorobenzoyl)morpholin-3-yl)methyl)-4-(5-(trifluoromethyl)-1,2,4-oxadiazol-3-yl)benzamide, or a salt thereof,
N-(((3S)-4-((1-methyl-1H-pyrazol-5-yl)carbonyl)morpholin-3-yl)methyl)-4-(5-(trifluoromethyl)-1,2,4-oxadiazol-3-yl)benzamide, or a salt thereof, and
N-(((3S)-4-((2-methyl-2H-indazol-3-yl)carbonyl)morpholin-3-yl)methyl)-4-(5-(trifluoromethyl)-1,2,4-oxadiazol-3-yl)benzamide, or a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts 3G with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]
The production method of the compound of the present invention is explained in the followings.
The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;

organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like, and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, t-butylhydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin etc.). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, examples of the reagent to be used include a nucleophile (e.g., an amine, imidazole etc.) and a base (e.g., a basic salt, an organic base etc.).

When nucleophilic addition reaction by a carbo anion, nucleophilic 1,4-addition reaction (Michael addition reaction) by a carbo anion or nucleophilic displacement reaction by a carbo anion is carried out in each step, examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine) palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases, basic salts and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis (4-methoxyphenyl-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of t-butyl ester, formic acid, triethylsilane and the like may be added to reductively-trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When Curtius rearrangement reaction is carried out in each step, examples of the reagent to be used include diphenylphosphoryl azide, trimethylsilylazide, sodium azide and the like.

Compound (I) can be produced according to the below method.

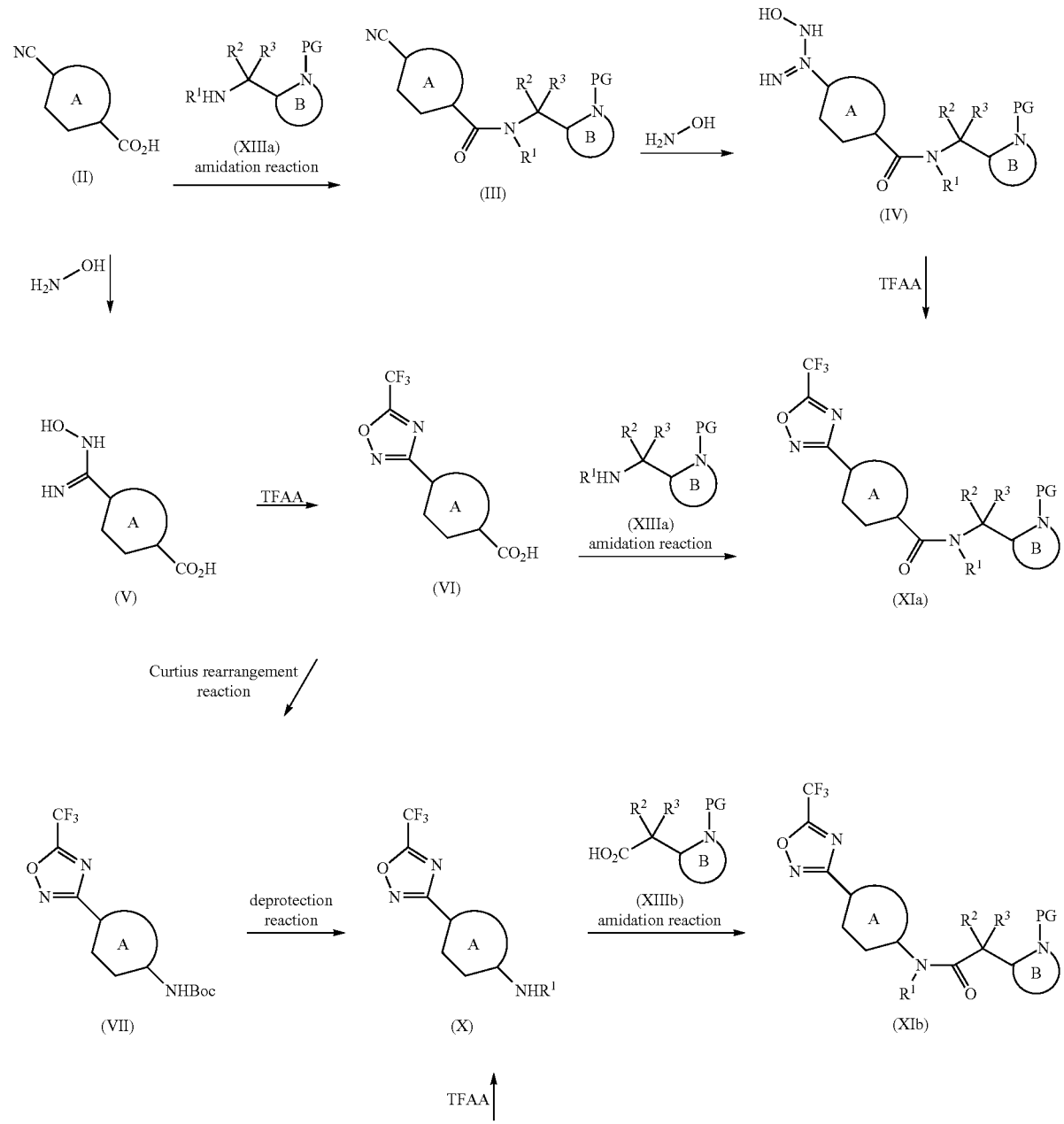

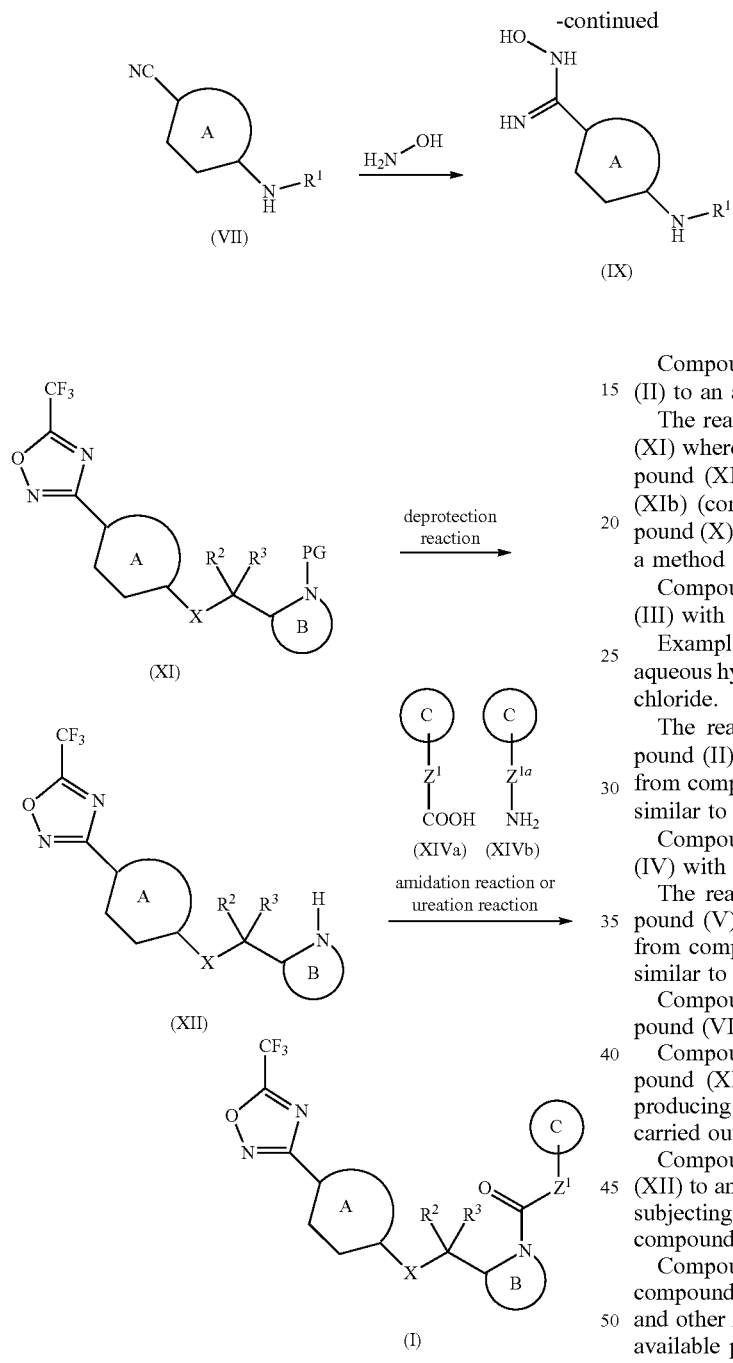

Compound (III) can be produced by subjecting compound (II) to an amidation reaction with compound (XIIIa).

The reaction for producing compound (XIa) (compound (XI) wherein X is $CONR^1$) from compound (VI) and compound (XIIIa), and the reaction for producing compound (XIb) (compound (XI) wherein X is $NR^1CO$) from compound (X) and compound (XIIIb) can also be carried out by a method similar to this reaction.

Compound (IV) can be produced by reacting compound (III) with a hydroxylamine reagent.

Examples of the hydroxylamine reagent include 50% aqueous hydroxylamine solution, and hydroxylamine hydrochloride.

The reaction for producing compound (V) from compound (II), and the reaction for producing compound (IX) from compound (VIII) can also be carried out by a method similar to this reaction.

Compound (XIa) can be produced by reacting compound (IV) with trifluoroacetic anhydride.

The reaction for producing compound (VI) from compound (V), and the reaction for producing compound (X) from compound (IX) can also be carried out by a method similar to this reaction.

Compound (VII) can be produced by subjecting compound (VI) to Curtius rearrangement reaction.

Compound (XII) can be produced by subjecting compound (XI) to a deprotection reaction. The reaction for producing compound (X) from compound (VII) can also be carried out by a method similar to this reaction.

Compound (I) can be produced by subjecting compound (XII) to an amidation reaction with compound (XIVa) or by subjecting compound (XII) to an ureation reaction with compound (XIVb).

Compound (II), compound (VIII), compound (XIIIa), compound (XIIIb), compound (XIVa), compound (XIVb) and other raw material compounds may be a commercially available product, or can also be produced according to a method known per se or a method analogous thereto.

In each intermediate, each substituent in Ring A, X, $R^2$, $R^3$, Ring B, $Z^1$, $Z^{1a}$ and Ring C may be converted to the other substituent according to a method known per se or a method analogous thereto.

When compound (I) has an optical isomer, a stereoisomer, a regioisomer or a rotamer, these are also encompassed in compound (I), and can be obtained as a single product according to a synthesis method and separation method known per se (e.g., concentration, solvent extraction, column chromatography, recrystallization etc.). For example, when compound (I) has an optical isomer, the optical isomer resolved from the compound is also encompassed in compound (I).

The optical isomer can be produced according to a method known per se. Specifically, the optical isomer is wherein
Ring A, X, $R^1$, $R^2$, $R^3$, Ring B,
$Z^1$ and Ring C are each as defined above,
PG is a protecting group, and
$Z^{1a}$ is a bond or a spacer in which the number of atoms in the main chain is 1 to 2.

Examples of the "spacer in which the number of atoms in the main chain is 1 to 2" for $Z^{1a}$ include spacers in which the number of atoms in the main chain is 1 to 2, from among the spacers exemplified as the "spacer in which the number of atoms in the main chain is 1 to 3" for $Z^1$.

Compound (XIa) is compound (XI) wherein X is $-CONR^1-$, and compound (XIb) is compound (XI) wherein X is $-NR^1CO-$.

obtained using an optically active synthetic intermediate or by subjecting the racemic final product to an optical resolution according to a known method.

The optical resolution may be a method known per se, such as a fractional recrystallization method, a chiral column method, a diastereomer method etc.

1) Fractional Recrystallized Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallized method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, 2-propanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallized method, a chromatography method etc.) and the like, and is subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl) phenylacetic acid], (−)-menthoxyacetic acid etc.) and the like are subjected to condensation reaction to give diastereomers of the ester compound or the amide compound, respectively. When compound (I) has a carboxy group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, 1,4-dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, 2-propanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0 to 50° C., preferably 0 to 20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a medicament.

Compound (I) of the present invention is superior in vivo kinetics (e.g., plasma drug half-life, intracerebral migration, metabolic stability), and shows low toxicity (e.g., more excellent as a medicament in terms of acute toxicity, chronic toxicity, genetic toxicity, reproductive toxicity, cardiotoxicity, drug interaction, carcinogenicity and the like). Therefore, compound (I) can be safely administered orally or parenterally directly as a medicament, or as a pharmaceutical composition mixed with a pharmacologically acceptable carrier to a mammal (e.g., human, monkey, bovine, horses, pig, mouse, rat, hamster, rabbit, cat, dog, sheep, goat, etc.). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like. Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, and the like); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

In addition, compound (I) may be a compound labeled or substituted with an isotope (e.g., $^2$H, $^3$H, $^{11}$C, $^{14}$C, $^{18}$F, $^{35}$S, $^{125}$I and the like) and the like. The compound labeled or substituted with an isotope can be used, for example, as a tracer (PET tracer) used in positron emission tomography (PET), and useful in the field of medical diagnosis and the like.

Compound (I) also encompasses a deuterium conversion form wherein $^1$H is converted to $^2$H(D).

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Since the compound of the present invention has a superior HDAC inhibitory action, preferably class II HDAC inhibitory action, more preferably HDAC6 inhibitory action, it is also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for HDAC-associated diseases, preferably class II HDAC-associated diseases, more preferably HDAC6-associated diseases, more specifically, the diseases described in (1)-(7) below.

(1) inflammatory diseases (e.g., acute pancreatitis, chronic pancreatitis, asthma, adult respiratory distress syndrome, chronic obstructive pulmonary disease (COPD), idiopathic pulmonary fibrosis, inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis, diabetic nephropathy, uveitis, suppurative hidradenitis etc.), (2) autoimmune diseases (e.g., rheumatoid arthritis, psoriasis, inflammatory bowel disease (e.g., Crohn's disease, ulcerative colitis etc.), Sjogren's syndrome, Behcet's disease, multiple sclerosis, systemic lupus erythematosus, lupus nephritis, discoid lupus erythematosus, Castleman's disease, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I diabetes, autoimmune hemolytic anemia, autoimmune neutropenia, thrombocytopenia, atopic dermatitis, pemphigus, chronic active hepatitis, myasthenia gravis, graft versus host disease, Addison's disease, abnormal immunoresponse, arthritis, dermatitis, radiodermatitis, primary biliary cirrhosis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, chronic sarcoma, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, adult T cell leukemia, chronic bone marrow proliferative disease, pancreatic endocrine tumor fibrous histiocytoma, leiomyosarcoma, rhabdomyosarcoma, cancer of unknown primary), leukemia (e.g., acute leukemia (e.g., acute lymphatic leukemia, acute myelocytic leukemia etc.), chronic leukemia (e.g., chronic lymphatic leukemia, chronic myelocytic leukemia etc.), myelodysplastic syndrome), uterine sarcoma (e.g., mixed mesodermal tumor, uterine leiomyosarcoma, endometrial stromal tumor etc.), myelofibrosis etc.], (5) neurodegenerative diseases and/or central diseases (i) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autistic spectrum syndrome, fragile X syndrome, Rett syndrome, adjustment disorder, bipolar disorder, neurosis, schizophrenia (e.g., positive symptom, negative symptom, cognitive symptom), cognitive dysfunction associated with schizophrenia, chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, hreditary sastic praplegia], (ii) neurodegenerative diseases [e.g., Alzheimer's disease, dementia of Alzheimer type, Alzheimer-type senile dementia, Parkinson's disease, muscular dystrophy, Parkinson's disease associated with dementia, Huntington's disease, multi-infarct dementia, frontotemporal dementia, Parkinson's type dementia, progressive supranuclear palsy, Pick's syndrome, Niemann-Pick syndrome, corticobasal degeneration, Down's disease, vascular dementia, postencephalitic parkinsonism, Lewy body dementia, Rubinstein-Taybi syndrome, Charcot-Marie-Tooth disease, HIV dementia, amyotrophic lateral sclerosis (ALS), motor neurogenesis disease (MND), Creutzfeldt-Jakob disease or prion disease, cerebral palsy, multiple sclerosis, Riley-Day syndrome], (iii) age-related cognition memory disorders [e.g., age-related memory disorders, senile dementia], (iv) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (v) respiratory depression caused by anesthetics, traumatic disease, or neurodegenerative disease and the like, (vi) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, peptic ulcer, diarrhea, constipation, postoperative ileus, (vii) pain, (6) chronic heart failure or acute heart failure, acute decompensated heart failure, ischemic heart disease, cardiomyopathy, myocarditis, valvular disease, (7) peripheral neuropathy and the like.

The medicament of the present invention can be preferably used as an agent for the prophylaxis or treatment of autoimmune disease, inflammatory disease, osteoarticular degenerative disease, neurodegenerative disease, central disease, neoplastic disease, or peripheral neuropathy, more preferably inflammatory bowel disease (inflammatory bowel disease) (preferably Crohn's disease or ulcerative colitis, systemic lupus erythematosus, rheumatoid arthritis, psoriasis, Sjogren's syndrome, Behcet's syndrome, multiple sclerosis, graft versus host disease, Alzheimer's disease (preferably dementia of Alzheimer type), schizophrenia, dementia with Lewy Bodies, frontotemporal dementia, progressive supranuclea palsy, corticobasal degeneration, Parkinson's disease, Huntington's disease, Rubinstein-Taybi Syndrome, muscular dystrophy, Rett Syndrome, amyotrophic lateral sclerosis, Charcot-Marie-Tooth disease, depression, hreditary sastic praplegia, Riley-Day syndrome, Castleman's disease, leukemia, uterine leiomyosarcoma, prostate cancer, colon cancer, multiple myeloma, cachexia or myelofibrosis, chronic heart failure or acute heart failure, acute decompensated heart failure, ischemic heart disease, cardiomyopathy, myocarditis, valvular disease, peripheral neuropathy and the like.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and direct administration to the lesion).

The content of the compound of the present invention in the medicament of the present invention is about 0.01 to 100% by weight of the entire medicament. The dose varies depending on administration subject, administration route, disease and the like. For example, for oral administration to patients (body weight about 60 kg) with psoriasis, rheumatoid arthritis, inflammatory bowel disease, Sjogren's syndrome, Behcet's disease, multiple sclerosis or systemic lupus erythematosus, about 0.01 mg/kg body weight-about 500 mg/kg body weight, preferably about 0.1 mg/kg body weight-about 50 mg/kg body weight, more preferably about 1 mg/kg body weight-about 30 mg/kg body weight of an active ingredient (compound (I)) may be administered once to several portions per day.

The pharmaceutically acceptable carrier, which is used for the production of the medicament of the present invention, is exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as a HDAC inhibitor, preferably a class II HDAC inhibitor, more preferably a HDAC6 inhibitor, it can be used together with the following drugs.

(1) non-steroidal anti-inflammatory drug (NSAIDs)
(i) Classical NSAIDs
  alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, ketophenylbutazone, loxoprofen sodium, phenylbutazone, indomethacin, ibuprofen, ketoprofen, naproxen, oxaprozin, flurbiprofen, fenbufen, pranoprofen, floctafenine, piroxicam, tenoxicam, epirizole, tiaramide hydrochloride, zaltoprofen, gabexate mesylate, camostat mesylate, ulinastatin, colchicine, probenecid, sulfinpyrazone, bucolome, benzbromarone, allopurinol, sodium aurothiomalate, hyaluronate sodium, sodium salicylate, salicylic acid, atropine, scopolamine, levorphanol, oxymorphone or a salt thereof and the like.

(ii) cyclooxygenase inhibitor (COX-1 selective inhibitor, COX-2 selective inhibitor etc.)
  salicylic acid derivatives (e.g., celecoxib, aspirin), etoricoxib, valdecoxib, diclofenac sodium, indomethacin, loxoprofen and the like.

(iii) nitric oxide-releasing NSAIDs.

(iv) JAK inhibitor
  tofacitinib, ruxolitinib and the like.

(2) disease-modifying anti-rheumatic drugs (DMARDs)
(i) Gold preparation
  auranofin, sodium aurothiomalate and the like.

(ii) penicillamine
  D-penicillamine.

(iii) aminosalicylic acid preparation
  sulfasalazine, mesalazine, olsalazine, balsalazide and the like.

(iv) antimalarial drug
  chloroquine and the like.

(v) pyrimidine synthesis inhibitor
  leflunomide and the like.

(vi) prograf (3) anti-cytokine drug
(I) protein drug
(i) TNF inhibitor
etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(v) interleukin-12/23 inhibitor
ustekinumab, briakinumab (anti-interleukin-12/23 antibody) and the like.
(II) non-protein drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
denileukin diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor, soluble TNF-α receptor and the like.
(xii) antisense compound
ISIS 104838 and the like.
(4) integrin inhibitor
natalizumab, vedolizumab, AJM300, TRK-170, E-6007 and the like.
(5) immunomodulator (immunosuppressant)
methotrexate, cyclophosphamide, MX-68, atiprimod dihydrochloride, BMS-188667, CKD-461, rimexolone, cyclosporine, tacrolimus, gusperimus, azathipurine, anti-lymphocyte serum, freeze-dried sulfonated normal immunoglobulin, erythropoietin, colony stimulating factor, interleukin, interferon and the like.
(6) steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol, paramethasone acetate, fludrocortisone acetate, clobetasol propionate, diflorasone acetate, dexamethasone propionate, difluprednate, betamethasone dipropionate, budesonide, diflucortolone valerate, amcinonide, halcinonide, mometasone furoate, hydrocortisone butyrate propionate, flumetasone pivalate, clobetasone butyrate, dexametasone acetate and the like.

(7) angiotensin converting enzyme inhibitor
enalapril, captopril, ramipril, lisinopril, cilazapril, perindopril and the like.
(8) angiotensin II receptor antagonist
candesartan, candesartan cilexetil, azilsartan, azilsartan medoxomil, valsartan, irbesartan, olmesartan, eprosartan and the like.
(9) diuretic drug
hydrochlorothiazide, spironolactone, furosemide, indapamide, bendrofluazide, cyclopenthiazide and the like.
(10) cardiotonic drug
digoxin, dobutamine and the like.
(11) β receptor antagonist
carvedilol, metoprolol, atenolol and the like.
(12) Ca sensitizer
MCC-135 and the like.
(13) Ca channel antagonist
nifedipine, diltiazem, verapamil, lomerizine hydrochloride, amlodipine besylate and the like.
(14) anti-platelet drug, anticoagulator
heparin, aspirin, warfarin, dabigatran, rivaroxaban, apixaban, edoxaban and the like.
(15) HMG-CoA reductase inhibitor
atorvastatin, simvastatin and the like.
(16) vasodilator
relaxin and the like.
(17) angiotensin receptor neprilysin inhibitor
LCZ696 and the like.
(18) heart rate-lowering drug
ivabradine and the like.
(19) hypouricemic drug
probenecid, allopurinol, febuxostat and the like.
(20) anti-aldosterone drug
spironolactone, eplerenone and the like.
(21) renin inhibitor
aliskiren and the like.
(22) α-blocker
doxazosin and the like.
(23) oraladsorptive agent
kremezin and the like.
(24) therapeutic drug for hyperkalemia
*calcicol* and the like.
(25) therapeutic drug for hyperphosphatemia
sevelamer, lanthanum carbonate and the like.
(26) metabolic acidosis improving drug
sodium bicarbonate and the like.
(27) activity type vitamin
(28) calcium receptor agonists
cinacalcet and the like.
(29) intravenous cardiotonic drug
h-ANP and the like.
(30) contraceptive
(i) sex hormone or derivatives thereof
gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
ormeloxifene, mifepristone, Org-33628 and the like.
(iii) spermatocide
ushercell and the like.
(31) others
(i) T cell inhibitors
(ii) inosine monophosphate dehydrogenase (IMPDH) inhibitor
mycophenolate mofetil and the like.
(iii) adhesion molecule inhibitor
ISIS-2302, selectin inhibitor, ELAM-1, VCAM-1, ICAM-1 and the like.
(iv) thalidomide
(v) cathepsin inhibitor
(vi) matrix metalloprotease (MMPs) inhibitor
V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor
roflumilast, CG-1088 and the like.
(x) phospholipase $A_2$ inhibitor
(xi) iNOS inhibitor
VAS-203 and the like.
(xii) microtubule stimulating drug
paclitaxel, docetaxel hydrate and the like.
(xiii) microtuble inhibitor
reumacon and the like.
(xiv) MHC class II antagonist
(xv) prostacyclin agonist
iloprost and the like.
(xvi) CD4 antagonist
zanolimumab and the like.
(xvii) CD23 antagonist
(xviii) LTB4 receptor antagonist
DW-1305 and the like.
(xix) 5-lipoxygenase inhibitor
zileuton and the like.
(xx) acetylcholinesterase inhibitor
donepezil hydrochloride, galanthamine, rivastigmine, neostigmine bromide, pyridostigmine bromide, ambenonium chloride, edrophonium chloride and the like.
(xxi) tyrosine kinase inhibitor
Tyk2 inhibitor (WO2010142752) and the like.
(xxii) cathepsin B inhibitor
(xxiii) adenosine deaminase inhibitor
pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
synvisc (hylan G-F 20), orthovisc and the like.
(xxix) glucosamine sulfate
(xxx) amiprilose
(xxxi) CD-20 inhibitor
rituximab, ibritumomab, tositumomab, ofatumumab and the like.
(xxxii) BAFF inhibitor
belimumab, tabalumab, atacicept, A-623 and the like.
(xxxiii) CD52 inhibitor
alemtuzumab and the like.
(xxxiv) IL-17 inhibitor
secukinumab (AIN-457), LY-2439821, AMG827 and the like.
(xxxv) PDE4 inhibitor
Roflumilast, Apremilast and the like.
(xxxvi) therapeutic drug for Alzheimer's disease memantine and the like.
(xxxvii) therapeutic drug for Parkinson's disease levodopa, droxidopa, amantadine hydrochloride, bromocriptine mesylate, trihexyphenidyl hydrochloride, selegiline hydrochloride and the like.
(xxxviii) ALS therapeutic drug
riluzole, neurotrophic factor and the like.
(xxxix) therapeutic drug for insomnia
etizolam, zopiclone, triazolam, zolpidem, ramelteon, indiplon and the like.
(xxxx) anti-ADHD drug
methylphenidate hydrochloride, methamphetamine hydrochloride and the like.

Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant and therapeutic drug for manic psychosis, antiallergic drug, cardiac stimulants, therapeutic drug for arrhythmia, vasodilator, vasoconstrictor, hypotensive diuretic, therapeutic drug for diabetes, antiobesity drug, antinarcotic, vitamin, vitamin derivative, antiasthmatic, therapeutic agent for pollakisuria/anischuria, antipruritic drug, therapeutic agent for atopic dermatitis, therapeutic agent for allergic rhinitis, hypertensor, narcotic analgesic, non-narcotic analgesic, therapeutic drug for ocular disease, therapeutic drug for nausea and vomiting, therapeutic drug for coprostasis and diarrhea, therapeutic drug for osteoporosis, therapeutic drug for thyroid dysfunction, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.
(1) Antibacterial agent
(i) sulfa drug
sulfamethizole, sulfisoxazole, sulfamonomethoxine, salazosulfapyridine, silver sulfadiazine and the like.
(ii) quinolone antibacterial agent
nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
diaphenylsulfone, rifampicin and the like.
(v) antiviral drug
idoxuridine, acyclovir, vidarabine, gancyclovir, foscarnet sodium, influenza HA vaccine, zanamivir, oseltamivir phosphate, amantadine hydrochloride and the like.
(vi) anti-HIV agent
zidovudine, didanosine, zalcitabine, indinavir sulfate ethanolate, ritonavir, lamivudine, abacavir sulfate, nevirapine, efavirenz, saquinavir mesylate, nelfinavir mesylate, amprenavir and the like.
(vii) antispirochetele
(viii) antibiotic tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxyl-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like], ceftriaxone sodium, vancomycin hydrochloride, benzylpenicillin potassium, chloramphenicol, amoxicillin, amoxicillin-clavulanate potassium, sulfamethoxazole-trimethoprim, erythromycin, norfloxacin, ciprofloxacin hydrochloride, imipenem-cilastatin sodium, ampicillin-cloxacillin, cefoxitin sodium, cefotetan sodium, clindamycin hydrochlorid, clarithromycin, netilmicin sulfate, sulbenicillin sodium, ampicillin sodium-sulbactam sodium, cefuroxime sodium, aztreonam and the like.

(2) antifungal agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) antiprotozoal agent
metronidazole, tinidazole, diethylcarbamazine citrate, quinine hydrochloride, quinine sulfate and the like.

(4) antitussive and expectorant drug
ephedrine hydrochloride, noscapine hydrochloride, codeine phosphate, dihydrocodeine phosphate, isoproterenol hydrochloride, methylephedrine hydrochloride, alloclamide, chlophedianol, picoperidamine, cloperastine, protokylol, isoproterenol, salbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative
chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) anesthetic
(6-1) local anesthetic
cocaine hydrochloride, procaine hydrochloride, lidocaine, dibucaine hydrochloride, tetracaine hydrochloride, mepivacaine hydrochloride, bupivacaine hydrochloride, oxybupurocaine hydrochloride, ethyl aminobenzoate, oxethazaine and the like.

(6-2) general anesthetic
(i) inhalation anesthetic (e.g., ether, halothane, nitrous oxide, isoflurane, enflurane),
(ii) intravenous anesthetic (e.g., ketamine hydrochloride, droperidol, thiopental sodium, thiamylal sodium, pentobarbital) and the like.

(7) antiulcer drug
histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin, propantheline bromide, misoprostol, ornoprostil and the like.

(8) antiarrhythmic agent
(i) sodium channel blocker (e.g., quinidine, procainamide, disopyramide, ajmaline, lidocaine, mexiletine, phenytoin, flecainide acetate, propafenone hydrochloride),
(ii) β-blocker (e.g., propranolol, alprenolol, bufetolol hydrochloride, oxprenolol, atenolol, acebutolol, metoprolol, bisoprolol, pindolol, carteolol, arotinolol hydrochloride),
(iii) potassium channel blocker (e.g., amiodarone, sotalol hydrochloride),
(iv) calcium channel blocker (e.g., verapamil, diltiazem),
(v) nitrate (e.g., nitroglycerin, isosorbide dinitrate) and the like.

(9) hypotensive diuretic drug
hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline, carperitide, torasemide and the like.

(10) anticoagulant
heparin sodium, sodium citrate, activated protein C, tissue factor pathway inhibitor, antithrombin III, dalteparin sodium, warfarin potassium, argatroban, gabexate, ozagrel sodium, ethyl icosapentate, beraprost sodium, alprostadil, ticlopidine hydrochloride, pentoxifylline, dipyridamole, tisokinase, urokinase, streptokinase, alteplase and the like.

(11) tranquilizer
diazepam, lorazepam, clorazepate dipotassium, oxazepam, chlordiazepoxide, medazepam, oxazolam, cloxazolam, clotiazepam, bromazepam, etizolam, fludiazepam, hydroxyzine, nitrazepam, triazolam, alprazolam and the like.

(12) antipsychotic
chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, clozapine, trifluoperazine dihydrochloride, fluphenazine hydrochloride, olanzapine, quetiapine fumarate, risperidone, aripiprazole, bromperidol, spiperone, reserpine, clocapramine hydrochloride, sulpiride, zotepine, tiotixene and the like.

(13) antitumor drug
(i) cytotoxic cancer drug
6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, peplomycin sulfate, vincristine sulfate, vinblastine sulfate, irinotecan hydrochloride, cyclophosphamide, melphalan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate, ifosfamide, busulfan, ranimustine, dacarbazine, nedaplatin, carboplatin, gemcitabine hydrochloride, fludarabine hydrochloride, vinorelbine ditartarate, etoposide, L-asparaginase and the like.

(ii) therapeutic drug for hormone tamoxifen citrate, toremifene citrate, fadrozole hydrochloride hydrate, flutamide, bicalutamide and the like.

(14) hypolipidemic drug and therapeutic drug for arteriosclerosis clofibrate, ethyl 2-chloro-3-[4-(2-methyl-2-phenylpropoxy)phenyl]propionate [Chemical and Pharmaceutical Bulletin, 1990, 38, 2792-2796], pravastatin, simvastatin, probucol, bezafibrate, clinofibrate, nicomol, cholestyramine, dextran sulfate sodium, fluvastatin sodium, cerivastatin sodium, colestimide, nicotinic acid, niceritrol, clofibrate, fenofibrate and the like.

(15) muscle relaxant pridinol, tubcurarine, pancuronium, tolperisone hydrochloride, chlorphenesin carbamate, baclofen, chlormezanone, mephenesin, chlorzoxazone, eperisone, tizanidine and the like.

(16) antiepileptic drug phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) antidepressant and therapeutic drug for manic psychosis imipramine, clomipramine, desipramine hydrochloride, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride, paroxetine hydrochloride hydrate, lithium carbonate, selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenalin reuptake inhibitor (venlafaxine hydrochloride, duloxetine hydrochloride, venlafaxine hydrochloride etc.), noradrenalin reuptake inhibitor (reboxetine mesylate etc.), noradrenalin-dopamine reuptake inhibitor (bupropion hydrochloride etc.), mirtazapine, trazodone hydrochloride, nefazodone hydrochloride, bupropion hydrochloride, setiptiline maleate, 5-HT1A agonist (buspirone hydrochloride, tandospirone citrate, osemozotan hydrochloride) and the like.

(18) antiallergic drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like:

(19) cardiac stimulants trans-π-oxocamphor, terephyllol, aminophylline, etilefrine, dopamine, dobutamine, denopamine, amrinone, pimobendan, ubidecarenone, digitoxin, digoxin, methyldigoxin, lanatoside C, G-strophanthin, milrinone, vesnarinone, docarpamine and the like.

(20) vasodilator oxyfedrine, diltiazem, tolazoline, hexobendine, bamethan, clonidine, methyldopa, guanabenz, hydralazine hydrochloride and the like.

(21) vasoconstrictor dopamine, dobutamine, denopamine and the like.

(22) hypotensive diuretic hexamethonium bromide, pentolinium, mecamylamine, ecarazine, clonidine, diltiazem, nifedipine and the like.

(23) therapeutic drug for diabetes tolbutamide, chlorpropamide, acetohexamide, glibenclamide, tolazamide, acarbose, epalrestat, troglitazone, glucagon, glymidine, glipizide, phenformin, buformin, metformin, gliclazide, nateglinide, voglibose, insulin and the like.

(24) antiobesity drugs glucagon-like peptide-1 (GLP-1) preparation and the like.

(25) antinarcotic levallorphan, nalorphine, naloxone or a salt thereof and the like.

(26) liposoluble vitamins (i) vitamin A: vitamin $A_1$, vitamin $A_2$ and retinol palmitate (ii) vitamin D: alfacalcidol, calcitriol, vitamin $D_1$, $D_2$, $D_3$, $D_4$ and $D_5$ (iii) vitamin E: α-tocopherol, β-tocopherol, γ-tocopherol, δ-tocopherol, dl-α-tocopherol nicotinate (iv) vitamin K: menatetrenone, vitamin $K_1$, $K_2$, $K_3$ and $K_4$ (v) folic acid (vitamin M) and the like.

(27) vitamin derivative various derivatives of vitamins, for example, vitamin $D_3$ derivatives such as 5,6-trans-cholecalciferol, 2,5-hydroxycholecalciferol, 1-α-hydroxycholecalciferol and the like, vitamin $D_2$ derivatives such as 5,6-trans-ergocalciferol and the like, and the like.

(28) antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate, epinephrine, fluticasone propionate, zafirlukast and the like.

(29) therapeutic agent for pollakisuria/anischuria flavoxate hydrochloride and the like.

(30) therapeutic agent for atopic dermatitis sodium cromoglicate and the like.

(31) therapeutic agent for allergic rhinitis sodium cromoglicate, chlorpheniramine maleate, alimemazine tartrate, clemastine fumarate, homochlorcyclizine hydrochloride, fexofenadine, mequitazine and the like.

(32) hypertensor dopamine, dobutamine, denopamine, digitoxin, digoxin, methyldigoxin, lanatoside C, G-strophanthin and the like.

(33) narcotic analgesic morphine hydrochloride, morphine sulfate sustained tablet, morphine-atropine, pethidine hydrochloride, fentanyl citrate and the like.

(34) non-narcotic analgesic pentazocine, buprenorphine hydrochloride and the like.

(35) therapeutic drug for ocular disease pilocarpine hydrochloride, distigmine bromide, ecothiopate iodide, timolol maleate, carteolol hydrochloride, phenylephrine hydrochloride, epinephrine, dorzolamide, isopropyl unoprostone, latanoprost and the like.

(36) therapeutic drug for nausea and vomiting domperidone, prochlorperazine, chlorpromazine, promethazine hydrochloride, diphenhydramine hydrochloride-diprophylline combination drug, scopolamine butylbromide, granisetron hydrochloride, ondansetron hydrochloride, azasetron hydrochloride, ramosetron hydrochloride and the like.

(37) therapeutic drug for coprostasis and diarrhea carmellose sodium, lactulose, D-sorbitol, magnesium citriate, magnesium oxide, senna extract, sennoside, picosulfate sodium, bisacodyl, cisapride, itopride hydrochloride, loperamide hydrochloride and the like.

(38) therapeutic drug for osteoporosis alfacalcidol, calcitriol, estriol, elcatonin, salmon calcitonin, etidronate disodium, pamidronate disodium, alendronate sodium hydrate and the like.

(39) therapeutic drug for thyroid dysfunction liothyronine sodium, propylthiouracil, thiamazole, potassium iodide, sodium iodide, levothyroxine sodium and the like.

(40) others diacerein, megestrol acetate, nicergoline, prostaglandins.

(41) therapeutic drug for central disease and the like benzodiazepine (chlordiazepoxide, diazepam, clorazepate dipotassium, lorazepam, clonazepam, alprazolam etc.), L-type calcium channel inhibitor (pregabalin etc.), tricyclic or tetracyclic antidepressant drug (imipramine hydrochloride, amitriptyline hydrochloride, desipramine hydrochloride, clomipramine hydrochloride, etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenalin reuptake inhibitor (venlafaxine hydrochloride, duloxetine hydrochloride, venlafaxine hydrochloride etc.), noradrenalin reuptake inhibitor (reboxetine mesylate etc.), noradrenalin-dopamine reuptake inhibitor (bupropion hydrochloride etc.), mirtazapine, trazodone hydrochloride, nefazodone hydrochloride, bupropion hydrochloride, setiptiline maleate, 5-HT1A agonist (buspirone hydrochloride, tandospirone citrate, osemozotan hydrochloride), $5-HT_3$ antagonist (cyamemazine etc.), heart non-selective β inhibitor (propranolol hydrochloride, oxiprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), drug that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, type II carbonic anhydrase inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioids antagonist, opioids agonist, uridine, nicotinic acid receptor agonists, thyroid hormone (T3, T4), TSH, TRH, MAO inhibitor (acidphenelzine sulfate, tranylcypromine sulfate, moclobemide etc.), $5-HT_{2A}$ antagonist, $5-HT_{2A}$ inverse agonist, COMT inhibitor (entacapone, etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug forfibromyalgia, therapeutic drug for headache, therapeutic drug for insomnia (etizolam, zopiclone, triazolam, xolpidem, ramelteon, indiplon etc.), therapeutic drug for quitting smoking, therapeutic drug for myasthenia gravis, therapeutic drug for cerebral infarction, therapeutic drug for manic psychosis, therapeutic drug for hypersomnia, therapeutic drug for pain, therapeutic drug for dysthymia, therapeutic drug for dysautonomia, therapeutic drug for male and female sexual dysfunction, therapeutic drug for migraine, therapeutic drug for pathological gambling, therapeutic drug for restless legs syndrome, therapeutic drug for substance dependence, therapeutic drug for alcohol-related disease, therapeutic drug for irritable bowel syndrome, therapeutic drug for Alzheimer's disease (donepezil, galanthamine, memantine, rivastigmine, etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination thereof etc.), therapeutic drug for Parkinson's disease associated with dementia (rivastigmine), therapeutic drug for Lewy body dementia (donepezil), therapeutic drug for ALS (riluzole, neurotrophic factor, etc.), therapeutic drug for hyperlipidemia such as cholesterol-lowering drug (statin series (pravastatin sodium, atorvastatin, simvastatin, rosuvastatin, etc.), fibrate (clofibrate etc.), squalene synthase inhibitor), therapeutic drug for abnormal behavior or dementia-related wandering (sedative drug, antianxiety drug, etc.), apoptosis inhibitor, antiobesity drug, antidiabetic drug, therapeutic drug for hypertension, therapeutic drug for hypotension, therapeutic drug for rheumatism (DMARD), anticancer drug, therapeutic drug for hypoparathyroidism (PTH), calcium receptor antagonist, sex hormone or derivative thereof (progesterone, estradiol, estradiol benzoate etc.), neuron differentiation accelerator, neurogeneration promotor, non-steroidal anti-inflammatory drug (meloxicam, tenoxicam, indomethacin, ibuprofen, celecoxib, rofecoxib, aspirin etc.), steroid (dexamethasone, cortisone acetate, etc.), anti-cytokine drug (TNF inhibitor, MAP kinase inhibitor, etc.), antibody medicament, nucleic acid or nucleic acid derivative, aptamer and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, "basic" means use of aminopropylsilane-bound silica gel. The ratios of elution solvents are volume mixing ratios, unless otherwise specified.

In Examples, the following abbreviations are used.
DMF: N,N-dimethylformamide
THF: tetrahydrofuran
EDCI: 1-ethyl-3-(3-dimethylaminopropyl)carbodiimide
DMSO: dimethyl sulfoxide
HOBt: 1-hydroxybenzotriazole
HATU: O-(7-azabenzotriazol-1-yl)-N,N,N',N',-tetramethyluroniumhexafluorophosphoric acid
TEA: triethylamine
DIEA: N,N-diisopropylethylamine
DME: 1,2-dimethoxyethane
CPME: cyclopentyl methyl ether
N: normal
M: mol concentration $^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

The following abbreviations are used for $^1$H NMR measurement.

s: singlet, d: doublet, dd: double doublet, dt: double triplet, t: triplet, q: quartet, m: multiplet, brs: broad singlet, quin: quintet, J: coupling constant, Hz: hertz.

MS (mass spectrum) was measured by LC/MS (liquid chromatography mass spectrometer). As ionization method, ESI (Electro Spray Ionization) method or APCI (Atmospheric Pressure Chemical Ionization) method was used. The data indicates those found.

Example 1

N-((4-benzoylmorpholin-3-yl)methyl)-4-(5-(trifluoromethyl)-1,2,4-oxadiazol-3-yl)benzamide (Step A)

A mixture of 4-(5-(trifluoromethyl)-1,2,4-oxadiazol-3-yl)benzoic acid (300 mg), tert-butyl 3-(aminomethyl)morpholine-4-carboxylate (264 mg), HATU (464 mg), DIEA (0.406 mL) and DMF (7 mL) was stirred overnight at room temperature. The reaction solution was diluted with saturated aqueous sodium hydrogencarbonate solution, and extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give tert-butyl 3-(((4-(5-(trifluoromethyl)-1,2,4-oxadiazol-3-yl)benzoyl)amino)methyl)morpholine-4-carboxylate (439 mg).

$^1$H NMR (300 MHz, CDCl$_3$) δ 1.37 (9H, s), 3.13-3.57 (3H, m), 3.60-4.00 (4H, m), 4.33 (2H, brs), 7.01 (1H, brs), 7.94 (2H, d, J=8.7 Hz), 8.17 (2H, d, J=8.3 Hz).

(Step B)

To a solution of tert-butyl 3-(((4-(5-(trifluoromethyl)-1,2,4-oxadiazol-3-yl)benzoyl)amino)methyl)morpholine-4-carboxylate obtained in Step A (86 mg) in methanol (1.5 mL) was added 4N hydrochloric acid-CPME solution (1.413 mL), and the mixture was stirred at room temperature for 3 hr. The reaction solution was neutralized with 1N aqueous sodium hydroxide solution, and extracted with ethyl acetate. The extract was washed with water and saturated brine, and dried over anhydrous magnesium sulfate, and the solvent was evaporated under reduced pressure to give a crude product (35 mg) of N-(morpholin-3-ylmethyl)-4-(5-(trifluoromethyl)-1,2,4-oxadiazol-3-yl)benzamide. The compound was used in the next step without further purification.
(Step C)

To a solution of the crude product (16 mg) of N-(morpholin-3-ylmethyl)-4-(5-(trifluoromethyl)-1,2,4-oxadiazol-3-yl)benzamide, which was obtained in Step B, in THF (3.0 mL) were added benzoyl chloride (6.25 μL) and TEA (7.51 μL), and the mixture was stirred overnight at room temperature. The reaction solution was diluted with saturated aqueous sodium hydrogencarbonate solution, and the solvent was evaporated under reduced pressure. The residue was purified by silica gel column chromatography (hexane/ethyl acetate), and recrystallized from ethyl acetate-hexane to give the title compound (11.7 mg).

$^1$H NMR (300 MHz, CDCl$_3$) δ 3.21-3.62 (3H, m), 3.63-4.11 (4H, m), 4.56-5.08 (2H, m), 7.19 (1H, brs), 7.23-7.30 (2H, m), 7.30-7.44 (3H, m), 7.90 (2H, d, J=8.3 Hz), 8.07 (2H, d, J=7.6 Hz).

Example 2

N-phenyl-3-(((4-(5-(trifluoromethyl)-1,2,4-oxadiazol-3-yl)benzoyl)amino)methyl)morpholine-4-carboxamide To a solution of the crude product (18 mg) of N-(morpholin-3-ylmethyl)-4-(5-(trifluoromethyl)-1,2,4-oxadiazol-3-yl)benzamide in THF (3.0 mL) was added isocyanatobenzene (8.26 μL), and the mixture was stirred overnight at room temperature. The reaction solution was concentrated under reduced pressure, and the residue was purified by silica gel column chromatography (hexane/ethyl acetate), and recrystallized from ethyl acetate-hexane to give the title compound (18 mg).

$^1$H NMR (300 MHz, CDCl$_3$) δ 3.09-3.28 (1H, m), 3.51-3.74 (3H, m), 3.83-4.08 (4H, m), 4.19 (1H, brs), 6.89-6.98 (1H, m), 7.01 (1H, s), 7.21-7.32 (2H, m), 7.54 (2H, d, J=7.9 Hz), 7.93 (2H, d, J=8.7 Hz), 8.04 (1H, brs), 8.16 (2H, d, J=8.7 Hz).

Examples 3 to 32

The compounds of Examples 3 to 32 were obtained using a crude product of N-(morpholin-3-ylmethyl)-4-(5-(trifluoromethyl)-1,2,4-oxadiazol-3-yl)benzamide hydrochloride by a method similar to the below-mentioned Example 33.

Example 33

N-((4-((2-methyl-2H-indazol-3-yl)carbonyl)morpholin-3-yl)methyl)-4-(5-(trifluoromethyl)-1,2,4-oxadiazol-3-yl)benzamide (Step A)
To a solution of tert-butyl 3-(((4-(5-(trifluoromethyl)-1,2,4-oxadiazol-3-yl)benzoyl)amino)methyl)morpholine-4-carboxylate (1520 mg) in methanol (15 mL) was added 4N hydrochloric acid-CPME solution (25.0 mL, 100 mmol), and the mixture was stirred at room temperature for 4 hr. The reaction solution was concentrated to give a crude product (1345 mg) of N-(morpholin-3-ylmethyl)-4-(5-(trifluoromethyl)-1,2,4-oxadiazol-3-yl)benzamide hydrochloride. The compound was used in the next step without further purification.
(Step B)

A mixture of the crude product (100 mg) of N-(morpholin-3-ylmethyl)-4-(5-(trifluoromethyl)-1,2,4-oxadiazol-3-yl)benzamide hydrochloride, which was obtained in Step A, 2-methyl-2H-indazole-3-carboxylic acid (49.3 mg), N-(3-(dimethylamino)propyl)-N'-ethylcarbodiimide hydrochloride (53.7 mg), 1H-benzotriazol-1-ol monohydrate (34.4 mg), DIEA (0.133 mL) and DMF (4.0 mL) was stirred overnight at room temperature. To the reaction mixture was added saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate), and recrystallized from ethyl acetate-hexane to give the title compound (59 mg).

$^1$H NMR (300 MHz, CDCl$_3$) δ 3.32-4.39 (11H, m), 4.83 (2H, brs), 7.15 (1H, t, J=5.3 Hz), 7.26 (1H, s), 7.47 (1H, d, J=8.3 Hz), 7.69 (1H, d, J=8.3 Hz), 7.75-8.51 (4H, m).

Examples 34 and 35

The compounds of Examples 34 and 35 were obtained by a method similar to Example 33.

Example 36

N-(((3S)-4-benzoylmorpholin-3-yl)methyl)-4-(5-(trifluoromethyl)-1,2,4-oxadiazol-3-yl)benzamide (Step A)
A racemate (3.48 g) of tert-butyl 3-(((4-(5-(trifluoromethyl)-1,2,4-oxadiazol-3-yl)benzoyl)amino)methyl)morpholine-4-carboxylate was resolved by HPLC (column: CHIRALPAK AD (LF001), 50 mmID×500 mmL, manufactured by Daicel Chemical Industries, mobile phase: hexane/ethanol=85/15) to give tert-butyl (3S)-3-(((4-(5-(trifluoromethyl)-1,2,4-oxadiazol-3-yl)benzoyl)amino)methyl)morpholine-4-carboxylate (1.78 g) as a compound having a shorter retention time.

$^1$H NMR (300 MHz, CDCl$_3$) δ 1.37 (9H, s), 3.16-3.58 (3H, m), 3.60-4.01 (4H, m), 4.33 (2H, brs), 7.04 (1H, brs), 7.94 (2H, d, J=8.7 Hz), 8.17 (2H, d, J=8.3 Hz).
(Step B)

To a solution of tert-butyl (3S)-3-(((4-(5-(trifluoromethyl)-1,2,4-oxadiazol-3-yl)benzoyl)amino)methyl)morpholine-4-carboxylate obtained in Step A (468 mg) in methanol (7.5 mL) was added 4N hydrochloric acid-CPME solution (7.69 mL), and the mixture was stirred at room temperature for 2 hr. The reaction solution was concentrated to give a crude product (385 mg) of N-((3S)-morpholin-3-ylmethyl)-4-(5-(trifluoromethyl)-1,2,4-oxadiazol-3-yl)benzamide hydrochloride. The compound was used in the next step without further purification.
(Step C)

To a solution of the crude product (120 mg) of N-((3S)-morpholin-3-ylmethyl)-4-(5-(trifluoromethyl)-1,2,4-oxadiazol-3-yl)benzamide hydrochloride, which was obtained in Step B, in THF (3.0 mL) were added benzoyl chloride (39 μL) and TEA (89 μL), and the mixture was stirred at room temperature for 2 hr. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and recrystallized from ethyl acetate-hexane to give the title compound (125 mg).

$^1$H NMR (400 MHz, CDCl$_3$) δ 3.34 (1H, d, J=12.5 Hz), 3.40-3.58 (2H, m), 3.73-3.94 (3H, m), 4.01 (1H, d, J=11.7 Hz), 4.69-4.86 (1H, m), 4.89-5.10 (1H, m), 7.26-7.30 (2H, m), 7.31-7.46 (4H, m), 7.79-7.87 (2H, m), 7.90 (2H, brs).

Example 37

N-(((3S)-4-(3,5-dichlorobenzoyl)morpholin-3-yl)methyl)-4-(5-(trifluoromethyl)-1,2,4-oxadiazol-3-yl)benzamide To a solution of N-((3S)-morpholin-3-ylmethyl)-4-(5-(trifluoromethyl)-1,2,4-oxadiazol-3-yl)benzamide hydrochloride (110 mg) in THF (3.0 mL) were added 3,5-dichlorobenzoyl chloride (64.5 mg) and TEA (82 µL), and the mixture was stirred at room temperature for 1 hr. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was recrystallized from ethyl acetate-hexane to give the title compound (140 mg).

The absolute configurations of Examples 36, 37, 111 and 112 were identified by X-ray crystal structural analysis of Example 37.

$^1$H NMR (300 MHz, CDCl$_3$) δ 3.31 (2H, d, J=11.7 Hz), 3.47 (1H, t, J=11.5 Hz), 3.77 (1H, dd, J=12.3, 3.2 Hz), 3.85-4.06 (3H, m), 4.66-5.01 (2H, m), 7.13 (3H, s), 7.36 (1H, t, J=1.9 Hz), 7.78-7.90 (2H, m), 7.96 (2H, d, J=7.2 Hz).

Example 38

N-(((3S)-4-((1-methyl-1H-pyrazol-5-yl)carbonyl)morpholin-3-yl)methyl)-4-(5-(trifluoromethyl)-1,2,4-oxadiazol-3-yl)benzamide (Step A)

A mixture of 4-(5-(trifluoromethyl)-1,2,4-oxadiazol-3-yl)benzoic acid (5.00 g), tert-butyl (3S)-3-(aminomethyl)morpholine-4-carboxylate (4.40 g), HATU (7.73 g), DIEA (6.77 ml) and DMF (140 mL) was stirred overnight at room temperature. The reaction solution was diluted with saturated aqueous sodium hydrogencarbonate solution, and extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give tert-butyl (3S)-3-(((4-(5-(trifluoromethyl)-1,2,4-oxadiazol-3-yl)benzoyl)amino)methyl)morpholine-4-carboxylate (7.10 g).

$^1$H NMR (300 MHz, CDCl$_3$) δ 1.37 (9H, s), 3.20-3.57 (3H, m), 3.60-3.99 (4H, m), 4.33 (2H, brs), 7.04 (1H, brs), 7.94 (2H, d, J=8.7 Hz), 8.17 (2H, d, J=8.7 Hz).

(Step B)

To a solution of tert-butyl (3S)-3-(((4-(5-(trifluoromethyl)-1,2,4-oxadiazol-3-yl)benzoyl)amino)methyl)morpholine-4-carboxylate obtained in Step A (7.10 g) in methanol (120 mL) was added 4N hydrochloric acid-CPME solution (117 mL), and the mixture was stirred at room temperature for 2 hr. The reaction solution was concentrated, and the residue was suspended in hexane, and collected by filtration to give a crude product (5.97 g) of N-((3S)-morpholin-3-ylmethyl)-4-(5-(trifluoromethyl)-1,2,4-oxadiazol-3-yl)benzamide hydrochloride. The compound was used in the next step without further purification.

(Step C)

A mixture of the crude product (160 mg) of N-((3S)-morpholin-3-ylmethyl)-4-(5-(trifluoromethyl)-1,2,4-oxadiazol-3-yl)benzamide hydrochloride, which was obtained in Step B, 1-methyl-1H-pyrazole-5-carboxylic acid (56.5 mg), HATU (186 mg), DIEA (0.213 mL) and DMF (140 mL) was stirred overnight at room temperature. The reaction solution was diluted with saturated aqueous sodium hydrogencarbonate solution, and extracted with ethyl acetate. The extract was washed with water and saturated brine, and dried over anhydrous sodium sulfate, and the solvent was evaporated under reduced pressure. The residue was purified by silica gel column chromatography (ethyl acetate/methanol) and basic silica gel column chromatography (hexane/ethyl acetate), and the purified product was suspended in hexane, and collected by filtration to give the title compound.

$^1$H NMR (300 MHz, CDCl$_3$) δ 3.20-3.63 (2H, m), 3.65-4.17 (8H, m), 4.54-5.03 (2H, m), 6.26 (1H, brs), 6.94 (1H, brs), 7.39 (1H, s), 7.82 (2H, d, J=8.3 Hz), 8.05 (2H, brs).

Examples 39 and 40

The compounds of Examples 39 and 40 were obtained using N-((3S)-morpholin-3-ylmethyl)-4-(5-(trifluoromethyl)-1,2,4-oxadiazol-3-yl)benzamide hydrochloride by a method similar to Example 38.

Examples 41 to 81

The compounds of Examples 41 to 81 were obtained using N-((3S)-morpholin-3-ylmethyl)-4-(5-(trifluoromethyl)-1,2,4-oxadiazol-3-yl)benzamide hydrochloride by a method similar to Example 33.

Example 82

N-(((3S)-4-((2-methyl-2H-indazol-3-yl)carbonyl)morpholin-3-yl)methyl)-4-(5-(trifluoromethyl)-1,2,4-oxadiazol-3-yl)benzamide A mixture of the crude product (234 mg) of N-((3S)-morpholin-3-ylmethyl)-4-(5-(trifluoromethyl)-1,2,4-oxadiazol-3-yl)benzamide hydrochloride, 2-methyl-2H-indazole-3-carboxylic acid (100 mg), N-(3-(dimethylamino)propyl)-N'-ethylcarbodiimide hydrochloride (131 mg), 1H-benzotriazol-1-ol monohydrate (96 mg), TEA (60 mg) and DMF (5.0 mL) was stirred overnight at room temperature. To the reaction mixture was added saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate), and the obtained compound was suspended in hexane, and collected by filtration to give the title compound (217 mg).

$^1$H NMR (300 MHz, CDCl$_3$) δ 3.22-4.45 (11H, m), 4.52-5.43 (2H, m), 7.18 (1H, d, J=7.2 Hz), 7.23-7.37 (1H, m), 7.47 (1H, d, J=8.3 Hz), 7.63-8.38 (5H, m).

Examples 83 to 87

The compounds of Examples 83 to 87 were obtained using N-((3S)-morpholin-3-ylmethyl)-4-(5-(trifluoromethyl)-1,2,4-oxadiazol-3-yl)benzamide hydrochloride by a method similar to Example 33.

Example 88

N-(((3S)-4-((3,5-dimethyl-1,2-oxazol-4-yl)carbonyl)morpholin-3-yl)methyl)-4-(5-(trifluoromethyl)-1,2,4-oxadiazol-3-yl)benzamide A mixture of N-((3S)-morpholin-3-ylmethyl)-4-(5-(trifluoromethyl)-1,2,4-oxadiazol-3-yl)benzamide hydrochloride (100 mg), 3,5-dimethyl-1,2-oxazole-4-carboxylic acid (54 mg), N-(3-(dimethylamino)propyl)-N'-ethylcarbodiimide hydrochloride (98 mg), 1H-benzotriazol-1-ol monohydrate (78 mg), DIEA (132 mg) and DMF (1.3 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure.

The residue was purified by silica gel column chromatography (hexane/ethyl acetate) to give the title compound (77 mg).

$^1$H NMR (300 MHz, CDCl$_3$) δ 2.10 (3H, s), 2.23 (3H, s), 3.24-3.58 (3H, m), 3.66-3.84 (2H, m), 3.91-4.10 (2H, m), 4.60-5.00 (2H, m), 7.03 (1H, brs), 7.92 (2H, d, J=8.3 Hz), 8.17 (2H, d, J=8.3 Hz).

Example 89

N-(((3S)-4-(piperidin-1-ylcarbonyl)morpholin-3-yl)methyl)-4-(5-(trifluoromethyl)-1,2,4-oxadiazol-3-yl)benzamide A mixture of N-((3S)-morpholin-3-ylmethyl)-4-(5-(trifluoromethyl)-1,2,4-oxadiazol-3-yl)benzamide hydrochloride (100 mg), piperidine-1-carbonyl chloride (56 mg), DIEA (99 mg) and THF (1.3 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (99 mg).

Example 90

2-((3S)-4-((2-methyl-2H-indazol-3-yl)carbonyl)morpholin-3-yl)-N-(4-(5-(trifluoromethyl)-1,2,4-oxadiazol-3-yl)phenyl)acetamide The title compound was obtained using 2-methyl-2H-indazole-3-carboxylic acid by a method similar to the below-mentioned Example 160.

Examples 91 to 93

The compounds of Examples 91 to 93 were obtained using N-((3S)-morpholin-3-ylmethyl)-4-(5-(trifluoromethyl)-1,2,4-oxadiazol-3-yl)benzamide hydrochloride by a method similar to Example 33.

Example 94

N-(((3S)-4-((3-methyl-1,2-oxazol-4-yl)carbonyl)morpholin-3-yl)methyl)-4-(5-(trifluoromethyl)-1,2,4-oxadiazol-3-yl)benzamide A mixture of N-((3S)-morpholin-3-ylmethyl)-4-(5-(trifluoromethyl)-1,2,4-oxadiazol-3-yl)benzamide hydrochloride (100 mg), 3-methyl-1,2-oxazole-4-carboxylic acid (39 mg), N-(3-(dimethylamino)propyl)-N'-ethylcarbodiimide hydrochloride (98 mg), 1H-benzotriazol-1-ol monohydrate (78 mg), DIEA (132 mg) and DMF (1.3 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol) to give the title compound (46 mg).

$^1$H NMR (300 MHz, CDCl$_3$) δ 2.27 (3H, s), 3.18-3.36 (1H, m), 3.41-3.60 (2H, m), 3.66-3.83 (1H, m), 3.89-4.07 (3H, m), 4.55-4.96 (2H, m), 6.77 (1H, brs), 7.84 (2H, d, J=8.3 Hz), 8.13 (2H, d, J=7.9 Hz), 8.32 (1H, brs).

Examples 95 to 97

The compounds of Examples 95 to 97 were obtained using N-((3S)-morpholin-3-ylmethyl)-4-(5-(trifluoromethyl)-1,2,4-oxadiazol-3-yl)benzamide hydrochloride by a method similar to Example 33.

Examples 98 to 100

The compounds of Examples 98 to 100 were obtained using N-((3S)-morpholin-3-ylmethyl)-4-(5-(trifluoromethyl)-1,2,4-oxadiazol-3-yl)benzamide hydrochloride by a method similar to Example 89.

Example 101

N-(((3S)-4-(2-methyl-2-(1H-pyrazol-1-yl)propanoyl)morpholin-3-yl)methyl)-4-(5-(trifluoromethyl)-1,2,4-oxadiazol-3-yl)benzamide A mixture of N-((3S)-morpholin-3-ylmethyl)-4-(5-(trifluoromethyl)-1,2,4-oxadiazol-3-yl)benzamide hydrochloride (100 mg), 2-methyl-2-(1H-pyrazol-1-yl)propanoic acid (100 mg), 50% 2,4,6-tripropyl-1,3,5,2,4,6-trioxatriphosphinane 2,4,6-trioxide ethyl acetate solution (0.76 mL), DIEA (279 mg), N,N-dimethylpyridin-4-amine (53 mg) and ethyl acetate (4.5 mL) was stirred overnight at 80° C. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (135 mg).

Example 102

N-(((3S)-4-((3-ethyl-5-methyl-1,2-oxazol-4-yl)carbonyl)morpholin-3-yl)methyl)-4-(5-(trifluoromethyl)-1,2,4-oxadiazol-3-yl)benzamide A mixture of N-((3S)-morpholin-3-ylmethyl)-4-(5-(trifluoromethyl)-1,2,4-oxadiazol-3-yl)benzamide hydrochloride (100 mg), 3-ethyl-5-methyl-1,2-oxazole-4-carboxylic acid (59 mg), N-(3-(dimethylamino)propyl)-NT-ethylcarbodiimide hydrochloride (98 mg), 1H-benzotriazol-1-ol monohydrate (78 mg), DIEA (132 mg) and DMF (1.3 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (78 mg).

$^1$H NMR (400 MHz, CDCl$_3$) δ 1.09 (3H, brs), 2.22 (3H, brs), 2.52 (2H, brs), 3.21-3.55 (3H, m), 3.65-3.82 (2H, m), 3.90-4.06 (2H, m), 4.71 (1H, brs), 4.89 (1H, brs), 7.13 (1H, brs), 7.93 (2H, d, J=8.1 Hz), 8.16 (2H, d, J=8.6 Hz).

Example 103

N-(((3S)-4-((3-phenyloxetan-3-yl)carbonyl)morpholin-3-yl)methyl)-4-(5-(trifluoromethyl)-1,2,4-oxadiazol-3-yl)benzamide The title compound was obtained using 3-phenyloxetane-3-carboxylic acid by a method similar to Example 101.

Examples 104 to 106

The compounds of Examples 104 to 106 were obtained using N-((3S)-morpholin-3-ylmethyl)-4-(5-(trifluoromethyl)-1,2,4-oxadiazol-3-yl)benzamide hydrochloride by a method similar to Example 33.

Example 107

N-(((3S)-4-(((2S)-2-(hydroxymethyl)pyrrolidin-1-yl)carbonyl)morpholin-3-yl)methyl)-4-(5-(trifluoromethyl)-1,2,4-oxadiazol-3-yl)benzamide Example 108

N-(((3S)-4-(((2R)-2-(hydroxymethyl)pyrrolidin-1-yl)carbonyl)morpholin-3-yl)methyl)-4-(5-(trifluoromethyl)-1,2,4-oxadiazol-3-yl)benzamide To a mixture of N-((3S)-morpholin-3-ylmethyl)-4-(5-(trifluoromethyl)-1,2,4-oxadiazol-3-yl)benzamide hydrochloride (100 mg), TEA (64 mg) and THF (2.5 mL) was added bis(trichloromethyl) carbonate (26 mg) at 0° C., and the mixture was stirred overnight at room temperature. To the reaction mixture was added pyrrolidin-2-ylmethanol (52 mg), and the mixture was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol) to give the compound 108 (30 mg). The residue was purified by high-performance liquid chromatography to give the compound 107 (28 mg).

compound 107; $^1$H NMR (300 MHz, CDCl$_3$) δ 1.52-1.67 (1H, m), 1.74-1.97 (2H, m), 2.02-2.19 (1H, m), 3.19 (1H, brs), 3.35-3.74 (9H, m), 3.86-3.99 (2H, m), 4.07-4.16 (1H, m), 4.18-4.28 (1H, m), 4.29-4.43 (1H, m), 7.95-8.03 (2H, m), 8.13-8.23 (2H, m), 8.34 (1H, brs).

compound 108; $^1$H NMR (300 MHz, CDCl$_3$) δ 1.40-1.55 (1H, m), 1.64-1.76 (1H, m), 1.77-1.87 (1H, m), 1.88-2.00 (1H, m), 3.25-3.48 (5H, m), 3.49-3.62 (2H, m), 3.68-3.78 (2H, m), 3.81-4.06 (4H, m), 4.08-4.16 (1H, m), 4.17-4.27 (1H, m), 6.81 (1H, t, J=4.9 Hz), 7.88-7.97 (2H, m), 8.12-8.28 (2H, m).

Example 109

N-(((3S)-4-(3-oxa-8-azabicyclo[3.2.1]oct-8-ylcarbonyl)morpholin-3-yl)methyl)-4-(5-(trifluoromethyl)-1,2,4-oxadiazol-3-yl)benzamide To a mixture of N-((3S)-morpholin-3-ylmethyl)-4-(5-(trifluoromethyl)-1,2,4-oxadiazol-3-yl)benzamide hydrochloride (100 mg), TEA (64 mg) and THF (2.5 mL) was added bis(trichloromethyl) carbonate (26 mg) at 0° C., and the mixture was stirred overnight at room temperature. To the reaction mixture were added 3-oxa-8-azabicyclo[3.2.1]octane hydrochloride (76 mg) and TEA (52 mg), and the mixture was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol), and the solvent was evaporated. The residue was purified by high-performance liquid chromatography to give the title compound (71 mg).

$^1$H NMR (300 MHz, CDCl$_3$) δ 1.68-1.97 (4H, m), 3.36-3.63 (7H, m), 3.64-3.75 (2H, m), 3.77-4.01 (4H, m), 4.17-4.41 (2H, m), 7.47 (1H, brs), 7.92-8.01 (2H, m), 8.15-8.24 (2H, m).

Example 110

N-(((3S)-4-(8-oxa-3-azabicyclo[3.2.1]oct-3-ylcarbonyl)morpholin-3-yl)methyl)-4-(5-(trifluoromethyl)-1,2,4-oxadiazol-3-yl)benzamide To a mixture of N-((3S)-morpholin-3-ylmethyl)-4-(5-(trifluoromethyl)-1,2,4-oxadiazol-3-yl)benzamide hydrochloride (100 mg), TEA (64 mg) and THF (2.5 mL) was added bis(trichloromethyl) carbonate (26 mg) at 0° C., and the mixture was stirred overnight at room temperature. To the reaction mixture was added 8-oxa-3-azabicyclo[3.2.1]octane (58 mg), and the mixture was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol), and the solvent was evaporated. The residue was purified by high-performance liquid chromatography to give the title compound (42 mg).

$^1$H NMR (300 MHz, CDCl$_3$) δ 1.71-1.96 (4H, m), 3.01-3.26 (3H, m), 3.28-3.60 (5H, m), 3.70 (1H, dd, J=11.5, 2.8 Hz), 3.81-4.07 (3H, m), 4.12-4.35 (3H, m), 7.79 (1H, brs), 7.97 (2H, d, J=8.3 Hz), 8.19 (2H, d, J=8.3 Hz).

Example 111

N-(((3R)-4-benzoylmorpholin-3-yl)methyl)-4-(5-(trifluoromethyl)-1,2,4-oxadiazol-3-yl)benzamide (Step A)
A racemate (3.48 g) of tert-butyl 3-(((4-(5-(trifluoromethyl)-1,2,4-oxadiazol-3-yl)benzoyl)amino)methyl)morpholine-4-carboxylate was resolved by HPLC (column: CHIRALPAK AD(LF001), 50 mmID×500 mmL, manufactured by Daicel Chemical Industries, mobile phase: hexane/ethanol=85/15) to give tert-butyl (3R)-3-(((4-(5-(trifluoromethyl)-1,2,4-oxadiazol-3-yl)benzoyl)amino)methyl) morpholine-4-carboxylate (1.78 g) as a compound having a longer retention time.

$^1$H NMR (300 MHz, CDCl$_3$) δ 1.37 (s, 9H) 3.16-3.98 (m, 7H) 4.21-4.53 (m, 2H) 7.03 (br. s., 1H) 7.94 (d, J=8.69 Hz, 2H) 8.17 (d, J=8.31 Hz, 2H).

(Step B)

To a solution of tert-butyl (3R)-3-(((4-(5-(trifluoromethyl)-1,2,4-oxadiazol-3-yl)benzoyl)amino)methyl)morpholine-4-carboxylate obtained in Step A (468 mg, 1.03 mmol) in methanol (7.5 mL) was added 4N hydrochloric acid-CPME solution (7.69 mL, 30.76 mmol), and the mixture was stirred at room temperature for 2 hr. The reaction solution was concentrated to give a crude product (406 mg) of N-((3R)-morpholin-3-ylmethyl)-4-(5-(trifluoromethyl)-1,2,4-oxadiazol-3-yl)benzamide hydrochloride. The compound was used in the next step without further purification.

(Step C)

To a solution of the crude product (120 mg) of N-((3R)-morpholin-3-ylmethyl)-4-(5-(trifluoromethyl)-1,2,4-oxadiazol-3-yl)benzamide hydrochloride, which was obtained in Step B, in THF (4.0 mL) were added benzoyl chloride (39 μL) and TEA (89 μL), and the mixture was stirred at room temperature for 2 hr. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and recrystallized from ethyl acetate-hexane to give the title compound (112 mg).

$^1$H NMR (400 MHz, CDCl$_3$) δ 3.35 (1H, d, J=13.2 Hz), 3.40-3.59 (2H, m), 3.73-3.94 (3H, m), 4.01 (1H, d, J=12.2 Hz), 4.64-4.86 (1H, m), 4.96 (1H, d, J=9.3 Hz), 7.27-7.43 (6H, m), 7.86 (2H, d, J=8.3 Hz), 7.96 (2H, d, J=6.8 Hz).

Example 112

N-(((3R)-4-(3,5-dichlorobenzoyl)morpholin-3-yl) methyl)-4-(5-(trifluoromethyl)-1,2,4-oxadiazol-3-yl) benzamide The title compound was obtained using the crude product of N-((3R)-morpholin-3-ylmethyl)-4-(5-(trifluoromethyl)-1,2,4-oxadiazol-3-yl)benzamide hydrochloride by a method similar to Example 37.

Examples 113 to 156

The compounds of Examples 113 to 156 were obtained using N-((3R)-morpholin-3-ylmethyl)-4-(5-(trifluoromethyl)-1,2,4-oxadiazol-3-yl)benzamide hydrochloride by a method similar to Example 33.

Example 157

N-(((3R)-4-((2-methyl-2H-indazol-3-yl)carbonyl) morpholin-3-yl)methyl)-4-(5-(trifluoromethyl)-1,2,4-oxadiazol-3-yl)benzamide The title compound was obtained using N-((3R)-morpholin-3-ylmethyl)-4-(5-(trifluoromethyl)-1,2,4-oxadiazol-3-yl)benzamide hydrochloride and 2-methyl-2H-indazole-3-carboxylic acid by a method similar to Example 38.

Example 158

N-(((3R)-4-(piperidin-1-ylcarbonyl)morpholin-3-yl) methyl)-4-(5-(trifluoromethyl)-1,2,4-oxadiazol-3-yl) benzamide The title compound was obtained using N-((3R)-morpholin-3-ylmethyl)-4-(5-(trifluoromethyl)-1,2,4-oxadiazol-3-yl)benzamide hydrochloride by a method similar to Example 89.

Example 159

N-((4-benzoylmorpholin-3-yl)methyl)-N-methyl-4-(5-(trifluoromethyl)-1,2,4-oxadiazol-3-yl)benzamide (Step A)

To a solution of tert-butyl 3-(aminomethyl)morpholine-4-carboxylate (287 mg) in THF (10 mL) were added benzyl chloroformate (226 mg) and TEA (134 mg), and the mixture was stirred at room temperature for 2 hr. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure to give tert-butyl 3-((((benzyloxy)carbonyl)amino)methyl)morpholine-4-carboxylate (464 mg).

$^1$H NMR (300 MHz, CDCl$_3$) δ 1.43 (9H, s), 2.94-3.37 (2H, m), 3.44 (1H, td, J=11.8, 2.8 Hz), 3.57 (1H, dd, J=11.7, 3.4 Hz), 3.65-3.93 (4H, m), 4.02-4.19 (1H, m), 5.00 (1H, brs), 5.09 (2H, s), 7.28-7.43 (5H, m).

(Step B)

To a solution of tert-butyl 3-((((benzyloxy)carbonyl) amino)methyl)morpholine-4-carboxylate obtained in Step A (464 mg) in methanol (10 mL) was added 4N hydrochloric acid-CPME solution (9.89 mL), and the mixture was stirred at room temperature for 2 hr. The reaction solution was concentrated to give a crude product (376 mg) of benzyl (morpholin-3-ylmethyl)carbamate hydrochloride. The compound was used in the next step without further purification.

(Step C)

To a solution of the crude product (200 mg) of benzyl (morpholin-3-ylmethyl)carbamate hydrochloride, which was obtained in Step B, in THF (6.0 mL) were added benzoyl chloride (89 μL) and TEA (204 μL), and the mixture was stirred at room temperature for 2 hr. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give benzyl ((4-benzoylmorpholin-3-yl)methyl)carbamate (247 mg).

$^1$H NMR (300 MHz, CDCl$_3$) δ 3.04-3.54 (3H, m), 3.68 (2H, dd, J=12.1, 3.0 Hz), 3.84 (2H, brs), 4.19 (1H, brs), 4.77 (1H, brs), 5.09 (3H, brs), 7.27-7.50 (10H, m).

(Step D)

To a solution of benzyl ((4-benzoylmorpholin-3-yl) methyl)carbamate obtained in Step C (245 mg) in DMF (5.0 mL) was added 60% sodium hydride (41.5 mg) under ice-cooling. The reaction solution was stirred under ice-cooling for 20 min, and methyl iodide (118 mg) was added thereto. The reaction solution was stirred at room temperature for 2 hr, to the reaction mixture was added saturated ammonium chloride aqueous solution, and the mixture was extracted with ethyl acetate. The extract was washed with water and saturated brine, and dried over anhydrous sodium sulfate, and the solvent was evaporated under reduced pressure. The residue was purified by basic silica gel column chromatography (hexane/ethyl acetate) to give benzyl ((4-benzoylmorpholin-3-yl)methyl)methylcarbamate (239 mg).

$^1$H NMR (300 MHz, CDCl$_3$) δ 2.69 (1H, brs), 3.02 (2H, brs), 3.37 (2H, brs), 3.56-4.07 (5H, m), 4.18-5.28 (4H, m), 7.27-7.47 (10H, m).

(Step E)

To a solution of benzyl ((4-benzoylmorpholin-3-yl)methyl)methylcarbamate obtained in Step D (235 mg) in methanol (6.0 mL) was added 10% palladium-carbon (70 mg), and the mixture was stirred at room temperature for 3 hr under hydrogen atmosphere. The reaction solution was filtrated through Celite, and the filtrate was concentrated to give a crude product (136 mg) of (3-((methylamino)methyl)morpholin-4-yl) (phenyl)methanone. The compound was used in the next step without further purification.

(Step F)

A mixture of the crude product (136 mg) of (3-((methylamino)methyl)morpholin-4-yl)(phenyl)methanone, which was obtained in Step E, 4-(5-(trifluoromethyl)-1,2,4-oxadiazol-3-yl)benzoic acid (160 mg), 1-methyl-1H-pyrazole-5-carboxylic acid (157 mg), HATU (265 mg), DIEA (0.203 ml) and DMF (4 mL) was stirred overnight at room temperature. The reaction solution was diluted with water, and extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give the title compound (253 mg).

$^1$H NMR (300 MHz, CDCl$_3$) δ 2.85 (1H, d, J=14.4 Hz), 3.11 (3H, s), 3.40 (2H, d, J=10.6 Hz), 3.73-3.90 (2H, m), 3.91-4.00 (1H, m), 4.01-4.10 (1H, m), 5.12 (1H, d, J=11.3 Hz), 5.27-5.49 (1H, m), 7.28-7.60 (7H, m), 8.07 (2H, d, J=7.9 Hz).

Example 160

2-((3S)-4-benzoylmorpholin-3-yl)-N-(4-(5-(trifluoromethyl)-1,2,4-oxadiazol-3-yl)phenyl)acetamide (Step A)

A mixture of 4-(5-(trifluoromethyl)-1,2,4-oxadiazol-3-yl)benzoic acid (4.0 g), TEA (4.7 g), tert-butyl alcohol (1.72 g), diphenylphosphoryl azide (5.5 g) and toluene was stirred overnight at 80° C. The reaction solution was diluted with water, and extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give tert-butyl (4-(5-(trifluoromethyl)-1,2,4-oxadiazol-3-yl)phenyl)carbamate (3.77 g).

$^1$H NMR (300 MHz, DMSO-d$_6$) δ 1.50 (9H, s), 7.61-7.76 (2H, m), 7.89-8.03 (2H, m), 9.82 (1H, s).

(Step B)

To a solution of tert-butyl (4-(5-(trifluoromethyl)-1,2,4-oxadiazol-3-yl)phenyl)carbamate obtained in Step A in methanol (20 mL)-ethyl acetate (10 mL) was added 4N hydrochloric acid-CPME solution (42.9 mL), and the mixture was stirred at room temperature for 2.5 hr. The reaction solution was concentrated. The residue was suspended in hexane, collected by filtration, and washed with diisopropyl ether to give a crude product (2.82 g) of 4-(5-(trifluoromethyl)-1,2,4-oxadiazol-3-yl)aniline hydrochloride. The compound was used in the next step without further purification.

(Step C)

A mixture of the crude product (133 mg) of 4-(5-(trifluoromethyl)-1,2,4-oxadiazol-3-yl)aniline hydrochloride, which was obtained in Step B, ((3S)-4-(tert-butoxycarbonyl)morpholin-3-yl)acetic acid (129 mg), HATU (228 mg), DIEA (0.262 mL) and DMF (4 mL) was stirred at room temperature for 5 hr. To the reaction solution were added ((3S)-4-(tert-butoxycarbonyl)morpholin-3-yl)acetic acid (129 mg) and HATU (114 mg), and the mixture was stirred at room temperature for 2 hr. The reaction solution was diluted with saturated aqueous sodium hydrogencarbonate solution, and extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give a crude product (298 mg) of tert-butyl (3S)-3-(2-oxo-2-((4-(5-(trifluoromethyl)-1,2,4-oxadiazol-3-yl)phenyl)amino)ethyl)morpholine-4-carboxylate. The compound was used in the next step without further purification.

(Step D)

To a solution of the crude product (228 mg) of tert-butyl (3S)-3-(2-oxo-2-((4-(5-(trifluoromethyl)-1,2,4-oxadiazol-3-yl)phenyl)amino)ethyl)morpholine-4-carboxylate, which was obtained in Step C, in methanol (3.0 mL) was added 4N hydrochloric acid-CPME solution (3.75 mL), and the mixture was stirred at room temperature for 1.5 hr. The reaction solution was concentrated to give a crude product (295 mg) of 2-((3S)-morpholin-3-yl)-N-(4-(5-(trifluoromethyl)-1,2,4-oxadiazol-3-yl)phenyl)acetamide hydrochloride. The compound was used in the next step without further purification.

(Step E)

To a solution of the crude product (295 mg) of 2-((3S)-morpholin-3-yl)-N-(4-(5-(trifluoromethyl)-1,2,4-oxadiazol-3-yl)phenyl)acetamide hydrochloride, which was obtained in Step D, in THF (5.0 mL) were added benzoyl chloride (70 μL) and TEA (153 μL), and the mixture was stirred overnight at room temperature. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and recrystallized from ethyl acetate-hexane to give the title compound (70 mg).

$^1$H NMR (300 MHz, CDCl$_3$) δ 2.80-3.30 (2H, m), 3.53 (3H, brs), 3.67-4.08 (3H, m), 5.08 (1H, brs), 7.29-7.51 (5H, m), 7.74 (2H, d, J=6.4 Hz), 8.02 (2H, d, J=8.7 Hz), 9.19 (1H, brs).

Example 161

2-((3S)-4-benzoylmorpholin-3-yl)-N-methyl-N-(4-(5-(trifluoromethyl)-1,2,4-oxadiazol-3-yl)phenyl)acetamide (Step A)

A mixture of 4-(methylamino)benzonitrile (250 mg), 50% aqueous hydroxylamine solution (0.580 mL) and ethanol (5.0 mL) was stirred overnight at 80° C. The reaction solution was concentrated, and the residue was subjected to an azeotropic process with toluene to give a crude product (342 mg) of N'-hydroxy-4-(methylamino)benzenecarboximidamide. The compound was used in the next step without further purification.

(Step B)

A mixture of the crude product (342 mg) of N'-hydroxy-4-(methylamino)benzenecarboximidamide, which was obtained in Step A, trifluoroacetic anhydride (595 mg) and THF (10 mL) was stirred overnight at room temperature. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) and basic silica gel column chromatography (hexane/ethyl acetate) to give a crude product (249 mg) of N-methyl-4-(5-(trifluoromethyl)-1,2,4-oxadiazol-3-yl)aniline. The compound was used in the next step without further purification.

(Step C)

A mixture of the crude product (249 mg) of N-methyl-4-(5-(trifluoromethyl)-1,2,4-oxadiazol-3-yl)aniline, which was obtained in Step B, ((3S)-4-(tert-butoxycarbonyl)morpholin-3-yl)acetic acid (276 mg), HATU (467 mg), DIEA (0.358 ml) and DMF (5 mL) was stirred at room temperature for 3 days. The reaction solution was diluted with water, and extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give a crude product (77 mg) of tert-butyl (3S)-3-(2-(methyl(4-(5-(trifluoromethyl)-1,2,4-oxadiazol-3-yl)phenyl)amino)-2-oxoethyl)morpholine-4-carboxylate. The compound was used in the next step without further purification.

(Step D)

To a solution of tert-butyl (3S)-3-(2-(methyl(4-(5-(trifluoromethyl)-1,2,4-oxadiazol-3-yl)phenyl)amino)-2-oxoethyl)morpholine-4-carboxylate obtained in Step C (77 mg) in methanol (2.0 mL) was added 4N hydrochloric acid-CPME solution (1.23 mL), and the mixture was stirred at room temperature for 1 hr. The reaction solution was concentrated to give a crude product (78 mg) of N-methyl-2-((3S)-morpholin-3-yl)-N-(4-(5-(trifluoromethyl)-1,2,4-oxadiazol-3-yl)phenyl)acetamide hydrochloride. The compound was used in the next step without further purification.

(Step E)

To a solution of the crude product (78 mg) of N-methyl-2-((3S)-morpholin-3-yl)-N-(4-(5-(trifluoromethyl)-1,2,4-oxadiazol-3-yl)phenyl)acetamide hydrochloride, which was obtained in Step D, in THF (3.0 mL) were added benzoyl chloride (56 μL) and TEA (100 μL), and the mixture was stirred at room temperature for 1 hr. The reaction solution was diluted with saturated aqueous sodium hydrogencarbonate solution, and the solvent was evaporated under reduced pressure. The residue was purified by silica gel column chromatography (hexane/ethyl acetate) and basic silica gel column chromatography (hexane/ethyl acetate) to give the title compound (33 mg).

$^1$H NMR (300 MHz, CDCl$_3$) δ 2.40-3.06 (2H, m), 3.08-4.00 (9H, m), 4.18-5.10 (1H, m), 7.29-7.77 (7H, m), 8.21 (2H, d, J=8.3 Hz).

Example 162

N-((1-benzoylpyrrolidin-2-yl)methyl)-4-(5-(trifluoromethyl)-1,2,4-oxadiazol-3-yl)benzamide The title compound was obtained using 4-(5-(trifluoromethyl)-1,2,4-oxadiazol-3-yl)benzoic acid and tert-butyl 2-(aminomethyl)pyrrolidine-1-carboxylate by a method similar to Example 1.

Example 163

N-((1-benzoylpiperidin-2-yl)methyl)-4-(5-(trifluoromethyl)-1,2,4-oxadiazol-3-yl)benzamide The title compound was obtained using 4-(5-(trifluoromethyl)-1,2,4-oxadiazol-3-yl)benzoic acid and tert-butyl 2-(aminomethyl)piperidine-1-carboxylate by a method similar to Example 1.

Example 164

N-(((2R)-1-((1-methyl-1H-pyrazol-5-yl)carbonyl)piperidin-2-yl)methyl)-4-(5-(trifluoromethyl)-1,2,4-oxadiazol-3-yl)benzamide The title compound was obtained using 4-(5-(trifluoromethyl)-1,2,4-oxadiazol-3-yl)benzoic acid and tert-butyl (2R)-2-(aminomethyl)piperidine-1-carboxylate by a method similar to Example 38.

Example 165

N-((1,4-dibenzoylpiperazin-2-yl)methyl)-4-(5-(trifluoromethyl)-1,2,4-oxadiazol-3-yl)benzamide (Step A)

A mixture of tert-butyl (piperazin-2-ylmethyl)carbamate (100 mg), benzoyl chloride (196 mg), TEA (235 mg) and THF (2.4 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (ethyl acetate/methanol) to give tert-butyl ((1,4-dibenzoylpiperazin-2-yl)methyl)carbamate (138 mg).

$^1$H NMR (300 MHz, CDCl$_3$) δ 1.43 (9H, s), 2.75-5.22 (10H, m), 7.30-7.59 (10H, m).

(Step B)

To a mixture of tert-butyl ((1,4-dibenzoylpiperazin-2-yl)methyl)carbamate obtained in Step A (138 mg) and ethyl acetate (1.6 mL) was added 4N hydrochloric acid-ethyl acetate solution (0.82 mL), and the mixture was stirred overnight at room temperature. The solvent was removed from the reaction mixture to give (2-(aminomethyl)piperazine-1,4-diyl)bis(phenylmethanone)hydrochloride (85 mg). The compound was used in Step C without further purification.

(Step C)

A mixture of 4-(5-(trifluoromethyl)-1,2,4-oxadiazol-3-yl)benzoic acid (56 mg), (2-(aminomethyl)piperazine-1,4-diyl)bis(phenylmethanone)hydrochloride obtained in Step B (85 mg), N-(3-(dimethylamino)propyl)-N'-ethylcarbodiimide hydrochloride (83 mg), 1H-benzotriazol-1-ol monohydrate (66 mg), DIEA (112 mg) and DMF (1.1 mL) was stirred overnight at room temperature. To the reaction mixture was added water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (74 mg).

$^1$H NMR (300 MHz, CDCl$_3$) δ 2.80-5.33 (9H, m), 7.09-7.59 (11H, m), 7.77-8.27 (4H, m).

Example 166

N-((1-(cyclopropylcarbonyl)-2,3-dihydro-1H-indol-2-yl)methyl)-4-(5-(trifluoromethyl)-1,2,4-oxadiazol-3-yl)benzamide (Step A)
To a solution of triphenylphosphine (1.6 g) in THF (10 mL) was added diisopropyl (E)-diazene-1,2-dicarboxylate (1.2 mL) at 0° C. Then, a solution of tert-butyl 2-(hydroxymethyl)indoline-1-carboxylate (800 mg) in THF (5 mL) and a solution of phthalimide (1.6 g) in THF (5 mL) were added thereto at 0° C., and the mixture was stirred at room temperature 16 hr. The reaction mixture was diluted with water, and extracted with ethyl acetate. The extract was washed with water, and dried over anhydrous sodium sulfate, and the solvent was evaporated under reduced pressure. The residue was purified by silica gel column chromatography (hexane/ethyl acetate) to give tert-butyl 2-((1,3-dioxo-1,3-dihydro-2H-isoindol-2-yl)methyl)indoline-1-carboxylate (900 mg).

MS: [M+H]$^+$ 379.2.
(Step B)
tert-Butyl 2-((1,3-dioxo-1,3-dihydro-2H-isoindol-2-yl)methyl)indoline-1-carboxylate (900 mg) and hydrazine monohydrate (6 mL) were suspended in ethanol (3 mL) and THF (1 mL), and the suspension was stirred at 80° C. for 16 hr. The reaction mixture was allowed to be cooled to room temperature, and extracted with ethyl acetate (100 mL). The extract was washed with saturated aqueous sodium hydrogencarbonate solution, and dried over anhydrous sodium sulfate, and the solvent was evaporated under reduced pressure. To the residue were added diethyl ether/n-heptane, and the resulting solid was removed by filtration. The filtrate was concentrated under reduced pressure to give tert-butyl 2-(aminomethyl)indoline-1-carboxylate (500 mg).

MS: [M+H]$^+$ 248.9.
(Step C)
tert-Butyl 2-(((4-(5-(trifluoromethyl)-1,2,4-oxadiazol-3-yl)benzoyl)amino)methyl)indoline-1-carboxylate was obtained using tert-butyl 2-(aminomethyl)indoline-1-carboxylate obtained in Step B by a method similar to Step A of Example 38.

$^1$H NMR (300 MHz, DMSO-d$_6$) δ 1.42 (9H, s), 3.60-3.77 (2H, m), 4.49-4.60 (1H, m), 4.66-4.70 (1H, m), 5.19-5.25 (1H, m), 7.23-7.33 (4H, m), 7.92-7.96 (2H, m), 8.11-8.13 (2H, m), 8.73-8.74 (1H, m).
(Step D)
N-(2,3-Dihydro-1H-indol-2-ylmethyl)-4-(5-(trifluoromethyl)-1,2,4-oxadiazol-3-yl)benzamide hydrochloride was obtained using tert-butyl 2-(((4-(5-(trifluoromethyl)-1,2,4-oxadiazol-3-yl)benzoyl)amino)methyl)indoline-1-carboxylate obtained in Step C by a method similar to Step B of Example 38.

MS: [M+H]$^+$ 389.0.

(Step E)
The title compound was obtained using N-(2,3-dihydro-1H-indol-2-ylmethyl)-4-(5-(trifluoromethyl)-1,2,4-oxadiazol-3-yl)benzamide hydrochloride obtained in Step D by a method similar to Example 1.

Example 167

N-((1-benzoyl-2,3-dihydro-1H-indol-2-yl)methyl)-4-(5-(trifluoromethyl)-1,2,4-oxadiazol-3-yl)benzamide The title compound was obtained using N-(2,3-dihydro-1H-indol-2-ylmethyl)-4-(5-(trifluoromethyl)-1,2,4-oxadiazol-3-yl)benzamide hydrochloride by a method similar to Example 1.

Example 168

N-((1-(3,5-dichlorobenzoyl)-2,3-dihydro-1H-indol-2-yl)methyl)-4-(5-(trifluoromethyl)-1,2,4-oxadiazol-3-yl)benzamide The title compound was obtained using N-(2,3-dihydro-1H-indol-2-ylmethyl)-4-(5-(trifluoromethyl)-1,2,4-oxadiazol-3-yl)benzamide hydrochloride by a method similar to Example 1.

Example 169

N-((2-(cyclopropylcarbonyl)-2,3-dihydro-1H-isoindol-1-yl)methyl)-4-(5-(trifluoromethyl)-1,2,4-oxadiazol-3-yl)benzamide The title compound was obtained using tert-butyl 1-(aminomethyl)-1,3-dihydro-2H-isoindole-2-carboxylate by a method similar to Example 166.

Example 170

N-((2-benzoyl-2,3-dihydro-1H-isoindol-1-yl)methyl)-4-(5-(trifluoromethyl)-1,2,4-oxadiazol-3-yl)benzamide The title compound was obtained using tert-butyl 1-(aminomethyl)-1,3-dihydro-2H-isoindole-2-carboxylate by a method similar to Example 166.

Example 171

N-((2-(3,5-dichlorobenzoyl)-2,3-dihydro-1H-isoindol-1-yl)methyl)-4-(5-(trifluoromethyl)-1,2,4-oxadiazol-3-yl)benzamide The title compound was obtained using tert-butyl 1-(aminomethyl)-1,3-dihydro-2H-isoindole-2-carboxylate by a method similar to Example 166.

Example 172

N-((1-(cyclopropylcarbonyl)-1,2,3,4-tetrahydroquinolin-2-yl)methyl)-4-(5-(trifluoromethyl)-1,2,4-oxadiazol-3-yl)benzamide The title compound was obtained using tert-butyl 2-(aminomethyl)-3,4-dihydroquinoline-1(2H)-carboxylate by a method similar to Example 166.

Example 173

N-((1-benzoyl-1,2,3,4-tetrahydroquinolin-2-yl)
methyl)-4-(5-(trifluoromethyl)-1,2,4-oxadiazol-3-yl)
benzamide The title compound was obtained using tert-butyl 2-(aminomethyl)-3,4-dihydroquinoline-1(2H)-carboxylate by a method similar to Example 166.

Example 174

N-((2-(cyclopropylcarbonyl)-1,2,3,4-tetrahydroiso-
quinolin-3-yl)methyl)-4-(5-(trifluoromethyl)-1,2,4-
oxadiazol-3-yl)benzamide The title compound was obtained using tert-butyl 3-(aminomethyl)-3,4-dihydroisoquinoline-2(1H)-carboxylate by a method similar to Example 166.

Example 175

N-((2-benzoyl-1,2,3,4-tetrahydroisoquinolin-3-yl)
methyl)-4-(5-(trifluoromethyl)-1,2,4-oxadiazol-3-yl)
benzamide The title compound was obtained using tert-butyl 3-(aminomethyl)-3,4-dihydroisoquinoline-2(1H)-carboxylate by a method similar to Example 166.

Example 176

N-((2-(3,5-dichlorobenzoyl)-1,2,3,4-tetrahydroiso-
quinolin-3-yl)methyl)-4-(5-(trifluoromethyl)-1,2,4-
oxadiazol-3-yl)benzamide The title compound was obtained using tert-butyl 3-(aminomethyl)-3,4-dihydroisoquinoline-2(1H)-carboxylate by a method similar to Example 166.

Example 177

N-((4-benzoylmorpholin-3-yl)methyl)-2-fluoro-4-(5-
(trifluoromethyl)-1,2,4-oxadiazol-3-yl)benzamide The title compound was obtained using 4-cyano-2-fluorobenzoic acid and tert-butyl 3-(aminomethyl)morpholine-4-carboxylate by a method similar to the below-mentioned Example 193.

Example 178

N-((4-benzoylmorpholin-3-yl)methyl)-2-methyl-4-
(5-(trifluoromethyl)-1,2,4-oxadiazol-3-yl)benzamide The title compound was obtained using 4-cyano-2-methylbenzoic acid and tert-butyl 3-(aminomethyl)morpholine-4-carboxylate by a method similar to the below-mentioned Example 193.

Example 179

N-((4-benzoylmorpholin-3-yl)methyl)-3-methyl-4-
(5-(trifluoromethyl)-1,2,4-oxadiazol-3-yl)benzamide The title compound was obtained using 4-cyano-3-methylbenzoic acid and tert-butyl 3-(aminomethyl)morpholine-4-carboxylate by a method similar to the below-mentioned Example 193.

Example 180

N-((4-benzoylmorpholin-3-yl)methyl)-6-(5-(trifluoromethyl)-1,2,4-oxadiazol-3-yl)nicotinamide The title compound was obtained using 6-cyanonicotinic acid and tert-butyl 3-(aminomethyl)morpholine-4-carboxylate by a method similar to the below-mentioned Example 193.

Examples 181 and 182

The compounds of Examples 181 and 182 were obtained using 5-cyanopyridine-2-carboxylic acid and tert-butyl 3-(aminomethyl)morpholine-4-carboxylate by a method similar to the below-mentioned Example 193.

Example 183

N-(((3S)-4-(3,5-dichlorobenzoyl)morpholin-3-yl)
methyl)-5-(5-(trifluoromethyl)-1,2,4-oxadiazol-3-yl)
pyridine-2-carboxamide The title compound was obtained using tert-butyl (3S)-3-((((5-(5-(trifluoromethyl)-1,2,4-oxadiazol-3-yl)pyridin-2-yl)carbonyl)amino)methyl)morpholine-4-carboxylate and 3,5-dichlorobenzoyl chloride by a method similar to Example 1.

Examples 184 to 192

The compounds of Examples 184 to 192 were obtained using tert-butyl (3S)-3-((((5-(5-(trifluoromethyl)-1,2,4-oxadiazol-3-yl)pyridin-2-yl)carbonyl)amino)methyl)morpholine-4-carboxylate by a method similar to Example 33.

Example 193

N-(((3S)-4-((5-methyl-1,2-oxazol-4-yl)carbonyl)
morpholin-3-yl)methyl)-5-(5-(trifluoromethyl)-1,2,4-
oxadiazol-3-yl)pyridine-2-carboxamide (Step A)
A mixture of 5-cyanopyridine-2-carboxylic acid (1.94 g), tert-butyl (3S)-3-(aminomethyl)morpholine-4-carboxylate (2.83 g), HATU (5.22 g), DIEA (4.57 mL) and DMF (50 mL) was stirred overnight at room temperature. The reaction solution was diluted with water, and extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give tert-butyl (3D)-3-((((5-cyanopyridin-2-yl)-carbonyl)amino)methyl)morpholine-4-carboxylate (3.40 g).

$^1$H NMR (300 MHz, CDCl$_3$) δ 1.34 (9H, s), 3.15-3.35 (1H, m), 3.48 (2H, td, J=11.8, 2.8 Hz), 3.65 (1H, dd, J=12.1, 3.4 Hz), 3.70-3.98 (3H, m), 4.00-4.46 (2H, m), 8.13 (1H, dd, J=7.9, 1.9 Hz), 8.22 (1H, brs), 8.33 (1H, d, J=7.6 Hz), 8.81 (1H, dd, J=2.1, 0.9 Hz).

(Step B)
A mixture of tert-butyl (3D)-3-((((5-cyanopyridin-2-yl)carbonyl)amino)methyl)morpholine-4-carboxylate obtained in Step A (3.40 g), 50% aqueous hydroxylamine solution (1.805 mL) and ethanol (100 mL) was stirred overnight at 80° C. The reaction solution was concentrated, and the residue was diluted with water, and the mixture was extracted with ethyl acetate. The extract was dried over anhydrous sodium sulfate, and concentrated under reduced pressure to give a crude product (3.80 g) of tert-butyl (3S)-3-((((5-(N'-hydroxycarbamimidoyl)pyridin-2-yl)carbonyl)amino)methyl)morpholine-4-carboxylate.
(Step C)

A mixture of the crude product (3.80 g) of tert-butyl (3S)-3-((((5-(N'-hydroxycarbamimidoyl)pyridin-2-yl)carbonyl)amino)methyl)morpholine-4-carboxylate, which was obtained in Step B, trifluoroacetic anhydride (3.16 g) and THF (100 mL) was stirred overnight at room temperature. The reaction mixture was concentrated, saturated aqueous sodium hydrogencarbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give tert-butyl (3S)-3-((((5-(5-(trifluoromethyl)-1,2,4-oxadiazol-3-yl)pyridin-2-yl)carbonyl)amino)methyl)morpholine-4-carboxylate (4.05 g).

$^1$H NMR (300 MHz, CDCl$_3$) δ 1.35 (9H, s), 3.17-3.37 (1H, m), 3.40-3.59 (2H, m), 3.65 (1H, dd, J=12.1, 3.4 Hz), 3.74-3.99 (3H, m), 4.01-4.22 (1H, m), 4.30 (1H, brs), 8.29 (1H, brs), 8.37 (1H, d, J=8.3 Hz), 8.56 (1H, dd, J=8.1, 2.1 Hz), 9.26 (1H, dd, J=2.3, 0.8 Hz).
(Step D)

To a solution of tert-butyl (3S)-3-((((5-(5-(trifluoromethyl)-1,2,4-oxadiazol-3-yl)pyridin-2-yl)carbonyl)amino)methyl)morpholine-4-carboxylate obtained in Step C (4.05 g) in methanol (60 mL) was added 4N hydrochloric acid-CPME solution (66.4 mL), and the mixture was stirred at room temperature for 2 hr. The reaction solution was concentrated, and the residue was suspended in hexane, collected by filtration, and washed with diisopropyl ether (3.78 g). A mixture of a part (120 mg) of the obtained residue, 5-methyl-1,2-oxazole-4-carboxylic acid (39 mg), 50% 2,4,6-tripropyl-1,3,5,2,4,6-trioxatriphosphinane 2,4,6-trioxide ethyl acetate solution (0.49 mL), DIEA (0.24 mL), N,N-dimethylpyridin-4-amine (34 mg) and ethyl acetate (4.0 mL) was stirred at 80° C. for 4 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and the purified product was suspended in a mixed solvent of hexane-diethyl ether, and collected by filtration to give the title compound (35 mg).

$^1$H NMR (300 MHz, CDCl$_3$) δ 2.41 (3H, s), 3.27-3.82 (4H, m), 3.98 (3H, d, J=12.1 Hz), 4.28-5.17 (2H, m), 8.20 (1H, brs), 8.31 (2H, dd, J=8.3, 0.8 Hz), 8.54 (1H, dd, J=8.1, 2.1 Hz), 9.26 (1H, d, J=1.1 Hz).

Examples 194 to 205

The compounds of Examples 194 to 205 were obtained using tert-butyl (3S)-3-((((5-(5-(trifluoromethyl)-1,2,4-oxadiazol-3-yl)pyridin-2-yl)carbonyl)amino)methyl)morpholine-4-carboxylate by a method similar to Example 33.

Example 206

N-(((3S)-4-(2-methyl-2-phenylpropanoyl)morpholin-3-yl)methyl)-5-(5-(trifluoromethyl)-1,2,4-oxadiazol-3-yl)pyridine-2-carboxamide The title compound was obtained using tert-butyl (3S)-3-((((5-(5-(trifluoromethyl)-1,2,4-oxadiazol-3-yl)pyridin-2-yl)carbonyl)amino)methyl)morpholine-4-carboxylate and 2-methyl-2-phenylpropanoyl chloride by a method similar to Example 1.

Example 207

N-(((3S)-4-(difluoro(phenyl)acetyl)morpholin-3-yl)methyl)-5-(5-(trifluoromethyl)-1,2,4-oxadiazol-3-yl)pyridine-2-carboxamide The title compound was obtained using difluoro(phenyl)acetic acid by a method similar to Example 193.

Example 208

N-(((3R)-4-((1-phenylcyclopropyl)carbonyl)morpholin-3-yl)methyl)-5-(5-(trifluoromethyl)-1,2,4-oxadiazol-3-yl)pyridine-2-carboxamide The title compound was obtained using 5-cyanopyridine-2-carboxylic acid, tert-butyl (3R)-3-(aminomethyl)morpholine-4-carboxylate and 1-phenylcyclopropylcarboxylic acid by a method similar to Example 193.

Example 209

N-(((3R)-4-(3,5-dichlorobenzoyl)morpholin-3-yl)methyl)-5-(5-(trifluoromethyl)-1,2,4-oxadiazol-3-yl)pyridine-2-carboxamide The title compound was obtained using 5-cyanopyridine-2-carboxylic acid, tert-butyl (3R)-3-(aminomethyl)morpholine-4-carboxylate and 3,5-dichlorobenzoic acid by a method similar to Example 193.

Examples 210 and 211

A crude product of N-(morpholin-3-ylmethyl)-5-(5-(trifluoromethyl)-1,2,4-oxadiazol-3-yl)thiophene-2-carboxamide hydrochloride was synthesized from 5-cyanothiophene-2-carboxylic acid and tert-butyl 3-(aminomethyl)morpholine-4-carboxylate by a method similar to the below-mentioned Example 259. The compounds of Examples 210 and 211 were obtained using the obtained crude product by a method similar to Example 1.

Examples 212 to 256

A crude product of N-(morpholin-3-ylmethyl)-5-(5-(trifluoromethyl)-1,2,4-oxadiazol-3-yl)thiophene-2-carboxamide hydrochloride was synthesized from 5-cyanothiophene-2-carboxylic acid and tert-butyl 3-(aminomethyl)morpholine-4-carboxylate by a method similar to the below-mentioned Example 259. The compounds of Examples 212 to 256 were obtained using the obtained crude product by a method similar to Example 33.

Example 257

(R or S)—N-((4-benzoylmorpholin-3-yl)methyl)-5-(5-(trifluoromethyl)-1,2,4-oxadiazol-3-yl)thiophene-2-carboxamide A racemate (72 mg) of N-((4-benzoylmorpholin-3-yl)methyl)-5-(5-(trifluoromethyl)-1,2,4-oxadiazol-3-yl)thiophene-2-carboxamide was resolved by HPLC (column: CHIRALPAK OD(NL001), 50 mmID×500 mmL, manufactured by Daicel Chemical Industries, mobile phase: hexane/ ethanol=80/20) to give a compound (35.5 mg) having a shorter retention time. The obtained purified product was purified by basic silica gel column chromatography (hexane/ ethyl acetate) to give (R or S)—N-((4-benzoylmorpholin-3-yl)methyl)-5-(5-(trifluoromethyl)-1,2,4-oxadiazol-3-yl)thiophene-2-carboxamide (29 mg).

$^1$H NMR (300 MHz, CDCl$_3$) δ 3.32 (1H, d, J=12.1 Hz), 3.39-3.60 (2H, m), 3.72-3.93 (3H, m), 4.00 (1H, d, J=12.5 Hz), 4.61-4.82 (1H, m), 4.87-5.05 (1H, m), 7.19 (1H, brs), 7.29-7.57 (7H, m).

Example 258

(R or S)—N-((4-benzoylmorpholin-3-yl)methyl)-5-(5-(trifluoromethyl)-1,2,4-oxadiazol-3-yl)thiophene-2-carboxamide A racemate (72 mg) of N-((4-benzoylmorpholin-3-yl)methyl)-5-(5-(trifluoromethyl)-1,2,4-oxadiazol-3-yl)thiophene-2-carboxamide was resolved by HPLC (column: CHIRALPAK OD(NL001), 50 mmID×500 mmL, manufactured by Daicel Chemical Industries, mobile phase: hexane/ethanol=80/20) to give a compound (35.7 mg) having a shorter retention time. The obtained purified product was purified by basic silica gel column chromatography (hexane/ethyl acetate) to give (R or S)—N-((4-benzoylmorpholin-3-yl)methyl)-5-(5-(trifluoromethyl)-1,2,4-oxadiazol-3-yl)thiophene-2-carboxamide (32 mg).

$^1$H NMR (300 MHz, CDCl$_3$) δ 3.28-3.58 (3H, m), 3.69 (1H, s), 3.73-3.92 (2H, m), 3.99 (1H, d, J=11.7 Hz), 4.64 (1H, s), 4.89 (1H, brs), 7.14 (1H, brs), 7.28-7.46 (6H, m), 7.70 (1H, brs).

Example 259

N-(((3S)-4-((5-methyl-1,2-oxazol-4-yl)carbonyl)morpholin-3-yl)methyl)-5-(5-(trifluoromethyl)-1,2,4-oxadiazol-3-yl)thiophene-2-carboxamide (Step A)
A mixture of 5-cyanothiophene-2-carboxylic acid (2.0 g), tert-butyl (3S)-3-(aminomethyl)morpholine-4-carboxylate (2.96 g), N-(3-(dimethylamino)propyl)-NT-ethylcarbodiimide hydrochloride (3.0 g), 1H-benzotriazol-1-ol monohydrate (2.2 g) and DMF (65 mL) was stirred overnight at room temperature. To the reaction mixture was added saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate) to give tert-butyl (3S)-3-((((5-cyano-2-thienyl)carbonyl)amino)methyl)morpholine-4-carboxylate (4.15 g).

$^1$H NMR (300 MHz, CDCl$_3$) δ 1.37 (9H, s), 3.16-3.39 (2H, m), 3.47 (1H, td, J=11.8, 2.8 Hz), 3.60-3.79 (2H, m), 3.80-3.96 (2H, m), 4.27 (2H, brs), 7.02 (1H, brs), 7.38 (1H, d, J=3.8 Hz), 7.54 (1H, d, J=4.2 Hz).
(Step B)
A mixture of tert-butyl (3S)-3-((((5-cyano-2-thienyl)carbonyl)amino)methyl)morpholine-4-carboxylate obtained in Step A (4.15 g), 50% aqueous hydroxylamine solution (2.171 mL) and ethanol (100 mL) was stirred at 80° C. for 2 hr. The reaction solution was concentrated, and the residue was diluted with saturated aqueous sodium hydrogencarbonate solution, and the mixture was extracted with ethyl acetate. The extract was washed with saturated brine, dried over anhydrous sodium sulfate, and concentrated under reduced pressure to give a crude product (4.87 g) of tert-butyl (3S)-3-((((5-(N-hydroxycarbamimidoyl)-2-thienyl)carbonyl)amino)methyl)morpholine-4-carboxylate.
(Step C)
A mixture of the crude product (4.87 g) of tert-butyl (3S)-3-((((5-(N-hydroxycarbamimidoyl)-2-thienyl)carbonyl)amino)methyl)morpholine-4-carboxylate, which was obtained in Step B, trifluoroacetic anhydride (3.19 g) and THF (100 mL) was stirred overnight at room temperature. The reaction mixture was concentrated, saturated aqueous sodium hydrogencarbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give tert-butyl (3S)-3-((((5-(5-(trifluoromethyl)-1,2,4-oxadiazol-3-yl)-2-thienyl)carbonyl)amino)methyl)morpholine-4-carboxylate (4.57 g).

$^1$H NMR (300 MHz, CDCl$_3$) δ 1.38 (9H, s), 3.17-3.55 (3H, m), 3.57-3.97 (4H, m), 4.29 (2H, brs), 6.92 (1H, brs), 7.48 (1H, d, J=4.2 Hz), 7.79 (1H, d, J=3.8 Hz).
(Step D)
To a solution of tert-butyl (3S)-3-((((5-(5-(trifluoromethyl)-1,2,4-oxadiazol-3-yl)-2-thienyl)carbonyl)amino)methyl)morpholine-4-carboxylate obtained in Step C (4.57 g) in methanol (75 mL) was added 4N hydrochloric acid-CPME solution (74.1 mL), and the mixture was stirred at room temperature for 1.5 hr. The reaction solution was concentrated to give a crude product (3.75 g) of N-((3S)-morpholin-3-ylmethyl)-5-(5-(trifluoromethyl)-1,2,4-oxadiazol-3-yl)thiophene-2-carboxamide hydrochloride.
(Step E)
A mixture of the crude product (150 mg) of N-((3S)-morpholin-3-ylmethyl)-5-(5-(trifluoromethyl)-1,2,4-oxadiazol-3-yl)thiophene-2-carboxamide hydrochloride, which was obtained in Step D, 5-methyl-1,2-oxazole-4-carboxylic acid (53 mg), N-(3-(dimethylamino)propyl)-N'-ethylcarbodiimide hydrochloride (87 mg), 1H-benzotriazol-1-ol monohydrate (63 mg), TEA (38 mg) and DMF (4.0 mL) was stirred at room temperature for 4 hr. To the reaction mixture was added saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate), and the obtained compound was suspended in hexane, and collected by filtration to give the title compound (57 mg).

$^1$H NMR (300 MHz, CDCl$_3$) δ 2.44 (3H, s), 3.14-3.60 (3H, m), 3.75 (1H, dd, J=12.1, 3.4 Hz), 3.98 (3H, d, J=12.1 Hz), 4.52-4.99 (2H, m), 7.07 (1H, brs), 7.33 (1H, brs), 7.61 (1H, brs), 8.19 (1H, brs).

Example 260

N-(((3S)-4-((4-methyl-1,2,5-oxadiazol-3-yl)carbonyl)morpholin-3-yl)methyl)-5-(5-(trifluoromethyl)-1,2,4-oxadiazol-3-yl)thiophene-2-carboxamide The title compound was obtained using N-((3S)-morpholin-3-ylmethyl)-5-(5-(trifluoromethyl)-1,2,4-oxadiazol-3- yl)thiophene-2-carboxamide hydrochloride and 4-methyl-1,2,5-oxadiazole-3-carboxylic acid by a method similar to Example 33.

Example 261

N-(((3S)-4-(difluoro(phenyl)acetyl)morpholin-3-yl)methyl)-5-(5-(trifluoromethyl)-1,2,4-oxadiazol-3-yl)thiophene-2-carboxamide The title compound was obtained using N-((3S)-morpholin-3-ylmethyl)-5-(5-(trifluoromethyl)-1,2,4-oxadiazol-3-yl)thiophene-2-carboxamide hydrochloride and difluoro(phenyl)acetic acid by a method similar to Example 101.

Example 262

N-(((3S)-4-(biphenyl-3-ylcarbonyl)morpholin-3-yl)methyl)-5-(5-(trifluoromethyl)-1,2,4-oxadiazol-3-yl)thiophene-2-carboxamide The title compound was obtained using N-((3S)-morpholin-3-ylmethyl)-5-(5-(trifluoromethyl)-1,2,4-oxadiazol-3-yl)thiophene-2-carboxamide hydrochloride and biphenyl-3-carboxylic acid by a method similar to Example 33.

Example 263

N-(((3S)-4-(2-methyl-2-phenylpropanoyl)morpholin-3-yl)methyl)-5-(5-(trifluoromethyl)-1,2,4-oxadiazol-3-yl)thiophene-2-carboxamide The title compound was obtained using N-((3S)-morpholin-3-ylmethyl)-5-(5-(trifluoromethyl)-1,2,4-oxadiazol-3-yl)thiophene-2-carboxamide hydrochloride and 2-methyl-2-phenylpropanoyl chloride by a method similar to Example 1.

Example 264

N-(((3R)-4-((4-methyl-1,2,5-oxadiazol-3-yl)carbonyl)morpholin-3-yl)methyl)-5-(5-(trifluoromethyl)-1,2,4-oxadiazol-3-yl)thiophene-2-carboxamide The title compound was obtained using N-((3R)-morpholin-3-ylmethyl)-5-(5-(trifluoromethyl)-1,2,4-oxadiazol-3-yl)thiophene-2-carboxamide hydrochloride (obtained from 5-cyanothiophene-2-carboxylic acid and tert-butyl (3R)-3-(aminomethyl)morpholine-4-carboxylate) and 4-methyl-1,2,5-oxadiazole-3-carboxylic acid by a method similar to Example 259.

Example 265

N-(((3R)-4-(difluoro(phenyl)acetyl)morpholin-3-yl)methyl)-5-(5-(trifluoromethyl)-1,2,4-oxadiazol-3-yl)thiophene-2-carboxamide N-((3R)-Morpholin-3-ylmethyl)-5-(5-(trifluoromethyl)-1,2,4-oxadiazol-3-yl)thiophene-2-carboxamide hydrochloride was obtained from 5-cyanothiophene-2-carboxylic acid and tert-butyl (3R)-3-(aminomethyl)morpholine-4-carboxylate by a method similar to Example 259. The title compound was obtained using the obtained N-((3R)-morpholin-3-ylmethyl)-5-(5-(trifluoromethyl)-1,2,4-oxadiazol-3-yl)thiophene-2-carboxamide hydrochloride and difluoro(phenyl)acetic acid by a method similar to Example 101.

Example 266

N-(((3R)-4-(cyclohexylcarbonyl)morpholin-3-yl)methyl)-5-(5-(trifluoromethyl)-1,2,4-oxadiazol-3-yl)thiophene-2-carboxamide The title compound was obtained using 5-cyanothiophene-2-carboxylic acid, tert-butyl (3R)-3-(aminomethyl)morpholine-4-carboxylate and cyclohexanecarboxylic acid by a method similar to Example 259.

Example 267

N-((4-benzoylmorpholin-3-yl)methyl)-5-(5-(trifluoromethyl)-1,2,4-oxadiazol-3-yl)thiophene-2-carboxamide A crude product of N-(morpholin-3-ylmethyl)-4-(5-(trifluoromethyl)-1,2,4-oxadiazol-3-yl)thiophene-2-carboxamide hydrochloride was obtained from 4-cyanothiophene-2-carboxylic acid and tert-butyl 3-(aminomethyl)morpholine-4-carboxylate by a method similar to Example 259. The title compound was obtained using the obtained crude product by a method similar to Example 1.

The structures and MS values (actual measured values) of the compounds of Examples 1 to 267 are shown in Table 1.

TABLE 1

| Example No. | IUPAC name | Structure | MS (found) |
|---|---|---|---|
| 1 | N-((4-benzoylmorpholin-3-yl)methyl)-4-(5-(trifluoromethyl)-1,2,4-oxadiazol-3-yl)benzamide | 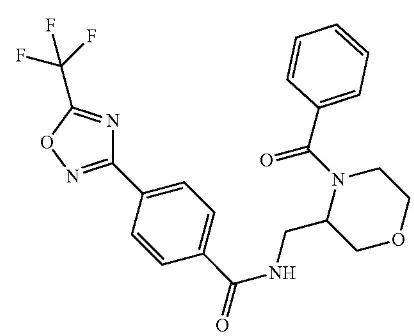 [SMILES: O=C(NCC1COCCN1C(=O)c1ccccc1)c1ccc(-c2noc(C(F)(F)F)n2)cc1] | 459.0 [M − H]− |

TABLE 1-continued

| Example No. | IUPAC name | Structure | MS (found) |
|---|---|---|---|
| 2 | N-phenyl-3-(((4-(5-(trifluoromethyl)-1,2,4-oxadiazol-3-yl)benzoyl)amino)methyl)morpholine-4-carboxamide | 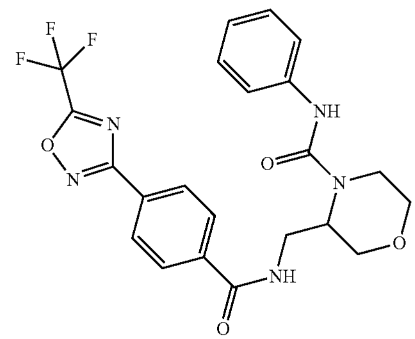 [SMILES: O=C(NCC1COCCN1C(=O)Nc1ccccc1)c1ccc(-c2noc(C(F)(F)F)n2)cc1] | 473.9 [M − H]− |
| 3 | N-((4-(2-fluorobenzoyl)morpholin-3-yl)methyl)-4-(5-trifluoromethyl)-1,2,4-oxadiazol-3-yl)benzamide | 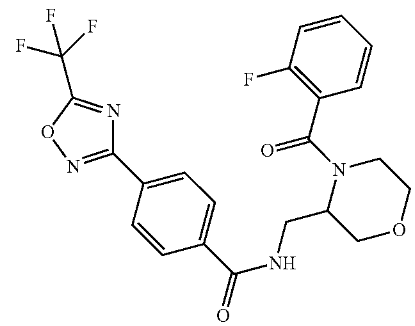 [SMILES: O=C(NCC1COCCN1C(=O)c1ccccc1F)c1ccc(-c2noc(C(F)(F)F)n2)cc1] | 479.1 [M + H]+ |
| 4 | N-((4-(3-fluorobenzoyl)morpholin-3-yl)methyl)-4-(5-(trifluoromethyl)-1,2,4-oxadiazol-3-yl)benzamide | 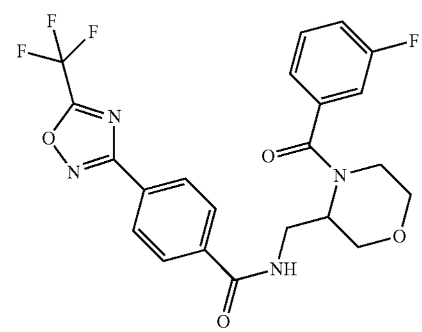 [SMILES: O=C(NCC1COCCN1C(=O)c1cccc(F)c1)c1ccc(-c2noc(C(F)(F)F)n2)cc1] | 479.0 [M + H]+ |
| 5 | N-((4-(4-fluorobenzoyl)morpholin-3-yl)methyl)-4-(5-(trifluoromethyl)-1,2,4-oxadiazol-3-yl)benzamide | 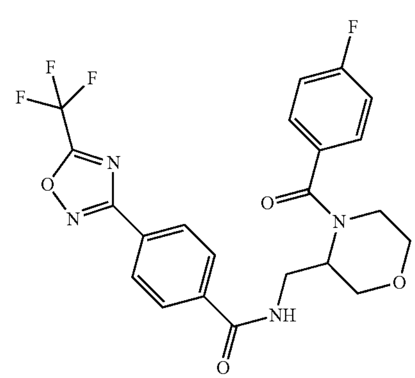 | 479.1 [M + H]+ |

TABLE 1-continued

| Example No. | IUPAC name | Structure | MS (found) |
|---|---|---|---|
| 6 | N-((4-(2-chlorobenzoyl)morpholin-3-yl)methyl)-4-(5-(trifluoromethyl)-1,2,4-oxadiazol-3-yl)benzamide | 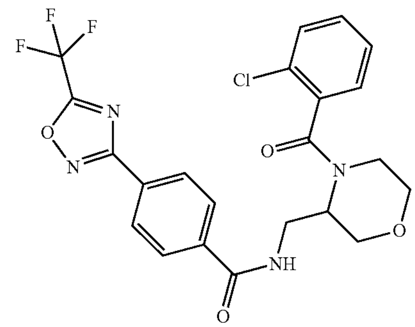 [SMILES: O=C(NCC1COCCN1C(=O)c1ccccc1Cl)c1ccc(-c2noc(C(F)(F)F)n2)cc1] | 495.0 [M + H]+ |
| 7 | N-((4-(3-chlorobenzoyl)morpholin-3-yl)methyl)-4-(5-(trifluoromethyl)-1,2,4-oxadiazol-3-yl)benzamide | 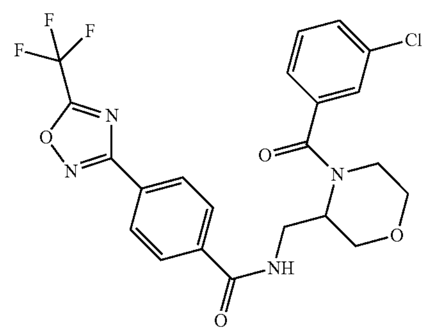 [SMILES: O=C(NCC1COCCN1C(=O)c1cccc(Cl)c1)c1ccc(-c2noc(C(F)(F)F)n2)cc1] | 495.1 [M + H]+ |
| 8 | N-((4-(4-chlorobenzoyl)morpholin-3-yl)methyl)-4-(5-trifluoromethyl)-1,2,4-oxadiazol-3-yl)benzamide | 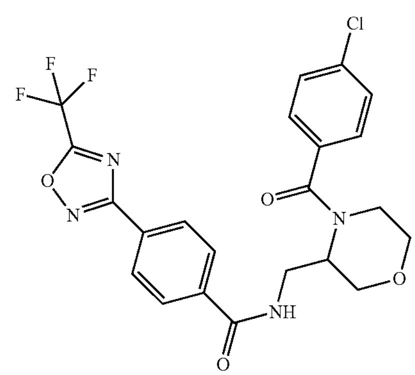 [SMILES: O=C(NCC1COCCN1C(=O)c1ccc(Cl)cc1)c1ccc(-c2noc(C(F)(F)F)n2)cc1] | 495.1 [M + H]+ |
| 9 | N-((4-(2-methylbenzoyl)morpholin-3-yl)methyl)-4-(5-(trifluoromethyl)-1,2,4-oxadiazol-3-yl)benzamide | 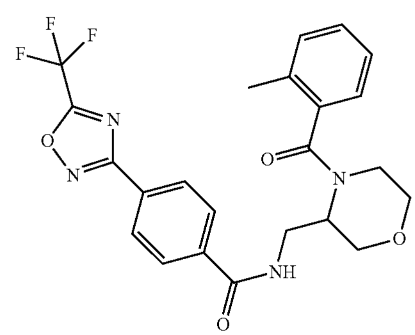 | 475.1 [M + H]+ |

TABLE 1-continued

| Example No. | IUPAC name | Structure | MS (found) |
|---|---|---|---|
| 10 | N-((4-(3-methylbenzoyl)morpholin-3-yl)methyl)-4-(5-(trifluoromethyl)-1,2,4-oxadiazol-3-yl)benzamide | 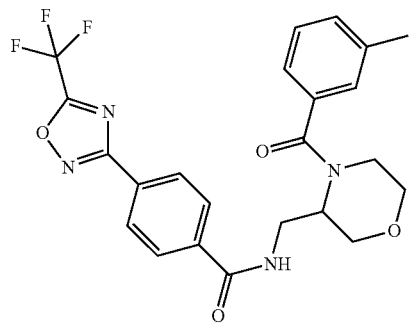 [SMILES: Cc1cccc(C(=O)N2CCOCC2CNC(=O)c2ccc(-c3noc(C(F)(F)F)n3)cc2)c1] | 475.1 [M + H]+ |
| 11 | N-((4-(4-methylbenzoyl)morpholin-3-yl)methyl)-4-(5-(trifluoromethyl)-1,2,4-oxadiazol-3-yl)benzamide | 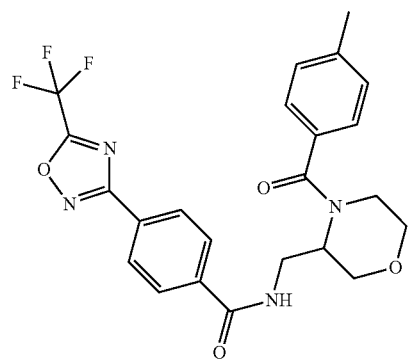 [SMILES: Cc1ccc(C(=O)N2CCOCC2CNC(=O)c2ccc(-c3noc(C(F)(F)F)n3)cc2)cc1] | 475.1 [M + H]+ |
| 12 | N-((4-(pyridin-2-ylcarbonyl)morpholin-3-yl)methyl)-4-(5-(trifluoromethyl)-1,2,4-oxadiazol-3-yl)benzamide | 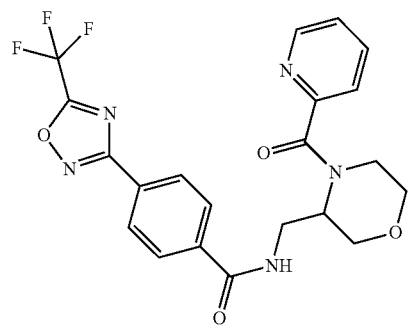 [SMILES: O=C(NCC1COCCN1C(=O)c1ccccn1)c1ccc(-c2noc(C(F)(F)F)n2)cc1] | 462.1 [M + H]+ |
| 13 | N-((4-(pyridin-3-ylcarbonyl)morpholin-3-yl)methyl)-4-(5-(trifluoromethyl)-1,2,4-oxadiazol-3-yl)benzamide | 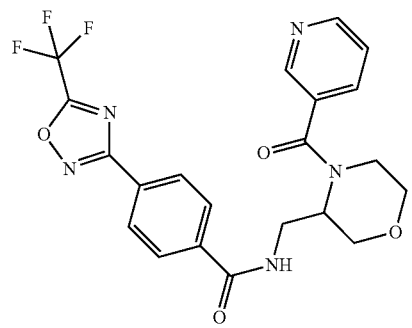 [SMILES: O=C(NCC1COCCN1C(=O)c1cccnc1)c1ccc(-c2noc(C(F)(F)F)n2)cc1] | 460.0 [M − H]− |

TABLE 1-continued

| Example No. | IUPAC name | Structure | MS (found) |
|---|---|---|---|
| 14 | N-((4-isonicotinoylmorpholin-3-yl)methyl)-4-(5-(trifluoromethyl)-1,2,4-oxadiazol-3-yl)benzamide | 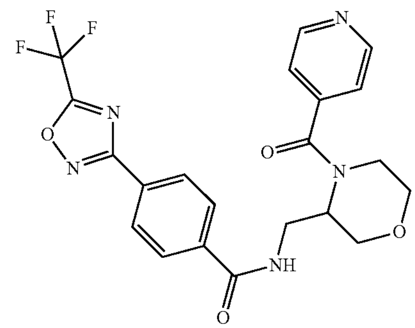 [SMILES: O=C(NCC1COCCN1C(=O)c1ccncc1)c1ccc(-c2noc(C(F)(F)F)n2)cc1] | 462.1 [M + H]+ |
| 15 | N-((4-(2-thienylcarbonyl)morpholin-3-yl)methyl)-4-(5-(trifluoromethyl)-1,2,4-oxadiazol-3-yl)benzamide | 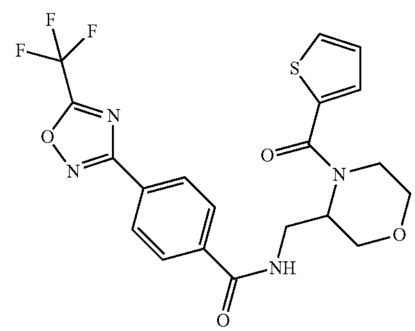 [SMILES: O=C(NCC1COCCN1C(=O)c1cccs1)c1ccc(-c2noc(C(F)(F)F)n2)cc1] | 467.0 [M + H]+ |
| 16 | N-((4-((1-methyl-1H-imidazol-2-yl)carbonyl)morpholin-3-yl)methyl)-4-(5-(trifluoromethyl)-1,2,4-oxadiazol-3-yl)benzamide | 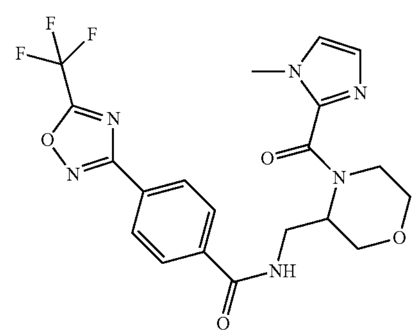 [SMILES: Cn1ccnc1C(=O)N1CCOCC1CNC(=O)c1ccc(-c2noc(C(F)(F)F)n2)cc1] | 465.0 [M + H]+ |
| 17 | N-((4-((1-methyl-1H-imidazol-4-yl)carbonyl)morpholin-3-yl)methyl)-4-(5-(trifluoromethyl)-1,2,4-oxadiazol-3-yl)benzamide | 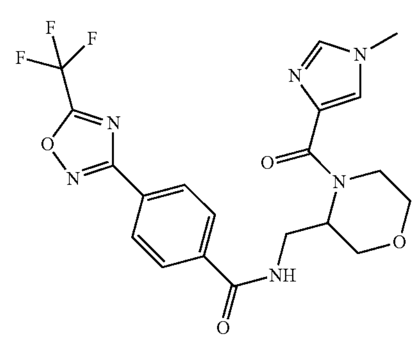 [SMILES: Cn1cnc(C(=O)N2CCOCC2CNC(=O)c2ccc(-c3noc(C(F)(F)F)n3)cc2)c1] | 465.0 [M + H]+ |

TABLE 1-continued

| Example No. | IUPAC name | Structure | MS (found) |
|---|---|---|---|
| 18 | N-((4-((1-methyl-1H-indazol-3-yl)carbonyl)morpholin-3-yl)methyl)-4-(5-(trifluoromethyl)-1,2,4-oxadiazol-3-yl)benzamide | 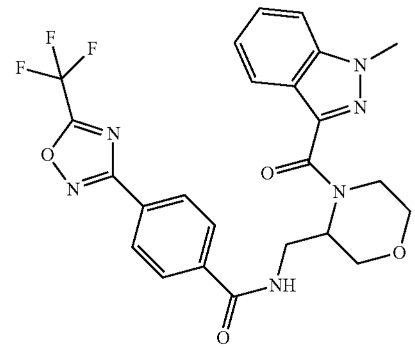 [SMILES: Cn1nc(C(=O)N2CCOCC2CNC(=O)c2ccc(-c3noc(C(F)(F)F)n3)cc2)c2ccccc21] | 515.1 [M + H]+ |
| 19 | N-((4-(1-benzofuran-2-ylcarbonyl)morpholin-3-yl)methyl)-4-(5-(trifluoromethyl)-1,2,4-oxadiazol-3-yl)benzamide | 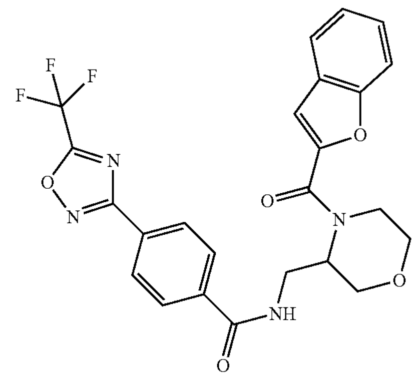 [SMILES: O=C(NCC1COCCN1C(=O)c1cc2ccccc2o1)c1ccc(-c2noc(C(F)(F)F)n2)cc1] | 501.1 [M + H]+ |
| 20 | N-((4-(imidazo[1,2-a]pyridin-6-ylcarbonyl)morpholin-3-yl)methyl)-4-(5-(trifluoromethyl)-1,2,4-oxadiazol-3-yl)benzamide | 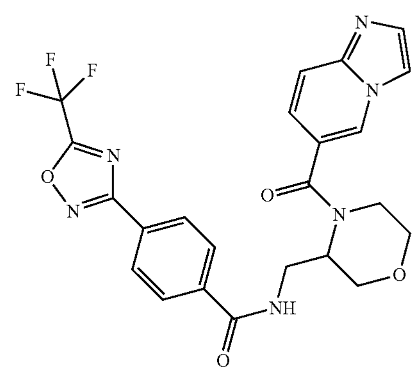 [SMILES: O=C(NCC1COCCN1C(=O)c1ccc2nccn2c1)c1ccc(-c2noc(C(F)(F)F)n2)cc1] | 501.1 [M + H]+ |
| 21 | N-((4-(2-thienylacetyl)morpholin-3-yl)methyl)-4-(5-(trifluoromethyl)-1,2,4-oxadiazol-3-yl)benzamide | 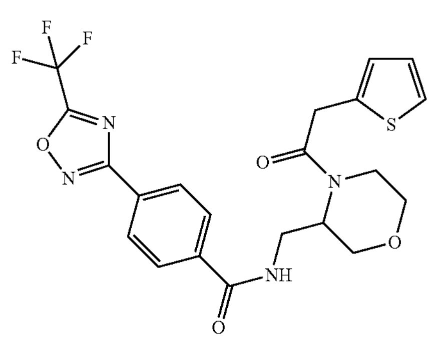 [SMILES: O=C(NCC1COCCN1C(=O)Cc1cccs1)c1ccc(-c2noc(C(F)(F)F)n2)cc1] | 478.9 [M − H]− |

TABLE 1-continued

| Example No. | IUPAC name | Structure | MS (found) |
|---|---|---|---|
| 22 | N-((4-(3-phenylpropanoyl)morpholin-3-yl)methyl)-4-(5-(trifluoromethyl)-1,2,4-oxadiazol-3-yl)benzamide | 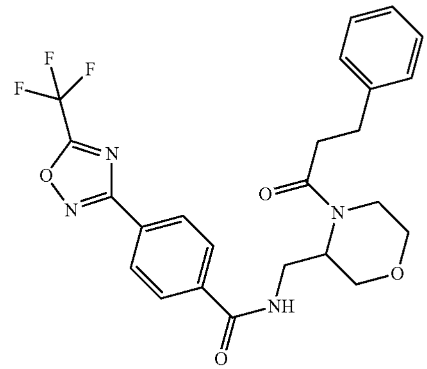 [SMILES: O=C(NCC1COCCN1C(=O)CCc1ccccc1)c1ccc(-c2noc(C(F)(F)F)n2)cc1] | 489.1 [M + H]+ |
| 23 | N-((4-(biphenyl-4-ylcarbonyl)morpholin-3-yl)methyl)-4-(5-(trifluoromethyl)-1,2,4-oxadiazol-3-yl)benzamide | 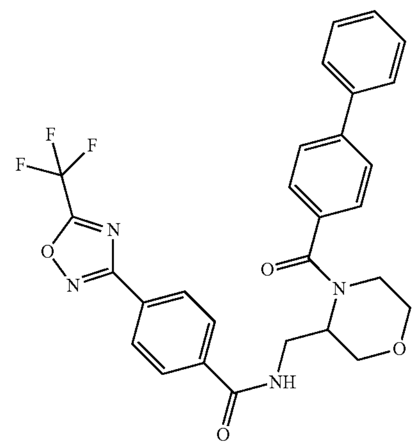 [SMILES: O=C(NCC1COCCN1C(=O)c1ccc(-c2ccccc2)cc1)c1ccc(-c2noc(C(F)(F)F)n2)cc1] | 537.1 [M + H]+ |
| 24 | N-((4-(cyclopropylcarbonyl)morpholin-3-yl)methyl)-4-(5-(trifluoromethyl)-1,2,4-oxadiazol-3-yl)benzamide | 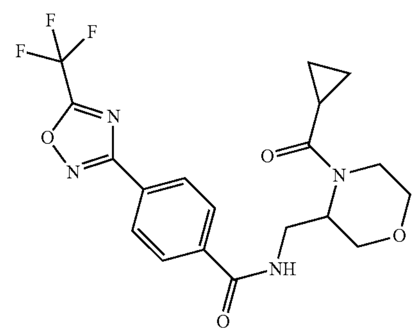 [SMILES: O=C(NCC1COCCN1C(=O)C1CC1)c1ccc(-c2noc(C(F)(F)F)n2)cc1] | 423.0 [M − H]− |
| 25 | N-((4-(cyclohexylcarbonyl)morpholin-3-yl)methyl)-4-(5-(trifluoromethyl)-1,2,4-oxadiazol-3-yl)benzamide | 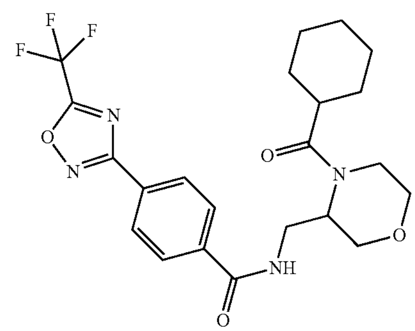 [SMILES: O=C(NCC1COCCN1C(=O)C1CCCCC1)c1ccc(-c2noc(C(F)(F)F)n2)cc1] | 465.0 [M − H]− |

TABLE 1-continued

| Example No. | IUPAC name | Structure | MS (found) |
|---|---|---|---|
| 26 | N-((4-(tetrahydro-2H-pyran-4-ylcarbonyl)morpholin-3-yl)methyl)-4-(5-(trifluoromethyl)-1,2,4-oxadiazol-3-yl)benzamide | 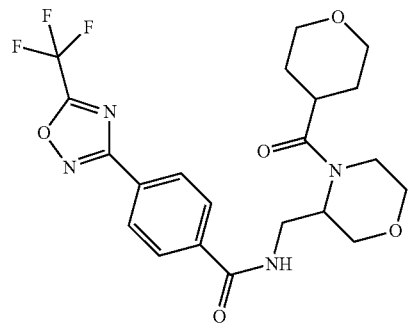 [SMILES: O=C(NCC1COCCN1C(=O)C1CCOCC1)c1ccc(-c2noc(C(F)(F)F)n2)cc1] | 467.0 [M − H]− |
| 27 | N-((4-(3-(trifluoromethyl)benzoyl)morpholin-3-yl)methyl)-4-(5-(trifluoromethyl)-1,2,4-oxadiazol-3-yl)benzamide | 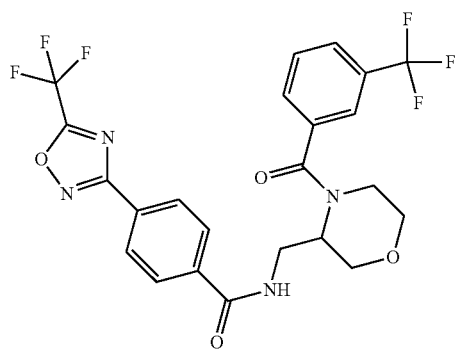 [SMILES: O=C(NCC1COCCN1C(=O)c1cccc(C(F)(F)F)c1)c1ccc(-c2noc(C(F)(F)F)n2)cc1] | 526.9 [M − H]− |
| 28 | N-((4-(3-cyanobenzoyl)morpholin-3-yl)methyl)-4-(5-(trifluoromethyl)-1,2,4-oxadiazol-3-yl)benzamide | 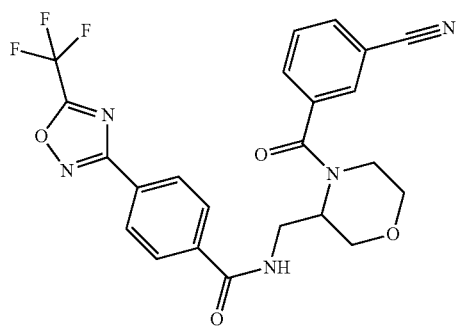 [SMILES: N#Cc1cccc(C(=O)N2CCOCC2CNC(=O)c2ccc(-c3noc(C(F)(F)F)n3)cc2)c1] | 486.1 [M + H]+ |
| 29 | N-((4-(3-methoxybenzoyl)morpholin-3-yl)methyl)-4-(5-(trifluoromethyl)-1,2,4-oxadiazol-3-yl)benzamide | 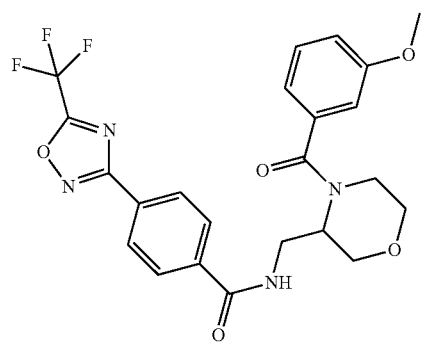 [SMILES: COc1cccc(C(=O)N2CCOCC2CNC(=O)c2ccc(-c3noc(C(F)(F)F)n3)cc2)c1] | 491.1 [M + H]+ |

TABLE 1-continued

| Example No. | IUPAC name | Structure | MS (found) |
|---|---|---|---|
| 30 | N-((4-(3,5-dichlorobenzoyl)morpholin-3-yl)methyl)-4-(5-(trifluoromethyl)-1,2,4-oxadiazol-3-yl)benzamide | 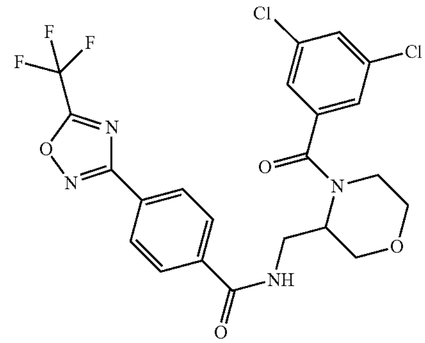 | 529.0 [M + H]+ |
| 31 | N-((4-(biphenyl-3-ylcarbonyl)morpholin-3-yl)methyl)-4-(5-(trifluoromethyl)-1,2,4-oxadiazol-3-yl)benzamide | 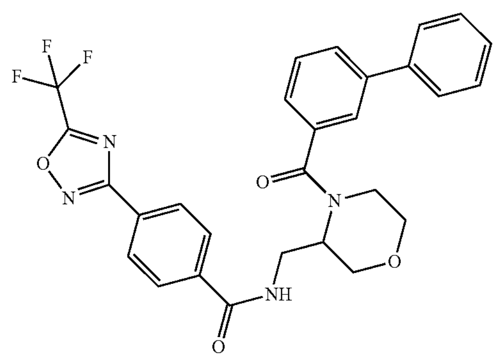 [SMILES: O=C(NCC1COCCN1C(=O)c1cccc(-c2ccccc2)c1)c1ccc(-c2noc(C(F)(F)F)n2)cc1] | 537.1 [M + H]+ |
| 32 | N-((4-(biphenyl-2-ylcarbonyl)morpholin-3-yl)methyl)-4-(5-(trifluoromethyl)-1,2,4-oxadiazol-3-yl)benzamide | 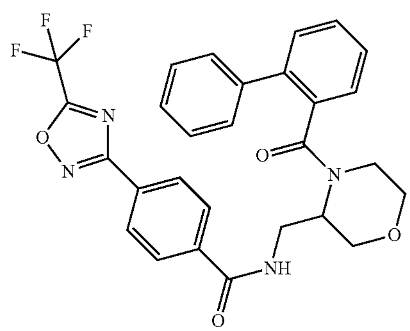 [SMILES: O=C(NCC1COCCN1C(=O)c1ccccc1-c1ccccc1)c1ccc(-c2noc(C(F)(F)F)n2)cc1] | 537.1 [M + H]+ |
| 33 | N-((4-((2-methyl-2H-indazol-3-yl)carbonyl)morpholin-3-yl)methyl)-4-(5-(trifluoromethyl)-1,2,4-oxadiazol-3-yl)benzamide | 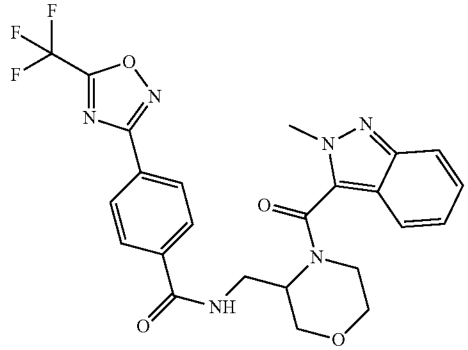 [SMILES: Cn1nc2ccccc2c1C(=O)N1CCOCC1CNC(=O)c1ccc(-c2noc(C(F)(F)F)n2)cc1] | 515.1 [M + H]+ |

TABLE 1-continued

| Example No. | IUPAC name | Structure | MS (found) |
|---|---|---|---|
| 34 | N-((4-(2-cyclopropylisonicotinoyl)morpholin-3-yl)methyl)-4-(5-(trifluoromethyl)-1,2,4-oxadiazol-3-yl)benzamide | 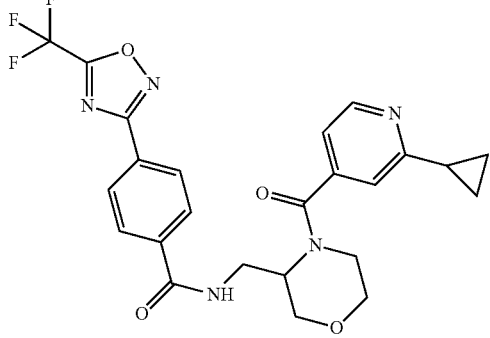 | 502.2 [M + H]+ |
| 35 | N-((4-(3,4-dihydro-2H-chromen-2-ylcarbonyl)morpholin-3-yl)methyl)-4-(5-(trifluoromethyl)-1,2,4-oxadiazol-3-yl)benzamide | 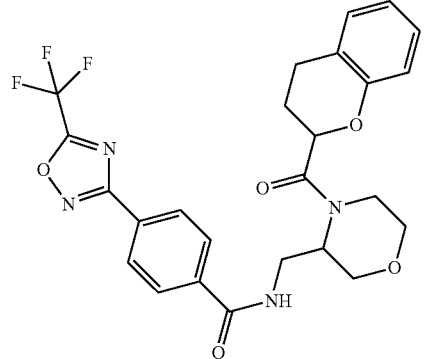 [SMILES: O=C(NCC1COCCN1C(=O)C1CCc2ccccc2O1)c1ccc(-c2noc(C(F)(F)F)n2)cc1] | 517.1 [M + H]+ |
| 36 | N-(((3S)-4-benzoylmorpholin-3-yl)methyl)-4-(5-(trifluoromethyl)-1,2,4-oxadiazol-3-yl)benzamide | 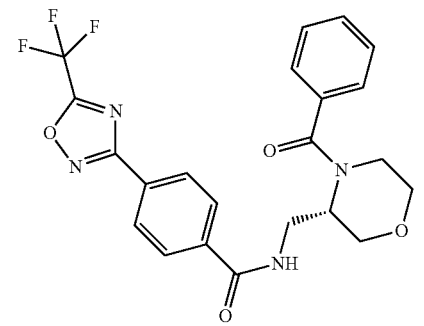 [SMILES: O=C(NC[C@H]1COCCN1C(=O)c1ccccc1)c1ccc(-c2noc(C(F)(F)F)n2)cc1] | 461.1 [M + H]+ |
| 37 | N-(((3S)-4-(3,5-dichlorobenzoyl)morpholin-3-yl)methyl)-4-(5-(trifluoromethyl)-1,2,4-oxadiazol-3-yl)benzamide | 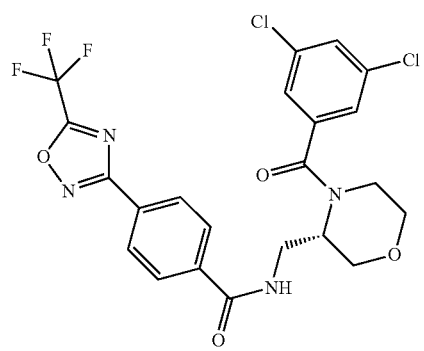 [SMILES: O=C(NC[C@H]1COCCN1C(=O)c1cc(Cl)cc(Cl)c1)c1ccc(-c2noc(C(F)(F)F)n2)cc1] | 529.0 [M + H]+<br>527.1 [M − H]− |

TABLE 1-continued

| Example No. | IUPAC name | Structure | MS (found) |
|---|---|---|---|
| 38 | N-(((3S)-4-((1-methyl-1H-pyrazol-5-yl)carbonyl)morpholin-3-yl)methyl)-4-(5-(trifluoromethyl)-1,2,4-oxadiazol-3-yl)benzamide | 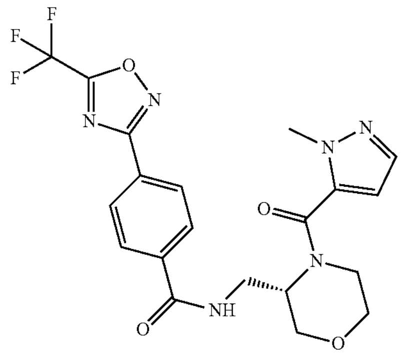 [SMILES: Cn1nccc1C(=O)N1CCOC[C@@H]1CNC(=O)c1ccc(-c2noc(C(F)(F)F)n2)cc1] | 465.1 [M + H]+ |
| 39 | N-(((3S)-4-(3,5-difluorobenzoyl)morpholin-3-yl)methyl)-4-(5-(trifluoromethyl)-1,2,4-oxadiazol-3-yl)benzamide | 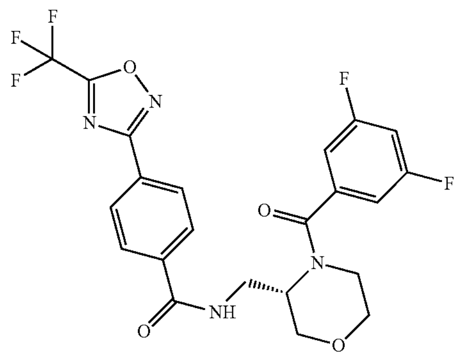 [SMILES: O=C(NC[C@H]1COCCN1C(=O)c1cc(F)cc(F)c1)c1ccc(-c2noc(C(F)(F)F)n2)cc1] | 497.0 [M + H]+ |
| 40 | N-(((3S)-4-(3-cyano-5-fluorobenzoyl)morpholin-3-yl)methyl)-4-(5-(trifluoromethyl)-1,2,4-oxadiazol-3-yl)benzamide | 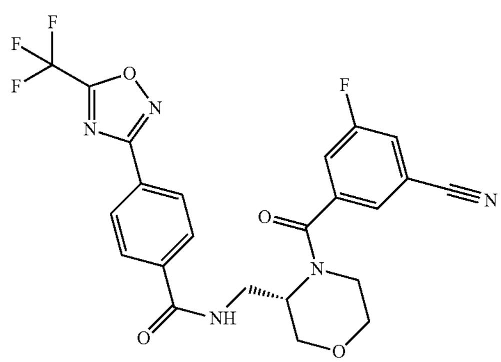 [SMILES: N#Cc1cc(F)cc(C(=O)N2CCOC[C@@H]2CNC(=O)c2ccc(-c3noc(C(F)(F)F)n3)cc2)c1] | 502.1 [M − H]− |
| 41 | N-(((3S)-4-(3-fluorobenzoyl)morpholin-3-yl)methyl)-4-(5-(trifluoromethyl)-1,2,4-oxadiazol-3-yl)benzamide | 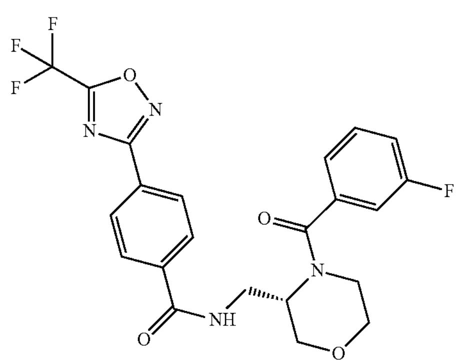 [SMILES: O=C(NC[C@H]1COCCN1C(=O)c1cccc(F)c1)c1ccc(-c2noc(C(F)(F)F)n2)cc1] | 479.1 [M + H]+ |

TABLE 1-continued

| Example No. | IUPAC name | Structure | MS (found) |
| --- | --- | --- | --- |
| 42 | N-(((3S)-4-(3-methoxybenzoyl)morpholin-3-yl)methyl)-4-(5-(trifluoromethyl)-1,2,4-oxadiazol-3-yl)benzamide | 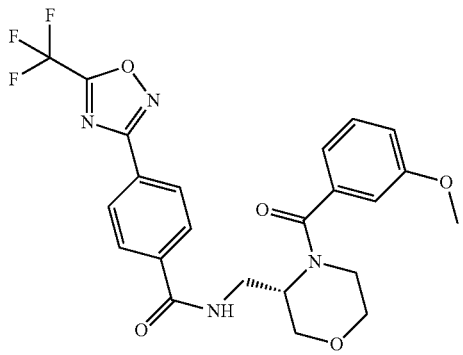 [SMILES: COc1cccc(C(=O)N2CCOC[C@@H]2CNC(=O)c2ccc(-c3noc(C(F)(F)F)n3)cc2)c1] | 491.1 [M + H]+ |
| 43 | N-(((3S)-4-(2-cyanobenzoyl)morpholin-3-yl)methyl)-4-(5-(trifluoromethyl)-1,2,4-oxadiazol-3-yl)benzamide | 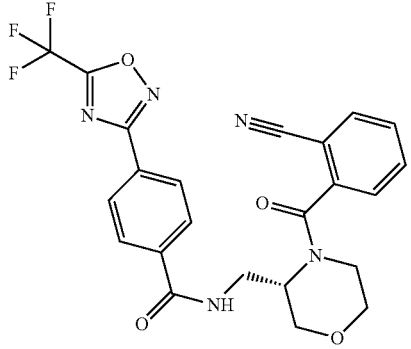 [SMILES: N#Cc1ccccc1C(=O)N1CCOC[C@@H]1CNC(=O)c1ccc(-c2noc(C(F)(F)F)n2)cc1] | 486.1 [M + H]+ |
| 44 | N-(((3S)-4-(3-cyanobenzoyl)morpholin-3-yl)methyl)-4-(5-(trifluoromethyl)-1,2,4-oxadiazol-3-yl)benzamide | 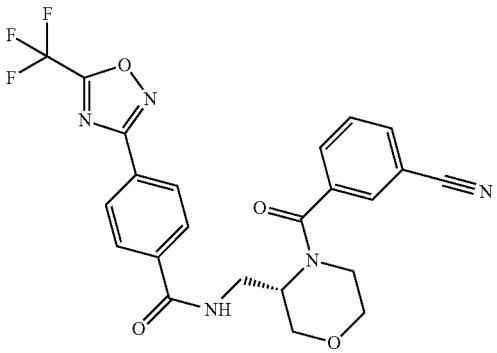 [SMILES: N#Cc1cccc(C(=O)N2CCOC[C@@H]2CNC(=O)c2ccc(-c3noc(C(F)(F)F)n3)cc2)c1] | 484.1 [M − H]− |
| 45 | N-(((3S)-4-(4-cyanobenzoyl)morpholin-3-yl)methyl)-4-(5-(trifluoromethyl)-1,2,4-oxadiazol-3-yl)benzamide | 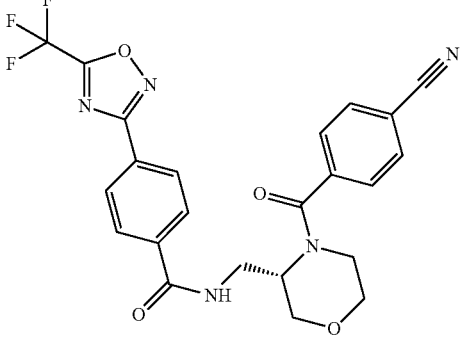 | 484.2 [M − H]− |

TABLE 1-continued

| Example No. | IUPAC name | Structure | MS (found) |
|---|---|---|---|
| 46 | N-(((3S)-4-(2-(morpholin-4-yl)benzoyl)morpholin-3-yl)methyl)-4-(5-(trifluoromethyl)-1,2,4-oxadiazol-3-yl)benzamide | 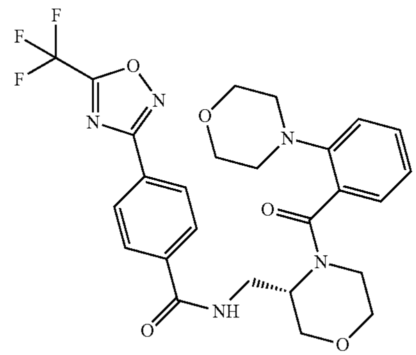 [SMILES: O=C(NC[C@H]1COCCN1C(=O)c1ccccc1N1CCOCC1)c1ccc(-c2noc(C(F)(F)F)n2)cc1] | 546.1 [M + H]+ |
| 47 | N-(((3S)-4-(3,4,5-trifluorobenzoyl)morpholin-3-yl)methyl)-4-(5-(trifluoromethyl)-1,2,4-oxadiazol-3-yl)benzamide | 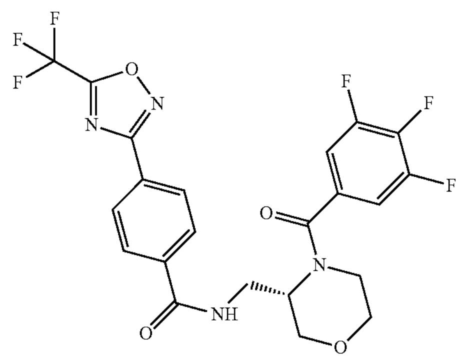 [SMILES: O=C(NC[C@H]1COCCN1C(=O)c1cc(F)c(F)c(F)c1)c1ccc(-c2noc(C(F)(F)F)n2)cc1] | 513.0 [M − H]− |
| 48 | N-(((3S)-4-isonicotinoylmorpholin-3-yl)methyl)-4-(5-(trifluoromethyl)-1,2,4-oxadiazol-3-yl)benzamide | 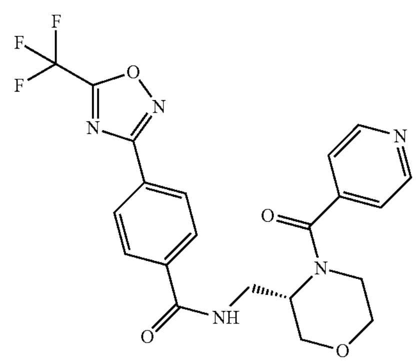 [SMILES: O=C(NC[C@H]1COCCN1C(=O)c1ccncc1)c1ccc(-c2noc(C(F)(F)F)n2)cc1] | 462.1 [M + H]+ |
| 49 | N-(((3S)-4-(2-methylisonicotinoyl)morpholin-3-yl)methyl)-4-(5-(trifluoromethyl)-1,2,4-oxadiazol-3-yl)benzamide | 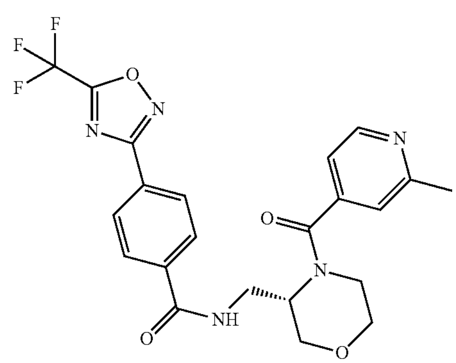 [SMILES: Cc1cc(C(=O)N2CCOC[C@@H]2CNC(=O)c2ccc(-c3noc(C(F)(F)F)n3)cc2)ccn1] | 476.1 [M + H]+ |

TABLE 1-continued

| Example No. | IUPAC name | Structure | MS (found) |
|---|---|---|---|
| 50 | N-(((3S)-4-(2-hydroxy-6-methylisonicotinoyl)morpholin-3-yl)methyl)-4-(5-(trifluoromethyl)-1,2,4-oxadiazol-3-yl)benzamide | 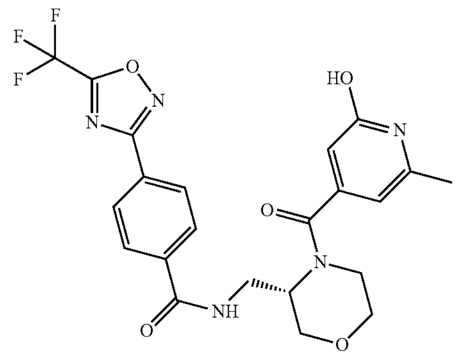 [SMILES: Cc1cc(C(=O)N2CCOC[C@@H]2CNC(=O)c2ccc(-c3noc(C(F)(F)F)n3)cc2)cc(O)n1] | 492.2 [M + H]+ |
| 51 | N-(((3S)-4-((6-(2,2,2-trifluoroethoxy)pyridin-3-yl)carbonyl)morpholin-3-yl)methyl)-4-(5-(trifluoromethyl)-1,2,4-oxadiazol-3-yl)benzamide | 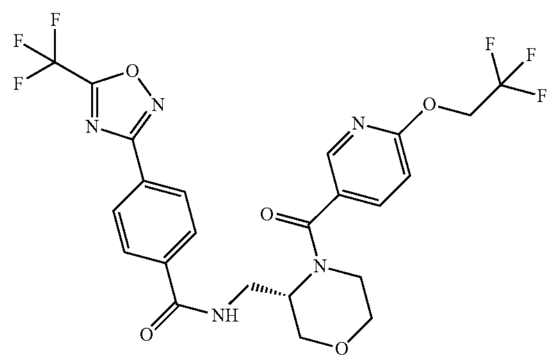 [SMILES: O=C(NC[C@H]1COCCN1C(=O)c1ccc(OCC(F)(F)F)nc1)c1ccc(-c2noc(C(F)(F)F)n2)cc1] | 560.1 [M + H]+ |
| 52 | N-(((3S)-4-(3,4-dihydro-2H-chromen-2-ylcarbonyl)morpholin-3-yl)methyl)-4-(5-(trifluoromethyl)-1,2,4-oxadiazol-3-yl)benzamide | 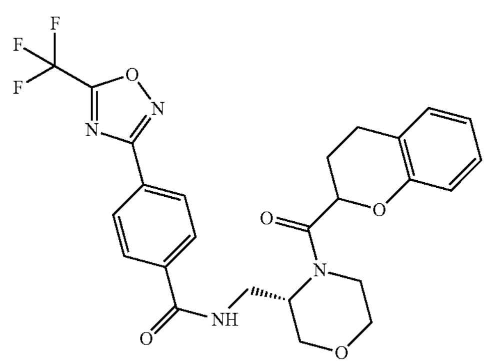 [SMILES: O=C(NC[C@H]1COCCN1C(=O)C1CCc2ccccc2O1)c1ccc(-c2noc(C(F)(F)F)n2)cc1] | 515.1 [M − H]− |
| 53 | N-(((3S)-4-(1-benzofuran-2-ylcarbonyl)morpholin-3-yl)methyl)-4-(5-(trifluoromethyl)-1,2,4-oxadiazol-3-yl)benzamide | 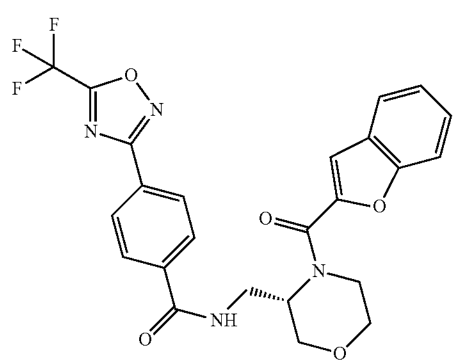 [SMILES: O=C(NC[C@H]1COCCN1C(=O)c1cc2ccccc2o1)c1ccc(-c2noc(C(F)(F)F)n2)cc1] | 501.1 [M + H]+ |

TABLE 1-continued

| Example No. | IUPAC name | Structure | MS (found) |
|---|---|---|---|
| 54 | N-(((3S)-4-(pyrazolo[1,5-a]pyrimidin-2-ylcarbonyl)morpholin-3-yl)methyl)-4-(5-(trifluoromethyl)-1,2,4-oxadiazol-3-yl)benzamide | 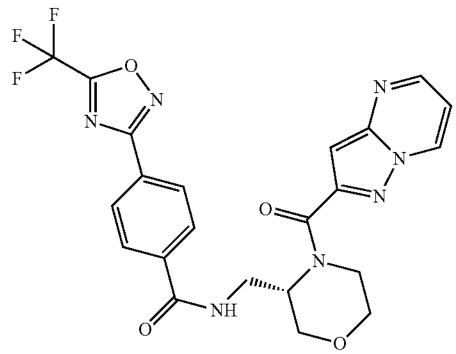 [SMILES: O=C(NC[C@H]1COCCN1C(=O)c1cc2ncccn2n1)c1ccc(-c2noc(C(F)(F)F)n2)cc1] | 502.1 [M + H]+ |
| 55 | N-(((3S)-4-((1-cyanocyclopropyl)carbonyl)morpholin-3-yl)methyl)-4-(5-(trifluoromethyl)-1,2,4-oxadiazol-3-yl)benzamide | 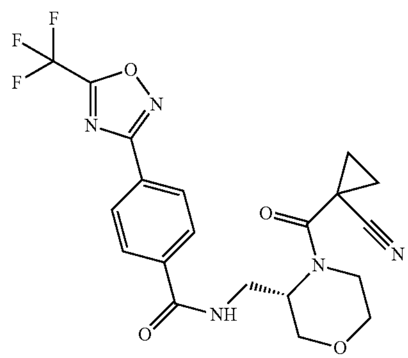 [SMILES: N#CC1(C(=O)N2CCOC[C@@H]2CNC(=O)c2ccc(-c3noc(C(F)(F)F)n3)cc2)CC1] | 450.1 [M + H]+ |
| 56 | N-(((3S)-4-((1-phenylcyclopropyl)carbonyl)morpholin-3-yl)methyl)-4-(5-(trifluoromethyl)-1,2,4-oxadiazol-3-yl)benzamide | 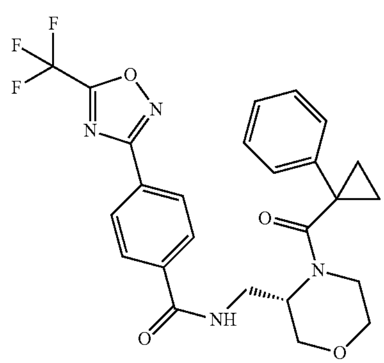 [SMILES: O=C(NC[C@H]1COCCN1C(=O)C1(c2ccccc2)CC1)c1ccc(-c2noc(C(F)(F)F)n2)cc1] | 501.2 [M + H]+ |
| 57 | N-(((3S)-4-(diphenylacetyl)morpholin-3-yl)methyl)-4-(5-(trifluoromethyl)-1,2,4-oxadiazol-3-yl)benzamide | 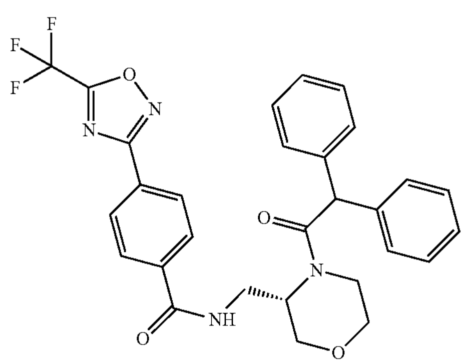 [SMILES: O=C(NC[C@H]1COCCN1C(=O)C(c1ccccc1)c1ccccc1)c1ccc(-c2noc(C(F)(F)F)n2)cc1] | 551.2 [M + H]+ |

TABLE 1-continued

| Example No. | IUPAC name | Structure | MS (found) |
|---|---|---|---|
| 58 | N-(((3S)-4-(phenoxyacetyl)morpholin-3-yl)methyl)-4-(5-(trifluoromethyl)-1,2,4-oxadiazol-3-yl)benzamide | 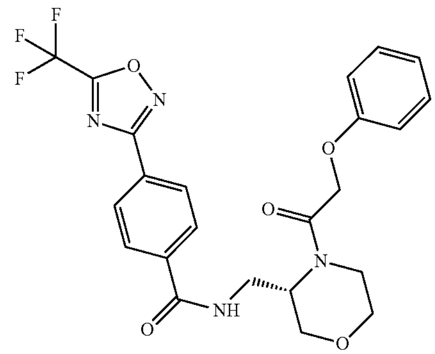 [SMILES: O=C(NC[C@H]1COCCN1C(=O)COc1ccccc1)c1ccc(-c2noc(C(F)(F)F)n2)cc1] | 491.1 [M + H]+ |
| 59 | N-(((3S)-4-((5-methyl-1,2-oxazol-4-yl)carbonyl)morpholin-3-yl)methyl)-4-(5-(trifluoromethyl)-1,2,4-oxadiazol-3-yl)benzamide | 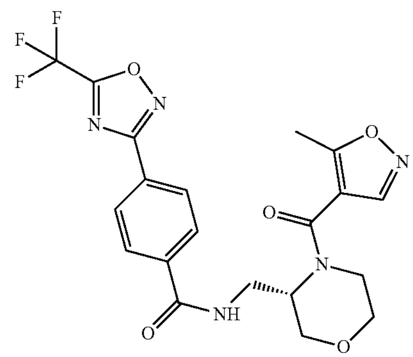 [SMILES: Cc1oncc1C(=O)N1CCOC[C@@H]1CNC(=O)c1ccc(-c2noc(C(F)(F)F)n2)cc1] | 466.1 [M + H]+ |
| 60 | N-(((3S)-4-((4-methyl-1,2,5-oxadiazol-3-yl)carbonyl)morpholin-3-yl)methyl)-4-(5-(trifluoromethyl)-1,2,4-oxadiazol-3-yl)benzamide | 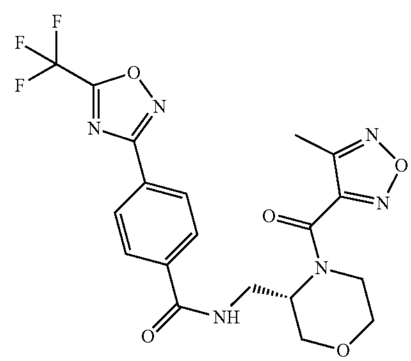 [SMILES: Cc1nonc1C(=O)N1CCOC[C@@H]1CNC(=O)c1ccc(-c2noc(C(F)(F)F)n2)cc1] | 467.0 [M + H]+ |
| 61 | N-(((3S)-4-(1,2-oxazol-5-ylcarbonyl)morpholin-3-yl)methyl)-4-(5-(trrfluoromethyl)-1,2,4-oxadiazol-3-yl)benzamide | 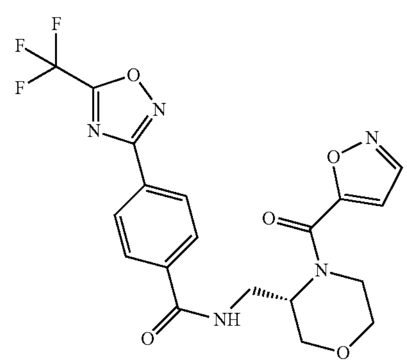 [SMILES: O=C(NC[C@H]1COCCN1C(=O)c1ccno1)c1ccc(-c2noc(C(F)(F)F)n2)cc1] | 452.1 [M + H]+ |

TABLE 1-continued

| Example No. | IUPAC name | Structure | MS (found) |
|---|---|---|---|
| 62 | N-(((3S)-4-((3-methyl-1,2-oxazol-5-yl)carbonyl)morpholin-3-yl)methyl)-4-(5-(trifluoromethyl)-1,2,4-oxadiazol-3-yl)benzamide | 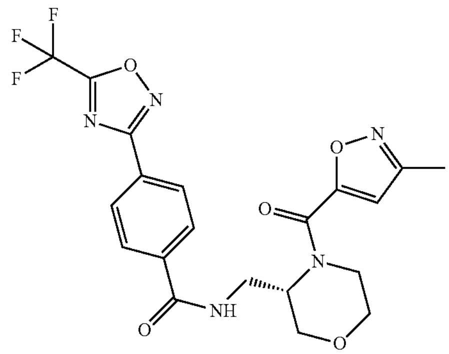 [SMILES: Cc1cc(C(=O)N2CCOC[C@@H]2CNC(=O)c2ccc(-c3noc(C(F)(F)F)n3)cc2)on1] | 466.1 [M + H]+ |
| 63 | N-(((3S)-4-((1,3-dimethyl-1H-pyrazol-5-yl)carbonyl)morpholin-3-yl)methyl)-4-(5-(trifluoromethyl)-1,2,4-oxadiazol-3-yl)benzamide | 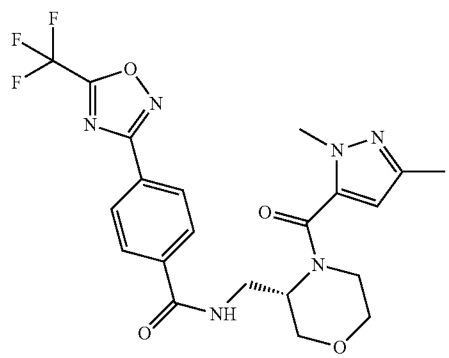 [SMILES: Cc1cc(C(=O)N2CCOC[C@@H]2CNC(=O)c2ccc(-c3noc(C(F)(F)F)n3)cc2)n(C)n1] | 479.1 [M + H]+ |
| 64 | N-(((3S)-4-((1-methyl-3-(trifluoromethyl)-1H-pyrazol-5-yl)carbonyl)morpholin-3-yl)methyl)-4-(5-(trifluoromethyl)-1,2,4-oxadiazol-3-yl)benzamide | 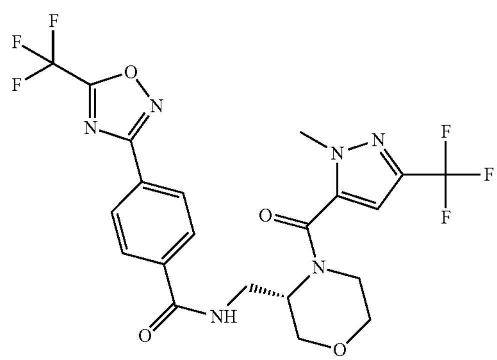 [SMILES: Cn1nc(C(F)(F)F)cc1C(=O)N1CCOC[C@@H]1CNC(=O)c1ccc(-c2noc(C(F)(F)F)n2)cc1] | 531.1 [M − H]− |
| 65 | N-(((3S)-4-((1-methyl-1H-pyrazol-3-yl)carbonyl)morpholin-3-yl)methyl)-4-(5-(trifluoromethyl)-1,2,4-oxadiazol-3-yl)benzamide | 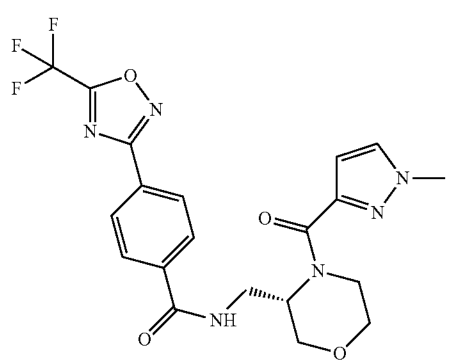 [SMILES: Cn1ccc(C(=O)N2CCOC[C@@H]2CNC(=O)c2ccc(-c3noc(C(F)(F)F)n3)cc2)n1] | 463.1 [M − H]− |

TABLE 1-continued

| Example No. | IUPAC name | Structure | MS (found) |
|---|---|---|---|
| 66 | N-(((3S)-4-((1-methyl-1H-pyrazol-4-yl)carbonyl)morpholin-3-yl)methyl)-4-(5-(trifluoromethyl)-1,2,4-oxadiazol-3-yl)benzamide | 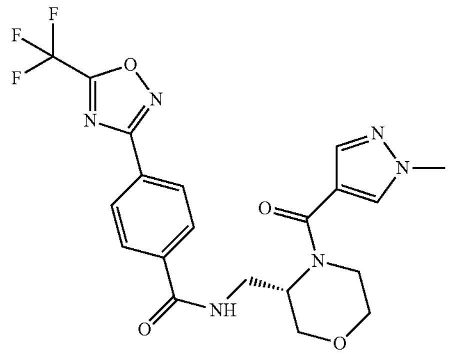 [SMILES: Cn1cc(C(=O)N2CCOC[C@@H]2CNC(=O)c2ccc(-c3noc(C(F)(F)F)n3)cc2)cn1] | 465.1 [M + H]+ |
| 67 | 4-(5-(trifluoromethyl)-1,2,4-oxadiazol-3-yl)-N-(((3S)-4-((1,3,5-trimethyl-1H-pyrazol-4-yl)carbonyl)morpholin-3-yl)methyl)benzamide | 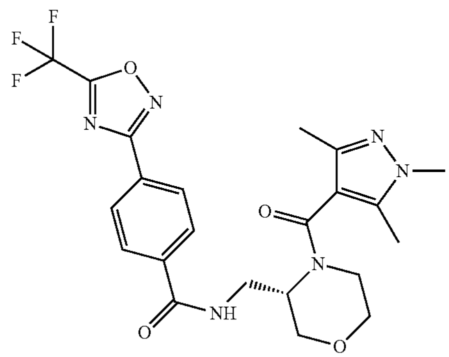 [SMILES: Cc1nn(C)c(C)c1C(=O)N1CCOC[C@@H]1CNC(=O)c1ccc(-c2noc(C(F)(F)F)n2)cc1] | 493.2 [M + H]+ |
| 68 | N-(((3S)-4-((4-methyl-1,2,3-thiadiazol-5-yl)carbonyl)morpholin-3-yl)methyl)-4-(5-(trifluoromethyl)-1,2,4-oxadiazol-3-yl)benzamide | 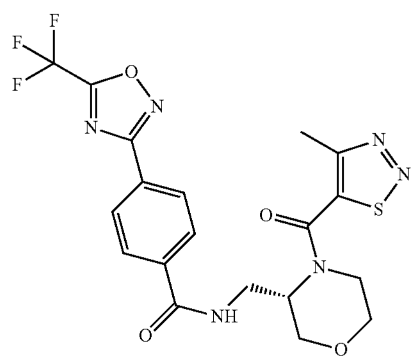 [SMILES: Cc1nnsc1C(=O)N1CCOC[C@@H]1CNC(=O)c1ccc(-c2noc(C(F)(F)F)n2)cc1] | 483.0 [M + H]+ |
| 69 | N-(((3S)-4-((4-methyl-1,3-thiazol-5-yl)carbonyl)morpholin-3-yl)methyl)-4-(5-(trifluoromethyl)-1,2,4-oxadiazol-3-yl)benzamide | 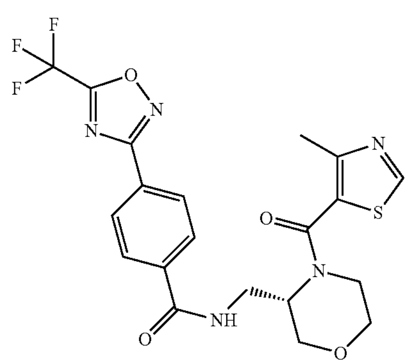 | 482.0 [M + H]+ |

TABLE 1-continued

| Example No. | IUPAC name | Structure | MS (found) |
|---|---|---|---|
| 70 | N-(((3S)-4-(1,2,3-thiadiazol-4-ylcarbonyl)morpholin-3-yl)methyl)-4-(5-(trifluoromethyl)-1,2,4-oxadiazol-3-yl)benzamide | 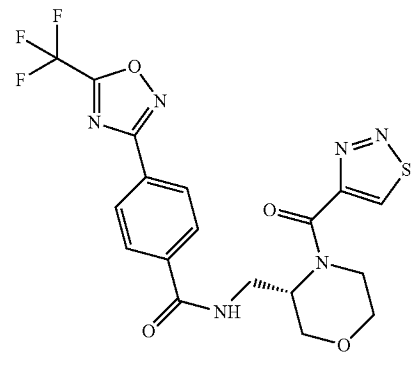 [SMILES: O=C(NC[C@H]1COCCN1C(=O)c1csnn1)c1ccc(-c2noc(C(F)(F)F)n2)cc1] | 469.1 [M + H]+ |
| 71 | N-(((3S)-4-(1H-pyrazol-3-ylcarbonyl)morpholin-3-yl)methyl)-4-(5-(trifluoromethyl)-1,2,4-oxadiazol-3-yl)benzamide | 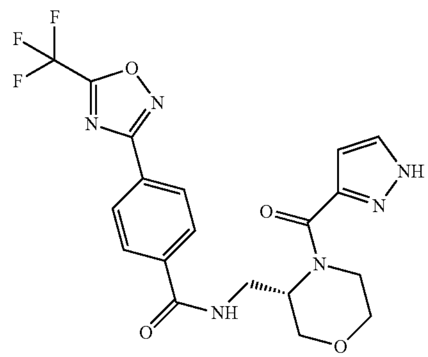 [SMILES: O=C(NC[C@H]1COCCN1C(=O)c1cc[nH]n1)c1ccc(-c2noc(C(F)(F)F)n2)cc1] | 451.1 [M + H]+ |
| 72 | N-(((3S)-4-((5-methyl-2-thienyl)carbonyl)morpholin-3-yl)methyl)-4-(5-(trifluoromethyl)-1,2,4-oxadiazol-3-yl)benzamide | 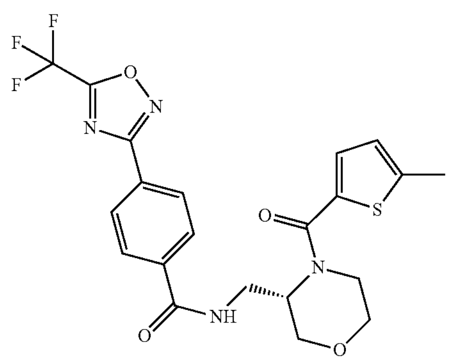 [SMILES: Cc1ccc(C(=O)N2CCOC[C@@H]2CNC(=O)c2ccc(-c3noc(C(F)(F)F)n3)cc2)s1] | 481.0 [M + H]+ |
| 73 | N-(((3S)-4-((4-methyl-2-thienyl)carbonyl)morpholin-3-yl)methyl)-4-(5-(trifluoromethyl)-1,2,4-oxadiazol-3-yl)benzamide | 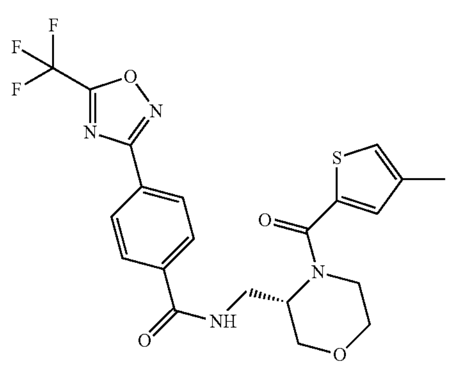 [SMILES: Cc1csc(C(=O)N2CCOC[C@@H]2CNC(=O)c2ccc(-c3noc(C(F)(F)F)n3)cc2)c1] | 481.0 [M + H]+ |

TABLE 1-continued

| Example No. | IUPAC name | Structure | MS (found) |
| --- | --- | --- | --- |
| 74 | N-(((3S)-4-((3-methyl-2-thienyl)carbonyl)morpholin-3-yl)methyl)-4-(5-(trifluoromethyl)-1,2,4-oxadiazol-3-yl)benzamide | 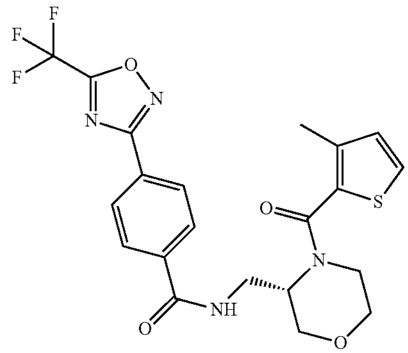 [SMILES: Cc1ccsc1C(=O)N1CCOC[C@@H]1CNC(=O)c1ccc(-c2noc(C(F)(F)F)n2)cc1] | 481.0 [M + H]+ |
| 75 | N-(((3S)-4-(cyclopropylcarbonyl)morpholin-3-yl)methyl)-4-(5-(trifluoromethyl)-1,2,4-oxadiazol-3-yl)benzamide | 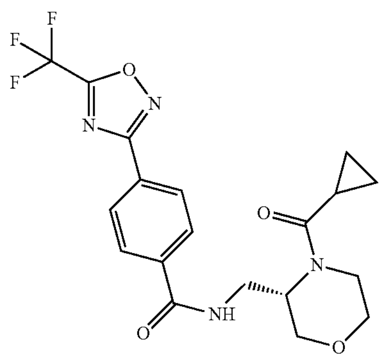 [SMILES: O=C(NC[C@H]1COCCN1C(=O)C1CC1)c1ccc(-c2noc(C(F)(F)F)n2)cc1] | 423.0 [M − H]− |
| 76 | N-(((3S)-4-(cyclopropylacetyl)morpholin-3-yl)methyl)-4-(5-(trifluoromethyl)-1,2,4-oxadiazol-3-yl)benzamide | 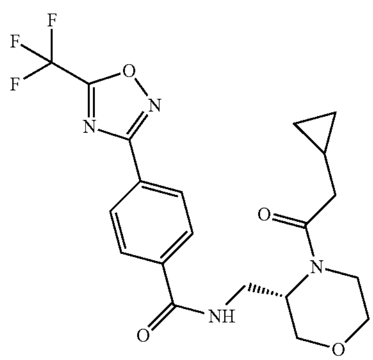 [SMILES: O=C(NC[C@H]1COCCN1C(=O)CC1CC1)c1ccc(-c2noc(C(F)(F)F)n2)cc1] | 437.1 [M − H]− |
| 77 | N-(((3S)-4-(cyclopentylcarbonyl)morpholin-3-yl)methyl)-4-(5-(trifluoromethyl)-1,2,4-oxadiazol-3-yl)benzamide | 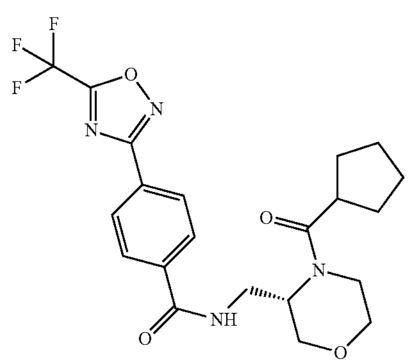 | 453.1 [M + H]+ |

TABLE 1-continued

| Example No. | IUPAC name | Structure | MS (found) |
| --- | --- | --- | --- |
| 78 | N-(((3S)-4-(tetrahydrofuran-2-ylcarbonyl)morpholin-3-yl)methyl)-4-(5-(trifluoromethyl)-1,2,4-oxadiazol-3-yl)benzamide | 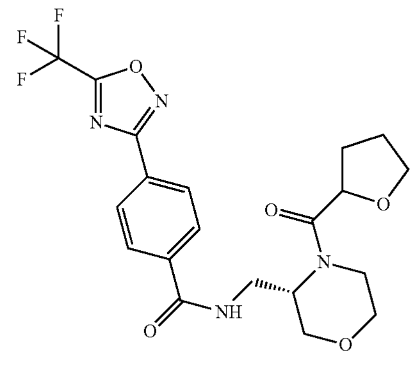 [SMILES: O=C(NC[C@H]1COCCN1C(=O)C1CCCO1)c1ccc(-c2noc(C(F)(F)F)n2)cc1] | 455.1 [M + H]+ |
| 79 | N-(((3S)-4-(tetrahydrofuran-3-ylcarbonyl)morpholin-3-yl)methyl)-4-(5-(trifluoromethyl)-1,2,4-oxadiazol-3-yl)benzamide | 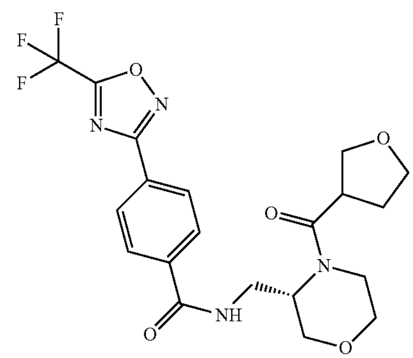 [SMILES: O=C(NC[C@H]1COCCN1C(=O)C1CCOC1)c1ccc(-c2noc(C(F)(F)F)n2)cc1] | 455.1 [M + H]+ |
| 80 | N-(((3S)-4-(cyclohexylcarbonyl)morpholin-3-yl)methyl)-4-(5-(trifluoromethyl)-1,2,4-oxadiazol-3-yl)benzamide | 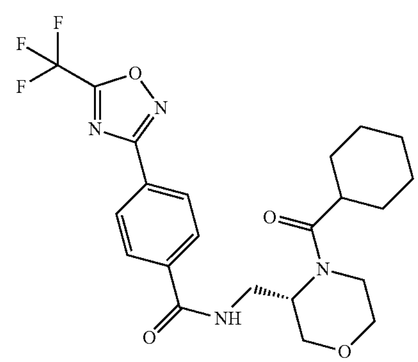 | 467.2 [M + H]+ |
| 81 | N-(((3S)-4-(tetrahydro-2H-pyran-4-ylcarbonyl)morpholin-3-yl)methyl)-4-(5-(trifluoromethyl)-1,2,4-oxadiazol-3-yl)benzamide | 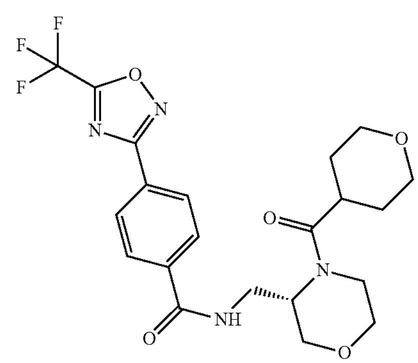 [SMILES: O=C(NC[C@H]1COCCN1C(=O)C1CCOCC1)c1ccc(-c2noc(C(F)(F)F)n2)cc1] | 469.2 [M + H]+ |

TABLE 1-continued

| Example No. | IUPAC name | Structure | MS (found) |
|---|---|---|---|
| 82 | N-(((3S)-4-((2-methyl-2H-indazol-3-yl)carbonyl)morpholin-3-yl)methyl)-4-(5-(trifluoromethyl)-1,2,4-oxadiazol-3-yl)benzamide | 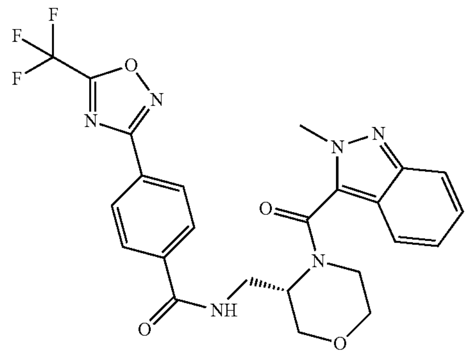 [SMILES: Cn1nc2ccccc2c1C(=O)N1CCOC[C@@H]1CNC(=O)c1ccc(-c2noc(C(F)(F)F)n2)cc1] | 515.1 [M + H]+ |
| 83 | N-(((3S)-4-((6-oxopyrimidin-1(6H)-yl)acetyl)morpholin-3-yl)methyl)-4-(5-(trifluoromethyl)-1,2,4-oxadiazol-3-yl)benzamide | 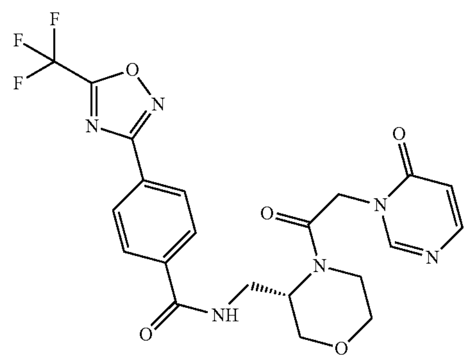 [SMILES: O=C(NC[C@H]1COCCN1C(=O)Cn1cnccc1=O)c1ccc(-c2noc(C(F)(F)F)n2)cc1] | 493.2 [M + H]+ |
| 84 | N-(((3S)-4-((1-isopropyl-1H-pyrazol-5-yl)carbonyl)morpholin-3-yl)methyl)-4-(5-(trifluoromethyl)-1,2,4-oxadiazol-3-yl)benzamide | 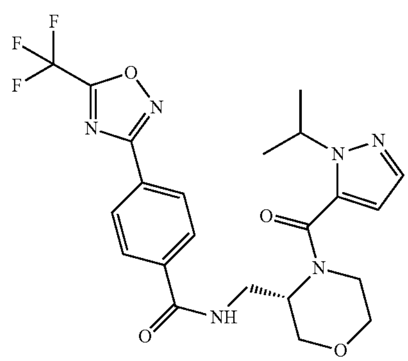 [SMILES: CC(C)n1nccc1C(=O)N1CCOC[C@@H]1CNC(=O)c1ccc(-c2noc(C(F)(F)F)n2)cc1] | 493.2 [M + H]+ |
| 85 | N-(((3S)-4-((2-methyl-2H-indazol-4-yl)carbonyl)morpholin-3-yl)methyl)-4-(5-(trifluoromethyl)-1,2,4-oxadiazol-3-yl)benzamide | 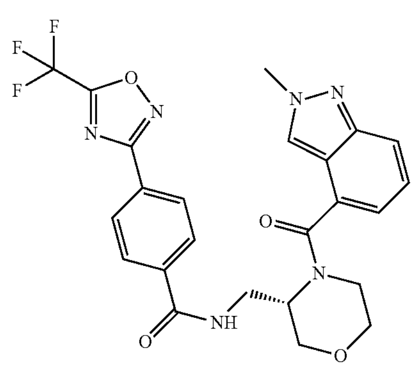 [SMILES: Cn1cc2c(C(=O)N3CCOC[C@@H]3CNC(=O)c3ccc(-c4noc(C(F)(F)F)n4)cc3)cccc2n1] | 515.0 [M + H]+ |

TABLE 1-continued

| Example No. | IUPAC name | Structure | MS (found) |
|---|---|---|---|
| 86 | N-(((3S)-4-(3-chloro-5-cyanobenzoyl)morpholin-3-yl)methyl)-4-(5-(trifluoromethyl)-1,2,4-oxadiazol-3-yl)benzamide | 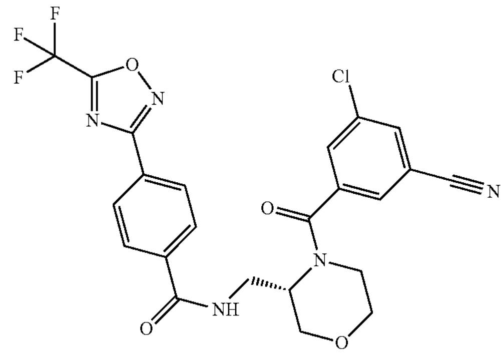 | 520.0 [M + H]+ |
| 87 | N-(((3S)-4-(4-cyano-2-methylbenzoyl)morpholin-3-yl)methyl)-4-(5-(trifluoromethyl)-1,2,4-oxadiazol-3-yl)benzamide | 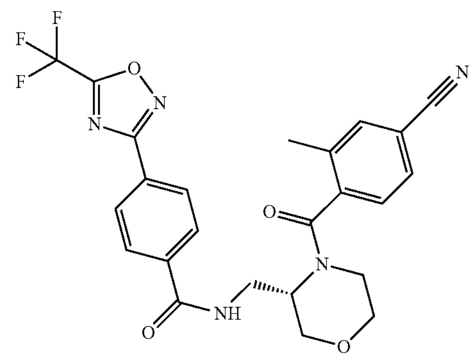 [SMILES: Cc1cc(C#N)ccc1C(=O)N1CCOC[C@@H]1CNC(=O)c1ccc(-c2noc(C(F)(F)F)n2)cc1] | 500.1 [M + H]+ |
| 88 | N-(((3S)-4-((3,5-dimethyl-1,2-oxazol-4-yl)carbonyl)morpholin-3-yl)methyl)-4-(5-(trifluoromethyl)-1,2,4-oxadiazol-3-yl)benzamide | 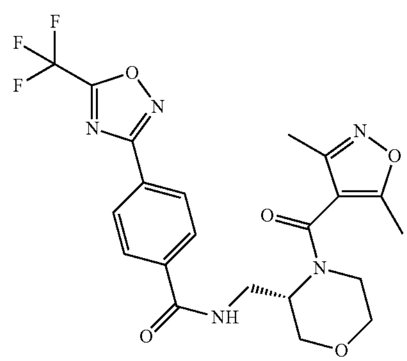 [SMILES: Cc1noc(C)c1C(=O)N1CCOC[C@@H]1CNC(=O)c1ccc(-c2noc(C(F)(F)F)n2)cc1] | 478.1 [M − H]− |
| 89 | N-(((3S)-4-(piperidin-1-ylcarbonyl)morpholin-3-yl)methyl)-4-(5-(trifluoromethyl)-1,2,4-oxadiazol-3-yl)benzamide | 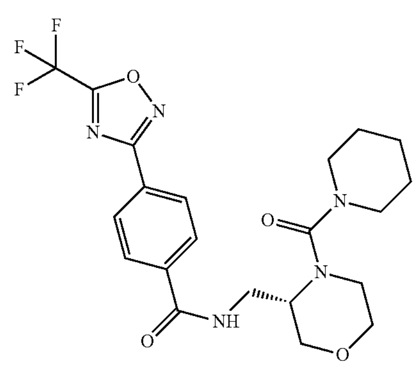 [SMILES: O=C(NC[C@H]1COCCN1C(=O)N1CCCCC1)c1ccc(-c2noc(C(F)(F)F)n2)cc1] | 466.1 [M − H]− |

TABLE 1-continued

| Example No. | IUPAC name | Structure | MS (found) |
|---|---|---|---|
| 90 | 2-((3S)-4-((2-methyl-2H-indazol-3-yl)carbonyl)morpholin-3-yl)-N-(4-(5-(trifluoromethyl)-1,2,4-oxadiazol-3-yl)phenyl)acetamide | 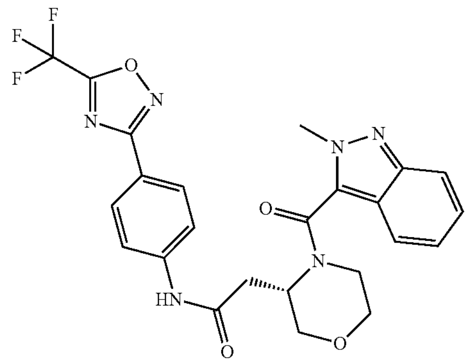 [SMILES: Cn1nc2ccccc2c1C(=O)N1CCOC[C@@H]1CC(=O)Nc1ccc(-c2noc(C(F)(F)F)n2)cc1] | 515.0 [M + H]+ |
| 91 | N-(((3S)-4-((6-methylimidazo[2,1-b][1,3]thiazol-5-yl)carbonyl)morpholin-3-yl)methyl)-4-(5-(trifluoromethyl)-1,2,4-oxadiazol-3-yl)benzamide | 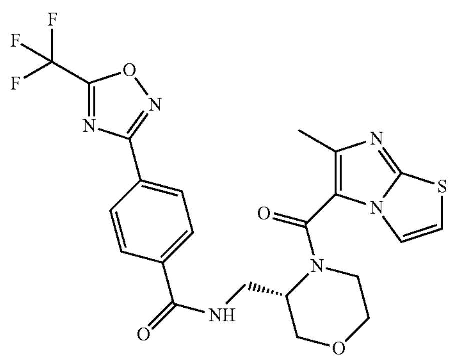 [SMILES: Cc1nc2sccn2c1C(=O)N1CCOC[C@@H]1CNC(=O)c1ccc(-c2noc(C(F)(F)F)n2)cc1] | 521.0 [M + H]+ |
| 92 | N-(((3S)-4-((2-methylimidazo[1,2-a]pyridin-3-yl)carbonyl)morpholin-3-yl)methyl)-4-(5-(trifluoromethyl)-1,2,4-oxadiazol-3-yl)benzamide | 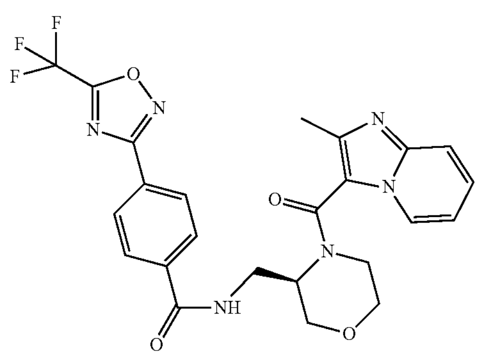 [SMILES: Cc1nc2ccccn2c1C(=O)N1CCOC[C@H]1CNC(=O)c1ccc(-c2noc(C(F)(F)F)n2)cc1] | 515.0 [M + H]+ |
| 93 | N-(((3S)-4-((2-methyl-4,5,6,7-tetrahydro-2H-indazol-3-yl)carbonyl)morpholin-3-yl)methyl)-4-(5-(trifluoromethyl)-1,2,4-oxadiazol-3-yl)benzamide | 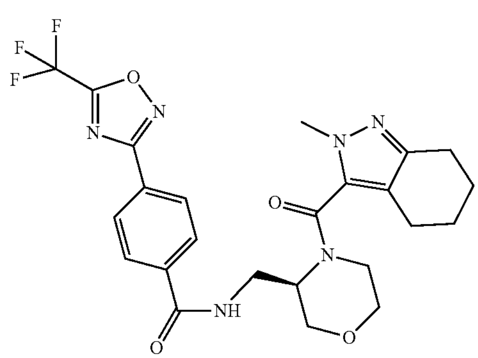 [SMILES: Cn1nc2c(c1C(=O)N1CCOC[C@H]1CNC(=O)c1ccc(-c3noc(C(F)(F)F)n3)cc1)CCCC2] | 519.1 [M + H]+ |

TABLE 1-continued

| Example No. | IUPAC name | Structure | MS (found) |
|---|---|---|---|
| 94 | N-(((3S)-4-((3-methyl-1,2-oxazol-4-yl)carbonyl)morpholin-3-yl)methyl)-4-(5-(trifluoromethyl)-1,2,4-oxadiazol-3-yl)benzamide | 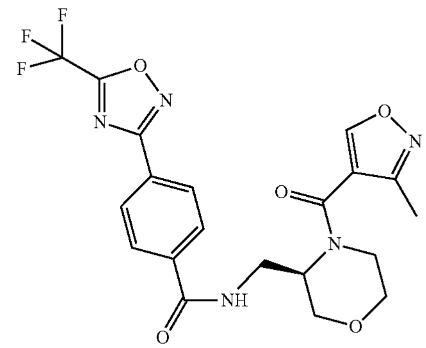 [SMILES: Cc1nocc1C(=O)N1CCOC[C@H]1CNC(=O)c1ccc(-c2noc(C(F)(F)F)n2)cc1] | 466.0 [M + H]+ |
| 95 | N-(((3S)-4-(2-methyl-2-phenylpropanoyl)morpholin-3-yl)methyl)-4-(5-(trifluoromethyl)-1,2,4-oxadiazol-3-yl)benzamide | 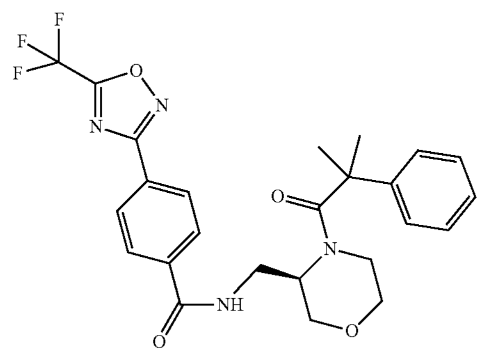 [SMILES: CC(C)(C(=O)N1CCOC[C@H]1CNC(=O)c1ccc(-c2noc(C(F)(F)F)n2)cc1)c1ccccc1] | 503.0 [M + H]+ |
| 96 | N-(((3S)-4-(difluoro(phenyl)acetyl)morpholin-3-yl)methyl)-4-(5-(trifluoromethyl)-1,2,4-oxadiazol-3-yl)benzamide | 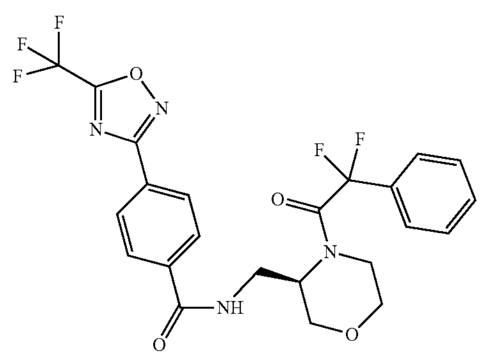 [SMILES: O=C(NC[C@@H]1COCCN1C(=O)C(F)(F)c1ccccc1)c1ccc(-c2noc(C(F)(F)F)n2)cc1] | 511.0 [M + H]+ |
| 97 | N-(((3S)-4-(adamantan-1-ylcarbonyl)morpholin-3-yl)methyl)-4-(5-(trifluoromethyl)-1,2,4-oxadiazol-3-yl)benzamide | 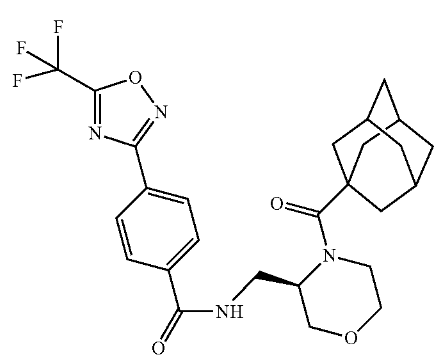 [SMILES: O=C(NC[C@@H]1COCCN1C(=O)C12CC3CC(CC(C3)C1)C2)c1ccc(-c2noc(C(F)(F)F)n2)cc1] | 519.0 [M + H]+ |

TABLE 1-continued

| Example No. | IUPAC name | Structure | MS (found) |
|---|---|---|---|
| 98 | (3S)-N-methyl-N-phenyl-3-(((4-(5-(trifluoromethyl)-1,2,4-oxadiazol-3-yl)benzoyl)amino)methyl)morpholine-4-carboxamide | 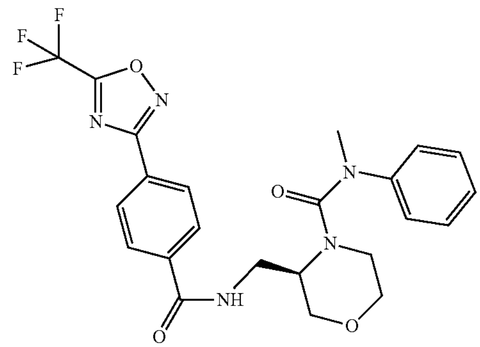 [SMILES: CN(C(=O)N1CCOC[C@H]1CNC(=O)c1ccc(-c2noc(C(F)(F)F)n2)cc1)c1ccccc1] | 490.1 [M + H]+ |
| 99 | N-(((3S)-4-(morpholin-4-ylcarbonyl)morpholin-3-yl)methyl)-4-(5-(trifluoromethyl)-1,2,4-oxadiazol-3-yl)benzamide | 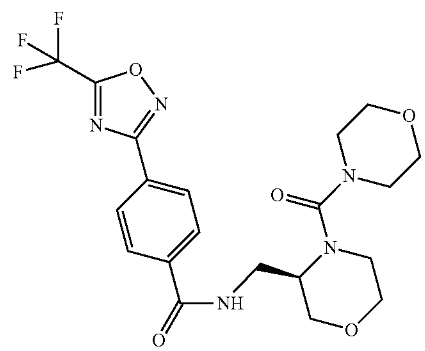 [SMILES: O=C(NC[C@@H]1COCCN1C(=O)N1CCOCC1)c1ccc(-c2noc(C(F)(F)F)n2)cc1] | 468.1 [M − H]− |
| 100 | N-(((3S)-4-(pyrrolidin-1-ylcarbonyl)morpholin-3-yl)methyl)-4-(5-(trifluoromethyl)-1,2,4-oxadiazol-3-yl)benzamide | 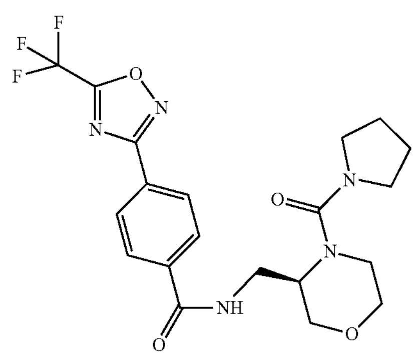 [SMILES: O=C(NC[C@@H]1COCCN1C(=O)N1CCCC1)c1ccc(-c2noc(C(F)(F)F)n2)cc1] | 454.0 [M + H]+ |
| 101 | N-(((3S)-4-(2-methyl-2-(1H-pyrazol-1-yl)propanoyl)morpholin-3-yl)methyl)-4-(5-(trifluoromethyl)-1,2,4-oxadiazol-3-yl)benzamide | 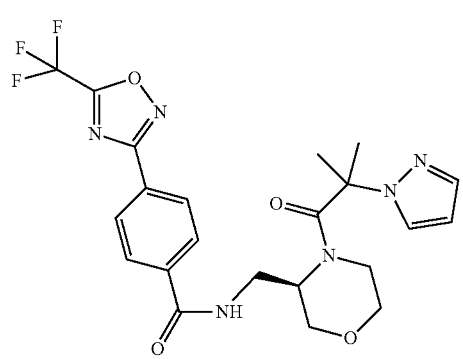 [SMILES: CC(C)(C(=O)N1CCOC[C@H]1CNC(=O)c1ccc(-c2noc(C(F)(F)F)n2)cc1)n1cccn1] | 493.1 [M + H]+ |

TABLE 1-continued

| Example No. | IUPAC name | Structure | MS (found) |
| --- | --- | --- | --- |
| 102 | N-(((3S)-4-((3-ethyl-5-methyl-1,2-oxazol-4-yl)carbonyl)morpholin-3-yl)methyl)-4-(5-(trifluoromethyl)-1,2,4-oxadiazol-3-yl)benzamide | 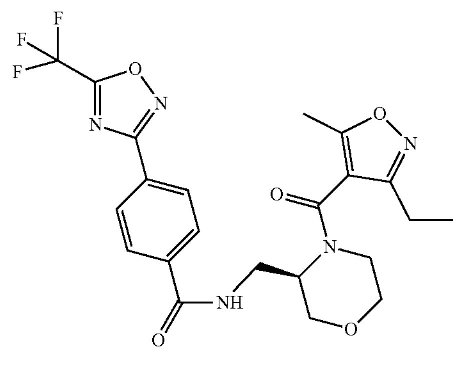 [SMILES: CCc1noc(C)c1C(=O)N1CCOC[C@H]1CNC(=O)c1ccc(-c2noc(C(F)(F)F)n2)cc1] | 494.0 [M + H]+ |
| 103 | N-(((3S)-4-((3-phenyloxetan-3-yl)carbonyl)morpholin-3-yl)methyl)-4-(5-(trifluoromethyl)-1,2,4-oxadiazol-3-yl)benzamide | 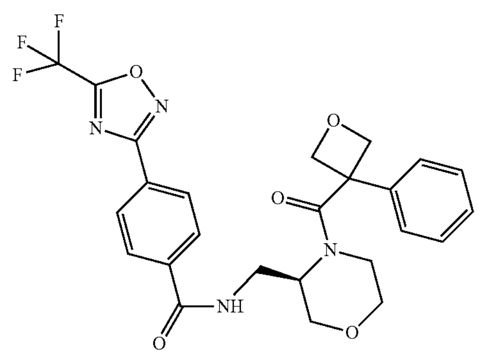 [SMILES: O=C(NC[C@@H]1COCCN1C(=O)C1(c2ccccc2)COC1)c1ccc(-c2noc(C(F)(F)F)n2)cc1] | 515.0 [M − H]− |
| 104 | N-(((3S)-4-((2-oxopyrrolidin-3-yl)carbonyl)morpholin-3-yl)methyl)-4-(5-(trifluoromethyl)-1,2,4-oxadiazol-3-yl)benzamide | 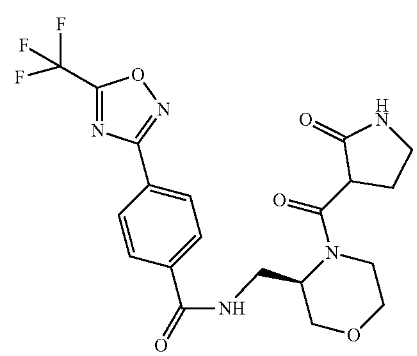 [SMILES: O=C(NC[C@@H]1COCCN1C(=O)C1CCNC1=O)c1ccc(-c2noc(C(F)(F)F)n2)cc1] | 468.0 [M + H]+ |
| 105 | N-(((3S)-4-((2-oxopyrrolidin-3-yl)carbonyl)morpholin-3-yl)methyl)-4-(5-(trifluoromethyl)-1,2,4-oxadiazol-3-yl)benzamide | 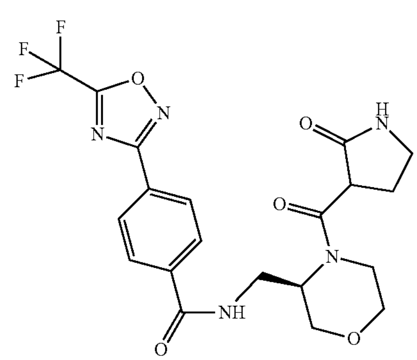 [SMILES: O=C(NC[C@@H]1COCCN1C(=O)C1CCNC1=O)c1ccc(-c2noc(C(F)(F)F)n2)cc1] | 468.0 [M + H]+ |

TABLE 1-continued

| Example No. | IUPAC name | Structure | MS (found) |
|---|---|---|---|
| 106 | N-(((3S)-4-((1-ethyl-1H-pyrazol-5-yl)carbonyl)morpholin-3-yl)methyl)-4-(5-(trifluoromethyl)-1,2,4-oxadiazol-3-yl)benzamide | 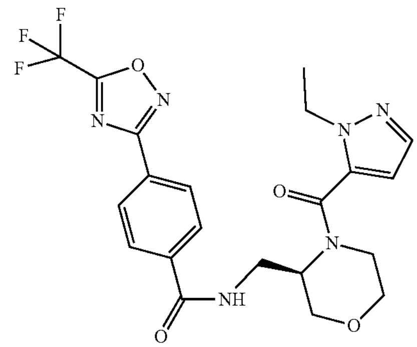 [SMILES: CCn1nccc1C(=O)N1CCOC[C@H]1CNC(=O)c1ccc(-c2noc(C(F)(F)F)n2)cc1] | 479.0 [M + H]+ |
| 107 | N-(((3S)-4-((2-(hydroxymethyl)pyrrolidin-1-yl)carbonyl)morpholin-3-yl)methyl)-4-(5-(trifluoromethyl)-1,2,4-oxadiazol-3-yl)benzamide | 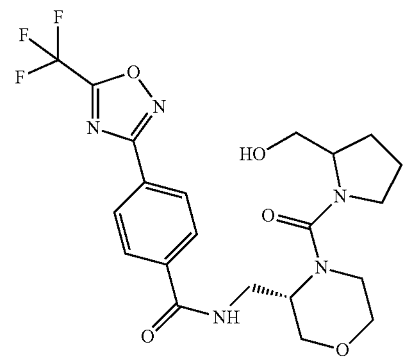 [SMILES: O=C(NC[C@H]1COCCN1C(=O)N1CCCC1CO)c1ccc(-c2noc(C(F)(F)F)n2)cc1] | 484.1 [M + H]+ |
| 108 | N-(((3S)-4-((2-(hydroxymethyl)pyrrolidin-1-yl)carbonyl)morpholin-3-yl)methyl)-4-(5-(trifluoromethyl)-1,2,4-oxadiazol-3-yl)benzamide | 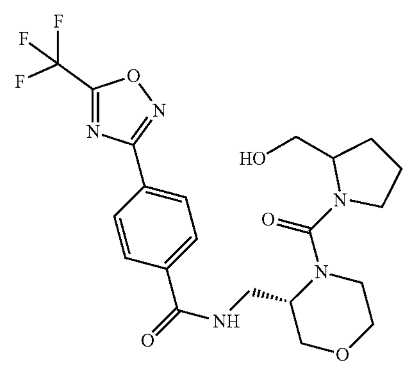 [SMILES: O=C(NC[C@H]1COCCN1C(=O)N1CCCC1CO)c1ccc(-c2noc(C(F)(F)F)n2)cc1] | 484.1 [M + H]+ |
| 109 | N-(((3S)-4-(3-oxa-8-azabicyclo[3.2.1]oct-8-ylcarbonyl)morpholin-3-yl)methyl)-4-(5-(trifluoromethyl)-1,2,4-oxadiazol-3-yl)benzamide | 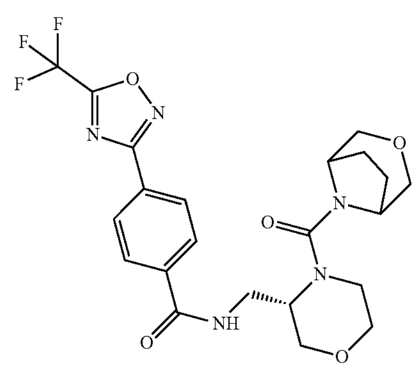 [SMILES: O=C(NC[C@H]1COCCN1C(=O)N1C2CCC1COC2)c1ccc(-c2noc(C(F)(F)F)n2)cc1] | 496.0 [M + H]+ |

TABLE 1-continued

| Example No. | IUPAC name | Structure | MS (found) |
|---|---|---|---|
| 110 | N-(((3S)-4-(8-oxa-3-azabicyclo[3.2.1]oct-3-ylcarbonyl)morpholin-3-yl)methyl)-4-(5-(trifluoromethyl)-1,2,4-oxadiazol-3-yl)benzamide | 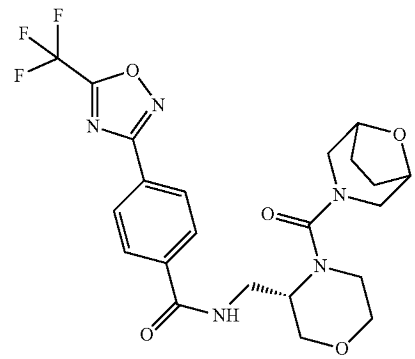 [SMILES: O=C(NC[C@H]1COCCN1C(=O)N1CC2CCC(C1)O2)c1ccc(-c2noc(C(F)(F)F)n2)cc1] | 496.1 [M + H]+ |
| 111 | N-(((3R)-4-benzoylmorpholin-3-yl)methyl)-4-(5-(trifluoromethyl)-1,2,4-oxadiazol-3-yl)benzamide | 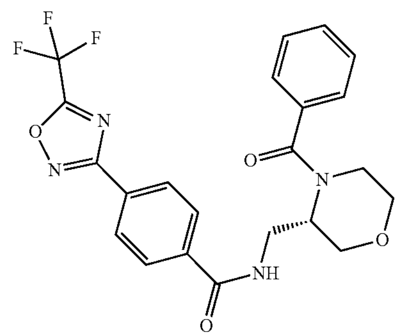 [SMILES: O=C(NC[C@H]1COCCN1C(=O)c1ccccc1)c1ccc(-c2noc(C(F)(F)F)n2)cc1] | 461.1 [M + H]+ |
| 112 | N-(((3R)-4-(3,5-dichlorobenzoyl)morpholin-3-yl)methyl)-4-(5-(trifluoromethyl)-1,2,4-oxadiazol-3-yl)benzamide | 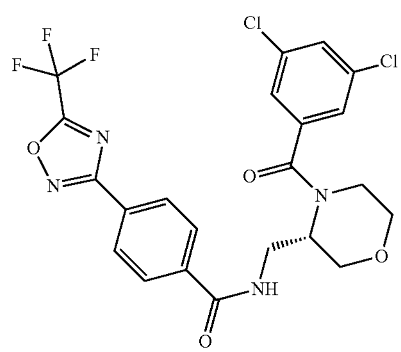 [SMILES: O=C(NC[C@H]1COCCN1C(=O)c1cc(Cl)cc(Cl)c1)c1ccc(-c2noc(C(F)(F)F)n2)cc1] | 529.0 [M + H]+ |
| 113 | N-(((3R)-4-(3-fluorobenzoyl)morpholin-3-yl)methyl)-4-(5-(trifluoromethyl)-1,2,4-oxadiazol-3-yl)benzamide | 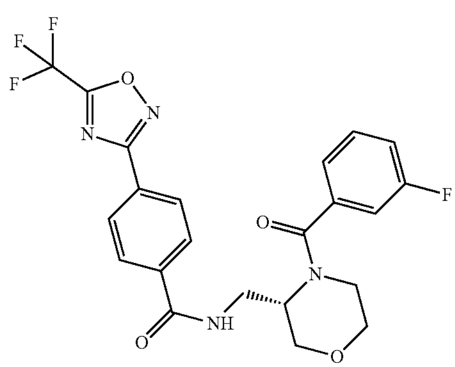 [SMILES: O=C(NC[C@H]1COCCN1C(=O)c1cccc(F)c1)c1ccc(-c2noc(C(F)(F)F)n2)cc1] | 479.1 [M + H]+ |

TABLE 1-continued

| Example No. | IUPAC name | Structure | MS (found) |
|---|---|---|---|
| 114 | N-(((3R)-4-(3-methoxybenzoyl)morpholin-3-yl)methyl)-4-(5-(trifluoromethyl)-1,2,4-oxadiazol-3-yl)benzamide | 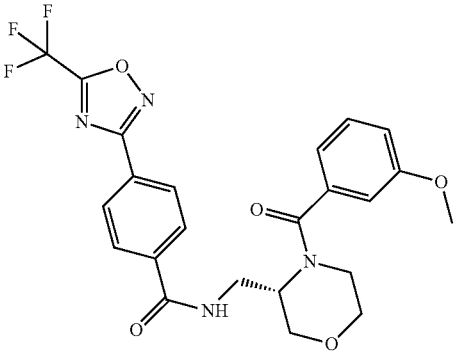 [SMILES: COc1cccc(C(=O)N2CCOC[C@@H]2CNC(=O)c2ccc(-c3noc(C(F)(F)F)n3)cc2)c1] | 491.1 [M + H]+ |
| 115 | N-(((3R)-4-(2-cyanobenzoyl)morpholin-3-yl)methyl)-4-(5-(trifluoromethyl)-1,2,4-oxadiazol-3-yl)benzamide | 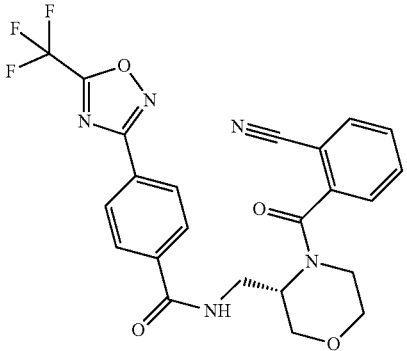 [SMILES: N#Cc1ccccc1C(=O)N1CCOC[C@@H]1CNC(=O)c1ccc(-c2noc(C(F)(F)F)n2)cc1] | 486.1 [M + H]+ |
| 116 | N-(((3R)-4-(3-cyanobenzoyl)morpholin-3-yl)methyl)-4-(5-(trifluoromethyl)-1,2,4-oxadiazol-3-yl)benzamide | 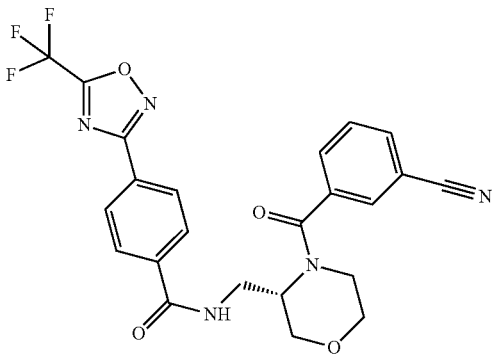 [SMILES: N#Cc1cccc(C(=O)N2CCOC[C@@H]2CNC(=O)c2ccc(-c3noc(C(F)(F)F)n3)cc2)c1] | 484.1 [M − H]− |
| 117 | N-(((3R)-4-(4-cyanobenzoyl)morpholin-3-yl)methyl)-4-(5-(trifluoromethyl)-1,2,4-oxadiazol-3-yl)benzamide | 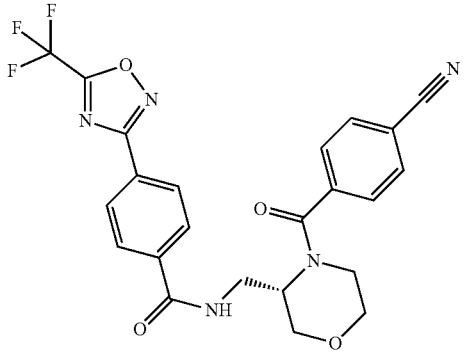 [SMILES: N#Cc1ccc(C(=O)N2CCOC[C@@H]2CNC(=O)c2ccc(-c3noc(C(F)(F)F)n3)cc2)cc1] | 486.1 [M + H]+ |

TABLE 1-continued

| Example No. | IUPAC name | Structure | MS (found) |
|---|---|---|---|
| 118 | N-(((3R)-4-(2-(morpholin-4-yl)benzoyl)morpholin-3-yl)methyl)-4-(5-(trifluoromethyl)-1,2,4-oxadiazol-3-yl)benzamide | 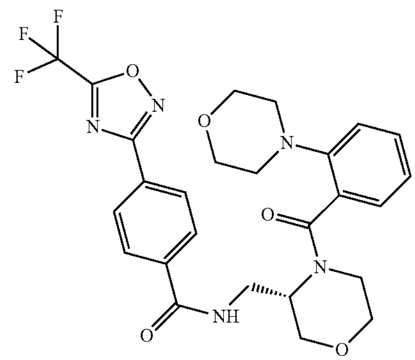 [SMILES: O=C(NC[C@H]1COCCN1C(=O)c1ccccc1N1CCOCC1)c1ccc(-c2noc(C(F)(F)F)n2)cc1] | 546.1 [M + H]+ |
| 119 | N-(((3R)-4-(3,4,5-trifluorobenzoyl)morpholin-3-yl)methyl)-4-(5-(trifluoromethyl)-1,2,4-oxadiazol-3-yl)benzamide | 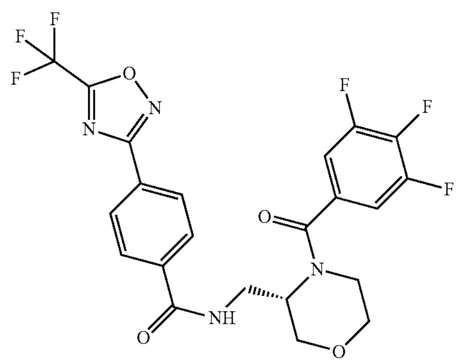 [SMILES: O=C(NC[C@H]1COCCN1C(=O)c1cc(F)c(F)c(F)c1)c1ccc(-c2noc(C(F)(F)F)n2)cc1] | 513.0 [M − H]− |
| 120 | N-(((3R)-4-isonicotinoylmorpholin-3-yl)methyl)-4-(5-(trifluoromethyl)-1,2,4-oxadiazol-3-yl)benzamide | 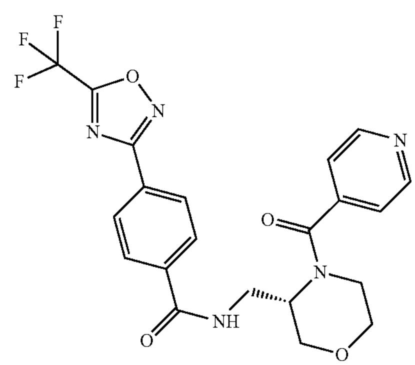 [SMILES: O=C(NC[C@H]1COCCN1C(=O)c1ccncc1)c1ccc(-c2noc(C(F)(F)F)n2)cc1] | 462.1 [M + H]+ |
| 121 | N-(((3R)-4-(2-methylisonicotinoyl)morpholin-3-yl)methyl)-4-(5-(trifluoromethyl)-1,2,4-oxadiazol-3-yl)benzamide | 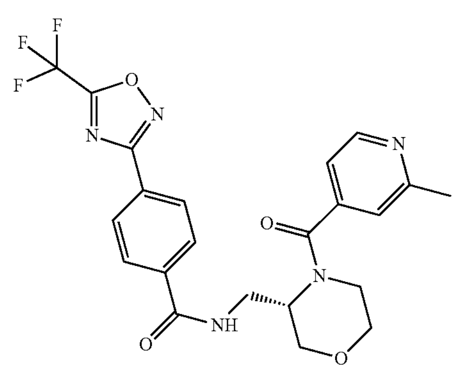 [SMILES: Cc1cc(C(=O)N2CCOC[C@@H]2CNC(=O)c2ccc(-c3noc(C(F)(F)F)n3)cc2)ccn1] | 476.1 [M + H]+ |

TABLE 1-continued

| Example No. | IUPAC name | Structure | MS (found) |
|---|---|---|---|
| 122 | N-(((3R)-4-(2-hydroxy-6-methylisonicotinoyl)morpholin-3-yl)methyl)-4-(5-(trifluoromethyl)-1,2,4-oxadiazol-3-yl)benzamide | 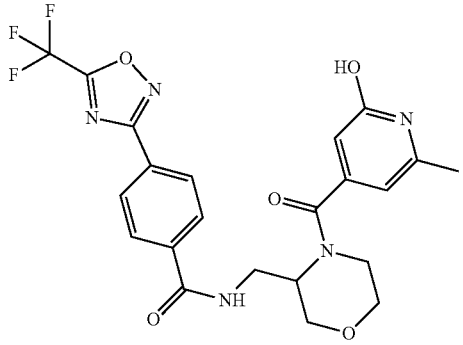 [SMILES: Cc1cc(C(=O)N2CCOCC2CNC(=O)c2ccc(-c3noc(C(F)(F)F)n3)cc2)cc(O)n1] | 492.2 [M + H]+ |
| 123 | N-(((3R)-4-((6-(2,2,2-trifluoroethoxy)pyridin-3-yl)carbonyl)morpholin-3-yl)methyl)-4-(5-(trifluoromethyl)-1,2,4-oxadiazol-3-yl)benzamide | 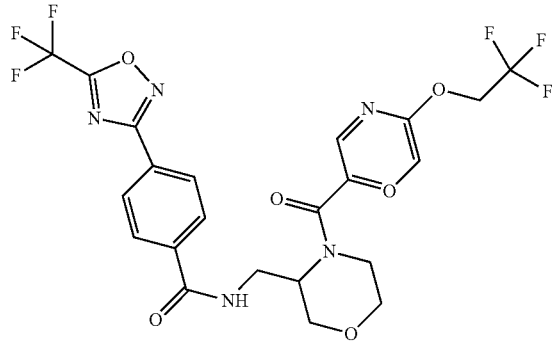 | 560.1 [M + H]+ |
| 124 | N-(((3R)-4-(3,4-dihydro-2H-chromen-2-ylcarbonyl)morpholin-3-yl)methyl)-4-(5-(trifluoromethyl)-1,2,4-oxadiazol-3-yl)benzamide | 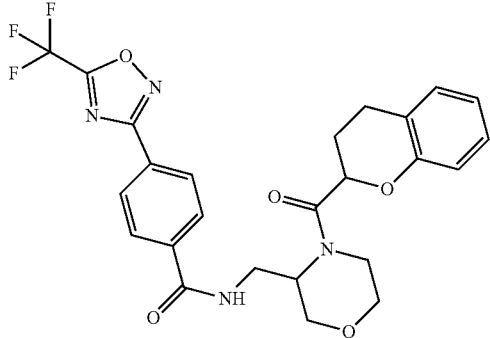 [SMILES: O=C(NCC1COCCN1C(=O)C1CCc2ccccc2O1)c1ccc(-c2noc(C(F)(F)F)n2)cc1] | 517.2 [M + H]+ |
| 125 | N-(((3R)-4-(1-benzofuran-2-ylcarbonyl)morpholin-3-yl)methyl)-4-(5-(trifluoromethyl)-1,2,4-oxadiazol-3-yl)benzamide | 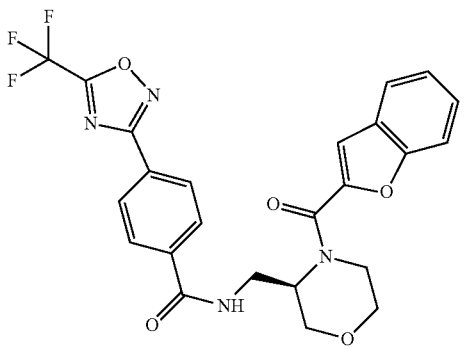 [SMILES: O=C(NC[C@@H]1COCCN1C(=O)c1cc2ccccc2o1)c1ccc(-c2noc(C(F)(F)F)n2)cc1] | 501.1 [M + H]+ |

TABLE 1-continued

| Example No. | IUPAC name | Structure | MS (found) |
|---|---|---|---|
| 126 | N-(((3R)-4-(pyrazolo[1,5-a]pyrimidin-2-ylcarbonyl)morpholin-3-yl)methyl)-4-(5-(trifluoromethyl)-1,2,4-oxadiazol-3-yl)benzamide | 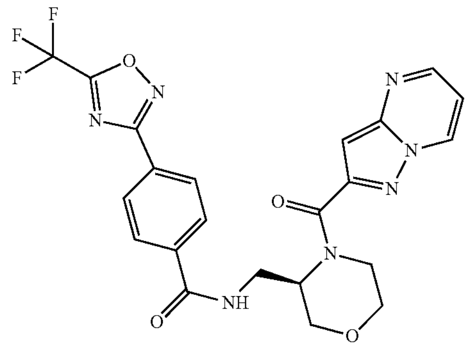 [SMILES: O=C(NC[C@@H]1COCCN1C(=O)c1cc2ncccn2n1)c1ccc(-c2noc(C(F)(F)F)n2)cc1] | 502.2 [M + H]+ |
| 127 | N-(((3R)-4-((1-cyanocyclopropyl)carbonyl)morpholin-3-yl)methyl)-4-(5-(trifluoromethyl)-1,2,4-oxadiazol-3-yl)benzamide | 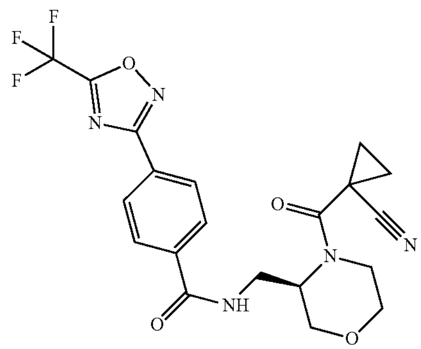 [SMILES: N#CC1(C(=O)N2CCOC[C@H]2CNC(=O)c2ccc(-c3noc(C(F)(F)F)n3)cc2)CC1] | 450.1 [M + H]+ |
| 128 | N-(((3R)-4-((1-phenylcyclopropyl)carbonyl)morpholin-3-yl)methyl)-4-(5-(trifluoromethyl)-1,2,4-oxadiazol-3-yl)benzamide | 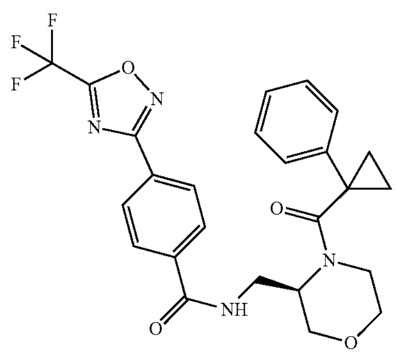 [SMILES: O=C(NC[C@@H]1COCCN1C(=O)C1(c2ccccc2)CC1)c1ccc(-c2noc(C(F)(F)F)n2)cc1] | 501.2 [M + H]+ |
| 129 | N-(((3R)-4-(diphenylacetyl)morpholin-3-yl)methyl)-4-(5-(trifluoromethyl)-1,2,4-oxadiazol-3-yl)benzamide | 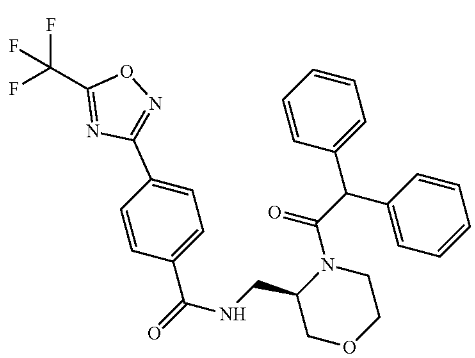 [SMILES: O=C(NC[C@@H]1COCCN1C(=O)C(c1ccccc1)c1ccccc1)c1ccc(-c2noc(C(F)(F)F)n2)cc1] | 551.1 [M + H]+ |

TABLE 1-continued

| Example No. | IUPAC name | Structure | MS (found) |
|---|---|---|---|
| 130 | N-(((3R)-4-(phenoxyacetyl)morpholin-3-yl)methyl)-4-(5-(trifluoromethyl)-1,2,4-oxadiazol-3-yl)benzamide | 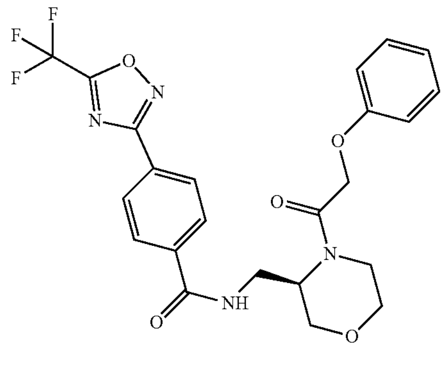 [SMILES: O=C(NC[C@@H]1COCCN1C(=O)COc1ccccc1)c1ccc(-c2noc(C(F)(F)F)n2)cc1] | 491.1 [M + H]+ |
| 131 | N-(((3R)-4-((5-methyl-1,2-oxazol-4-yl)carbonyl)morpholin-3-yl)methyl)-4-(5-(trifluoromethyl)-1,2,4-oxadiazol-3-yl)benzamide | 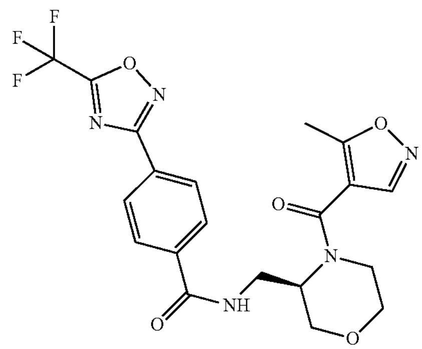 [SMILES: Cc1oncc1C(=O)N1CCOC[C@H]1CNC(=O)c1ccc(-c2noc(C(F)(F)F)n2)cc1] | 466.1 [M + H]+ |
| 132 | N-(((3R)-4-((4-methyl-1,2,5-oxadiazol-3-yl)carbonyl)morpholin-3-yl)methyl)-4-(5-(trifluoromethyl)-1,2,4-oxadiazol-3-yl)benzamide | 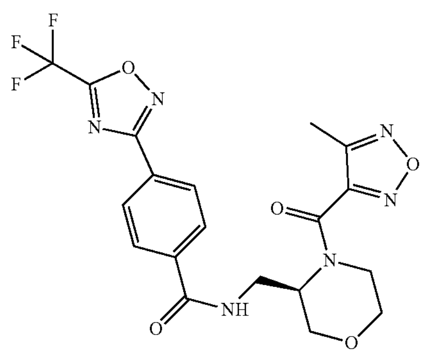 [SMILES: Cc1nonc1C(=O)N1CCOC[C@H]1CNC(=O)c1ccc(-c2noc(C(F)(F)F)n2)cc1] | 467.1 [M + H]+ |
| 133 | N-(((3R)-4-(1,2-oxazol-5-ylcarbonyl)morpholin-3-yl)methyl)-4-(5-(trifluoromethyl)-1,2,4-oxadiazol-3-yl)benzamide | 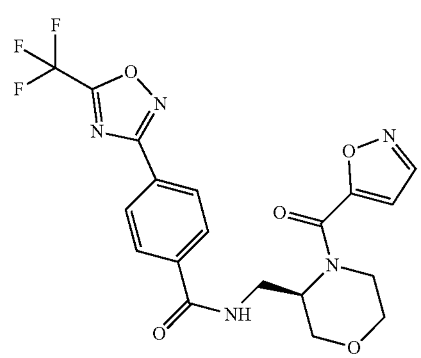 [SMILES: O=C(NC[C@@H]1COCCN1C(=O)c1ccno1)c1ccc(-c2noc(C(F)(F)F)n2)cc1] | 452.1 [M + H]+ |

TABLE 1-continued

| Example No. | IUPAC name | Structure | MS (found) |
|---|---|---|---|
| 134 | N-(((3R)-4-((3-methyl-1,2-oxazol-5-yl)carbonyl)morpholin-3-yl)methyl)-4-(5-(trifluoromethyl)-1,2,4-oxadiazol-3-yl)benzamide | 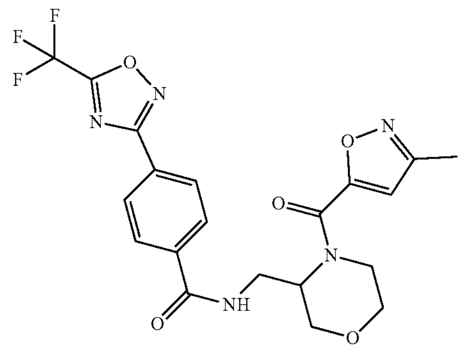 [SMILES: Cc1cc(C(=O)N2CCOCC2CNC(=O)c2ccc(-c3noc(C(F)(F)F)n3)cc2)on1] | 466.1 [M + H]+ |
| 135 | N-(((3R)-4-((1,3-dimethyl-1H-pyrazol-5-yl)carbonyl)morpholin-3-yl)methyl)-4-(5-(trifluoromethyl)-1,2,4-oxadiazol-3-yl)benzamide | 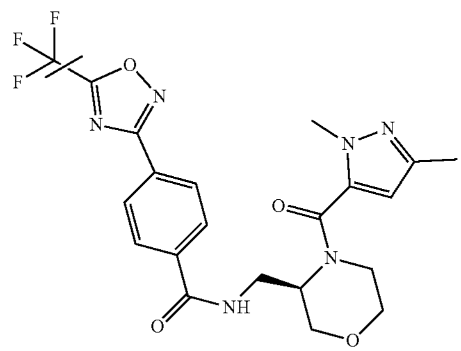 | 479.0 [M + H]+ |
| 136 | N-(((3R)-4-((1-methyl-3-(trifluoromethyl)-1H-pyrazol-5-yl)carbonyl)morpholin-3-yl)methyl)-4-(5-(trifluoromethyl)-1,2,4-oxadiazol-3-yl)benzamide | 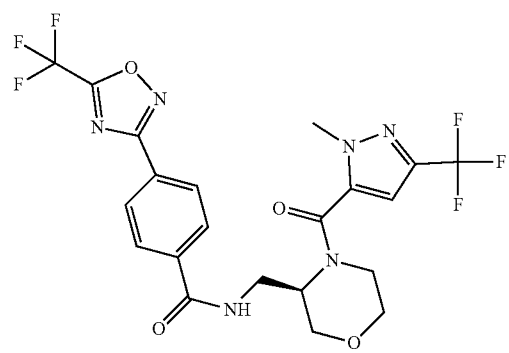 [SMILES: Cn1nc(C(F)(F)F)cc1C(=O)N1CCOC[C@H]1CNC(=O)c1ccc(-c2noc(C(F)(F)F)n2)cc1] | 531.1 [M − H]− |
| 137 | N-(((3R)-4-((1-methyl-1H-pyrazol-3-yl)carbonyl)morpholin-3-yl)methyl)-4-(5-(trifluoromethyl)-1,2,4-oxadiazol-3-yl)benzamide | 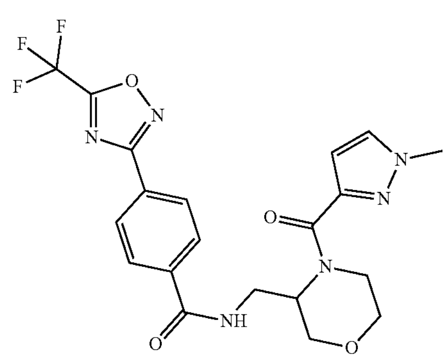 [SMILES: Cn1ccc(C(=O)N2CCOCC2CNC(=O)c2ccc(-c3noc(C(F)(F)F)n3)cc2)n1] | 465.1 [M + H]+ |

TABLE 1-continued

| Example No. | IUPAC name | Structure | MS (found) |
|---|---|---|---|
| 138 | N-(((3R)-4-((1-methyl-1H-pyrazol-4-yl)carbonyl)morpholin-3-yl)methyl)-4-(5-(trifluoromethyl)-1,2,4-oxadiazol-3-yl)benzamide | 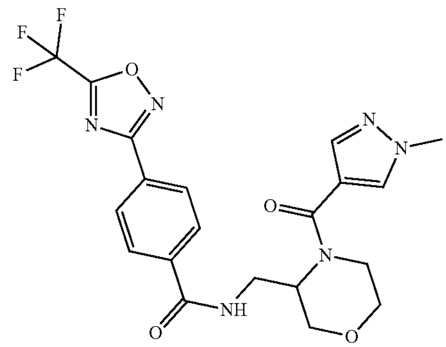 [SMILES: Cn1cc(C(=O)N2CCOCC2CNC(=O)c2ccc(-c3noc(C(F)(F)F)n3)cc2)cn1] | 465.1 [M + H]+ |
| 139 | 4-(5-(trifluoromethyl)-1,2,4-oxadiazol-3-yl)-N-(((3R)-4-((1,3,5-trimethyl-1H-pyrazol-4-yl)carbonyl)morpholin-3-yl)methyl)benzamide | 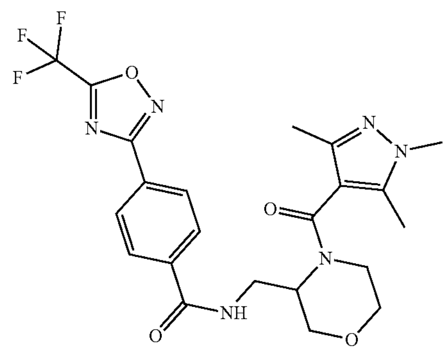 [SMILES: Cc1nn(C)c(C)c1C(=O)N1CCOCC1CNC(=O)c1ccc(-c2noc(C(F)(F)F)n2)cc1] | 493.2 [M + H]+ |
| 140 | N-(((3R)-4-((4-methyl-1,2,3-thiadiazol-5-yl)carbonyl)morpholin-3-yl)methyl)-4-(5-(trifluoromethyl)-1,2,4-oxadiazol-3-yl)benzamide | 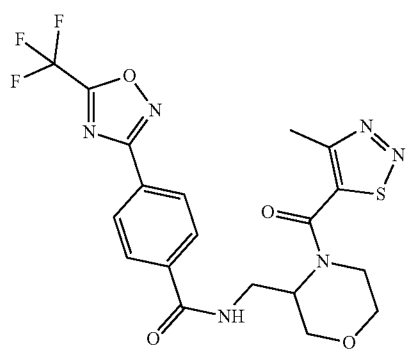 [SMILES: Cc1nnsc1C(=O)N1CCOCC1CNC(=O)c1ccc(-c2noc(C(F)(F)F)n2)cc1] | 483.0 [M + H]+ |
| 141 | N-(((3R)-4-((4-methyl-1,3-thiazol-5-yl)carbonyl)morpholin-3-yl)methyl)-4-(5-(trifluoromethyl)-1,2,4-oxadiazol-3-yl)benzamide | 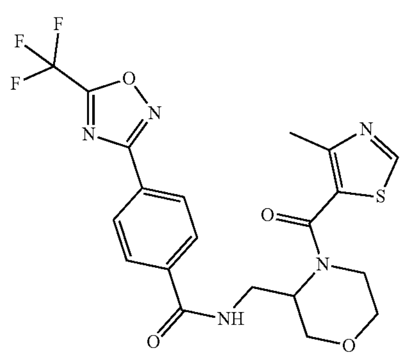 [SMILES: Cc1ncsc1C(=O)N1CCOCC1CNC(=O)c1ccc(-c2noc(C(F)(F)F)n2)cc1] | 482.0 [M + H]+ |

TABLE 1-continued

| Example No. | IUPAC name | Structure | MS (found) |
|---|---|---|---|
| 142 | N-(((3R)-4-(1,2,3-thiadiazol-4-ylcarbonyl)morpholin-3-yl)methyl)-4-(5-(trifluoromethyl)-1,2,4-oxadiazol-3-yl)benzamide | 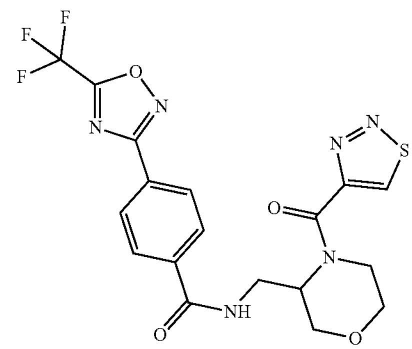 [SMILES: O=C(NCC1COCCN1C(=O)c1csnn1)c1ccc(-c2noc(C(F)(F)F)n2)cc1] | 469.1 [M + H]+ |
| 143 | N-(((3R)-4-(1H-pyrazol-3-ylcarbonyl)morpholin-3-yl)methyl)-4-(5-(trifluoromethyl)-1,2,4-oxadiazol-3-yl)benzamide | 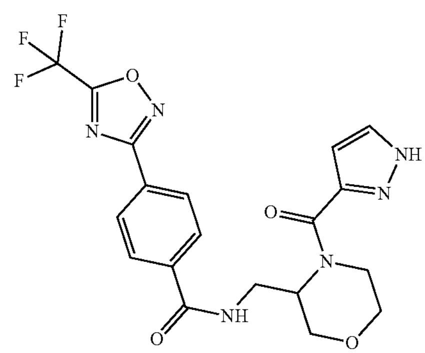 [SMILES: O=C(NCC1COCCN1C(=O)c1cc[nH]n1)c1ccc(-c2noc(C(F)(F)F)n2)cc1] | 451.1 [M + H]+ |
| 144 | N-(((3R)-4-((5-methyl-2-thienyl)carbonyl)morpholin-3-yl)methyl)-4-(5-(trifluoromethyl)-1,2,4-oxadiazol-3-yl)benzamide | 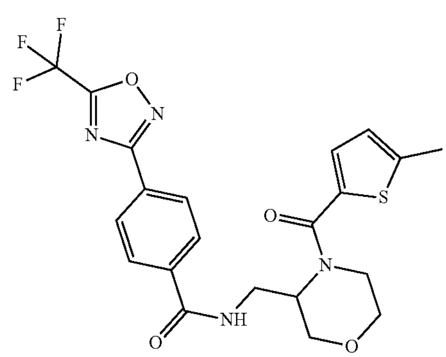 [SMILES: Cc1ccc(C(=O)N2CCOCC2CNC(=O)c2ccc(-c3noc(C(F)(F)F)n3)cc2)s1] | 481.0 [M + H]+ |
| 145 | N-(((3R)-4-((4-methyl-2-thienyl)carbonyl)morpholin-3-yl)methyl)-4-(5-(trifluoromethyl)-1,2,4-oxadiazol-3-yl)benzamide | 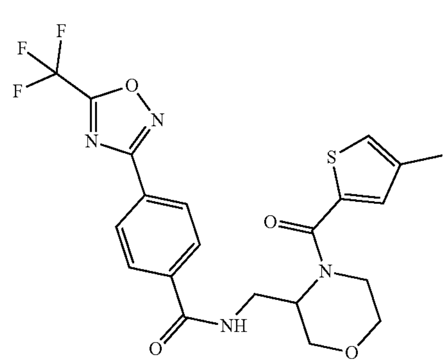 [SMILES: Cc1csc(C(=O)N2CCOCC2CNC(=O)c2ccc(-c3noc(C(F)(F)F)n3)cc2)c1] | 481.0 [M + H]+ |

TABLE 1-continued

| Example No. | IUPAC name | Structure | MS (found) |
|---|---|---|---|
| 146 | N-(((3R)-4-((3-methyl-2-thienyl)carbonyl)morpholin-3-yl)methyl)-4-(5-(trifluoromethyl)-1,2,4-oxadiazol-3-yl)benzamide | 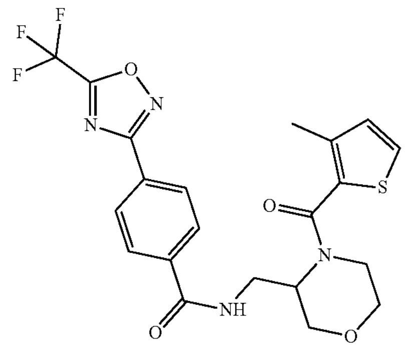 [SMILES: Cc1ccsc1C(=O)N1CCOCC1CNC(=O)c1ccc(-c2noc(C(F)(F)F)n2)cc1] | 481.0 [M + H]+ |
| 147 | N-(((3R)-4-(cyclopropylcarbonyl)morpholin-3-yl)methyl)-4-(5-(trifluoromethyl)-1,2,4-oxadiazol-3-yl)benzamide | 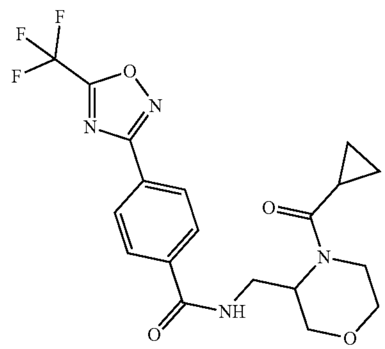 [SMILES: O=C(NCC1COCCN1C(=O)C1CC1)c1ccc(-c2noc(C(F)(F)F)n2)cc1] | 423.1 [M − H]− |
| 148 | N-(((3R)-4-(cyclopropylacetyl)morpholin-3-yl)methyl)-4-(5-(trifluoromethyl)-1,2,4-oxadiazol-3-yl)benzamide | 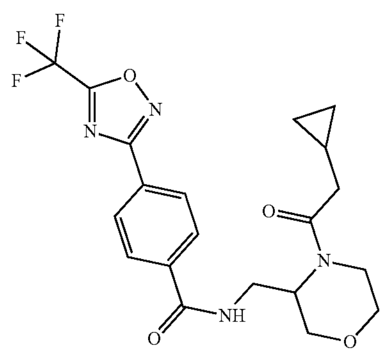 [SMILES: O=C(NCC1COCCN1C(=O)CC1CC1)c1ccc(-c2noc(C(F)(F)F)n2)cc1] | 437.1 [M − H]− |
| 149 | N-(((3R)-4-(cyclopentylcarbonyl)morpholin-3-yl)methyl)-4-(5-(trifluoromethyl)-1,2,4-oxadiazol-3-yl)benzamide | 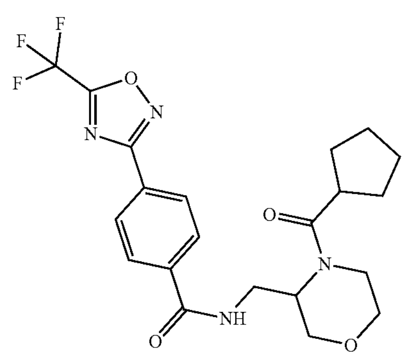 [SMILES: O=C(NCC1COCCN1C(=O)C1CCCC1)c1ccc(-c2noc(C(F)(F)F)n2)cc1] | 453.1 [M + H]+ |

TABLE 1-continued

| Example No. | IUPAC name | Structure | MS (found) |
|---|---|---|---|
| 150 | N-(((3R)-4-(tetrahydrofuran-2-ylcarbonyl)morpholin-3-yl)methyl)-4-(5-(trifluoromethyl)-1,2,4-oxadiazol-3-yl)benzamide | 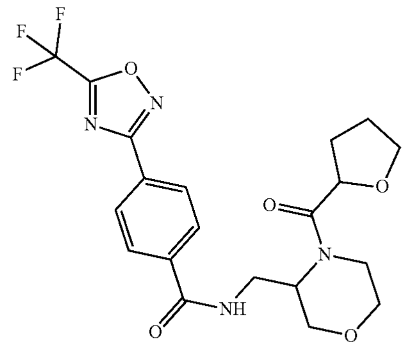 [SMILES: O=C(NCC1COCCN1C(=O)C1CCCO1)c1ccc(-c2noc(C(F)(F)F)n2)cc1] | 455.1 [M + H]+ |
| 151 | N-(((3R)-4-(tetrahydrofuran-3-ylcarbonyl)morpholin-3-yl)methyl)-4-(5-(trifluoromethyl)-1,2,4-oxadiazol-3-yl)benzamide | 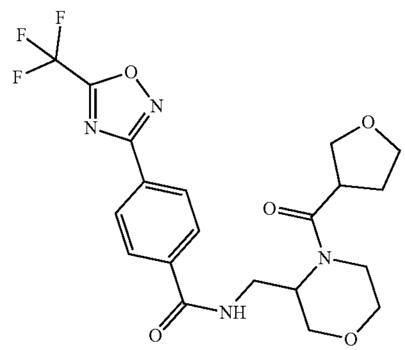 | 455.1 [M + H]+ |
| 152 | N-(((3R)-4-(cyclohexylcarbonyl)morpholin-3-yl)methyl)-4-(5-(trifluoromethyl)-1,2,4-oxadiazol-3-yl)benzamide | 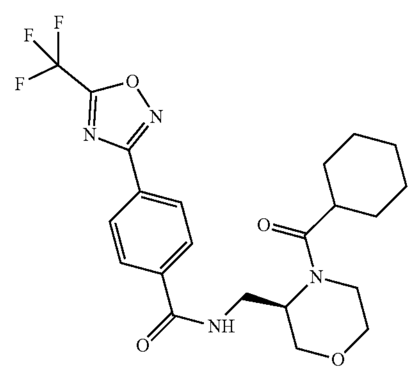 | 467.1 [M + H]+ |
| 153 | N-(((3R)-4-(tetrahydro-2H-pyran-4-ylcarbonyl)morpholin-3-yl)methyl)-4-(5-(trifluoromethyl)-1,2,4-oxadiazol-3-yl)benzamide | 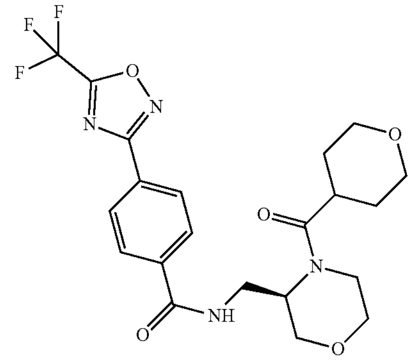 [SMILES: O=C(NC[C@@H]1COCCN1C(=O)C1CCOCC1)c1ccc(-c2noc(C(F)(F)F)n2)cc1] | 467.1 [M − H]− |

TABLE 1-continued

| Example No. | IUPAC name | Structure | MS (found) |
|---|---|---|---|
| 154 | N-(((3R)-4-((1-methyl-1H-pyrazol-5-yl)carbonyl)morpholin-3-yl)methyl)-4-(5-(trifluoromethyl)-1,2,4-oxadiazol-3-yl)benzamide | 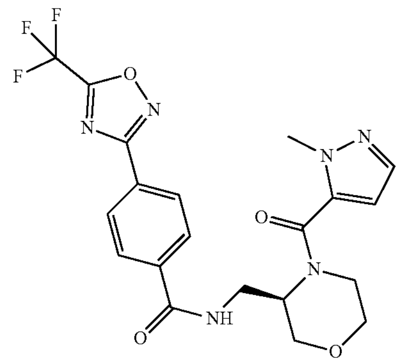 [SMILES: Cn1nccc1C(=O)N1CCOC[C@H]1CNC(=O)c1ccc(-c2noc(C(F)(F)F)n2)cc1] | 465.1 [M + H]+ |
| 155 | N-(((3R)-4-(3,5-difluorobenzoyl)morpholin-3-yl)methyl)-4-(5-(trifluoromethyl)-1,2,4-oxadiazol-3-yl)benzamide | 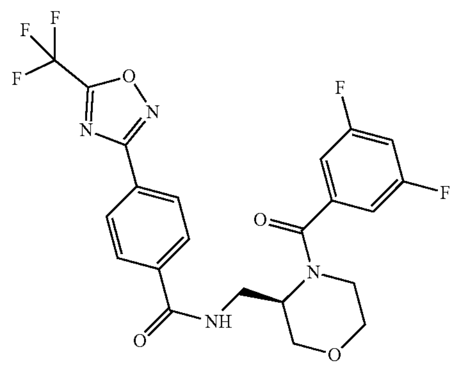 [SMILES: O=C(NC[C@@H]1COCCN1C(=O)c1cc(F)cc(F)c1)c1ccc(-c2noc(C(F)(F)F)n2)cc1] | 497.1 [M + H]+ |
| 156 | N-(((3R)-4-(3-cyano-5-fluorobenzoyl)morpholin-3-yl)methyl)-4-(5-(trifluoromethyl)-1,2,4-oxadiazol-3-yl)benzamide | 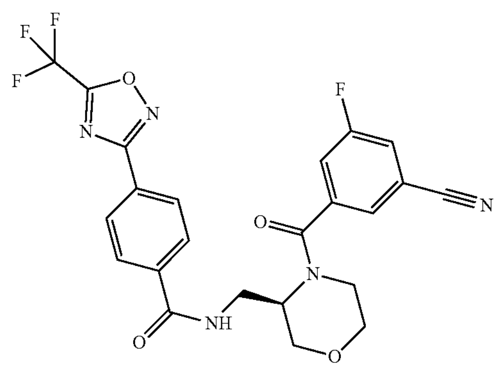 [SMILES: N#Cc1cc(F)cc(C(=O)N2CCOC[C@H]2CNC(=O)c2ccc(-c3noc(C(F)(F)F)n3)cc2)c1] | 502.0 [M − H]− |
| 157 | N-(((3R)-4-((2-methyl-2H-indazol-3-yl)carbonyl)morpholin-3-yl)methyl)-4-(5-(trifluoromethyl)-1,2,4-oxadiazol-3-yl)benzamide | 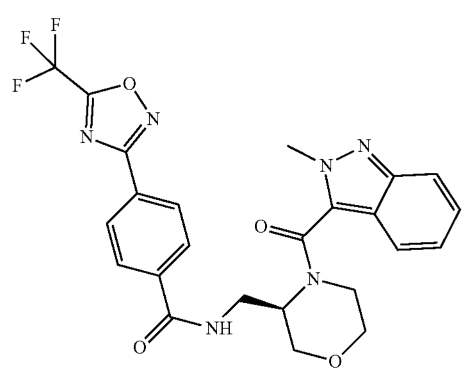 [SMILES: Cn1nc2ccccc2c1C(=O)N1CCOC[C@H]1CNC(=O)c1ccc(-c2noc(C(F)(F)F)n2)cc1] | 515.1 [M + H]+ |

TABLE 1-continued

| Example No. | IUPAC name | Structure | MS (found) |
|---|---|---|---|
| 158 | N-(((3R)-4-(piperidin-1-ylcarbonyl)morpholin-3-yl)methyl)-4-(5-(trifluoromethyl)-1,2,4-oxadiazol-3-yl)benzamide | 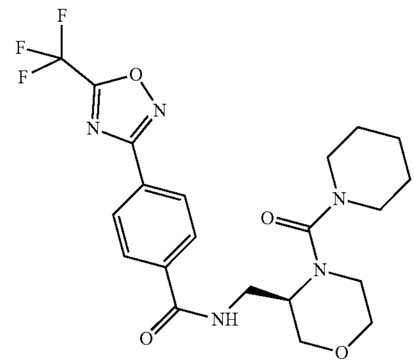 [SMILES: O=C(NC[C@@H]1COCCN1C(=O)N1CCCCC1)c1ccc(-c2noc(C(F)(F)F)n2)cc1] | 468.1 [M + H]+ |
| 159 | N-((4-benzoylmorpholin-3-yl)methyl)-N-methyl-4-(5-(trifluoromethyl)-1,2,4-oxadiazol-3-yl)benzamide | 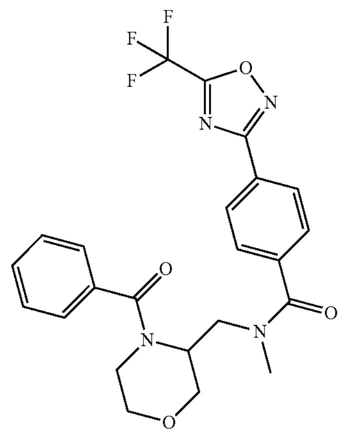 [SMILES: CN(CC1COCCN1C(=O)c1ccccc1)C(=O)c1ccc(-c2noc(C(F)(F)F)n2)cc1] | 475.1 [M + H]+ |
| 160 | 2-((3S)-4-benzoylmorpholin-3-yl)-N-(4-(5-(trifluoromethyl)-1,2,4-oxadiazol-3-yl)phenyl)acetamide | 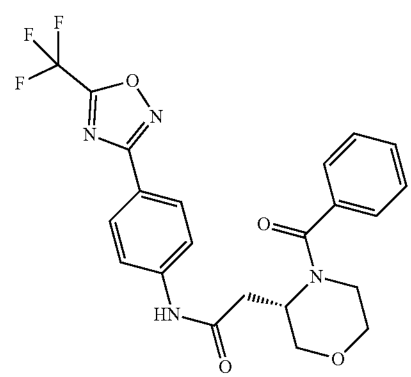 [SMILES: O=C(C[C@H]1COCCN1C(=O)c1ccccc1)Nc1ccc(-c2noc(C(F)(F)F)n2)cc1] | 461.1 [M + H]+ |
| 161 | 2-((3S)-4-benzoylmorpholin-3-yl)-N-methyl-N-(4-(5-(trifluoromethyl)-1,2,4-oxadiazol-3-yl)phenyl)acetamide | 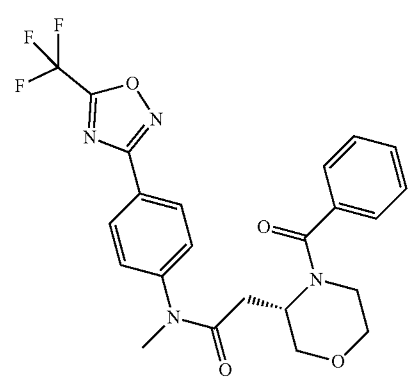 [SMILES: CN(C(=O)C[C@H]1COCCN1C(=O)c1ccccc1)c1ccc(-c2noc(C(F)(F)F)n2)cc1] | 475.0 [M + H]+ |

TABLE 1-continued

| Example No. | IUPAC name | Structure | MS (found) |
|---|---|---|---|
| 162 | N-((1-benzoylpyrrolidin-2-yl)methyl)-4-(5-(trifluoromethyl)-1,2,4-oxadiazol-3-yl)benzamide | 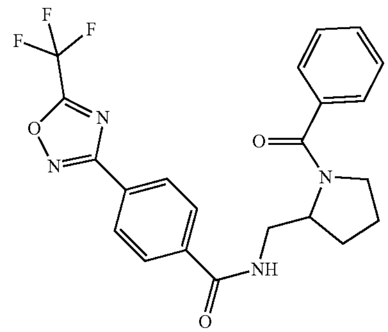 [SMILES: O=C(NCC1CCCN1C(=O)c1ccccc1)c1ccc(-c2noc(C(F)(F)F)n2)cc1] | 445.1 [M + H]+ |
| 163 | N-((1-benzoylpiperidin-2-yl)methyl)-4-(5-(trifluoromethyl)-1,2,4-oxadiazol-3-yl)benzamide | 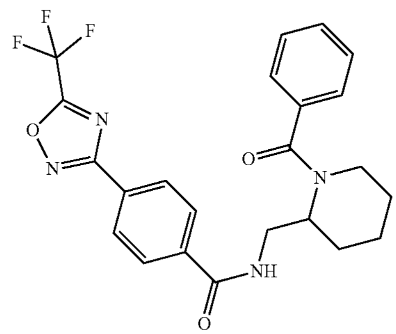 [SMILES: O=C(NCC1CCCCN1C(=O)c1ccccc1)c1ccc(-c2noc(C(F)(F)F)n2)cc1] | 459.1 [M + H]+ |
| 164 | N-(((2R)-1-((1-methyl-1H-pyrazol-5-yl)carbonyl)piperidin-2-yl)methyl)-4-(5-(trifluoromethyl)-1,2,4-oxadiazol-3-yl)benzamide | 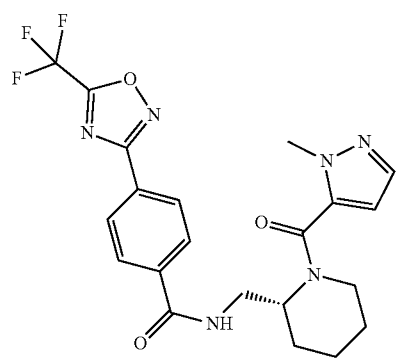 [SMILES: Cn1nccc1C(=O)N1CCCC[C@@H]1CNC(=O)c1ccc(-c2noc(C(F)(F)F)n2)cc1] | 463.0 [M + H]+ |
| 165 | N-((1,4-dibenzoylpiperazin-2-yl)methyl)-4-(5-(trifluoromethyl)-1,2,4-oxadiazol-3-yl)benzamide | 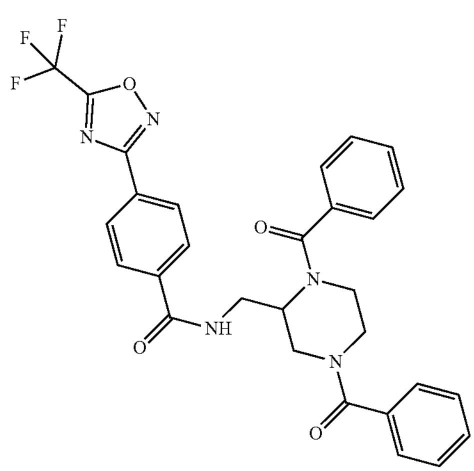 [SMILES: O=C(NCC1CN(C(=O)c2ccccc2)CCN1C(=O)c1ccccc1)c1ccc(-c2noc(C(F)(F)F)n2)cc1] | 564.1 [M + H]+ |

TABLE 1-continued

| Example No. | IUPAC name | Structure | MS (found) |
|---|---|---|---|
| 166 | N-((1-(cyclopropylcarbonyl)-2,3-dihydro-1H-indol-2-yl)methyl)-4-(5-(trifluoromethyl)-1,2,4-oxadiazol-3-yl)benzamide | 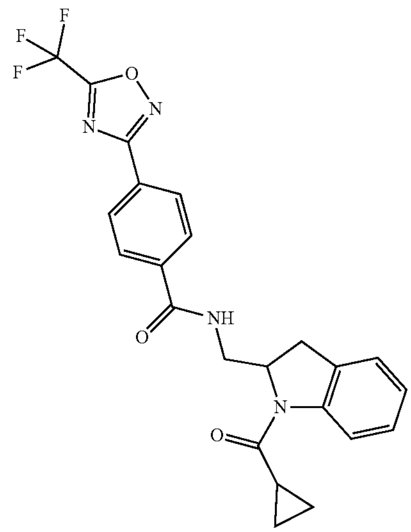 [SMILES: O=C(NCC1Cc2ccccc2N1C(=O)C1CC1)c1ccc(-c2noc(C(F)(F)F)n2)cc1] | 457.0 [M + H]+ |
| 167 | N-((1-benzoyl-2,3-dihydro-1H-indol-2-yl)methyl)-4-(5-(trifluoromethyl)-1,2,4-oxadiazol-3-yl)benzamide | 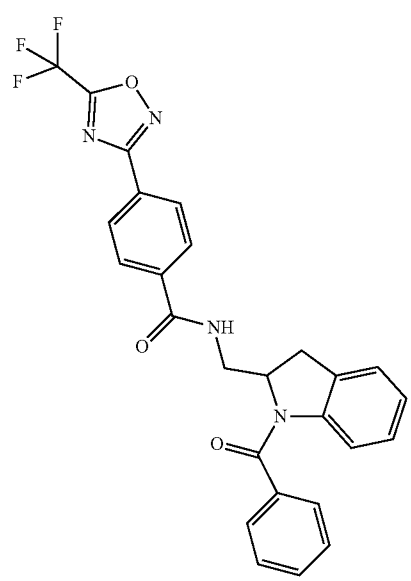 [SMILES: O=C(NCC1Cc2ccccc2N1C(=O)c1ccccc1)c1ccc(-c2noc(C(F)(F)F)n2)cc1] | 492.9 [M + H]+ |

TABLE 1-continued
| Example No. | IUPAC name | Structure | MS (found) |
|---|---|---|---|
| 168 | N-((1-(3,5-dichlorobenzoyl)-2,3-dihydro-1H-indol-2-yl)methyl)-4-(5-(trifluoromethyl)-1,2,4-oxadiazol-3-yl)benzamide | 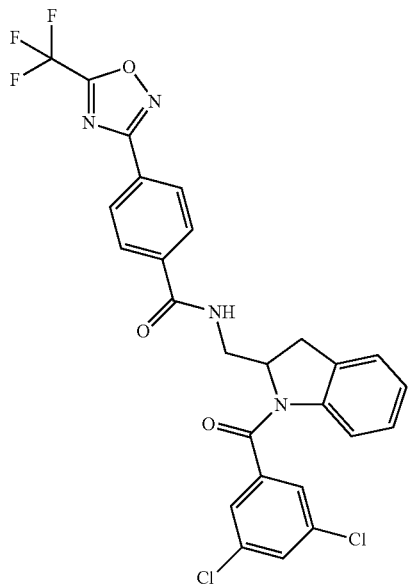 [SMILES: O=C(NCC1Cc2ccccc2N1C(=O)c1cc(Cl)cc(Cl)c1)c1ccc(-c2noc(C(F)(F)F)n2)cc1] | 560.9 [M + H]+ |
| 169 | N-((2-(cyclopropylcarbonyl)-2,3-dihydro-1H-isoindol-1-yl)methyl)-4-(5-(trifluoromethyl)-1,2,4-oxadiazol-3-yl)benzamide | 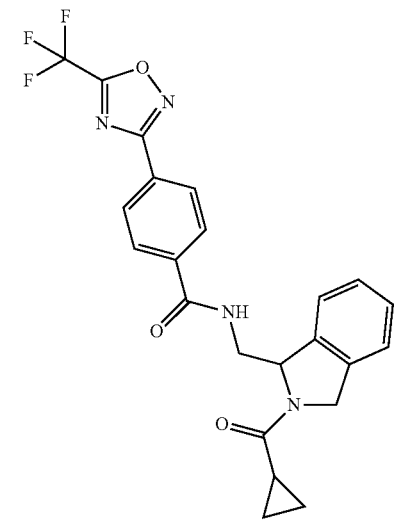 [SMILES: O=C(NCC1c2ccccc2CN1C(=O)C1CC1)c1ccc(-c2noc(C(F)(F)F)n2)cc1] | 454.9 [M − H]− |

TABLE 1-continued

| Example No. | IUPAC name | Structure | MS (found) |
|---|---|---|---|
| 170 | N-((2-benzoyl-2,3-dihydro-1H-isoindol-1-yl)methyl)-4-(5-(trifluoromethyl)-1,2,4-oxadiazol-3-yl)benzamide | 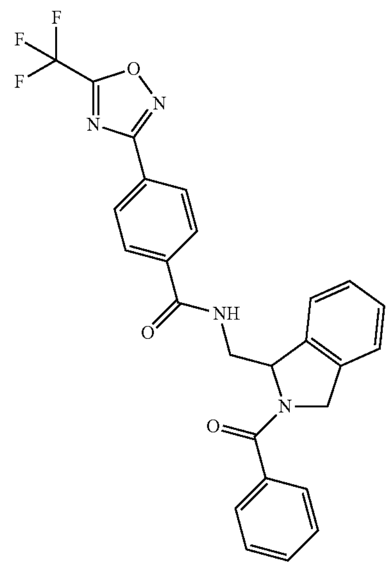 [SMILES: O=C(NCC1c2ccccc2CN1C(=O)c1ccccc1)c1ccc(-c2noc(C(F)(F)F)n2)cc1] | 493.1 [M + H]+ |
| 171 | N-((2-(3,5-dichlorobenzoyl)-2,3-dihydro-1H-isoindol-1-yl)methyl)-4-(5-(trifluoromethyl)-1,2,4-oxadiazol-3-yl)benzamide | 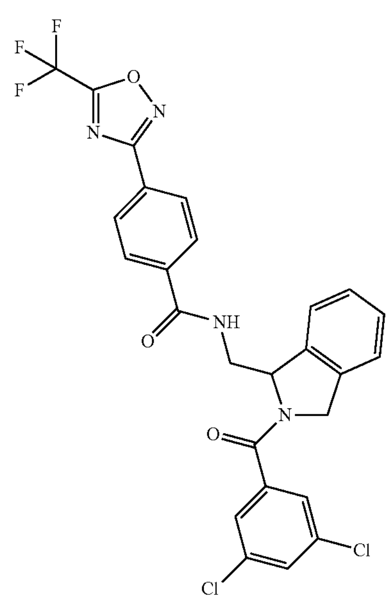 [SMILES: O=C(NCC1c2ccccc2CN1C(=O)c1cc(Cl)cc(Cl)c1)c1ccc(-c2noc(C(F)(F)F)n2)cc1] | 560.8 [M + H]+ |

TABLE 1-continued

| Example No. | IUPAC name | Structure | MS (found) |
|---|---|---|---|
| 172 | N-((1-(cyclopropylcarbonyl)-1,2,3,4-tetrahydroquinolin-2-yl)methyl)-4-(5-(trifluoromethyl)-1,2,4-oxadiazol-3-yl)benzamide | 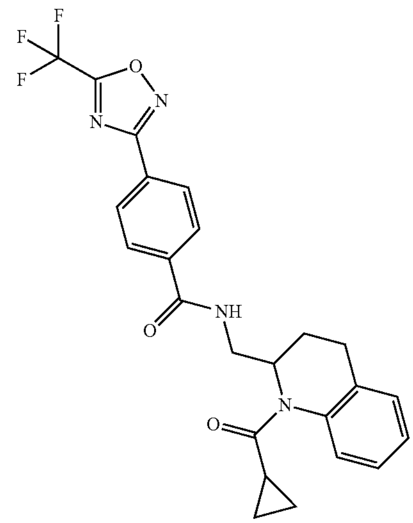 [SMILES: O=C(NCC1CCc2ccccc2N1C(=O)C1CC1)c1ccc(-c2noc(C(F)(F)F)n2)cc1] | 471.1 [M + H]+ |
| 173 | N-((1-benzoyl-1,2,3,4-tetrahydroquinolin-2-yl)methyl)-4-(5-(trifluoromethyl)-1,2,4-oxadiazol-3-yl)benzamide | 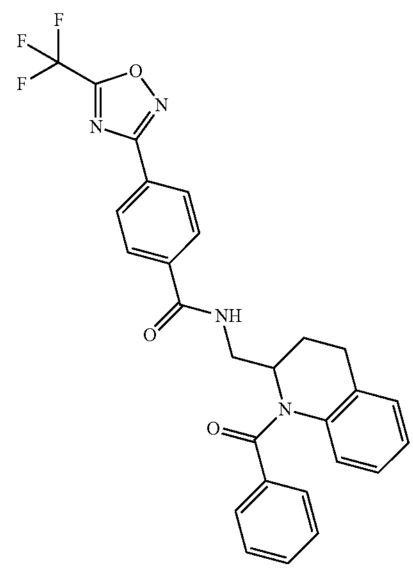 [SMILES: O=C(NCC1CCc2ccccc2N1C(=O)c1ccccc1)c1ccc(-c2noc(C(F)(F)F)n2)cc1] | 507.2 [M + H]+ |
| 174 | N-((2-(cyclopropylcarbonyl)-1,2,3,4-tetrahydroisoquinolin-3-yl)methyl)-4-(5-(trifluoromethyl)-1,2,4-oxadiazol-3-yl)benzamide | 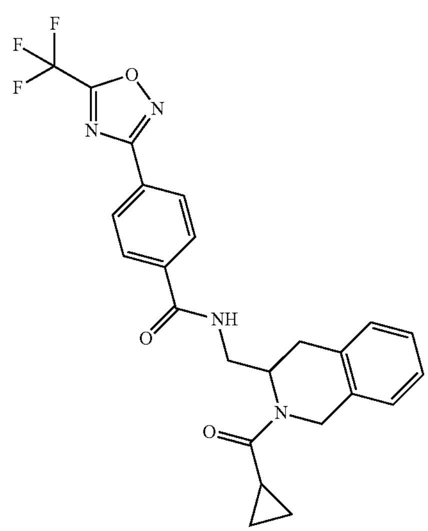 [SMILES: O=C(NCC1Cc2ccccc2CN1C(=O)C1CC1)c1ccc(-c2noc(C(F)(F)F)n2)cc1] | 471.1 [M + H]+ |

TABLE 1-continued

| Example No. | IUPAC name | Structure | MS (found) |
|---|---|---|---|
| 175 | N-((2-benzoyl-1,2,3,4-tetrahydroisoquinolin-3-yl)methyl)-4-(5-(trifluoromethyl)-1,2,4-oxadiazol-3-yl)benzamide | 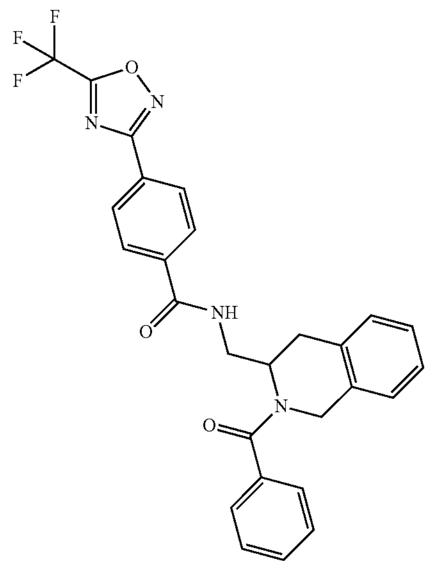 [SMILES: O=C(NCC1Cc2ccccc2CN1C(=O)c1ccccc1)c1ccc(-c2noc(C(F)(F)F)n2)cc1] | 507.0 [M + H]+ |
| 176 | N-((2-(3,5-dichlorobenzoyl)-1,2,3,4-tetrahydroisoquinolin-3-yl)methyl)-4-(5-(trifluoromethyl)-1,2,4-oxadiazol-3-yl)benzamide | 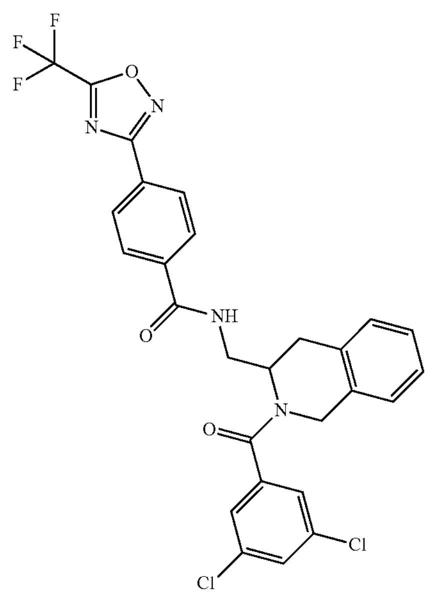 [SMILES: O=C(NCC1Cc2ccccc2CN1C(=O)c1cc(Cl)cc(Cl)c1)c1ccc(-c2noc(C(F)(F)F)n2)cc1] | 574.9 [M + H]+ |
| 177 | N-((4-benzoylmorpholin-3-yl)methyl)-2-fluoro-4-(5-(trifluoromethyl)-1,2,4-oxadiazol-3-yl)benzamide | 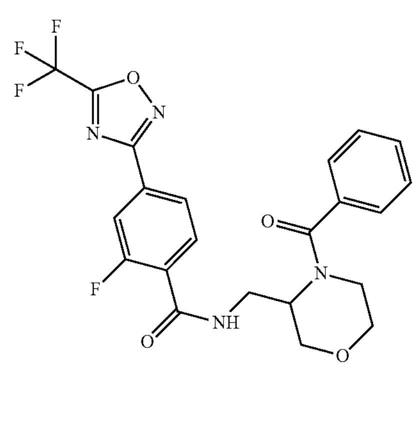 | 479.1 [M + H]+ |

TABLE 1-continued

| Example No. | IUPAC name | Structure | MS (found) |
|---|---|---|---|
| 178 | N-((4-benzoylmorpholin-3-yl)methyl)-2-methyl-4-(5-(trifluoromethyl)-1,2,4-oxadiazol-3-yl)benzamide | 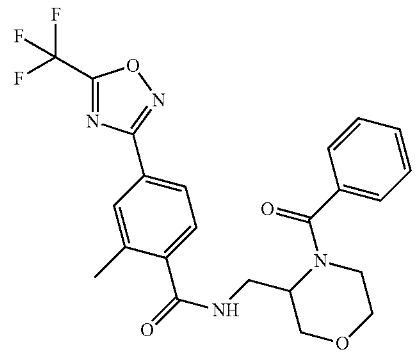 [SMILES: Cc1cc(-c2noc(C(F)(F)F)n2)ccc1C(=O)NCC1COCCN1C(=O)c1ccccc1] | 475.2 [M + H]+ |
| 179 | N-((4-benzoylmorpholin-3-yl)methyl)-3-methyl-4-(5-(trifluoromethyl)-1,2,4-oxadiazol-3-yl)benzamide | 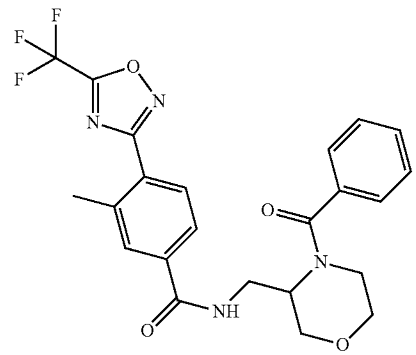 [SMILES: Cc1cc(C(=O)NCC2COCCN2C(=O)c2ccccc2)ccc1-c1noc(C(F)(F)F)n1] | 473.1 [M − H]− |
| 180 | N-((4-benzoylmorpholin-3-yl)methyl)-6-(5-(trifluoromethyl)-1,2,4-oxadiazol-3-yl)nicotinamide | 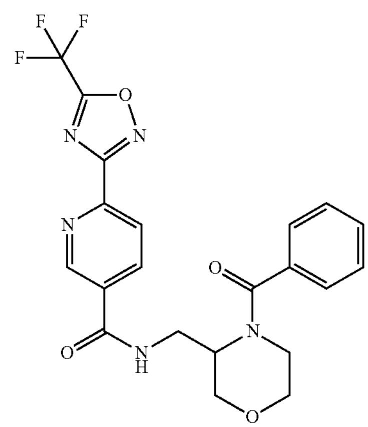 [SMILES: O=C(NCC1COCCN1C(=O)c1ccccc1)c1ccc(-c2noc(C(F)(F)F)n2)nc1] | 462.0 [M + H]+ |
| 181 | N-((4-benzoylmorpholin-3-yl)methyl)-5-(5-(trifluoromethyl)-1,2,4-oxadiazol-3-yl)pyridine-2-carboxamide | 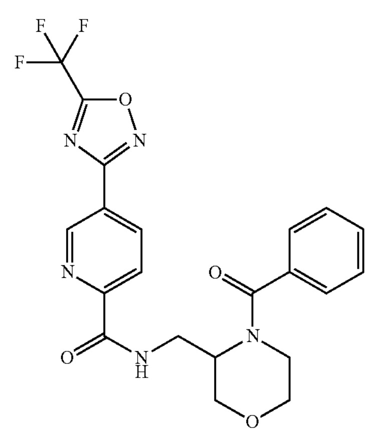 [SMILES: O=C(NCC1COCCN1C(=O)c1ccccc1)c1ccc(-c2noc(C(F)(F)F)n2)cn1] | 462.0 [M + H]+ |

TABLE 1-continued

| Example No. | IUPAC name | Structure | MS (found) |
|---|---|---|---|
| 182 | N-((4-(3,5-dichlorobenzoyl)morpholin-3-yl)methyl)-5-(5-(trifluoromethyl)-1,2,4-oxadiazol-3-yl)pyridine-2-carboxamide | 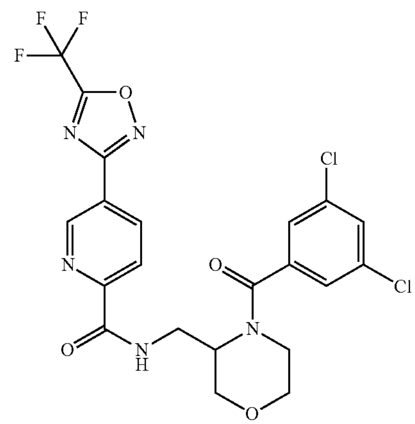 [SMILES: O=C(NCC1COCCN1C(=O)c1cc(Cl)cc(Cl)c1)c1ccc(-c2noc(C(F)(F)F)n2)cn1] | 529.9 [M + H]+ |
| 183 | N-(((3S)-4-(3,5-dichlorobenzoyl)morpholin-3-yl)methyl)-5-(5-(trifluoromethyl)-1,2,4-oxadiazol-3-yl)pyridine-2-carboxamide | 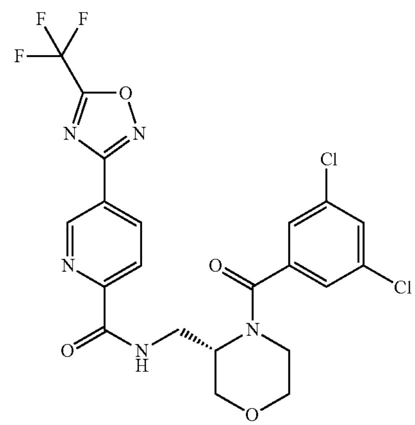 [SMILES: O=C(NC[C@H]1COCCN1C(=O)c1cc(Cl)cc(Cl)c1)c1ccc(-c2noc(C(F)(F)F)n2)cn1] | 530.0 [M + H]+ |
| 184 | N-(((3S)-4-((2-methyl-2H-indazol-3-yl)carbonyl)morpholin-3-yl)methyl)-5-(5-(trifluoromethyl)-1,2,4-oxadiazol-3-yl)pyridine-2-carboxamide | 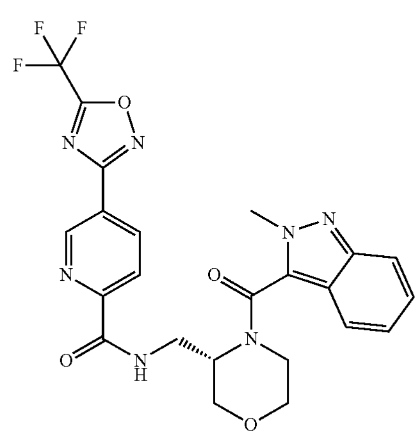 [SMILES: Cn1nc2ccccc2c1C(=O)N1CCOC[C@@H]1CNC(=O)c1ccc(-c2noc(C(F)(F)F)n2)cn1] | 516.1 [M + H]+ |

TABLE 1-continued

| Example No. | IUPAC name | Structure | MS (found) |
|---|---|---|---|
| 185 | N-(((3S)-4-(3-fluorobenzoyl)morpholin-3-yl)methyl)-5-(5-(trifluoromethyl)-1,2,4-oxadiazol-3-yl)pyridine-2-carboxamide | 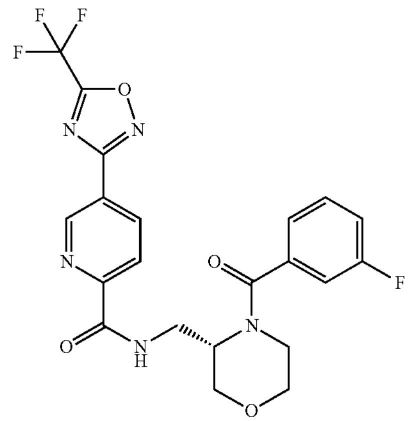 [SMILES: O=C(NC[C@H]1COCCN1C(=O)c1cccc(F)c1)c1ccc(-c2noc(C(F)(F)F)n2)cn1] | 480.1 [M + H]+ |
| 186 | N-(((3S)-4-(3,5-difluorobenzoyl)morpholin-3-yl)methyl)-5-(5-(trifluoromethyl)-1,2,4-oxadiazol-3-yl)pyridine-2-carboxamide | 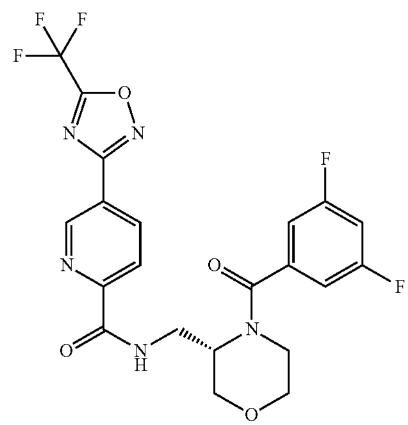 [SMILES: O=C(NC[C@H]1COCCN1C(=O)c1cc(F)cc(F)c1)c1ccc(-c2noc(C(F)(F)F)n2)cn1] | 498.1 [M + H]+ |
| 187 | N-(((3S)-4-(2-cyanobenzoyl)morpholin-3-yl)methyl)-5-(5-(trifluoromethyl)-1,2,4-oxadiazol-3-yl)pyridine-2-carboxamide | 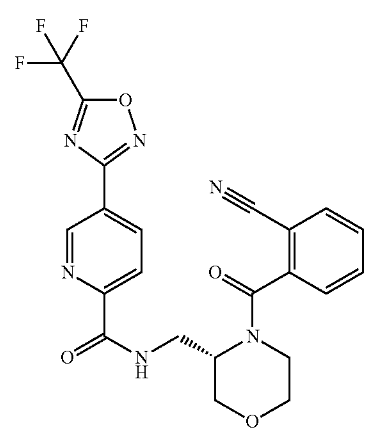 [SMILES: N#Cc1ccccc1C(=O)N1CCOC[C@@H]1CNC(=O)c1ccc(-c2noc(C(F)(F)F)n2)cn1] | 487.1 [M + H]+ |

TABLE 1-continued

| Example No. | IUPAC name | Structure | MS (found) |
|---|---|---|---|
| 188 | N-(((3S)-4-(3-cyanobenzoyl)morpholin-3-yl)methyl)-5-(5-(trifluoromethyl)-1,2,4-oxadiazol-3-yl)pyridine-2-carboxamide | 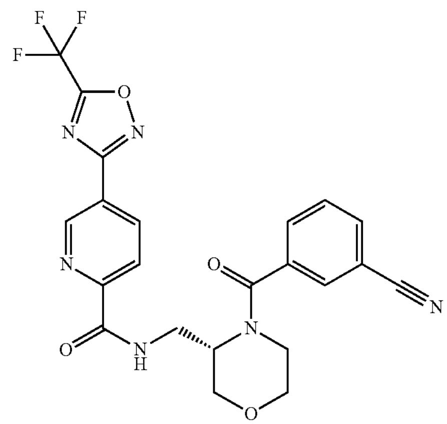 [SMILES: N#Cc1cccc(C(=O)N2CCOC[C@@H]2CNC(=O)c2ccc(-c3noc(C(F)(F)F)n3)cn2)c1] | 487.1 [M + H]+ |
| 189 | N-(((3S)-4-(3-cyano-5-fluorobenzoyl)morpholin-3-yl)methyl)-5-(5-(trifluoromethyl)-1,2,4-oxadiazol-3-yl)pyridine-2-carboxamide | 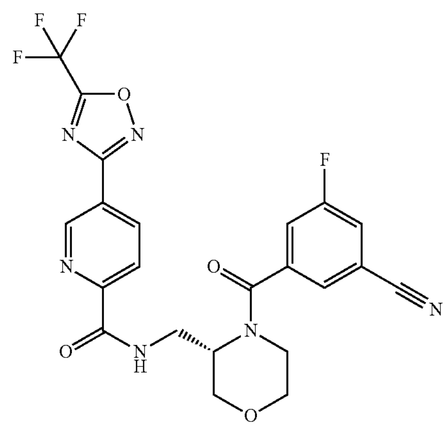 [SMILES: N#Cc1cc(F)cc(C(=O)N2CCOC[C@@H]2CNC(=O)c2ccc(-c3noc(C(F)(F)F)n3)cn2)c1] | 505.1 [M + H]+ |
| 190 | N-(((3S)-4-(4-cyanobenzoyl)morpholin-3-yl)methyl)-5-(5-(trifluoromethyl)-1,2,4-oxadiazol-3-yl)pyridine-2-carboxamide | 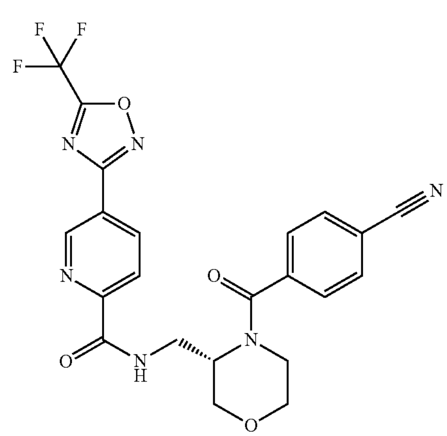 [SMILES: N#Cc1ccc(C(=O)N2CCOC[C@@H]2CNC(=O)c2ccc(-c3noc(C(F)(F)F)n3)cn2)cc1] | 487.1 [M + H]+ |

TABLE 1-continued

| Example No. | IUPAC name | Structure | MS (found) |
|---|---|---|---|
| 191 | N-(((3S)-4-isonicotinoylmorpholin-3-yl)methyl)-5-(5-(trifluoromethyl)-1,2,4-oxadiazol-3-yl)pyridine-2-carboxamide | 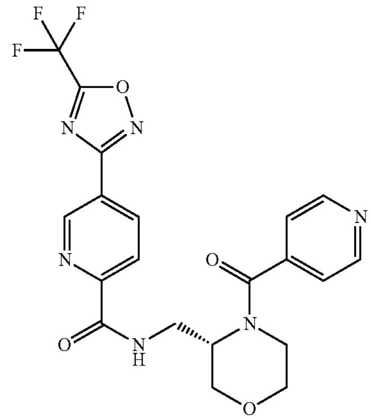 [SMILES: O=C(NC[C@H]1COCCN1C(=O)c1ccncc1)c1ccc(-c2noc(C(F)(F)F)n2)cn1] | 463.2 [M + H]+ |
| 192 | N-(((3S)-4-((1-methyl-1H-pyrazol-5-yl)carbonyl)morpholin-3-yl)methyl)-5-(5-(trifluoromethyl)-1,2,4-oxadiazol-3-yl)pyridine-2-carboxamide | 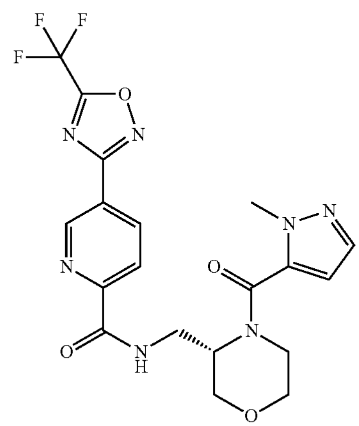 [SMILES: Cn1nccc1C(=O)N1CCOC[C@@H]1CNC(=O)c1ccc(-c2noc(C(F)(F)F)n2)cn1] | 466.1 [M + H]+ |
| 193 | N-(((3S)-4-((5-methyl-1,2-oxazol-4-yl)carbonyl)morpholin-3-yl)methyl)-5-(5-(trifluoromethyl)-1,2,4-oxadiazol-3-yl)pyridine-2-carboxamide | 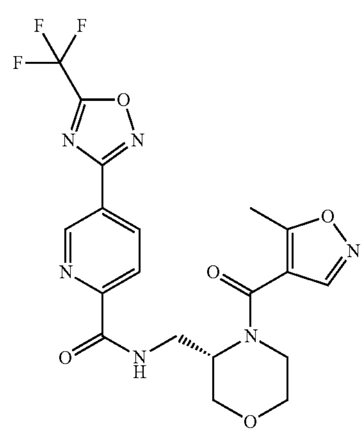 [SMILES: Cc1oncc1C(=O)N1CCOC[C@@H]1CNC(=O)c1ccc(-c2noc(C(F)(F)F)n2)cn1] | 466.9 [M + H]+<br>467.1 [M + H]+ |

TABLE 1-continued

| Example No. | IUPAC name | Structure | MS (found) |
|---|---|---|---|
| 194 | N-(((3S)-4-((4-methyl-1,2,5-oxadiazol-3-yl)carbonyl)morpholin-3-yl)methyl)-5-(5-(trifluoromethyl)-1,2,4-oxadiazol-3-yl)pyridine-2-carboxamide | 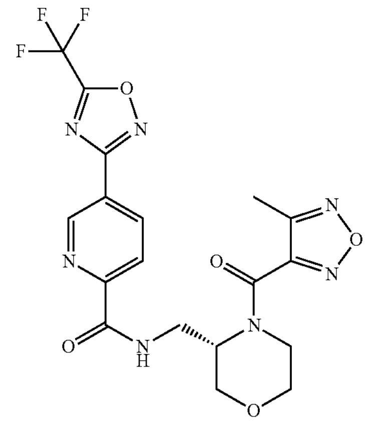 [SMILES: Cc1nonc1C(=O)N1CCOC[C@@H]1CNC(=O)c1ccc(-c2noc(C(F)(F)F)n2)cn1] | 468.1 [M + H]+ |
| 195 | N-(((3S)-4-((4-methyl-1,2,3-thiadiazol-5-yl)carbonyl)morpholin-3-yl)methyl)-5-(5-(trifluoromethyl)-1,2,4-oxadiazol-3-yl)pyridine-2-carboxamide | 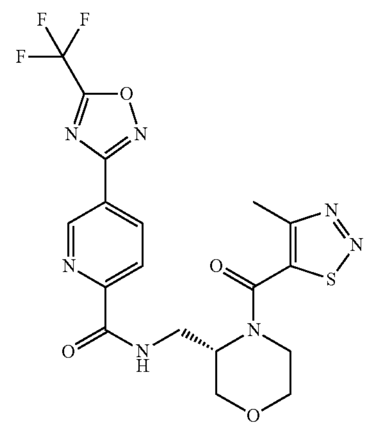 [SMILES: Cc1nnsc1C(=O)N1CCOC[C@@H]1CNC(=O)c1ccc(-c2noc(C(F)(F)F)n2)cn1] | 484.1 [M + H]+ |
| 196 | N-(((3S)-4-((4-methyl-1,3-thiazol-5-yl)carbonyl)morpholin-3-yl)methyl)-5-(5-(trifluoromethyl)-1,2,4-oxadiazol-3-yl)pyridine-2-carboxamide | 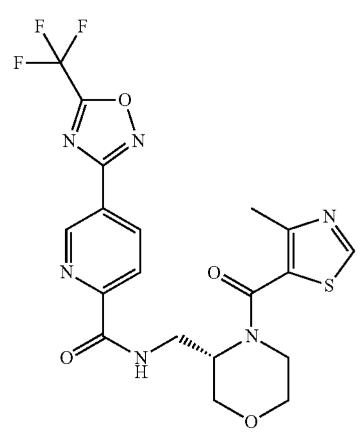 [SMILES: Cc1ncsc1C(=O)N1CCOC[C@@H]1CNC(=O)c1ccc(-c2noc(C(F)(F)F)n2)cn1] | 483.1 [M + H]+ |

TABLE 1-continued

| Example No. | IUPAC name | Structure | MS (found) |
|---|---|---|---|
| 197 | N-(((3S)-4-(2-thienylcarbonyl)morpholin-3-yl)methyl)-5-(5-(trifluoromethyl)-1,2,4-oxadiazol-3-yl)pyridine-2-carboxamide | 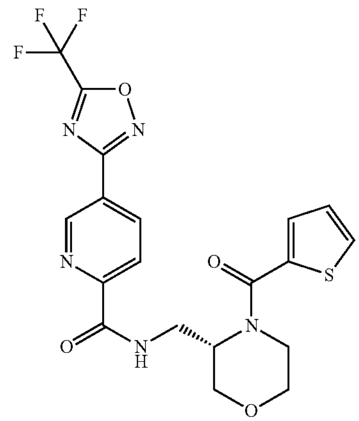 [SMILES: O=C(NC[C@H]1COCCN1C(=O)c1cccs1)c1ccc(-c2noc(C(F)(F)F)n2)cn1] | 468.1 [M + H]+ |
| 198 | N-(((3S)-4-((3-methyl-2-thienyl)carbonyl)morpholin-3-yl)methyl)-5-(5-(trifluoromethyl)-1,2,4-oxadiazol-3-yl)pyridine-2-carboxamide | 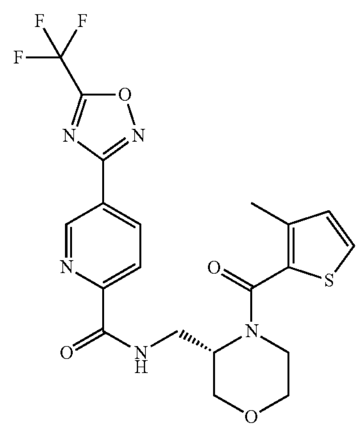 [SMILES: Cc1ccsc1C(=O)N1CCOC[C@@H]1CNC(=O)c1ccc(-c2noc(C(F)(F)F)n2)cn1] | 482.1 [M + H]+ |
| 199 | N-(((3S)-4-(3,4-dihydro-2H-chromen-2-ylcarbonyl)morpholin-3-yl)methyl)-5-(5-(trifluoromethyl)-1,2,4-oxadiazol-3-yl)pyridine-2-carboxamide | 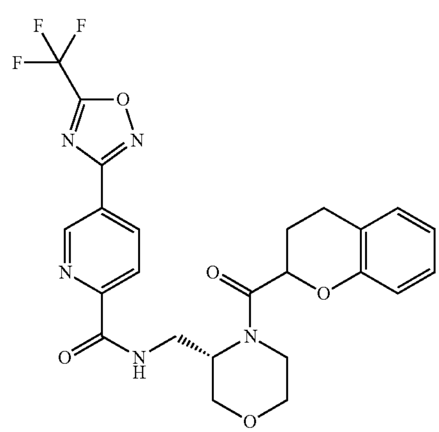 [SMILES: O=C(NC[C@H]1COCCN1C(=O)C1CCc2ccccc2O1)c1ccc(-c2noc(C(F)(F)F)n2)cn1] | 518.1 [M + H]+ |

TABLE 1-continued

| Example No. | IUPAC name | Structure | MS (found) |
|---|---|---|---|
| 200 | N-(((3S)-4-(1-benzofuran-2-ylcarbonyl)morpholin-3-yl)methyl)-5-(5-(trifluoromethyl)-1,2,4-oxadiazol-3-yl)pyridine-2-carboxamide | 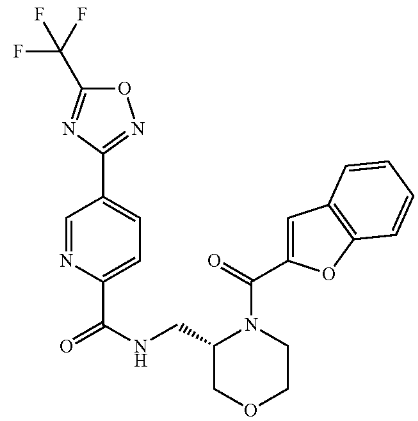 [SMILES: O=C(NC[C@H]1COCCN1C(=O)c1cc2ccccc2o1)c1ccc(-c2noc(C(F)(F)F)n2)cn1] | 502.2 [M + H]+ |
| 201 | N-(((3S)-4-(2-thienylacetyl)morpholin-3-yl)methyl)-5-(5-(trifluoromethyl)-1,2,4-oxadiazol-3-yl)pyridine-2-carboxamide | 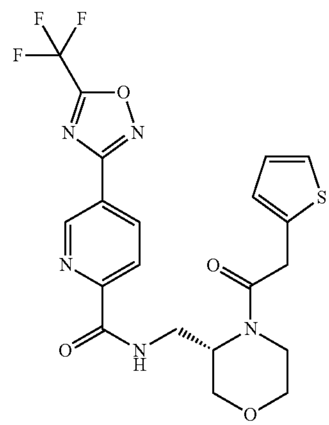 [SMILES: O=C(NC[C@H]1COCCN1C(=O)Cc1cccs1)c1ccc(-c2noc(C(F)(F)F)n2)cn1] | 482.1 [M + H]+ |
| 202 | N-(((3S)-4-((1-phenylcyclopropyl)carbonyl)morpholin-3-yl)methyl)-5-(5-(trifluoromethyl)-1,2,4-oxadiazol-3-yl)pyridine-2-carboxamide | 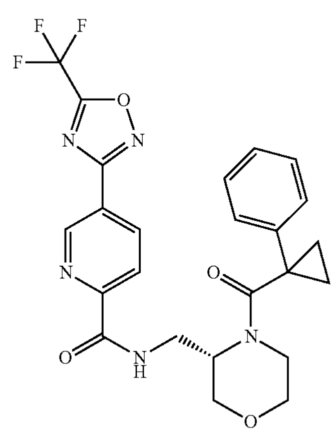 [SMILES: O=C(NC[C@H]1COCCN1C(=O)C1(c2ccccc2)CC1)c1ccc(-c2noc(C(F)(F)F)n2)cn1] | 502.2 [M + H]+ |

TABLE 1-continued

| Example No. | IUPAC name | Structure | MS (found) |
|---|---|---|---|
| 203 | N-(((3S)-4-(3-phenylpropanoyl)morpholin-3-yl)methyl)-5-(5-(trifluoromethyl)-1,2,4-oxadiazol-3-yl)pyridine-2-carboxamide | 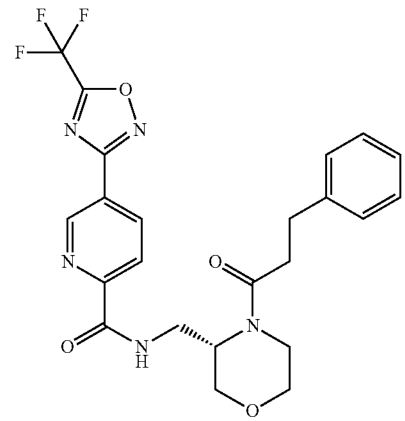 [SMILES: O=C(NC[C@H]1COCCN1C(=O)CCc1ccccc1)c1ccc(-c2noc(C(F)(F)F)n2)cn1] | 490.2 [M + H]+ |
| 204 | N-(((3S)-4-(cyclohexylcarbonyl)morpholin-3-yl)methyl)-5-(5-(trifluoromethyl)-1,2,4-oxadiazol-3-yl)pyridine-2-carboxamide | 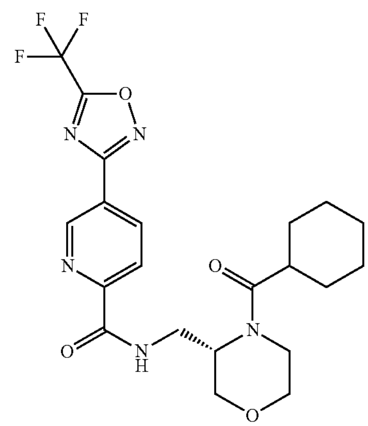 [SMILES: O=C(NC[C@H]1COCCN1C(=O)C1CCCCC1)c1ccc(-c2noc(C(F)(F)F)n2)cn1] | 466.2 [M − H]− |
| 205 | N-((4-(adamantan-2-ylcarbonyl)morpholin-3-yl)methy)-5-(5-(trifluoromethyl)-1,2,4-oxadiazol-3-yl)pyridine-2-carboxamide | 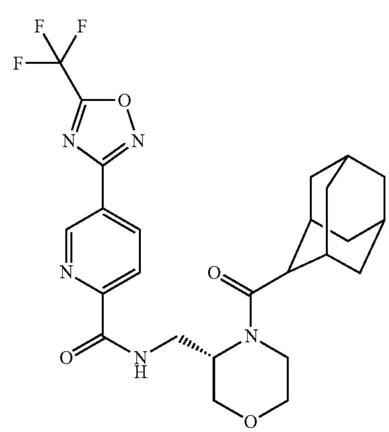 [SMILES: O=C(NC[C@H]1COCCN1C(=O)C1C2CC3CC(C2)CC1C3)c1ccc(-c2noc(C(F)(F)F)n2)cn1] | 520.2 [M + H]+ |

TABLE 1-continued

| Example No. | IUPAC name | Structure | MS (found) |
|---|---|---|---|
| 206 | N-(((3S)-4-(2-methyl-2-phenylpropanoyl)morpholin-3-yl)methyl)-5-(5-(trifluoromethyl)-1,2,4-oxadiazol-3-yl)pyridine-2-carboxamide | 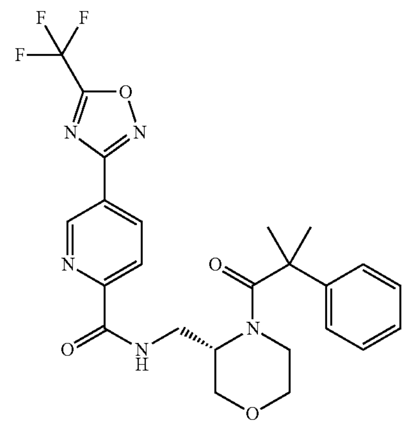 [SMILES: CC(C)(C(=O)N1CCOC[C@@H]1CNC(=O)c1ccc(-c2noc(C(F)(F)F)n2)cn1)c1ccccc1] | 504.0 [M + H]+ |
| 207 | N-(((3S)-4-(difluoro(phenyl)acetyl)morpholin-3-yl)methyl)-5-(5-(trifluoromethyl)-1,2,4-oxadiazol-3-yl)pyridine-2-carboxamide | 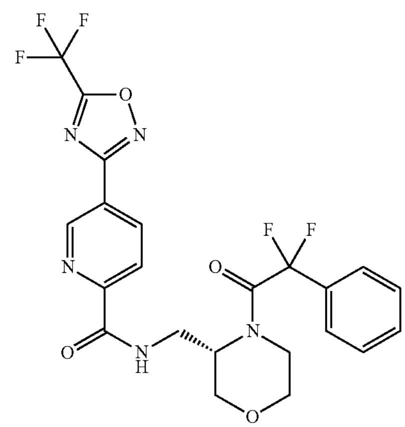 [SMILES: O=C(NC[C@H]1COCCN1C(=O)C(F)(F)c1ccccc1)c1ccc(-c2noc(C(F)(F)F)n2)cn1] | 512.0 [M + H]+ |
| 208 | N-(((3R)-4-((1-phenylcyclopropyl)carbonyl)morpholin-3-yl)methyl)-5-(5-(trifluoromethyl)-1,2,4-oxadiazol-3-yl)pyridine-2-carboxamide | 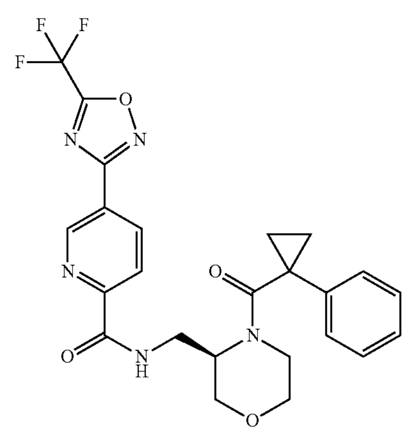 [SMILES: O=C(NC[C@@H]1COCCN1C(=O)C1(c2ccccc2)CC1)c1ccc(-c2noc(C(F)(F)F)n2)cn1] | 502.1 [M + H]+ |

TABLE 1-continued

| Example No. | IUPAC name | Structure | MS (found) |
|---|---|---|---|
| 209 | N-(((3R)-4-(3,5-dichlorobenzoyl)morpholin-3-yl)methyl)-5-(5-(trifluoromethyl)-1,2,4-oxadiazol-3-yl)pyridine-2-carboxamide | 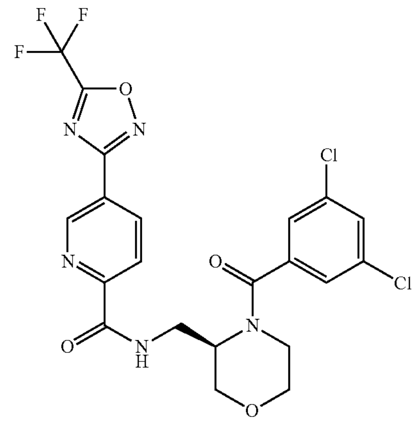 [SMILES: O=C(NC[C@@H]1COCCN1C(=O)c1cc(Cl)cc(Cl)c1)c1ccc(-c2noc(C(F)(F)F)n2)cn1] | 529.9 [M + H]+ |
| 210 | N-((4-benzoylmorpholin-3-yl)methyl)-5-(5-(trifluoromethyl)-1,2,4-oxadiazol-3-yl)thiophene-2-carboxamide | 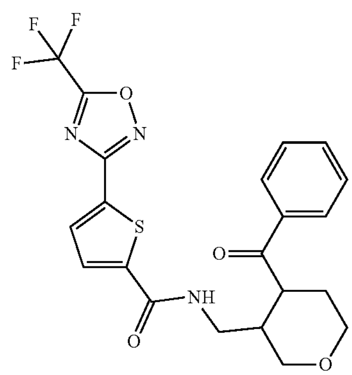 [SMILES: O=C(NCC1COCCC1C(=O)c1ccccc1)c1ccc(-c2noc(C(F)(F)F)n2)s1] | 467.0 [M + H]+ |
| 211 | N-((4-(3,5-dichlorobenzoyl)morpholin-3-yl)methyl)-5-(5-(trifluoromethyl)-1,2,4-oxadiazol-3-yl)thiophene-2-carboxamide | 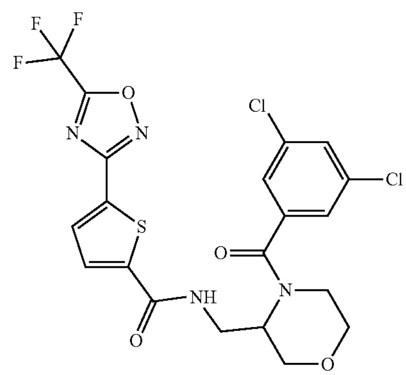 [SMILES: O=C(NCC1COCCN1C(=O)c1cc(Cl)cc(Cl)c1)c1ccc(-c2noc(C(F)(F)F)n2)s1] | 535.1 [M + H]+ |
| 212 | N-((4-(3-fluorobenzoyl)morpholin-3-yl)methyl)-5-(5-(trifluoromethyl)-1,2,4-oxadiazol-3-yl)thiophene-2-carboxamide | 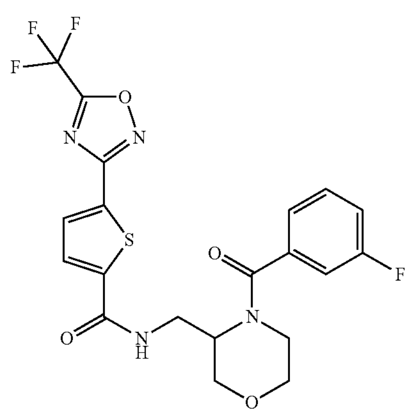 [SMILES: O=C(NCC1COCCN1C(=O)c1cccc(F)c1)c1ccc(-c2noc(C(F)(F)F)n2)s1] | 485.1 [M + H]+ |

TABLE 1-continued

| Example No. | IUPAC name | Structure | MS (found) |
|---|---|---|---|
| 213 | N-((4-(3,5-difluorobenzoyl)morpholin-3-yl)methyl)-5-(5-(trifluoromethyl)-1,2,4-oxadiazol-3-yl)thiophene-2-carboxamide | 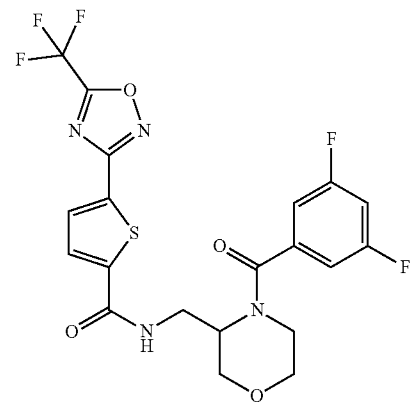 [SMILES: O=C(NCC1COCCN1C(=O)c1cc(F)cc(F)c1)c1ccc(-c2noc(C(F)(F)F)n2)s1] | 501.1 [M − H]− |
| 214 | N-((4-(2-chlorobenzoyl)morpholin-3-yl)methyl)-5-(5-(trifluoromethyl)-1,2,4-oxadiazol-3-yl)thiophene-2-carboxamide | 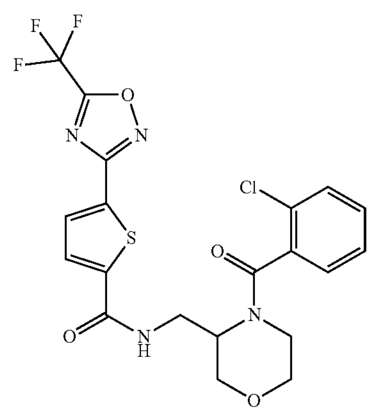 [SMILES: O=C(NCC1COCCN1C(=O)c1ccccc1Cl)c1ccc(-c2noc(C(F)(F)F)n2)s1] | 501.0 [M + H]+ |
| 215 | N-((4-(3-chlorobenzoyl)morpholin-3-yl)methyl)-5-(5-(trifluoromethyl)-1,2,4-oxadiazol-3-yl)thiophene-2-carboxamide | 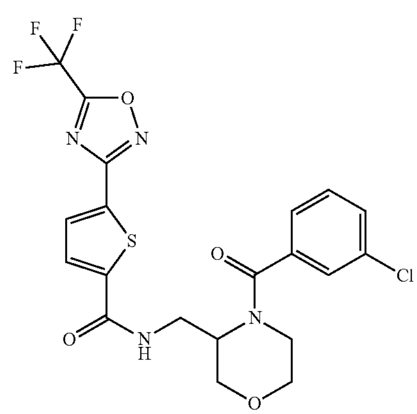 [SMILES: O=C(NCC1COCCN1C(=O)c1cccc(Cl)c1)c1ccc(-c2noc(C(F)(F)F)n2)s1] | 501.1 [M + H]+ |

TABLE 1-continued
| Example No. | IUPAC name | Structure | MS (found) |
|---|---|---|---|
| 216 | N-((4-(4-chlorobenzoyl)morpholin-3-yl)methyl)-5-(5-(trifluoromethyl)-1,2,4-oxadiazol-3-yl)thiophene-2-carboxamide | 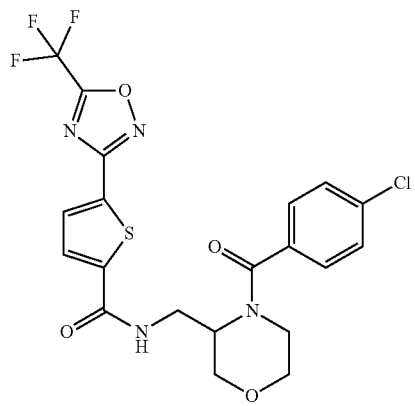 [SMILES: O=C(NCC1COCCN1C(=O)c1ccc(Cl)cc1)c1ccc(-c2noc(C(F)(F)F)n2)s1] | 501.0 [M + H]+ |
| 217 | N-((4-(2-cyanobenzoyl)morpholin-3-yl)methyl)-5-(5-(trifluoromethyl)-1,2,4-oxadiazol-3-yl)thiophene-2-carboxamide | 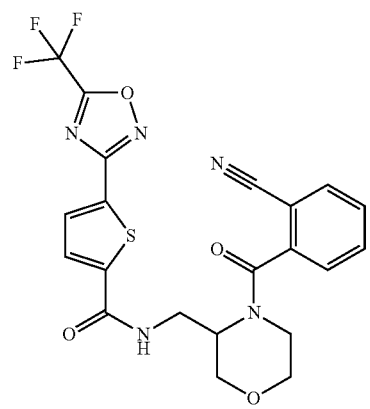 [SMILES: N#Cc1ccccc1C(=O)N1CCOCC1CNC(=O)c1ccc(-c2noc(C(F)(F)F)n2)s1] | 492.1 [M + H]+ |
| 218 | N-((4-(3-cyanobenzoyl)morpholin-3-yl)methyl)-5-(5-(trifluoromethyl)-1,2,4-oxadiazol-3-yl)thiophene-2-carboxamide | 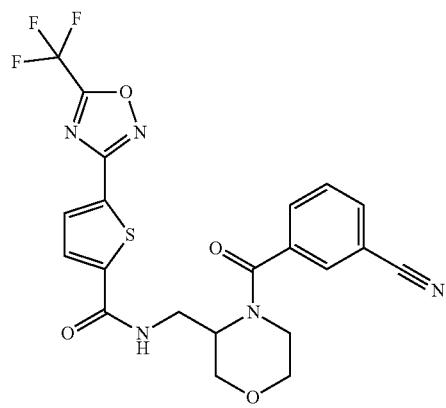 [SMILES: N#Cc1cccc(C(=O)N2CCOCC2CNC(=O)c2ccc(-c3noc(C(F)(F)F)n3)s2)c1] | 490.1 [M − H]− |

TABLE 1-continued

| Example No. | IUPAC name | Structure | MS (found) |
| --- | --- | --- | --- |
| 219 | N-((4-(4-cyanobenzoyl)morpholin-3-yl)methyl)-5-(5-(trifluoromethyl)-1,2,4-oxadiazol-3-yl)thiophene-2-carboxamide | 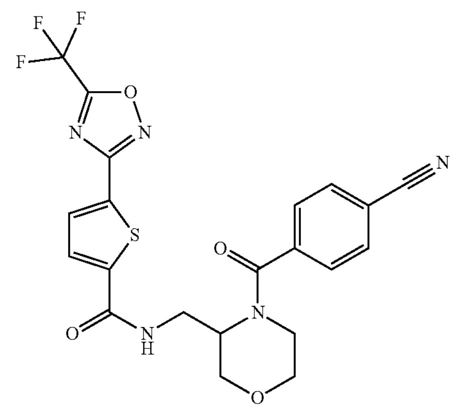 [SMILES: N#Cc1ccc(C(=O)N2CCOCC2CNC(=O)c2ccc(-c3noc(C(F)(F)F)n3)s2)cc1] | 490.1 [M − H]− |
| 220 | N-((4-(2-(morpholin-4-yl)benzoyl)morpholin-3-yl)methyl)-5-(5-(trifluoromethyl)-1,2,4-oxadiazol-3-yl)thiophene-2-carboxamide | 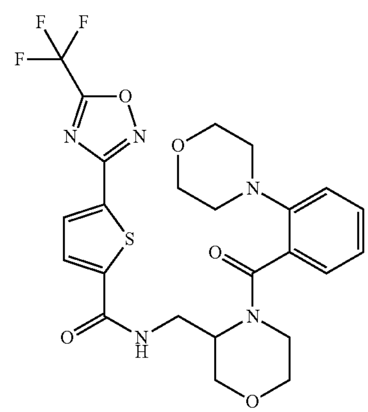 [SMILES: O=C(NCC1COCCN1C(=O)c1ccccc1N1CCOCC1)c1ccc(-c2noc(C(F)(F)F)n2)s1] | 552.2 [M + H]+ |
| 221 | N-((4-(biphenyl-2-ylcarbonyl)morpholin-3-yl)methyl)-5-(5-(trifluoromethyl)-1,2,4-oxadiazol-3-yl)thiophene-2-carboxamide | 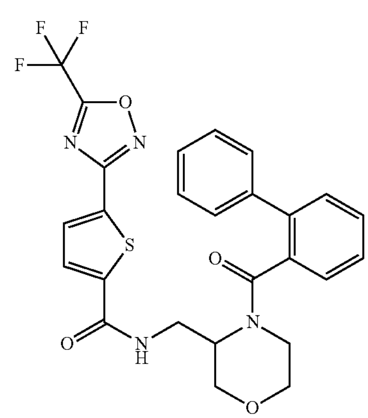 [SMILES: O=C(NCC1COCCN1C(=O)c1ccccc1-c1ccccc1)c1ccc(-c2noc(C(F)(F)F)n2)s1] | 543.1 [M + H]+ |

TABLE 1-continued

| Example No. | IUPAC name | Structure | MS (found) |
|---|---|---|---|
| 222 | N-((4-(biphenyl-3-ylcarbonyl)morpholin-3-yl)methyl)-5-(5-(trifluoromethyl)-1,2,4-oxadiazol-3-yl)thiophene-2-carboxamide | 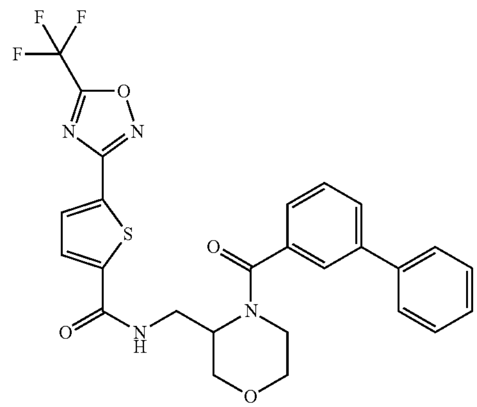 [SMILES: O=C(NCC1COCCN1C(=O)c1cccc(-c2ccccc2)c1)c1ccc(-c2noc(C(F)(F)F)n2)s1] | 543.1 [M + H]+ |
| 223 | N-((4-(biphenyl-4-ylcarbonyl)morpholin-3-yl)methyl)-5-(5-(trifluoromethyl)-1,2,4-oxadiazol-3-yl)thiophene-2-carboxamide | 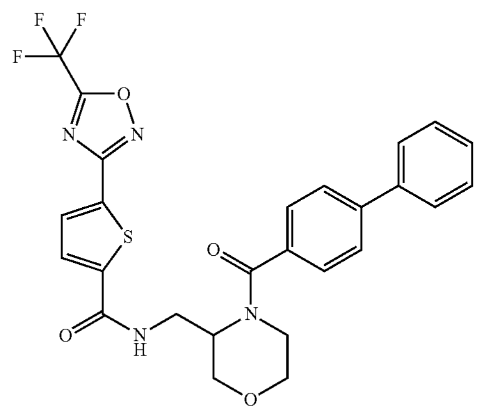 [SMILES: O=C(NCC1COCCN1C(=O)c1ccc(-c2ccccc2)cc1)c1ccc(-c2noc(C(F)(F)F)n2)s1] | 543.1 [M + H]+ |
| 224 | N-((4-(pyridin-2-ylcarbonyl)morpholin-3-yl)methyl)-5-(5-(trifluoromethyl)-1,2,4-oxadiazol-3-yl)thiophene-2-carboxamide | 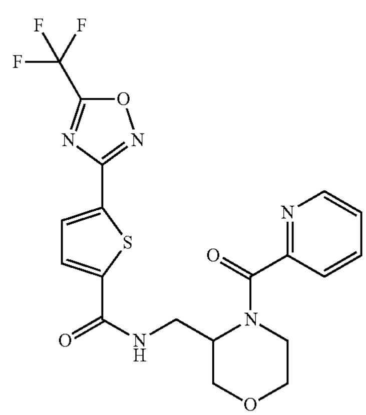 [SMILES: O=C(NCC1COCCN1C(=O)c1ccccn1)c1ccc(-c2noc(C(F)(F)F)n2)s1] | 468.1 [M + H]+ |

TABLE 1-continued

| Example No. | IUPAC name | Structure | MS (found) |
|---|---|---|---|
| 225 | N-((4-(pyridin-3-ylcarbonyl)morpholin-3-yl)methyl)-5-(5-(trifluoromethyl)-1,2,4-oxadiazol-3-yl)thiophene-2-carboxamide | 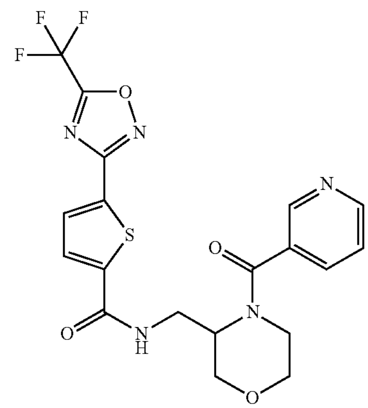 [SMILES: O=C(NCC1COCCN1C(=O)c1cccnc1)c1ccc(-c2noc(C(F)(F)F)n2)s1] | 466.1 [M − H]− |
| 226 | N-((4-isonicotinoylmorpholin-3-yl)methyl)-5-(5-(trifluoromethyl)-1,2,4-oxadiazol-3-yl)thiophene-2-carboxamide | 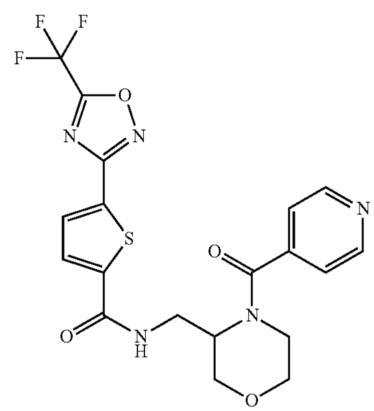 [SMILES: O=C(NCC1COCCN1C(=O)c1ccncc1)c1ccc(-c2noc(C(F)(F)F)n2)s1] | 468.1 [M + H]+ |
| 227 | N-((4-(2-methylisonicotinoyl)morpholin-3-yl)methyl)-5-(5-(trifluoromethyl)-1,2,4-oxadiazol-3-yl)thiophene-2-carboxamide | 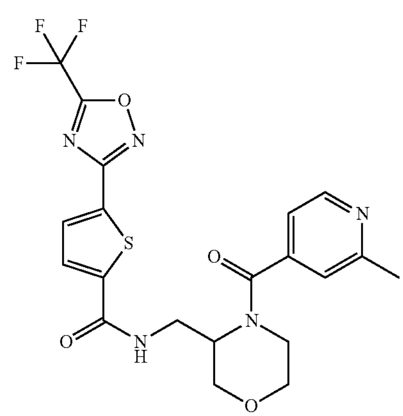 [SMILES: Cc1cc(C(=O)N2CCOCC2CNC(=O)c2ccc(-c3noc(C(F)(F)F)n3)s2)ccn1] | 480.2 [M − H]− |

TABLE 1-continued

| Example No. | IUPAC name | Structure | MS (found) |
|---|---|---|---|
| 228 | N-((4-((1-methyl-1H-imidazol-2-yl)carbonyl)morpholin-3-yl)methyl)-5-(5-(trifluoromethyl)-1,2,4-oxadiazol-3-yl)thiophene-2-carboxamide | 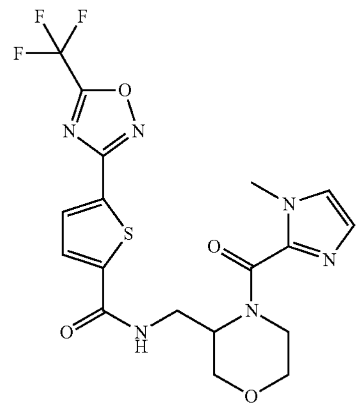 [SMILES: Cn1ccnc1C(=O)N1CCOCC1CNC(=O)c1ccc(-c2noc(C(F)(F)F)n2)s1] | 471.1 [M + H]+ |
| 229 | N-((4-((1-methyl-1H-pyrazol-5-yl)carbonyl)morpholin-3-yl)methyl)-5-(5-(trifluoromethyl)-1,2,4-oxadiazol-3-yl)thiophene-2-carboxamide | 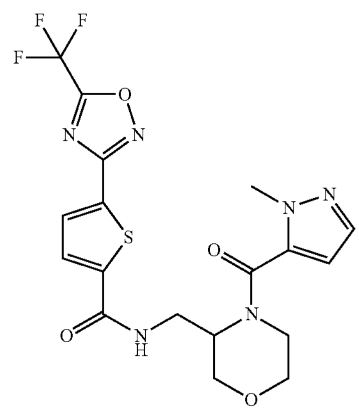 [SMILES: Cn1nccc1C(=O)N1CCOCC1CNC(=O)c1ccc(-c2noc(C(F)(F)F)n2)s1] | 471.1 [M + H]+ |
| 230 | N-((4-((1,3-dimethyl-1H-pyrazol-5-yl)carbonyl)morpholin-3-yl)methyl)-5-(5-(trifluoromethyl)-1,2,4-oxadiazol-3-yl)thiophene-2-carboxamide | 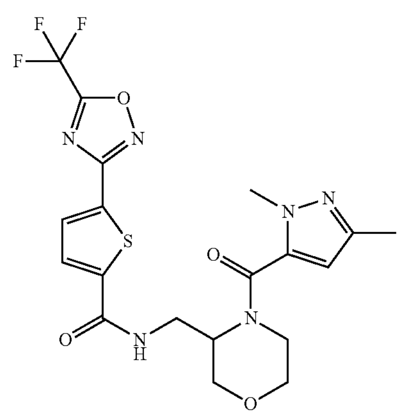 [SMILES: Cc1cc(C(=O)N2CCOCC2CNC(=O)c2ccc(-c3noc(C(F)(F)F)n3)s2)n(C)n1] | 485.1 [M + H]+ |

TABLE 1-continued

| Example No. | IUPAC name | Structure | MS (found) |
|---|---|---|---|
| 231 | N-((4-((1-methyl-3-(trifluoromethyl)-1H-pyrazol-5-yl)carbonyl)morpholin-3-yl)methyl)-5-(5-(trifluoromethyl)-1,2,4-oxadiazol-3-yl)thiophene-2-carboxamide | 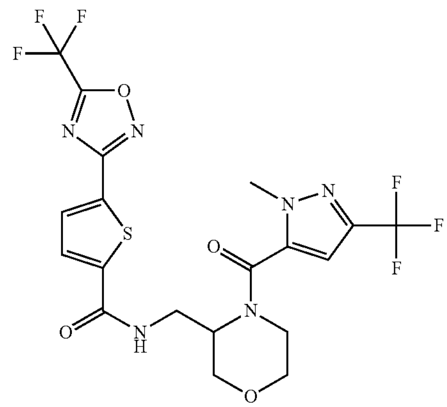 [SMILES: Cn1nc(C(F)(F)F)cc1C(=O)N1CCOCC1CNC(=O)c1ccc(-c2noc(C(F)(F)F)n2)s1] | 537.2 [M − H]− |
| 232 | N-((4-((1-methyl-1H-pyrazol-3-yl)carbonyl)morpholin-3-yl)methyl)-5-(5-(trifluoromethyl)-1,2,4-oxadiazol-3-yl)thiophene-2-carboxamide | 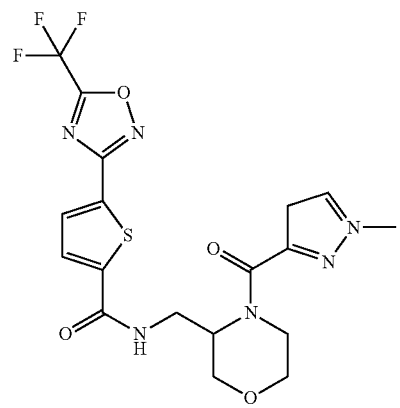 | 471.1 [M + H]+ |
| 233 | N-((4-((1-methyl-1H-pyrazol-4-yl)carbonyl)morpholin-3-yl)methyl)-5-(5-(trifluoromethyl)-1,2,4-oxadiazol-3-yl)thiophene-2-carboxamide | 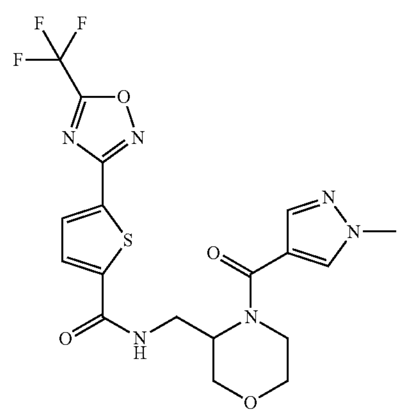 [SMILES: Cn1cc(C(=O)N2CCOCC2CNC(=O)c2ccc(-c3noc(C(F)(F)F)n3)s2)cn1] | 471.1 [M + H]+ |

TABLE 1-continued

| Example No. | IUPAC name | Structure | MS (found) |
| --- | --- | --- | --- |
| 234 | N-((4-((1-methyl-1H-imidazol-4-yl)carbonyl)morpholin-3-yl)methyl)-5-(5-(trifluoromethyl)-1,2,4-oxadiazol-3-yl)thiophene-2-carboxamide | 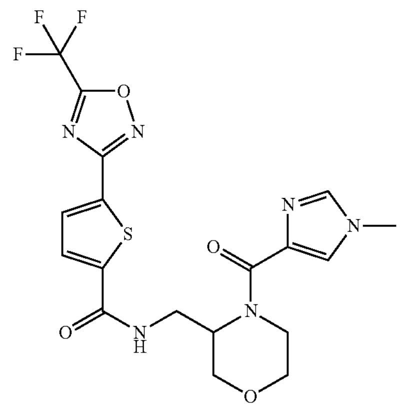 [SMILES: Cn1cnc(C(=O)N2CCOCC2CNC(=O)c2ccc(-c3noc(C(F)(F)F)n3)s2)c1] | 471.1 [M + H]+ |
| 235 | N-((4-((5-methyl-1,2-oxazol-4-yl)carbonyl)morpholin-3-yl)methyl)-5-(5-(trifluoromethyl)-1,2,4-oxadiazol-3-yl)thiophene-2-carboxamide | 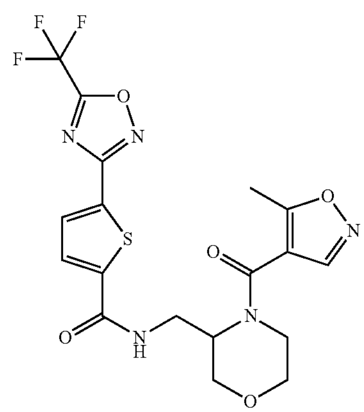 [SMILES: Cc1oncc1C(=O)N1CCOCC1CNC(=O)c1ccc(-c2noc(C(F)(F)F)n2)s1] | 472.0 [M + H]+ |
| 236 | N-((4-((4-methyl-1,2,5-oxadiazol-3-yl)carbonyl)morpholin-3-yl)methyl)-5-(5-(trifluoromethyl)-1,2,4-oxadiazol-3-yl)thiophene-2-carboxamide | 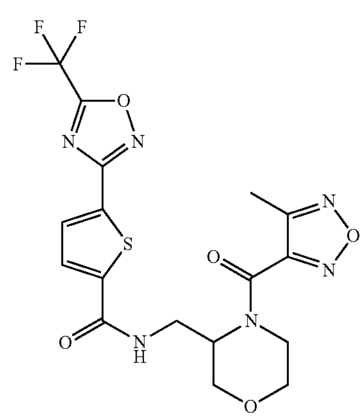 [SMILES: Cc1nonc1C(=O)N1CCOCC1CNC(=O)c1ccc(-c2noc(C(F)(F)F)n2)s1] | 473.1 [M + H]+ |

TABLE 1-continued

| Example No. | IUPAC name | Structure | MS (found) |
|---|---|---|---|
| 237 | N-((4-((4-methyl-1,2,3-thiadiazol-5-yl)carbonyl)morpholin-3-yl)methyl)-5-(5-(trifluoromethyl)-1,2,4-oxadiazol-3-yl)thiophene-2-carboxamide | 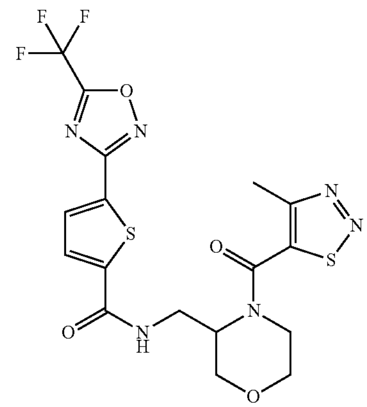 [SMILES: Cc1nnsc1C(=O)N1CCOCC1CNC(=O)c1ccc(-c2noc(C(F)(F)F)n2)s1] | 489.0 [M + H]+ |
| 238 | N-((4-((4-methyl-1,3-thiazol-5-yl)carbonyl)morpholin-3-yl)methyl)-5-(5-(trifluoromethyl)-1,2,4-oxadiazol-3-yl)thiophene-2-carboxamide | 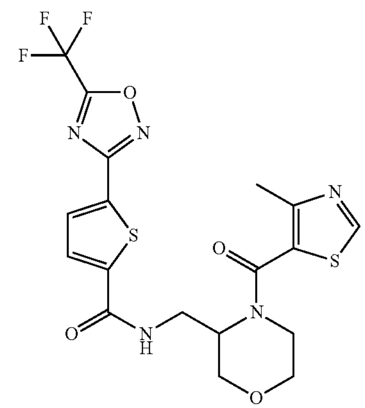 [SMILES: Cc1ncsc1C(=O)N1CCOCC1CNC(=O)c1ccc(-c2noc(C(F)(F)F)n2)s1] | 488.1 [M + H]+ |
| 239 | N-((4-(1,2-oxazol-5-ylcarbonyl)morpholin-3-yl)methyl)-5-(5-(trifluoromethyl)-1,2,4-oxadiazol-3-yl)thiophene-2-carboxamide | 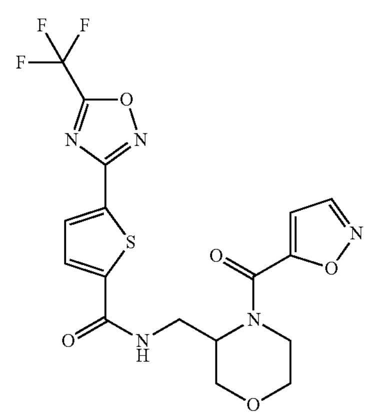 [SMILES: O=C(NCC1COCCN1C(=O)c1ccno1)c1ccc(-c2noc(C(F)(F)F)n2)s1] | 458.1 [M + H]+ |

TABLE 1-continued

| Example No. | IUPAC name | Structure | MS (found) |
|---|---|---|---|
| 240 | N-((4-((3-methyl-1,2-oxazol-5-yl)carbonyl)morpholin-3-yl)methyl)-5-(5-(trifluoromethyl)-1,2,4-oxadiazol-3-yl)thiophene-2-carboxamide | 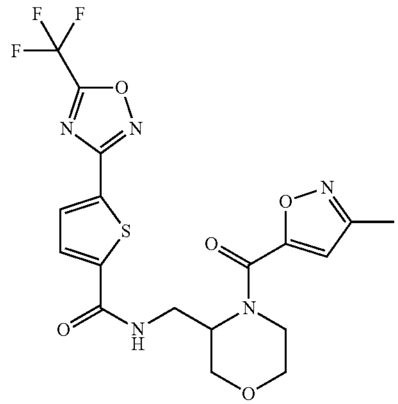 [SMILES: Cc1cc(C(=O)N2CCOCC2CNC(=O)c2ccc(-c3noc(C(F)(F)F)n3)s2)on1] | 472.0 [M + H]+ |
| 241 | N-((4-(2-thienylcarbonyl)morpholin-3-yl)methyl)-5-(5-(trifluoromethyl)-1,2,4-oxadiazol-3-yl)thiophene-2-carboxamide | 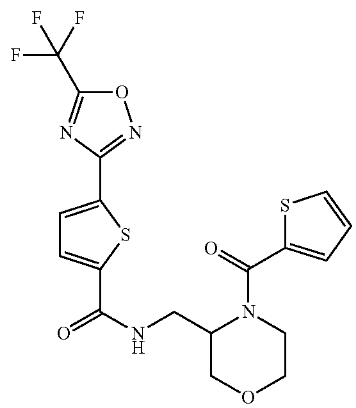 [SMILES: O=C(NCC1COCCN1C(=O)c1cccs1)c1ccc(-c2noc(C(F)(F)F)n2)s1] | 473.1 [M + H]+ |
| 242 | N-((4-((5-methyl-2-thienyl)carbonyl)morpholin-3-yl)methyl)-5-(5-(trifluoromethyl)-1,2,4-oxadiazol-3-yl)thiophene-2-carboxamide | 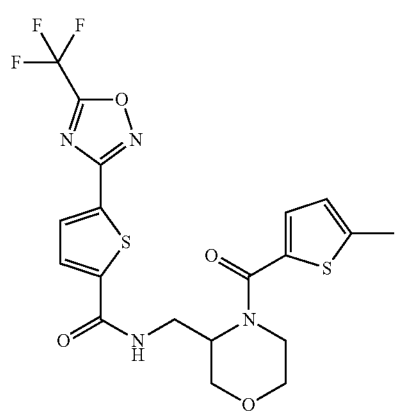 [SMILES: Cc1ccc(C(=O)N2CCOCC2CNC(=O)c2ccc(-c3noc(C(F)(F)F)n3)s2)s1] | 487.0 [M + H]+ |

TABLE 1-continued

| Example No. | IUPAC name | Structure | MS (found) |
|---|---|---|---|
| 243 | N-((4-((4-methyl-2-thienyl)carbonyl)morpholin-3-yl)methyl)-5-(5-(trifluoromethyl)-1,2,4-oxadiazol-3-yl)thiophene-2-carboxamide | 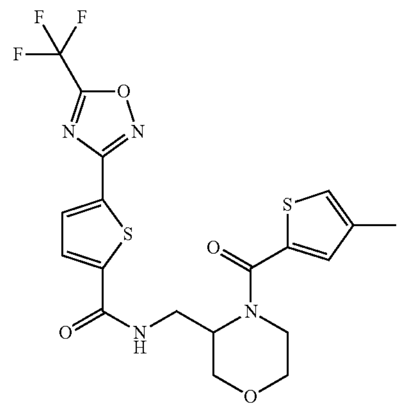 [SMILES: Cc1csc(C(=O)N2CCOCC2CNC(=O)c2ccc(-c3noc(C(F)(F)F)n3)s2)c1] | 487.0 [M + H]+ |
| 244 | N-((4-((3-methyl-2-thienyl)carbonyl)morpholin-3-yl)methyl)-5-(5-(trifluoromethyl)-1,2,4-oxadiazol-3-yl)thiophene-2-carboxamide | 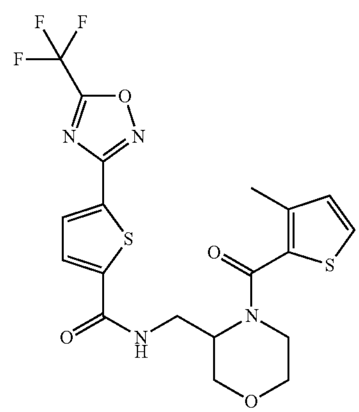 [SMILES: Cc1ccsc1C(=O)N1CCOCC1CNC(=O)c1ccc(-c2noc(C(F)(F)F)n2)s1] | 487.1 [M + H]+ |
| 245 | N-((4-(2-thienylacetyl)morpholin-3-yl)methyl)-5-(5-(trifluoromethyl)-1,2,4-oxadiazol-3-yl)thiophene-2-carboxamide | 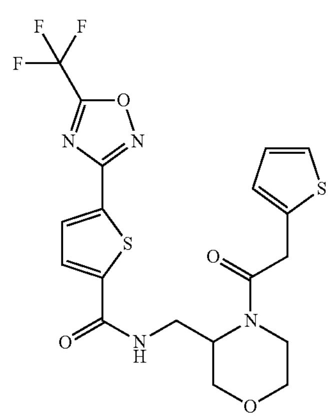 [SMILES: O=C(NCC1COCCN1C(=O)Cc1cccs1)c1ccc(-c2noc(C(F)(F)F)n2)s1] | 487.0 [M + H]+ |

TABLE 1-continued

| Example No. | IUPAC name | Structure | MS (found) |
|---|---|---|---|
| 246 | N-((4-(difluoro(phenyl)acetyl)morpholin-3-yl)methyl)-5-(5-(trifluoromethyl)-1,2,4-oxadiazol-3-yl)thiophene-2-carboxamide | 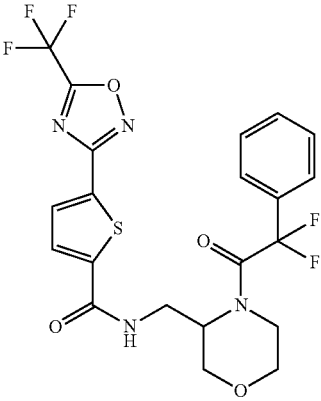 [SMILES: O=C(NCC1COCCN1C(=O)C(F)(F)c1ccccc1)c1ccc(-c2noc(C(F)(F)F)n2)s1] | 517.1 [M + H]+ |
| 247 | N-((4-(2-methyl-2-phenylpropanoyl)morpholin-3-yl)methyl)-5-(5-(trifluoromethyl)-1,2,4-oxadiazol-3-yl)thiophene-2-carboxamide | 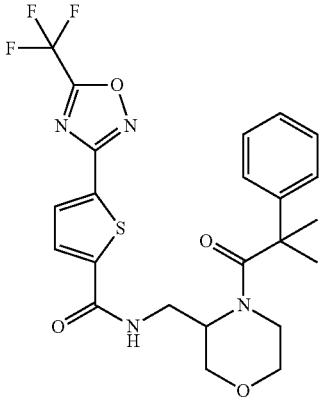 [SMILES: CC(C)(C(=O)N1CCOCC1CNC(=O)c1ccc(-c2noc(C(F)(F)F)n2)s1)c1ccccc1] | 509.2 [M + H]+ |
| 248 | N-((4-((1-phenylcyclopropyl)carbonyl)morpholin-3-yl)methyl)-5-(5-(trifluoromethyl)-1,2,4-oxadiazol-3-yl)thiophene-2-carboxamide | 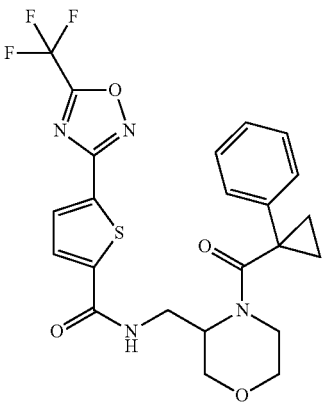 [SMILES: O=C(NCC1COCCN1C(=O)C1(c2ccccc2)CC1)c1ccc(-c2noc(C(F)(F)F)n2)s1] | 507.2 [M + H]+ |

TABLE 1-continued

| Example No. | IUPAC name | Structure | MS (found) |
|---|---|---|---|
| 249 | N-((4-((1-phenylcyclohexyl)carbonyl)morpholin-3-yl)methyl)-5-(5-(trifluoromethyl)-1,2,4-oxadiazol-3-yl)thiophene-2-carboxamide | 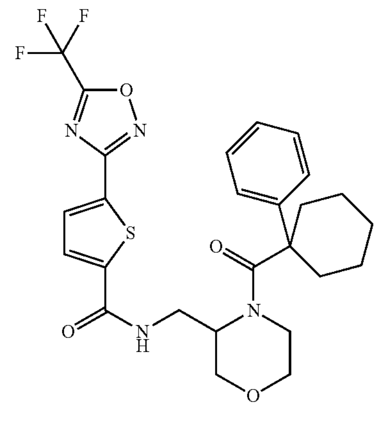 [SMILES: O=C(NCC1COCCN1C(=O)C1(c2ccccc2)CCCCC1)c1ccc(-c2noc(C(F)(F)F)n2)s1] | 549.1 [M + H]+ |
| 250 | N-((4-(3-phenylpropanoyl)morpholin-3-yl)methyl)-5-(5-(trifluoromethyl)-1,2,4-oxadiazol-3-yl)thiophene-2-carboxamide | 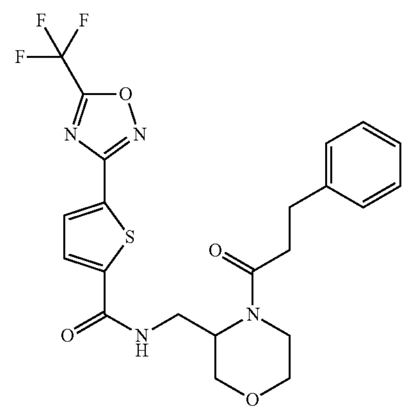 [SMILES: O=C(NCC1COCCN1C(=O)CCc1ccccc1)c1ccc(-c2noc(C(F)(F)F)n2)s1] | 495.1 [M + H]+ |
| 251 | N-((4-((2-methyl-2H-indazol-3-yl)carbonyl)morpholin-3-yl)methyl)-5-(5-(trifluoromethyl)-1,2,4-oxadiazol-3-yl)thiophene-2-carboxamide | 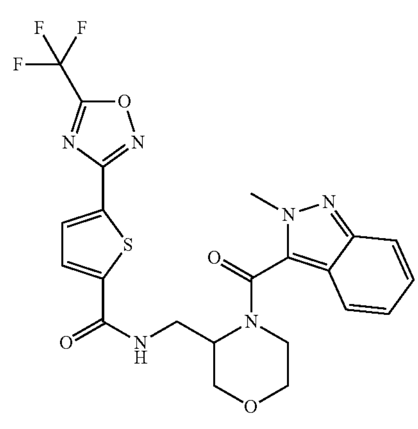 [SMILES: Cn1nc2ccccc2c1C(=O)N1CCOCC1CNC(=O)c1ccc(-c2noc(C(F)(F)F)n2)s1] | 521.1 [M + H]+ |

TABLE 1-continued

| Example No. | IUPAC name | Structure | MS (found) |
|---|---|---|---|
| 252 | N-((4-(2,3-dihydro-1-benzofuran-7-ylcarbonyl)morpholin-3-yl)methyl)-5-(5-(trifluoromethyl)-1,2,4-oxadiazol-3-yl)thiophene-2-carboxamide | 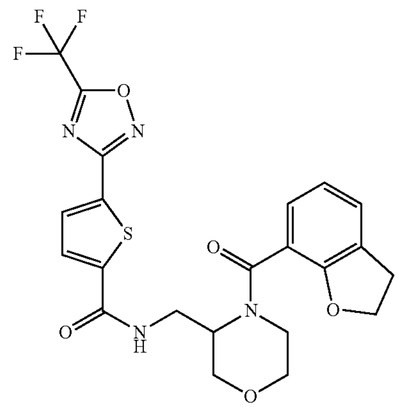 [SMILES: O=C(NCC1COCCN1C(=O)c1cccc2c1OCC2)c1ccc(-c2noc(C(F)(F)F)n2)s1] | 509.2 [M + H]+ |
| 253 | N-((4-(cyclopropylcarbonyl)morpholin-3-yl)methyl)-5-(5-(trifluoromethyl)-1,2,4-oxadiazol-3-yl)thiophene-2-carboxamide | 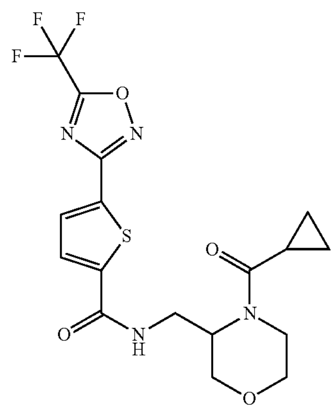 [SMILES: O=C(NCC1COCCN1C(=O)C1CC1)c1ccc(-c2noc(C(F)(F)F)n2)s1] | 431.0 [M + H]+ |
| 254 | N-((4-(cyclohexylcarbonyl)morpholin-3-yl)methyl)-5-(5-(trifluoromethyl)-1,2,4-oxadiazol-3-yl)thiophene-2-carboxamide | 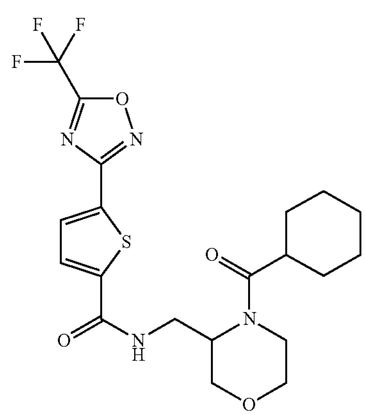 [SMILES: O=C(NCC1COCCN1C(=O)C1CCCCC1)c1ccc(-c2noc(C(F)(F)F)n2)s1] | 471.2 [M − H]− |

TABLE 1-continued

| Example No. | IUPAC name | Structure | MS (found) |
|---|---|---|---|
| 255 | N-((4-(tetrahydro-2H-pyran-4-ylcarbonyl)morpholin-3-yl)methyl)-5-(5-(trifluoromethyl)-1,2,4-oxadiazol-3-yl)thiophene-2-carboxamide | 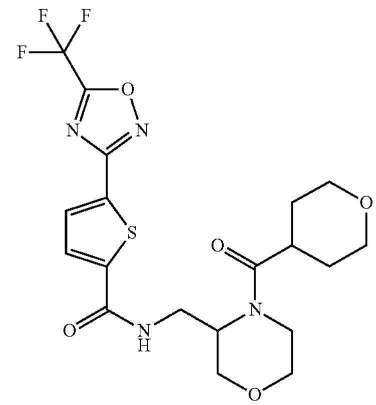 [SMILES: O=C(NCC1COCCN1C(=O)C1CCOCC1)c1ccc(-c2noc(C(F)(F)F)n2)s1] | 473.2 [M − H]− |
| 256 | N-((4-(adamantan-2-ylcarbonyl)morpholin-3-yl)methyl)-5-(5-(trifluoromethyl)-1,2,4-oxadiazol-3-yl)thiophene-2-carboxamide | 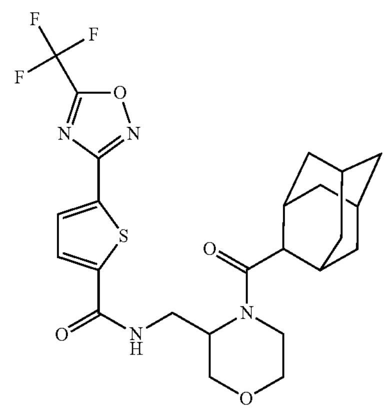 [SMILES: O=C(NCC1COCCN1C(=O)C1C2CC3CC(C2)CC1C3)c1ccc(-c2noc(C(F)(F)F)n2)s1] | 525.2 [M + H]+ |
| 257 | (R or S)-N-((4-benzoylmorpholin-3-yl)methyl)-5-(5-(trifluoromethyl)-1,2,4-oxadiazol-3-yl)thiophene-2-carboxamide | 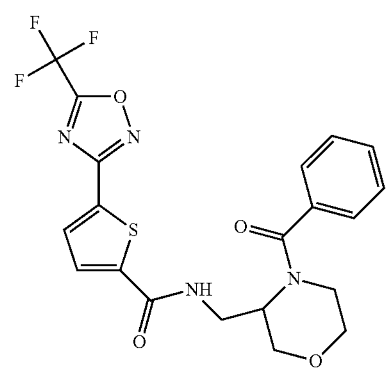 [SMILES: O=C(NCC1COCCN1C(=O)c1ccccc1)c1ccc(-c2noc(C(F)(F)F)n2)s1] | 467.1 [M + H]+ |
| 258 | (R or S)-N-((4-benzoylmorpholin-3-yl)methyl)-5-(5-(trifluoromethyl)-1,2,4-oxadiazol-3-yl)thiophene-2-carboxamide | 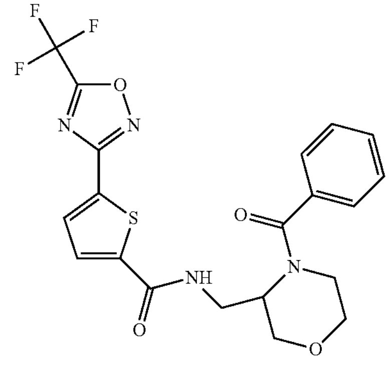 [SMILES: O=C(NCC1COCCN1C(=O)c1ccccc1)c1ccc(-c2noc(C(F)(F)F)n2)s1] | 467.0 [M + H]+ |

TABLE 1-continued

| Example No. | IUPAC name | Structure | MS (found) |
| --- | --- | --- | --- |
| 259 | N-(((3S)-4-((5-methyl-1,2-oxazol-4-yl)carbonyl)morpholin-3-yl)methyl)-5-(5-(trifluoromethyl)-1,2,4-oxadiazol-3-yl)thiophene-2-carboxamide | 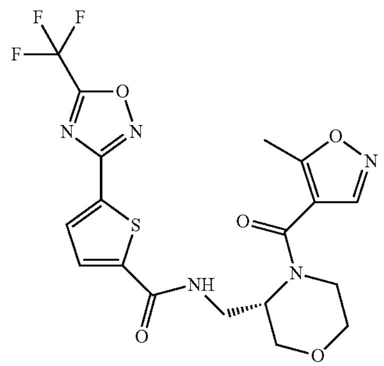 [SMILES: Cc1oncc1C(=O)N1CCOC[C@@H]1CNC(=O)c1ccc(-c2noc(C(F)(F)F)n2)s1] | 471.9 [M + H]+ |
| 260 | N-(((3S)-4-((4-methyl-1,2,5-oxadiazol-3-yl)carbonyl)morpholin-3-yl)methyl)-5-(5-(trifluoromethyl)-1,2,4-oxadiazol-3-yl)thiophene-2-carboxamide | 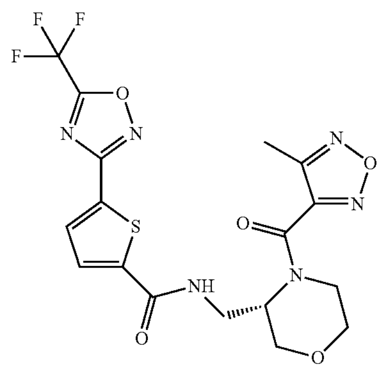 [SMILES: Cc1nonc1C(=O)N1CCOC[C@@H]1CNC(=O)c1ccc(-c2noc(C(F)(F)F)n2)s1] | 472.9 [M + H]+ |
| 261 | N-(((3S)-4-(difluoro(phenyl)acetyl)morpholin-3-yl)methyl)-5-(5-(trifluoromethyl)-1,2,4-oxadiazol-3-yl)thiophene-2-carboxamide | 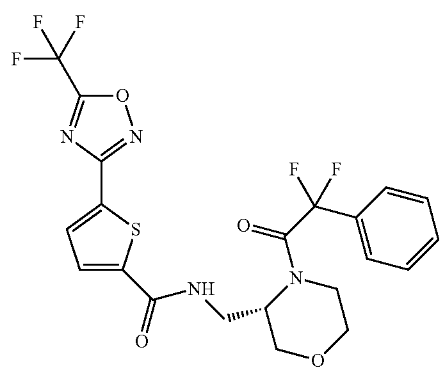 [SMILES: O=C(NC[C@H]1COCCN1C(=O)C(F)(F)c1ccccc1)c1ccc(-c2noc(C(F)(F)F)n2)s1] | 517.0 [M + H]+ |
| 262 | N-(((3S)-4-(biphenyl-3-ylcarbonyl)morpholin-3-yl)methyl)-5-(5-(trifluoromethyl)-1,2,4-oxadiazol-3-yl)thiophene-2-carboxamide | 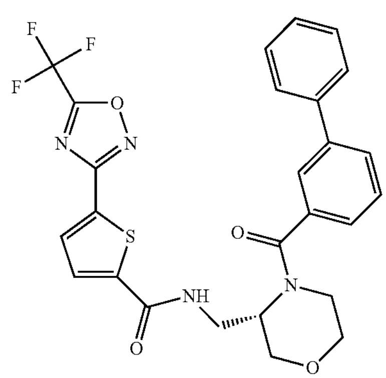 [SMILES: O=C(NC[C@H]1COCCN1C(=O)c1cccc(-c2ccccc2)c1)c1ccc(-c2noc(C(F)(F)F)n2)s1] | 543.0 [M + H]+ |

TABLE 1-continued

| Example No. | IUPAC name | Structure | MS (found) |
|---|---|---|---|
| 263 | N-(((3S)-4-(2-methyl-2-phenylpropanoyl)morpholin-3-yl)methyl)-5-(5-(trifluoromethyl)-1,2,4-oxadiazol-3-yl)thiophene-2-carboxamide | 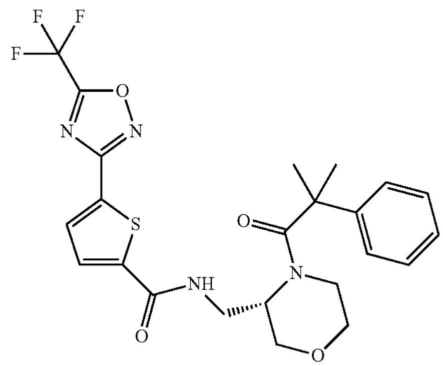 [SMILES: CC(C)(C(=O)N1CCOC[C@@H]1CNC(=O)c1ccc(-c2noc(C(F)(F)F)n2)s1)c1ccccc1] | 509.1 [M + H]+ |
| 264 | N-(((3R)-4-((4-methyl-1,2,5-oxadiazol-3-yl)carbonyl)morpholin-3-yl)methyl)-5-(5-(trifluoromethyl)-1,2,4-oxadiazol-3-yl)thiophene-2-carboxamide | 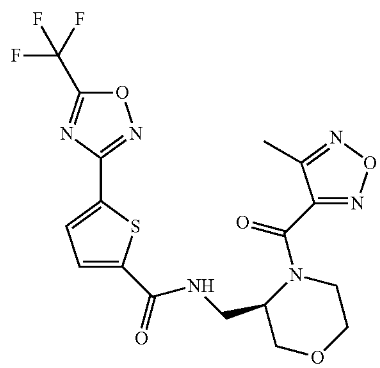 [SMILES: Cc1nonc1C(=O)N1CCOC[C@H]1CNC(=O)c1ccc(-c2noc(C(F)(F)F)n2)s1] | 472.9 [M + H]+ |
| 265 | N-(((3R)-4-(difluoro(phenyl)acetyl)morpholin-3-yl)methyl)-5-(5-(trifluoromethyl)-1,2,4-oxadiazol-3-yl)thiophene-2-carboxamide | 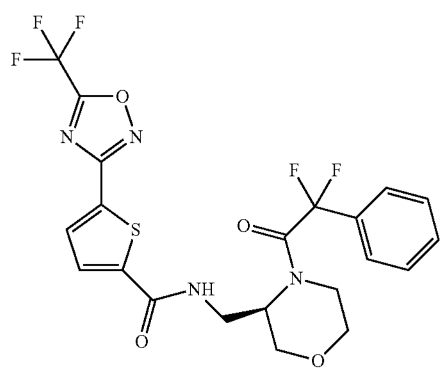 [SMILES: O=C(NC[C@@H]1COCCN1C(=O)C(F)(F)c1ccccc1)c1ccc(-c2noc(C(F)(F)F)n2)s1] | 517.0 [M + H]+ |
| 266 | N-(((3R)-4-(cyclohexylcarbonyl)morpholin-3-yl)methyl)-5-(5-(trifluoromethyl)-1,2,4-oxadiazol-3-yl)thiophene-2-carboxamide | 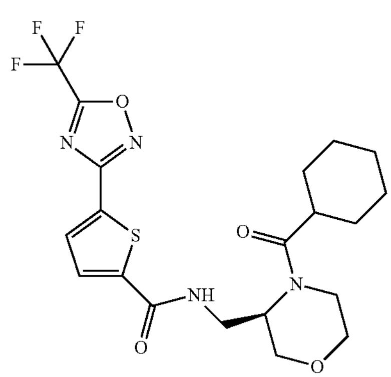 [SMILES: O=C(NC[C@@H]1COCCN1C(=O)C1CCCCC1)c1ccc(-c2noc(C(F)(F)F)n2)s1] | 473.0 [M + H]+ |

| Example No. | IUPAC name | Structure | MS (found) |
|---|---|---|---|
| 267 | N-((4-benzoylmorpholin-3-yl)methyl)-4-(5-(trifluoromethyl)-1,2,4-oxadiazol-3-yl)thiophene-2-carboxamide | 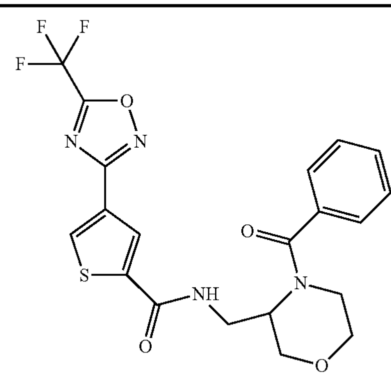 | 465.1 [M − H]− |

Example 268 methyl 3-(((3S)-3-(((4-(5-(trifluoromethyl)-1,2,4-oxadiazol-3-yl)benzoyl)amino)methyl)morpholin-4-yl)carbonyl)benzoate The title compound was obtained using N-((3S)-morpholin-3-ylmethyl)-4-(5-(trifluoromethyl)-1,2,4-oxadiazol-3-yl)benzamide hydrochloride and 3-methoxycarbonylbenzoic acid by a method similar to Example 82.

Example 269

3-(((3S)-3-(((4-(5-(trifluoromethyl)-1,2,4-oxadiazol-3-yl)benzoyl)amino)methyl)morpholin-4-yl)carbonyl)benzoic acid To a mixture of methyl 3-(((3S)-3-(((4-(5-(trifluoromethyl)-1,2,4-oxadiazol-3-yl)benzoyl)amino)methyl)morpholin-4-yl)carbonyl)benzoate (230 mg) and methanol (4 mL) was added a mixture of lithium hydroxidel hydrate (37.2 mg) and water (0.5 mL) at 0° C., and the reaction mixture was stirred at room temperature for 2 hr. The reaction mixture was neutralized with 1N hydrochloric acid, and extracted with ethyl acetate. The extract was washed with saturated brine, and dried over anhydrous sodium sulfate, and the solvent was evaporated under reduced pressure. The residue was purified by silica gel column chromatography (ethyl acetate/methanol) to give the title compound (67 mg).

Example 270

N-(((3S)-4-(1-methyl-L-prolyl)morpholin-3-yl)methyl)-4-(5-(trifluoromethyl)-1,2,4-oxadiazol-3-yl)benzamide The title compound was obtained using N-((3S)-morpholin-3-ylmethyl)-4-(5-(trifluoromethyl)-1,2,4-oxadiazol-3-yl)benzamide hydrochloride and 1-methyl-L-proline by a method similar to Example 33.

Example 271

N-(2-hydroxyethyl)-3-(((3S)-3-(((4-(5-(trifluoromethyl)-1,2,4-oxadiazol-3-yl)benzoyl)amino)methyl)morpholin-4-yl)carbonyl)benzamide A mixture of 3-(((3S)-3-(((4-(5-(trifluoromethyl)-1,2,4-oxadiazol-3-yl)benzoyl) amino)methyl)morpholin-4-yl)carbonyl)benzoic acid (56 mg), 2-aminoethanol (7.12 mg), N-(3-(dimethylamino)propyl)-NT-ethylcarbodiimide hydrochloride (25.5 mg), 1H-benzotriazol-1-ol monohydrate (18.7 mg) and DMF (3 mL) was stirred overnight at room temperature. To the reaction mixture was added saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (hexane/ethyl acetate), and recrystallized from ethyl acetate-hexane to give the title compound (26 mg).

Examples 272 to 295

The compounds of Examples 272 to 295 were obtained using N-((3S)-morpholin-3-ylmethyl)-4-(5-(trifluoromethyl)-1,2,4-oxadiazol-3-yl)benzamide hydrochloride and the corresponding carboxylic acid by a method similar to Example 107 or 108.

Example 296

N-(((3S)-4-((1-(2-hydroxyethyl)-1H-pyrazol-5-yl)carbonyl)morpholin-3-yl)methyl)-4-(5-(trifluoromethyl)-1,2,4-oxadiazol-3-yl)benzamide A mixture of N-((3S)-morpholin-3-ylmethyl)-4-(5-(trifluoromethyl)-1,2,4-oxadiazol-3-yl)benzamide hydrochloride (30 mg), 1-(2-hydroxyethyl)-1H-pyrazole-5-carboxylic acid (11.93 mg), 4-(4,6-dimethoxy-1,3,5-triazin-2-yl)-4-methylmorpholine-4-ium chloride (31.7 mg) and ethanol (1 mL) was stirred at room temperature for 3 days. To the reaction mixture was added DIEA (9.87 mg), and the mixture was stirred at 50° C. 3 hr. The reaction mixture was poured into water, and extracted with ethyl acetate. The extract was washed with saturated brine, and dried over anhydrous sodium sulfate, and the solvent was evaporated under reduced pressure. The residue was purified by silica gel column chromatography (ethyl acetate/methanol) and basic silica gel column chromatography (ethyl acetate/methanol) to give the title compound (11.9 mg).

Example 297

N-(((3S)-4-((1-methyl-1H-pyrazol-5-yl)acetyl)morpholin-3-yl)methyl)-4-(5-(trifluoromethyl)-1,2,4-oxadiazol-3-yl)benzamide The title compound was obtained using N-((3S)-morpholin-3-ylmethyl)-4-(5-(trifluoromethyl)-1,2,4-oxadiazol-3-yl)benzamide hydrochloride and (1-methyl-1H-pyrazol-5-yl)acetic acid by a method similar to Example 82.

Examples 298 to 301

The compounds of Examples 298 to 301 were obtained using N-((3S)-morpholin-3-ylmethyl)-4-(5-(trifluoromethyl)-1,2,4-oxadiazol-3-yl)benzamide hydrochloride and the corresponding carboxylic acid by a method similar to Example 107 or 108.

Example 302

N-(((3S)-4-(3-(2-hydroxyethoxy)benzoyl)morpholin-3-yl)methyl)-4-(5-(trifluoromethyl)-1,2,4-oxadiazol-3-yl)benzamide A mixture of N-((3S)-morpholin-3-ylmethyl)-4-(5-(trifluoromethyl)-1,2,4-oxadiazol-3-yl)benzamide hydrochloride (100 mg), 3-(2-hydroxyethoxy)benzoic acid (46.4 mg), 4-(4,6-dimethoxy-1,3,5-triazin-2-yl)-4-methylmorpholine-4-ium chloride (85 mg), TEA (25.8 mg) and methanol (3 mL) was stirred overnight at room temperature. The reaction mixture was poured into saturated aqueous sodium hydrogencarbonate solution, and extracted with ethyl acetate. The extract was washed with 1N hydrochloric acid and saturated brine, and dried over anhydrous sodium sulfate, and the solvent was evaporated under reduced pressure. The residue was purified by silica gel column chromatography (ethyl acetate/methanol) to give the title compound (69 mg).

Examples 303 to 307

The compounds of Examples 303 to 307 were obtained using N-((3S)-morpholin-3-ylmethyl)-4-(5-(trifluoromethyl)-1,2,4-oxadiazol-3-yl)benzamide hydrochloride and the corresponding carboxylic acid by a method similar to Example 107 or 108.

Example 308

N-(((3S)-4-((2-methyl-1-benzofuran-3-yl)carbonyl)morpholin-3-yl)methyl)-4-(5-(trifluoromethyl)-1,2,4-oxadiazol-3-yl)benzamide To a mixture of 2-methyl-1-benzofuran-3-carboxylic acid (37.4 mg), THF (3 mL) and DMF (0.01 mL) was added ethanedioyl dichloride (32.3 mg), and the mixture was stirred at room temperature for 3 hr. The solvent was evaporated under reduced pressure, and to the residue was added DMF (3 mL). To the reaction mixture were added N-((3S)-morpholin-3-ylmethyl)-4-(5-(trifluoromethyl)-1,2,4-oxadiazol-3-yl)benzamide hydrochloride (100 mg) and TEA (42.9 mg), and the mixture was stirred at room temperature for 5 hr. The reaction mixture was added to saturated aqueous sodium hydrogencarbonate solution, and extracted with ethyl acetate. The extract was washed with water and saturated brine, and dried over anhydrous sodium sulfate, and the solvent was evaporated under reduced pressure. The residue was purified by silica gel column chromatography (ethyl acetate) and basic silica gel column chromatography (hexane/ethyl acetate) to give the title compound (9.7 mg).

Examples 309 to 311

The compounds of Examples 309 to 311 were obtained using N-((3S)-morpholin-3-ylmethyl)-4-(5-(trifluoromethyl)-1,2,4-oxadiazol-3-yl)benzamide hydrochloride and the corresponding carboxylic acid by a method similar to Example 107 or 108.

The structures and MS values (actual measured values) of the compounds of Examples 268 to 311 are shown in Table 2.

TABLE 2

| Example No. | IUPAC Name | Structure | MS (found) |
| --- | --- | --- | --- |
| 268 | methyl 3-(((3S)-3-(((4-(5-(trifluoromethyl)-1,2,4-oxadiazol-3-yl)benzoyl)amino)methyl)morpholin-4-yl)carbonyl)benzoate | 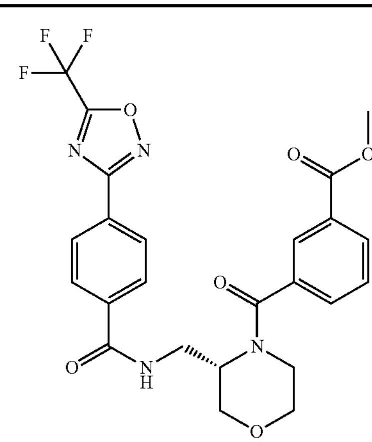 | 519.0 [M + H]+ |

TABLE 2-continued

| Example No. | IUPAC Name | Structure | MS (found) |
| --- | --- | --- | --- |
| 269 | 3-(((3S)-3-(((4-(5-(trifluoromethyl)-1,2,4-oxadiazol-3-yl)benzoyl)amino)methyl)morpholin-4-yl)carbonyl)benzoic acid | 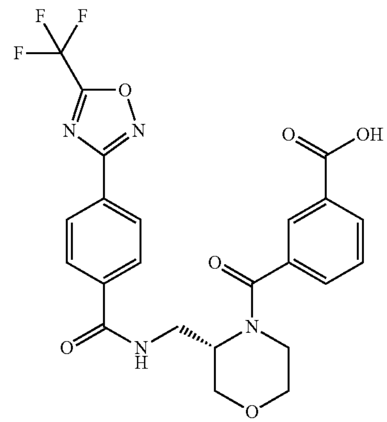 [SMILES: O=C(O)c1cccc(C(=O)N2CCOC[C@@H]2CNC(=O)c2ccc(-c3noc(C(F)(F)F)n3)cc2)c1] | 505.0 [M + H]+ |
| 270 | N-(((3S)-4-(1-methyl-L-prolyl)morpholin-3-yl)methyl)-4-(5-(trifluoromethyl)-1,2,4-oxadiazol-3-yl)benzamide | 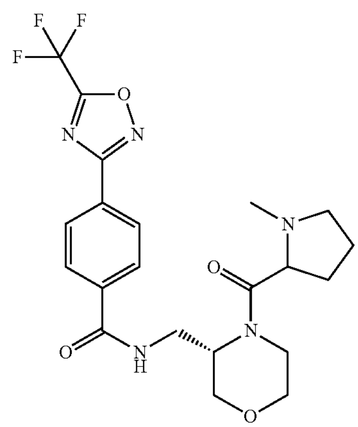 [SMILES: CN1CCCC1C(=O)N1CCOC[C@@H]1CNC(=O)c1ccc(-c2noc(C(F)(F)F)n2)cc1] | 468.0 [M + H]+ |
| 271 | N-(2-hydroxyethyl)-3-(((3S)-3-(((4-(5-(trifluoromethyl)-1,2,4-oxadiazol-3-yl)benzoyl)amino)methyl)morpholin-4-yl)carbonyl)benzamide | 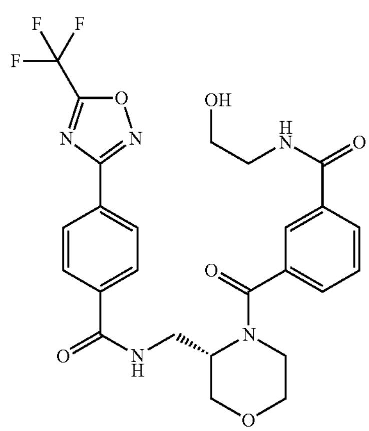 [SMILES: O=C(NCCO)c1cccc(C(=O)N2CCOC[C@@H]2CNC(=O)c2ccc(-c3noc(C(F)(F)F)n3)cc2)c1] | 548.0 [M + H]+ |

TABLE 2-continued

| Example No. | IUPAC Name | Structure | MS (found) |
|---|---|---|---|
| 272 | N-(((3S)-4-(((2R)-2-(methoxymethyl)pyrrolidin-1-yl)carbonyl)morpholin-3-yl)methyl)-4-(5-(trifluoromethyl)-1,2,4-oxadiazol-3-yl)benzamide | 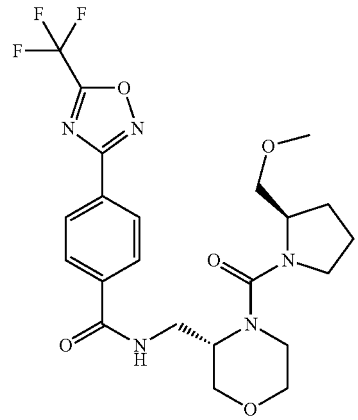 [SMILES: COC[C@H]1CCCN1C(=O)N1CCOC[C@@H]1CNC(=O)c1ccc(-c2noc(C(F)(F)F)n2)cc1] | 498.0 [M + H]+ |
| 273 | N-(((3S)-4-(((2S)-2-(methoxymethyl)pyrrolidin-1-yl)carbonyl)morpholin-3-yl)methyl)-4-(5-(trifluoromethyl)-1,2,4-oxadiazol-3-yl)benzamide | 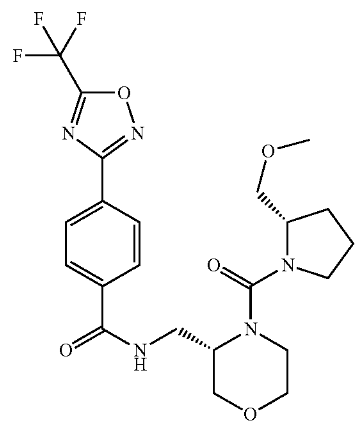 [SMILES: COC[C@@H]1CCCN1C(=O)N1CCOC[C@@H]1CNC(=O)c1ccc(-c2noc(C(F)(F)F)n2)cc1] | 498.1 [M + H]+ |
| 274 | N-(((3S)-4-(((3S)-3-hydroxypyrrolidin-1-yl)carbonyl)morpholin-3-yl)methyl)-4-(5-(trifluoromethyl)-1,2,4-oxadiazol-3-yl)benzamide | 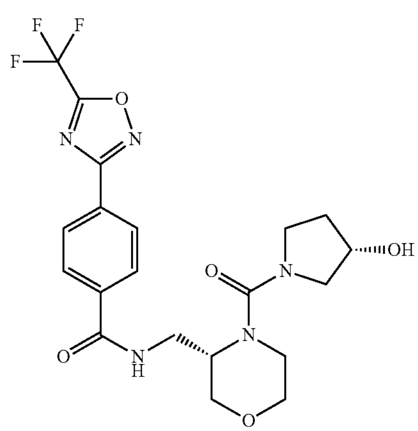 [SMILES: O=C(NC[C@H]1COCCN1C(=O)N1CC[C@H](O)C1)c1ccc(-c2noc(C(F)(F)F)n2)cc1] | 470.0 [M + H]+ |

TABLE 2-continued

| Example No. | IUPAC Name | Structure | MS (found) |
|---|---|---|---|
| 275 | N-(((3S)-4-(((3R)-3-hydroxypyrrolidin-1-yl)carbonyl)morpholin-3-yl)methyl)-4-(5-(trifluoromethyl)-1,2,4-oxadiazol-3-yl)benzamide | 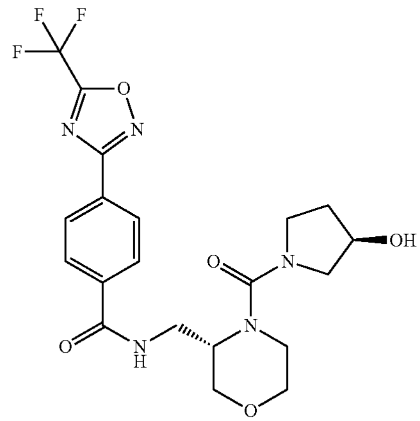 [SMILES: O=C(NC[C@H]1COCCN1C(=O)N1CC[C@@H](O)C1)c1ccc(-c2noc(C(F)(F)F)n2)cc1] | 470.0 [M + H]+ |
| 276 | N-(((3S)-4-((3-(hydroxymethyl)piperidin-1-yl)carbonyl)morpholin-3-yl)methyl)-4-(5-(trifluoromethyl)-1,2,4-oxadiazol-3-yl)benzamide | 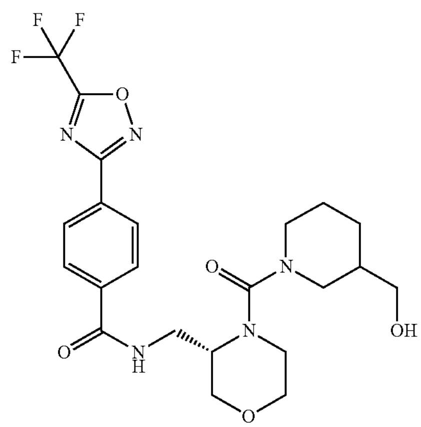 [SMILES: O=C(NC[C@H]1COCCN1C(=O)N1CCCC(CO)C1)c1ccc(-c2noc(C(F)(F)F)n2)cc1] | 498.0 [M + H]+ |
| 277 | N-(((3S)-4-((4,4-difluoropiperidin-1-yl)carbonyl)morpholin-3-yl)methyl)-4-(5-(trifluoromethyl)-1,2,4-oxadiazol-3-yl)benzamide | 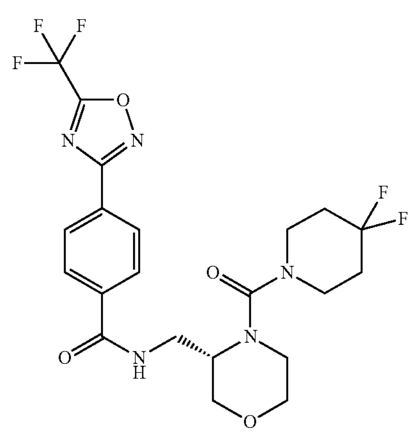 [SMILES: O=C(NC[C@H]1COCCN1C(=O)N1CCC(F)(F)CC1)c1ccc(-c2noc(C(F)(F)F)n2)cc1] | 504.0 [M + H]+ |

TABLE 2-continued

| Example No. | IUPAC Name | Structure | MS (found) |
|---|---|---|---|
| 278 | N-(((3S)-4-((4-(hydroxymethyl)piperidin-1-yl)carbonyl)morpholin-3-yl)methyl)-4-(5-(trifluoromethyl)-1,2,4-oxadiazol-3-yl)benzamide | 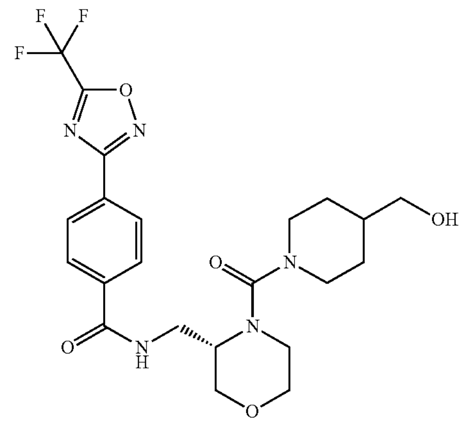 [SMILES: O=C(NC[C@H]1COCCN1C(=O)N1CCC(CO)CC1)c1ccc(-c2noc(C(F)(F)F)n2)cc1] | 497.8 [M + H]+ |
| 279 | N-(((3S)-4-((4-(2-hydroxyethyl)piperidin-1-yl)carbonyl)morpholin-3-yl)methyl)-4-(5-(trifluoromethyl)-1,2,4-oxadiazol-3-yl)benzamide | 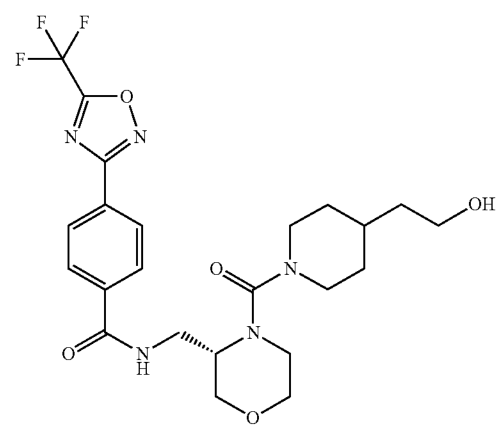 [SMILES: O=C(NC[C@H]1COCCN1C(=O)N1CCC(CCO)CC1)c1ccc(-c2noc(C(F)(F)F)n2)cc1] | 512.1 [M + H]+ |
| 281 | N-(((3S)-4-(2-oxa-6-azaspiro[3.5]non-6-ylcarbonyl)morpholin-3-yl)methyl)-4-(5-(trifluoromethyl)-1,2,4-oxadiazol-3-yl)benzamide | 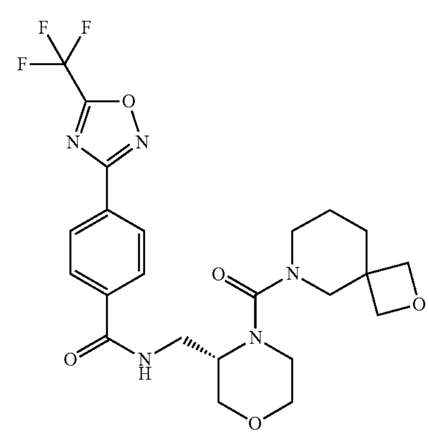 [SMILES: O=C(NC[C@H]1COCCN1C(=O)N1CCCC2(COC2)C1)c1ccc(-c2noc(C(F)(F)F)n2)cc1] | 510.1 [M + H]+ |

TABLE 2-continued

| Example No. | IUPAC Name | Structure | MS (found) |
|---|---|---|---|
| 282 | N-(((3S)-4-(2-oxa-7-azaspiro[3.5]non-7-ylcarbonyl)morpholin-3-yl)methyl)-4-(5-(trifluoromethyl)-1,2,4-oxadiazol-3-yl)benzamide | 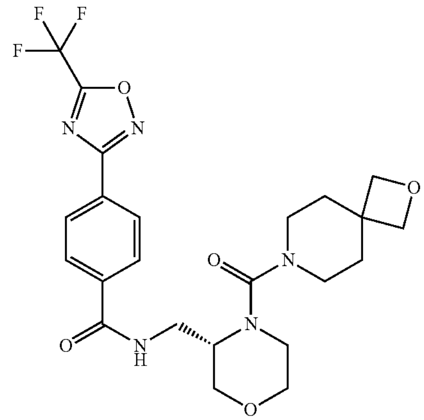 [SMILES: O=C(NC[C@H]1COCCN1C(=O)N1CCC2(CC1)COC2)c1ccc(-c2noc(C(F)(F)F)n2)cc1] | 510.1 [M + H]+ |
| 283 | 1-(((3S)-3-(((4-(5-(trifluoromethyl)-1,2,4-oxadiazol-3-yl)benzoyl)amino)methyl)morpholin-4-yl)carbonyl)-L-prolinamide | 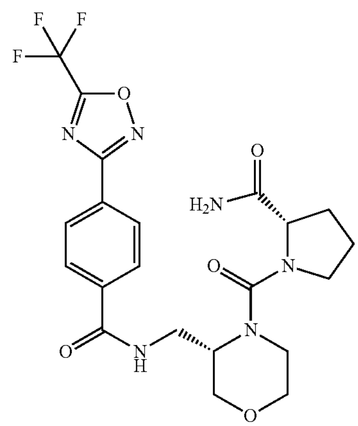 [SMILES: NC(=O)[C@@H]1CCCN1C(=O)N1CCOC[C@@H]1CNC(=O)c1ccc(-c2noc(C(F)(F)F)n2)cc1] | 497.0 [M + H]+ |
| 284 | N-(((3S)-4-(((2R)-2-cyanopyrrolidin-1-yl)carbonyl)morpholin-3-yl)methyl)-4-(5-(trifluoromethyl)-1,2,4-oxadiazol-3-yl)benzamide | 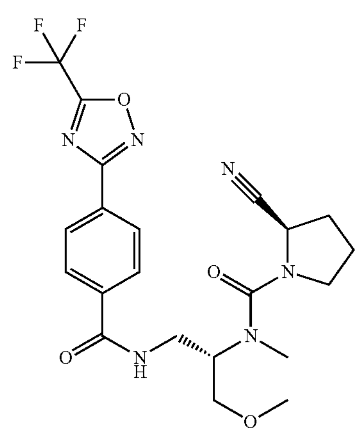 [SMILES: COC[C@H](CNC(=O)c1ccc(-c2noc(C(F)(F)F)n2)cc1)N(C)C(=O)N1CCC[C@@H]1C#N] | 479.0 [M + H]+ |

TABLE 2-continued

| Example No. | IUPAC Name | Structure | MS (found) |
|---|---|---|---|
| 285 | N-(((3S)-4-(((2S)-2-cyanopyrrolidin-1-yl)carbonyl)morpholin-3-yl)methyl)-4-(5-(trifluoromethyl)-1,2,4-oxadiazol-3-yl)benzamide | 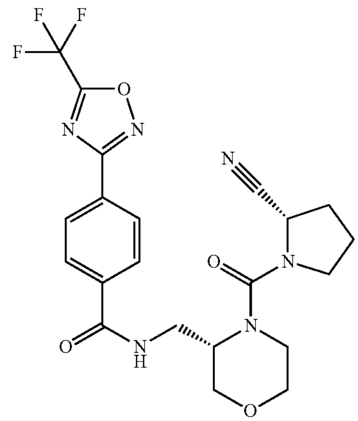 [SMILES: N#C[C@@H]1CCCN1C(=O)N1CCOC[C@@H]1CNC(=O)c1ccc(-c2noc(C(F)(F)F)n2)cc1] | 479.0 [M + H]+ |
| 286 | 4-(5-(trifluoromethyl)-1,2,4-oxadiazol-3-yl)-N-(((3S)-4-(((2R)-2-(trifluoromethyl)pyrrolidin-1-yl)carbonyl)morpholin-3-yl)methyl)benzamide | 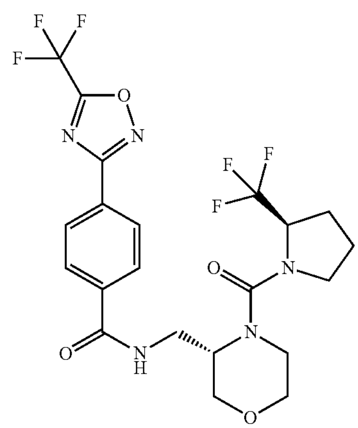 [SMILES: O=C(NC[C@H]1COCCN1C(=O)N1CCC[C@@H]1C(F)(F)F)c1ccc(-c2noc(C(F)(F)F)n2)cc1] | 522.0 [M + H]+ |
| 287 | 4-(5-(trifluoromethyl)-1,2,4-oxadiazol-3-yl)-N-(((3S)-4-(((2S)-2-(trifluoromethyl)pyrrolidin-1-yl)carbonyl)morpholin-3-yl)methyl)benzamide | 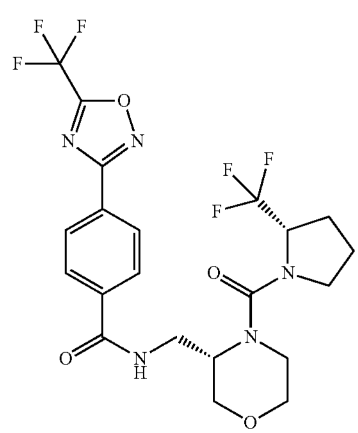 [SMILES: O=C(NC[C@H]1COCCN1C(=O)N1CCC[C@H]1C(F)(F)F)c1ccc(-c2noc(C(F)(F)F)n2)cc1] | 522.1 [M + H]+ |

TABLE 2-continued

| Example No. | IUPAC Name | Structure | MS (found) |
|---|---|---|---|
| 288 | N-(((3S)-4-(((2S)-2-methylpyrrolidin-1-yl)carbonyl)morpholin-3-yl)methyl)-4-(5-(trifluoromethyl)-1,2,4-oxadiazol-3-yl)benzamide | 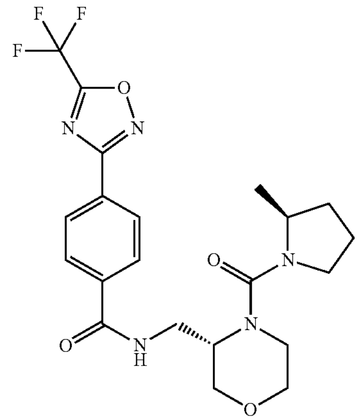 [SMILES: C[C@H]1CCCN1C(=O)N1CCOC[C@@H]1CNC(=O)c1ccc(-c2noc(C(F)(F)F)n2)cc1] | 468.0 [M + H]+ |
| 289 | N-(((3S)-4-(((2R)-2-methylpyrrolidin-1-yl)carbonyl)morpholin-3-yl)methyl)-4-(5-(trifluoromethyl)-1,2,4-oxadiazol-3-yl)benzamide | 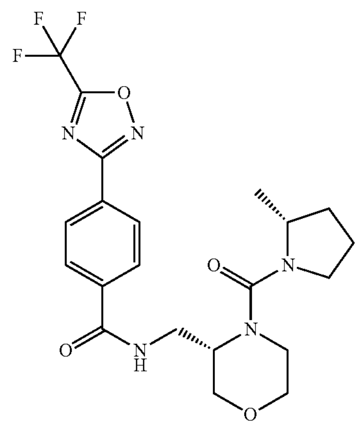 [SMILES: C[C@@H]1CCCN1C(=O)N1CCOC[C@@H]1CNC(=O)c1ccc(-c2noc(C(F)(F)F)n2)cc1] | 468.0 [M + H]+ |
| 290 | N-(((3S)-4-(1,4-oxazepan-4-ylcarbonyl)morpholin-3-yl)methyl)-4-(5-(trifluoromethyl)-1,2,4-oxadiazol-3-yl)benzamide | 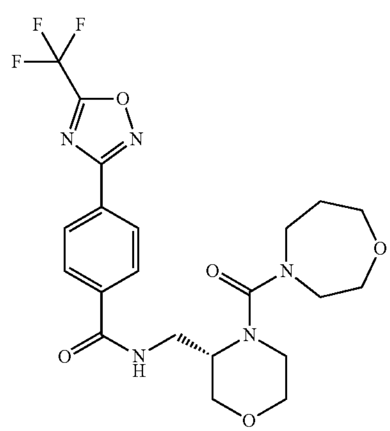 [SMILES: O=C(NC[C@H]1COCCN1C(=O)N1CCCOCC1)c1ccc(-c2noc(C(F)(F)F)n2)cc1] | 484.1 [M + H]+ |

TABLE 2-continued

| Example No. | IUPAC Name | Structure | MS (found) |
|---|---|---|---|
| 291 | N-(((3S)-4-((2-(hydroxymethyl)-1,4-oxazepan-4-yl)carbonyl)morpholin-3-yl)methyl)-4-(5-(trifluoromethyl)-1,2,4-oxadiazol-3-yl)benzamide | 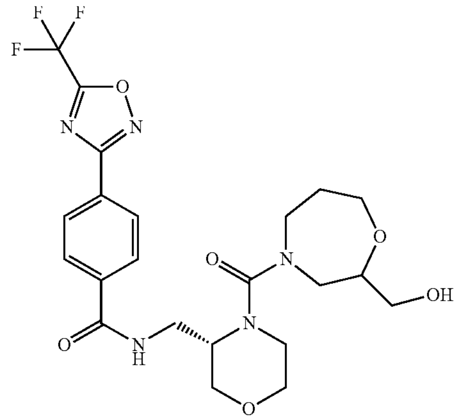 [SMILES: O=C(NC[C@H]1COCCN1C(=O)N1CCCOC(CO)C1)c1ccc(-c2noc(C(F)(F)F)n2)cc1] | 514.0 [M + H]+ |
| 292 | N-(((3S)-4-((2-(pyridin-3-yl)pyrrolidin-1-yl)carbonyl)morpholin-3-yl)methyl)-4-(5-(trifluoromethyl)-1,2,4-oxadiazol-3-yl)benzamide | 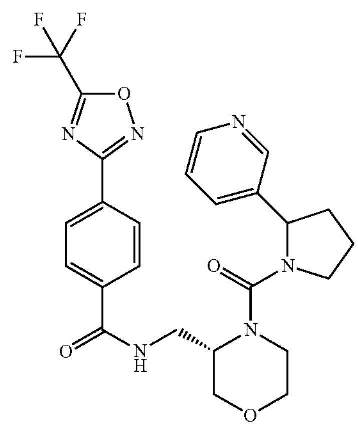 [SMILES: O=C(NC[C@H]1COCCN1C(=O)N1CCCC1c1cccnc1)c1ccc(-c2noc(C(F)(F)F)n2)cc1] | 531.1 [M + H]+ |
| 293 | N-(((3S)-4-((3-phenylpyrrolidin-1-yl)carbonyl)morpholin-3-yl)methyl)-4-(5-(trifluoromethyl)-1,2,4-oxadiazol-3-yl)benzamide | 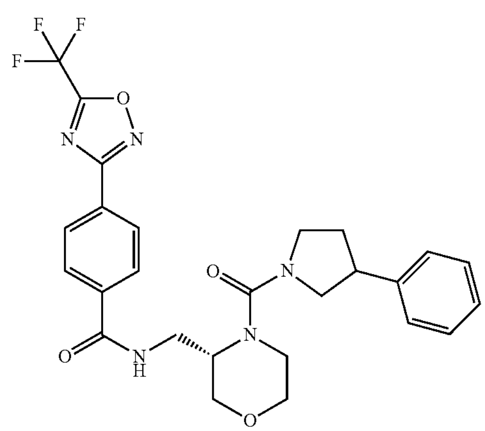 [SMILES: O=C(NC[C@H]1COCCN1C(=O)N1CCC(c2ccccc2)C1)c1ccc(-c2noc(C(F)(F)F)n2)cc1] | 530.0 [M + H]+ |

TABLE 2-continued

| Example No. | IUPAC Name | Structure | MS (found) |
| --- | --- | --- | --- |
| 294 | N-(((3S)-4-((3-(pyridin-3-yl)pyrrolidin-1-yl)carbonyl)morpholin-3-yl)methyl)-4-(5-(trifluoromethyl)-1,2,4-oxadiazol-3-yl)benzamide | 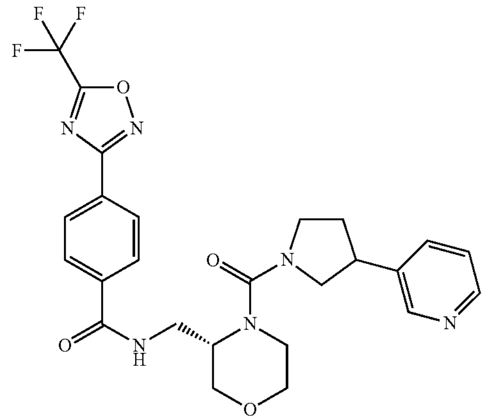 [SMILES: O=C(NC[C@H]1COCCN1C(=O)N1CCC(c2cccnc2)C1)c1ccc(-c2noc(C(F)(F)F)n2)cc1] | 531.0 [M + H]+ |
| 295 | N-(((3S)-4-((3-(pyridin-4-yl)pyrrolidin-1-yl)carbonyl)morpholin-3-yl)methyl)-4-(5-(trifluoromethyl)-1,2,4-oxadiazol-3-yl)benzamide | 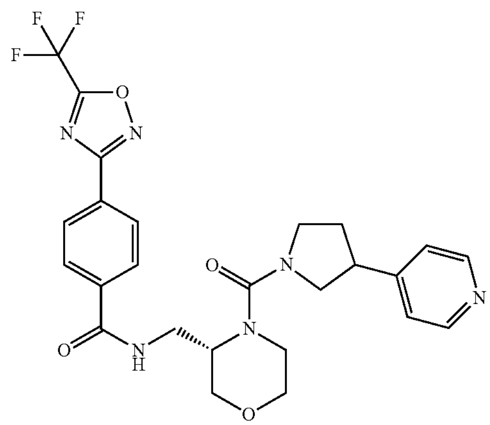 [SMILES: O=C(NC[C@H]1COCCN1C(=O)N1CCC(c2ccncc2)C1)c1ccc(-c2noc(C(F)(F)F)n2)cc1] | 531.0 [M + H]+ |
| 296 | N-(((3S)-4-((1-(2-hydroxyethyl)-1H-pyrazol-5-yl)carbonyl)morpholin-3-yl)methyl)-4-(5-(trifluoromethyl)-1,2,4-oxadiazol-3-yl)benzamide | 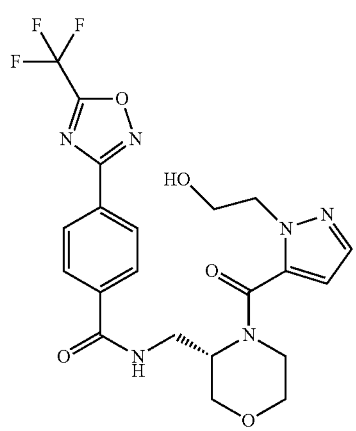 [SMILES: O=C(NC[C@H]1COCCN1C(=O)c1ccnn1CCO)c1ccc(-c2noc(C(F)(F)F)n2)cc1] | 495.0 [M + H]+ |

TABLE 2-continued

| Example No. | IUPAC Name | Structure | MS (found) |
| --- | --- | --- | --- |
| 297 | N-(((3S)-4-((1-methyl-1H-pyrazol-5-yl)acetyl)morpholin-3-yl)methyl)-4-(5-(trifluoromethyl)-1,2,4-oxadiazol-3-yl)benzamide | 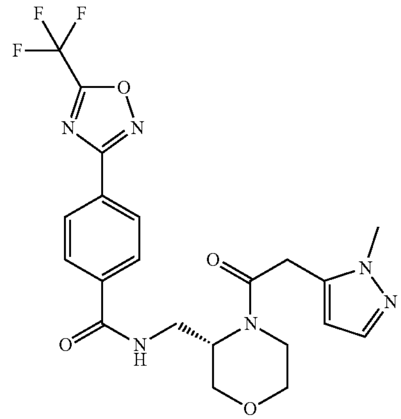 [SMILES: Cn1nccc1CC(=O)N1CCOC[C@@H]1CNC(=O)c1ccc(-c2noc(C(F)(F)F)n2)cc1] | 477.1 [M − H]− |
| 298 | N-(((3S)-4-((3-(hydroxymethyl)pyrrolidin-1-yl)carbonyl)morpholin-3-yl)methyl)-4-(5-(trifluoromethyl)-1,2,4-oxadiazol-3-yl)benzamide | 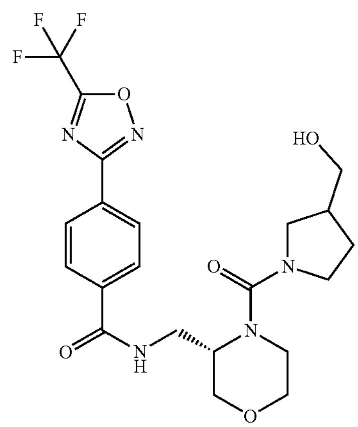 [SMILES: O=C(NC[C@H]1COCCN1C(=O)N1CCC(CO)C1)c1ccc(-c2noc(C(F)(F)F)n2)cc1] | 484.0 [M + H]+ |
| 299 | N-(((3S)-4-((3-(hydroxymethyl)pyrrolidin-1-yl)carbonyl)morpholin-3-yl)methyl)-4-(5-(trifluoromethyl)-1,2,4-oxadiazol-3-yl)benzamide | 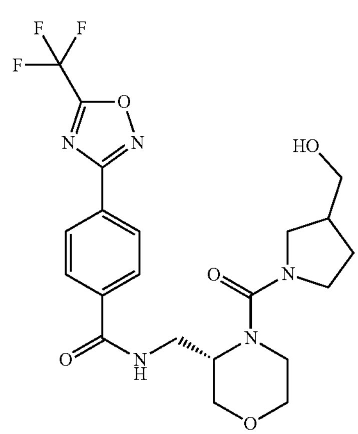 [SMILES: O=C(NC[C@H]1COCCN1C(=O)N1CCC(CO)C1)c1ccc(-c2noc(C(F)(F)F)n2)cc1] | 484.1 [M + H]+ |

TABLE 2-continued

| Example No. | IUPAC Name | Structure | MS (found) |
|---|---|---|---|
| 300 | N-(((3S)-4-((3-(2-hydroxyethyl)pyrrolidin-1-yl)carbonyl)morpholin-3-yl)methyl)-4-(5-(trifluoromethyl)-1,2,4-oxadiazol-3-yl)benzamide | 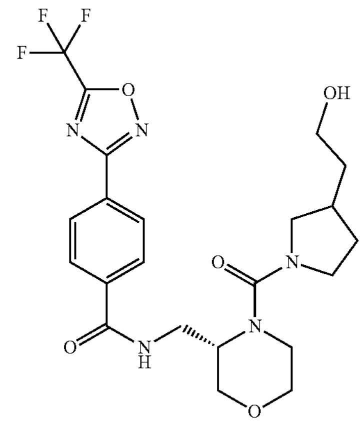 [SMILES: O=C(NC[C@H]1COCCN1C(=O)N1CCC(CCO)C1)c1ccc(-c2noc(C(F)(F)F)n2)cc1] | 498.0 [M + H]+ |
| 301 | N-(((3S)-4-((3-(2-hydroxyethyl)pyrrolidin-1-yl)carbonyl)morpholin-3-yl)methyl)-4-(5-(trifluoromethyl)-1,2,4-oxadiazol-3-yl)benzamide | 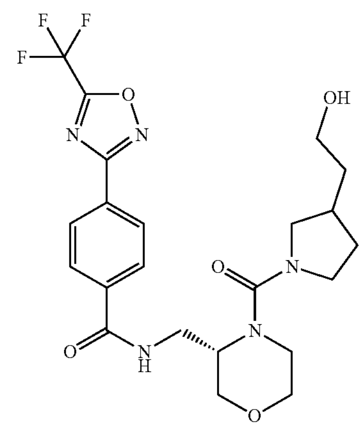 [SMILES: O=C(NC[C@H]1COCCN1C(=O)N1CCC(CCO)C1)c1ccc(-c2noc(C(F)(F)F)n2)cc1] | 498.0 [M + H]+ |
| 302 | N-(((3S)-4-(3-(2-hydroxyethoxy)benzoyl)morpholin-3-yl)methyl)-4-(5-(trifluoromethyl)-1,2,4-oxadiazol-3-yl)benzamide | 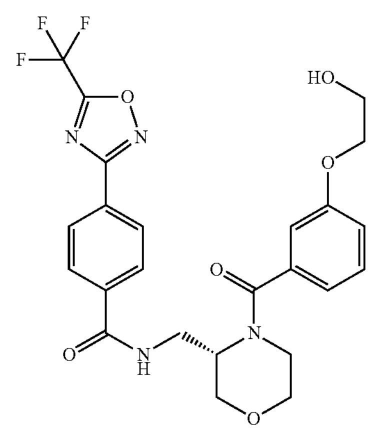 [SMILES: O=C(NC[C@H]1COCCN1C(=O)c1cccc(OCCO)c1)c1ccc(-c2noc(C(F)(F)F)n2)cc1] | 521.1 [M + H]+ |

TABLE 2-continued

| Example No. | IUPAC Name | Structure | MS (found) |
|---|---|---|---|
| 303 | N-(((3S)-4-((2-(hydroxymethyl)piperidin-1-yl)carbonyl)morpholin-3-yl)methyl)-4-(5-(trifluoromethyl)-1,2,4-oxadiazol-3-yl)benzamide | 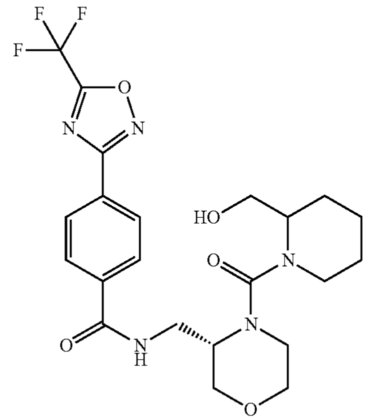 [SMILES: O=C(NC[C@H]1COCCN1C(=O)N1CCCCC1CO)c1ccc(-c2noc(C(F)(F)F)n2)cc1] | 498.0 [M + H]+ |
| 304 | N-(((3S)-4-((2-(hydroxymethyl)piperidin-1-yl)carbonyl)morpholin-3-yl)methyl)-4-(5-(trifluoromethyl)-1,2,4-oxadiazol-3-yl)benzamide | 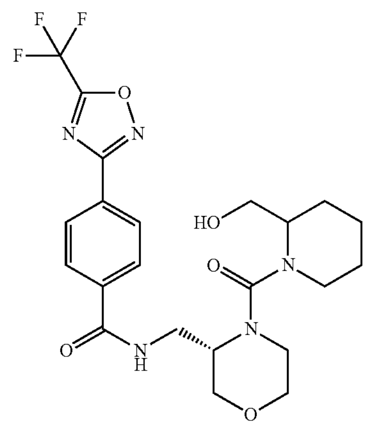 [SMILES: O=C(NC[C@H]1COCCN1C(=O)N1CCCCC1CO)c1ccc(-c2noc(C(F)(F)F)n2)cc1] | 498.0 [M + H]+ |
| 305 | N-(((3S)-4-((2-(2-hydroxyethyl)pyrrolidin-1-yl)carbonyl)morpholin-3-yl)methyl)-4-(5-(trifluoromethyl)-1,2,4-oxadiazol-3-yl)benzamide | 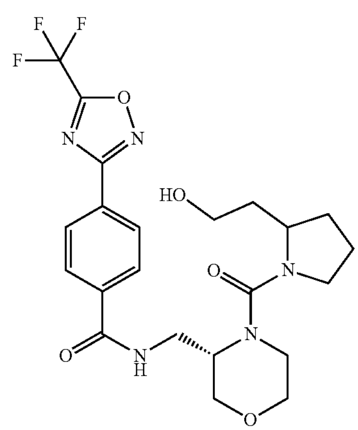 [SMILES: O=C(NC[C@H]1COCCN1C(=O)N1CCCC1CCO)c1ccc(-c2noc(C(F)(F)F)n2)cc1] | 498.0 [M + H]+ |

TABLE 2-continued

| Example No. | IUPAC Name | Structure | MS (found) |
|---|---|---|---|
| 306 | N-(((3S)-4-((2-(2-hydroxyethyl)pyrrolidin-1-yl)carbonyl)morpholin-3-yl)methyl)-4-(5-(trifluoromethyl)-1,2,4-oxadiazol-3-yl)benzamide | 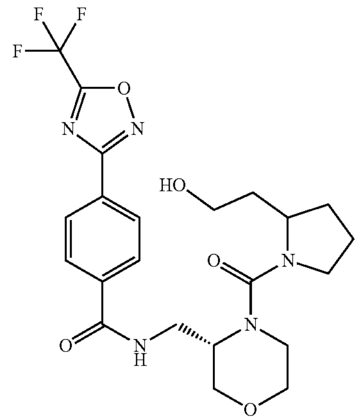 [SMILES: O=C(NC[C@H]1COCCN1C(=O)N1CCCC1CCO)c1ccc(-c2noc(C(F)(F)F)n2)cc1] | 498.0 [M + H]+ |
| 307 | N-(((3S)-4-((3,3-difluoropiperidin-1-yl)carbonyl)morpholin-3-yl)methyl)-4-(5-(trifluoromethyl)-1,2,4-oxadiazol-3-yl)benzamide | 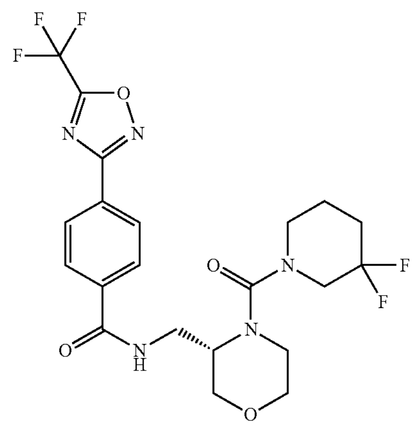 [SMILES: O=C(NC[C@H]1COCCN1C(=O)N1CCCC(F)(F)C1)c1ccc(-c2noc(C(F)(F)F)n2)cc1] | 504.1 [M + H]+ |
| 308 | N-(((3S)-4-((2-methyl-1-benzofuran-3-yl)carbonyl)morpholin-3-yl)methyl)-4-(5-(trifluoromethyl)-1,2,4-oxadiazol-3-yl)benzamide | 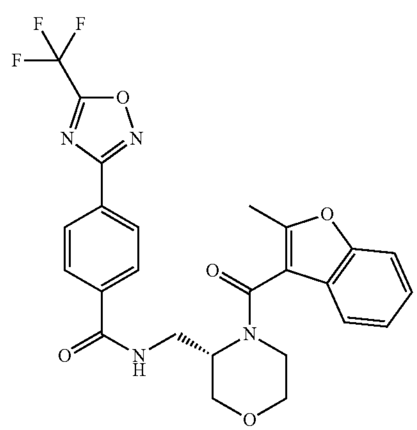 [SMILES: Cc1oc2ccccc2c1C(=O)N1CCOC[C@@H]1CNC(=O)c1ccc(-c2noc(C(F)(F)F)n2)cc1] | 515.0 [M + H]+ |

TABLE 2-continued

| Example No. | IUPAC Name | Structure | MS (found) |
|---|---|---|---|
| 309 | N-(((3S)-4-((6,6-difluoro-3-azabicyclo[3.1.0]hex-3-yl)carbonyl)morpholin-3-yl)methyl)-4-(5-(trifluoromethyl)-1,2,4-oxadiazol-3-yl)benzamide | 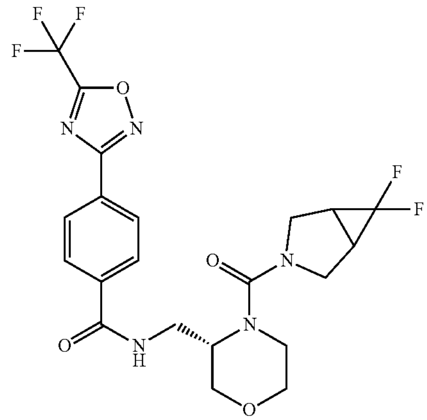 [SMILES: O=C(NC[C@H]1COCCN1C(=O)N1CC2C(C1)C2(F)F)c1ccc(-c2noc(C(F)(F)F)n2)cc1] | 502.1 [M + H]+ |
| 310 | N-(((3S)-4-((3-(hydroxymethyl)morpholin-4-yl)carbonyl)morpholin-3-yl)methyl)-4-(5-(trifluoromethyl)-1,2,4-oxadiazol-3-yl)benzamide | 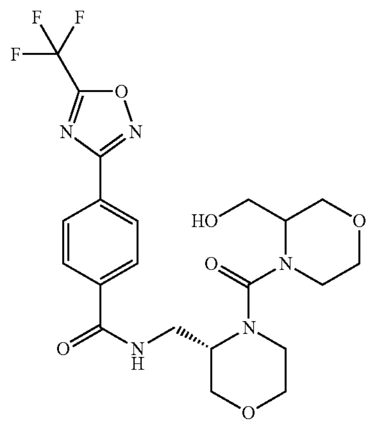 [SMILES: O=C(NC[C@H]1COCCN1C(=O)N1CCOCC1CO)c1ccc(-c2noc(C(F)(F)F)n2)cc1] | 500.1 [M + H]+ |
| 311 | N-(((3S)-4-((3-(hydroxymethyl)morpholin-4-yl)carbonyl)morpholin-3-yl)methyl)-4-(5-(trifluoromethyl)-1,2,4-oxadiazol-3-yl)benzamide | 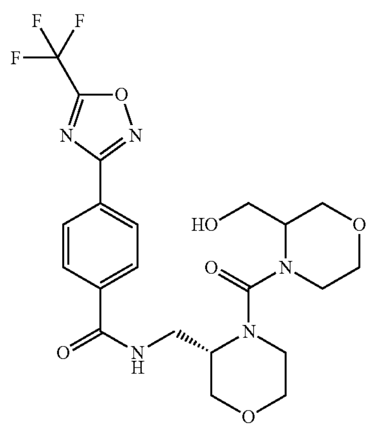 [SMILES: O=C(NC[C@H]1COCCN1C(=O)N1CCOCC1CO)c1ccc(-c2noc(C(F)(F)F)n2)cc1] | 500.1 [M + H]+ |

Experimental Example 1 HDAC1/6 Enzyme Inhibitory Assay

HDAC1 enzyme and HDAC6 enzyme each prepared by transducing full length HDAC1 and HDAC6 genes into Sf-9 insect cells and purifying by GST affinity column were purchased from SignalChem. Using these enzymes, HDAC1 and/or HDAC6 enzyme inhibitory activities of the compound of the present invention were evaluated. Enzymes were used after preserved at −70° C. HDAC1 or HDAC6 enzyme inhibitory activity of the compound of the present invention was measured using HDAC-Glo™ I/II Assay kit (Promega) according to the following experimental method.

The test compound diluted with assay buffer (24 mM Tris-HCl (pH 7.5), 1 mM $MgCl_2$, 0.35 mM KCl, 135 mM NaCl, 0.6 mM Glutathione, 0.01% Tween-20) was added to a 384-well plate by each 2 μL. Then, HDAC1 or HDAC6 enzyme solution diluted with assay buffer was added thereto by each 4 μL, and the plate was incubated at room temperature for 60 min. After incubated, HDAC substrate-Developer solution prepared according to Promega protocol attached to the assay kit was added to the 384-well plate by each 2 μL, and the enzyme reaction was started. After reacting at room temperature for 20 min, luminescence level was measured using plate reader Envision (PerkinElmer). The inhibitory activity of each compound was calculated as a relative activity value when luminescence level in wells without enzyme is considered as 100% inhibition.

The results are shown in the following Table 3.

TABLE 3

| compound of present invention (Ex. No.) | HDAC6 inhibitory rate (%) (1 μM) | HDAC1 inhibitory rate (%) (1 μM) |
| --- | --- | --- |
| 1 | 98% | 22% |
| 2 | 86% | — |
| 3 | 99% | 19% |
| 4 | 100% | 18% |
| 5 | 99% | 21% |
| 6 | 111% | 22% |
| 7 | 101% | 24% |
| 8 | 97% | 33% |
| 9 | 99% | 21% |
| 10 | 104% | 18% |
| 11 | 99% | 21% |
| 12 | 98% | 7% |
| 13 | 97% | 13% |
| 14 | 98% | 20% |
| 15 | 98% | 20% |
| 16 | 93% | — |
| 17 | 61% | — |
| 18 | 98% | 9% |
| 19 | 98% | 24% |
| 20 | 99% | 20% |
| 21 | 97% | 28% |
| 22 | 100% | 23% |
| 23 | 95% | 36% |
| 24 | 93% | 8% |
| 25 | 102% | 20% |
| 26 | 95% | 10% |
| 27 | 99% | 14% |
| 28 | 98% | 14% |
| 29 | 99% | 19% |
| 30 | 98% | 24% |
| 31 | 96% | 28% |
| 32 | 96% | 23% |
| 33 | 99% | 47% |
| 34 | 98% | 18% |
| 35 | 92% | 30% |
| 36 | 105% | 21% |
| 37 | 98% | 27% |
| 38 | 100% | 25% |
| 39 | 100% | 18% |
| 40 | 99% | 17% |
| 41 | 98% | 65% |
| 42 | 101% | 16% |
| 43 | 101% | 14% |
| 44 | 99% | 16% |
| 45 | 99% | 25% |
| 46 | 95% | 12% |
| 47 | 102% | 11% |
| 48 | 98% | 16% |
| 49 | 98% | 13% |
| 50 | 95% | — |
| 51 | 99% | 15% |
| 52 | 97% | 18% |
| 53 | 95% | — |
| 54 | 95% | — |
| 55 | 96% | 17% |
| 56 | 97% | 16% |
| 57 | 56% | — |
| 58 | 93% | — |
| 59 | 101% | 22% |
| 60 | 98% | 27% |
| 61 | 97% | 10% |
| 62 | 93% | — |
| 63 | 97% | 14% |
| 64 | 93% | 17% |
| 65 | 75% | — |
| 66 | 88% | — |
| 67 | 95% | 5% |
| 68 | 101% | 32% |
| 69 | 100% | 16% |
| 70 | 95% | 5% |
| 71 | 89% | — |
| 72 | 89% | — |
| 73 | 98% | — |
| 74 | 100% | 18% |
| 75 | 92% | — |
| 76 | 90% | — |
| 77 | 98% | 18% |
| 78 | 88% | — |
| 79 | 94% | — |
| 80 | 98% | 15% |
| 81 | 94% | — |
| 82 | 101% | 60% |
| 83 | 15% | 4% |
| 84 | 98% | 53% |
| 85 | 96% | 15% |
| 86 | 98% | 24% |
| 87 | 98% | 29% |
| 88 | 100% | 38% |
| 89 | 98% | 12% |
| 90 | 97% | 29% |
| 91 | 98% | 42% |
| 92 | 97% | 36% |
| 93 | 95% | 21% |
| 94 | 99% | 30% |
| 95 | 99% | 30% |
| 96 | 98% | 40% |
| 97 | 96% | 16% |
| 98 | 98% | 15% |
| 99 | 99% | 9% |
| 100 | 97% | 6% |
| 101 | 99% | 17% |
| 102 | 99% | 50% |
| 103 | 98% | 35% |
| 104 | 57% | 9% |
| 105 | 76% | 8% |
| 106 | 98% | 51% |
| 107 | 84% | 14% |
| 108 | 100% | 2% |
| 109 | 99% | 10% |
| 110 | 96% | 10% |
| 111 | 101% | 21% |
| 112 | 97% | 16% |
| 113 | 97% | 17% |
| 114 | 92% | — |
| 115 | 94% | — |
| 116 | 91% | — |
| 117 | 93% | — |
| 118 | 97% | 17% |
| 119 | 97% | 11% |
| 120 | 96% | — |
| 121 | 87% | — |
| 122 | 36% | — |
| 123 | 95% | — |
| 124 | 90% | — |
| 125 | 100% | 19% |
| 126 | 88% | — |
| 127 | 90% | — |
| 128 | 92% | 6% |
| 129 | 53% | — |
| 130 | 94% | — |
| 131 | 87% | — |
| 132 | 98% | 16% |
| 133 | 96% | 6% |
| 134 | 97% | 11% |
| 135 | 91% | — |
| 136 | 92% | — |
| 137 | 93% | — |
| 138 | 85% | — |
| 139 | 63% | — |
| 140 | 92% | — |
| 141 | 89% | — |
| 142 | 96% | 12% |
| 143 | 93% | — |
| 144 | 96% | 14% |
| 145 | 97% | 15% |
| 146 | 94% | — |
| 147 | 94% | 7% |
| 148 | 95% | 10% |
| 149 | 96% | 12% |

TABLE 3-continued

| compound of present invention (Ex. No.) | HDAC6 inhibitory rate (%) (1 μM) | HDAC1 inhibitory rate (%) (1 μM) |
|---|---|---|
| 150 | 90% | — |
| 151 | 90% | — |
| 152 | 99% | 20% |
| 153 | 92% | 3% |
| 154 | 89% | — |
| 155 | 99% | 15% |
| 156 | 95% | — |
| 157 | 92% | 31% |
| 158 | 97% | 12% |
| 159 | 42% | 11% |
| 160 | 98% | 15% |
| 161 | 48% | 6% |
| 162 | 97% | 16% |
| 163 | 97% | 25% |
| 164 | 98% | 17% |
| 165 | 99% | 17% |
| 166 | 98% | — |
| 167 | 93% | 15% |
| 168 | 70% | — |
| 169 | 84% | — |
| 170 | 80% | — |
| 171 | 66% | — |
| 172 | 95% | 8% |
| 173 | 90% | 16% |
| 174 | 94% | — |
| 175 | 97% | 18% |
| 176 | 82% | — |
| 177 | 99% | 27% |
| 178 | 24% | 3% |
| 179 | 36% | −1% |
| 180 | 91% | — |
| 181 | 97% | 29% |
| 182 | 97% | 42% |
| 183 | 97% | 57% |
| 184 | 99% | 77% |
| 185 | 97% | — |
| 186 | 99% | — |
| 187 | 94% | — |
| 188 | 95% | — |
| 189 | 95% | — |
| 190 | 95% | — |
| 191 | 96% | — |
| 192 | 94% | — |
| 193 | 97% | 33% |
| 194 | 97% | 36% |
| 195 | 98% | 40% |
| 196 | 96% | — |
| 197 | 97% | — |
| 198 | 99% | — |
| 199 | 94% | — |
| 200 | 91% | — |
| 201 | 95% | — |
| 202 | 98% | 20% |
| 203 | 95% | — |
| 204 | 97% | 22% |
| 205 | 99% | 59% |
| 206 | 98% | 33% |
| 207 | 99% | 41% |
| 208 | 92% | 16% |
| 209 | 95% | 21% |
| 210 | 96% | 23% |
| 211 | 96% | 15% |
| 212 | 97% | — |
| 213 | 95% | — |
| 214 | 96% | — |
| 215 | 94% | — |
| 216 | 93% | — |
| 217 | 94% | — |
| 218 | 91% | — |
| 219 | 90% | — |
| 220 | 94% | — |
| 221 | 91% | — |
| 222 | 89% | 7% |
| 223 | 93% | — |
| 224 | 92% | — |
| 225 | 92% | — |
| 226 | 95% | — |
| 227 | 91% | — |
| 228 | 77% | — |
| 229 | 97% | — |
| 230 | 88% | — |
| 231 | 92% | — |
| 232 | 85% | — |
| 233 | 78% | — |
| 234 | 38% | — |
| 235 | 99% | 17% |
| 236 | 98% | 43% |
| 237 | 98% | 27% |
| 238 | 98% | — |
| 239 | 97% | — |
| 240 | 89% | — |
| 241 | 94% | — |
| 242 | 89% | — |
| 243 | 93% | — |
| 244 | 96% | — |
| 245 | 95% | — |
| 246 | 99% | 52% |
| 247 | 98% | 18% |
| 248 | 97% | 18% |
| 249 | 83% | — |
| 250 | 98% | — |
| 251 | 96% | 36% |
| 252 | 91% | — |
| 253 | 97% | — |
| 254 | 98% | 33% |
| 255 | 93% | — |
| 256 | 99% | 34% |
| 257 | 97% | 23% |
| 258 | 96% | 31% |
| 259 | 100% | 25% |
| 260 | 98% | 44% |
| 261 | 101% | 53% |
| 262 | 94% | 16% |
| 263 | 99% | 32% |
| 264 | 99% | 48% |
| 265 | 99% | 76% |
| 266 | 98% | 30% |
| 267 | 52% | — |
| 268 | 96% | 15% |
| 269 | 89% | 7% |
| 270 | 59% | −1% |
| 271 | 94% | 7% |
| 272 | 99% | 5% |
| 273 | 87% | 3% |
| 274 | 94% | 3% |
| 275 | 85% | 5% |
| 276 | 89% | 9% |
| 277 | 101% | 8% |
| 278 | 90% | 6% |
| 279 | 90% | 10% |
| 281 | 93% | 7% |
| 282 | 83% | 5% |
| 283 | 73% | −1% |
| 284 | 95% | 1% |
| 285 | 83% | 3% |
| 286 | 95% | 2% |
| 287 | 91% | 2% |
| 288 | 102% | 3% |
| 289 | 85% | 4% |
| 290 | 97% | 3% |
| 291 | 90% | 1% |
| 292 | 76% | 2% |
| 293 | 90% | 14% |
| 294 | 82% | 5% |
| 295 | 85% | 8% |
| 296 | 100% | 32% |
| 297 | 93% | 5% |
| 298 | 88% | 3% |
| 299 | 94% | 4% |
| 300 | 90% | 4% |
| 301 | 92% | 3% |
| 302 | 98% | 10% |
| 303 | 99% | 8% |
| 304 | 99% | 9% |

TABLE 3-continued

| compound of present invention (Ex. No.) | HDAC6 inhibitory rate (%) (1 µM) | HDAC1 inhibitory rate (%) (1 µM) |
|---|---|---|
| 305 | 99% | 5% |
| 306 | 88% | 5% |
| 307 | 98% | 9% |
| 308 | 100% | 46% |
| 309 | 96% | 4% |
| 310 | 98% | 3% |
| 311 | 96% | 7% |

Experimental Example 2 Measurement of Acetylated Tubulin by Compounds A and B (1) Administration and Recovery of Sample:

Compound A (compound of Example 36) and compound B (compound of Example 37) were each orally administered to BALE/c mice (female, Charles River Japan, 8-weeks old when used) at a dose of 30 mg/kg. Compound A and compound B were each suspended in 0.5% methyl cellulose solution, and the suspensions were each orally administered at a dose of 10 mL/kg. For control group, 0.5% methyl cellulose solution was administered. After administration, a part (about 30 mg) of the spleen was recovered into tube containing beads (Lysing Matrix I, Cat. 6918-100, MP Biomedicals), and cryopreserved at −80° C. until used.

0.5 mL RIPA buffer containing protease inhibitor (Cat. 25955-11, Nacalai tesque) was added to the spleen placed in Lysing Matrix I tube, and the spleen was crushed over 20 sec by FastPrep-24. The sample tube was centrifuged (15,000 rpm, 4° C.,) for 5 min, and the supernatant was transferred to another tube. The tube was centrifuged again, and the supernatant was dispensed to a 96-well plate, and preserved at −80° C. until Western blotting measurement. The protein amount of the sample was measured using BCA protein assay kit (Cat. 23227, Pierce). For each administration group, three examples were performed per one group, and data was shown as the mean±standard error.

(2) Western Blotting Method 0.1 M DTT/sample buffer solution prepared by ten-fold diluting 1 M DTT solution (Cat. 646563, Sigma) with sample buffer (Cat. 161-0737, BioRAD) was mixed with the spleen sample in the proportion of 1:1, and the sample was boiled at 100° C. for 3 min. The sample was applied to 15% gel (Cat. NTH-747P10, DRC) so that the protein amount was 5 µg/lane, and electrophoresed at 42 mA/gel for 40 min. After electrophoresed, the protein in the gel was transferred to PVDF membrane by semidryblotting (2 mA/cm$^2$, 60 min).

The membrane was immersed in blocking reagent (Cat. NYPBR01, TOYOBO) at room temperature for 1 hr, washed, and reacted with primary antibody overnight at 4° C. After washed, the membrane was reacted with secondary antibody at room temperature for 1 hr, and immersed in ECL prime detecting solution (Cat. RPN2232, GE), and the chemiluminescence was detected by luminoimage analyzer LAS3000.

The chemiluminescence detected around molecular weights 52 KDa and 37 KD were quantified, and the protein expression levels of acetylated tubulin and GAPDH were evalated as fold increase relative to 0.5% methyl cellulose solution administration group (Veh in graph of Example).

Acetylated tubulin antibody (Cat. T7451, Sigma) and GAPDH antibody (Cat. 21185, Cell Signaling Technology (CST)) were used as a primary antibody. Anti-mouse IgG-HRP antibody (Cat. 7076, CST) and anti-rabbit IgG-HRP antibody (Cat. 7074, CST) were used as a secondary antibody.

(3) Results

Figure 2:
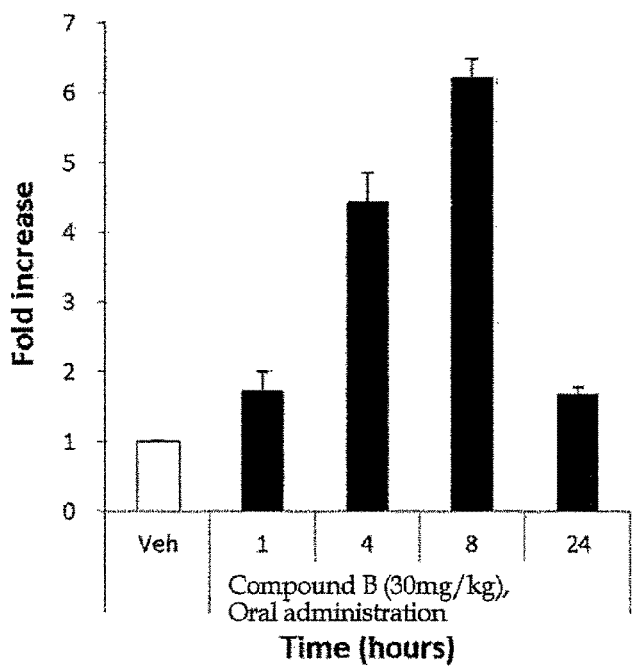
FIG. 2 shows increase in acetylated tubulin by compound B (compound of Example 37).

The results are shown in FIG. 1 and FIG. 2. As clear from FIG. 1 and FIG. 2, compound A and compound B increased most acetylation of tubulin in spleen 8 hr after administration.

| Formulation Example 1 (production of capsule) | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin

| Formulation Example 2 (production of tablet) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has a HDAC inhibitory action, and is useful for the treatment of autoimmune diseases and/or inflammatory diseases (inflammatory bowel disease, rheumatoid arthritis, psoriasis, multiple sclerosis, Sjogren's syndrome, Behcet's disease, systemic lupus erythematosus, etc.), graft versus host disease (GvHD), cancers (multiple myeloma, leukemia, uterine leiomyosarcoma, prostate cancer, cachexia, myelofibrosis, etc.), central nervous diseases including neurodegenerative diseases (Alzheimer's disease, Parkinson's disease, Huntington's disease, etc.) and the like.

This application is based on patent application No. 2014-172058 filed on Aug. 26, 2014 in Japan, the contents of which are encompassed in full herein.

The invention claimed is:

1. A compound represented by the formula (I):

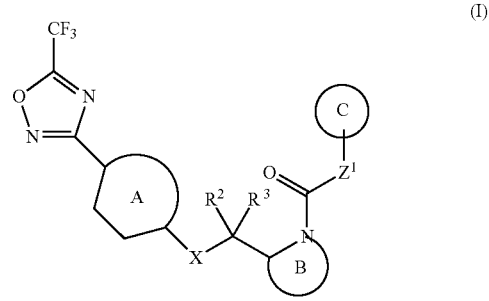

wherein
Ring A is an optionally further substituted 5- or 6-membered aromatic or non-aromatic ring,
X is —CONR$^1$— or —NR$^1$CO—,
R$^1$ is a hydrogen atom or a substituent,
R$^2$ and R$^3$ are the same or different and each is a hydrogen atom or a substituent,
Ring B is an optionally further substituted nitrogen-containing heterocycle,
Z$^1$ is a bond, or a spacer in which the number of atoms in the main chain is 1 to 3, and
Ring C is an optionally further substituted ring,
or a salt thereof.

2. The compound or salt of claim 1, wherein
Ring A is a 5- or 6-membered ring optionally further substituted by 1 to 3 substituents selected from
  (1) a halogen atom, and
  (2) a C$_{1-6}$ alkyl group;
X is —CONR$^1$— or —NR$^1$CO—, and R$^1$ is a hydrogen atom or a C$_{1-6}$ alkyl group;
R$^2$ and R$^3$ are hydrogen atoms;
Ring B is a nitrogen-containing heterocycle optionally further substituted by 1 to 3 C$_{6-14}$ aryl-carbonyl groups;
Z$^1$ is a bond, —NR$^a$—, —CR$^b_2$—, —CR$^b_2$—CR$^b_2$— or —CR$^b_2$—O—;
wherein
  R$^a$ is a hydrogen atom or a C$_{1-6}$ alkyl group; and
  R$^b$ are each independently a hydrogen atom, a halogen atom, a C$_{1-6}$ alkyl group or a C$_{6-14}$ aryl group; and
Ring C is a ring optionally further substituted by 1 to 3 substituents selected from
  (a) a halogen atom,
  (b) a C$_{1-6}$ alkyl group optionally substituted by 1 to 3 substituents selected from
    (i) a halogen atom,
    (ii) a hydroxy group, and
    (iii) a C$_{1-6}$ alkoxy group,
  (c) a C$_{6-14}$ aryl group,
  (d) a cyano group,
  (e) a C$_{1-6}$ alkoxy group optionally substituted by 1 to 3 substituents selected from
    (i) a halogen atom, and
    (ii) a hydroxy group,
  (f) a 3- to 14-membered non-aromatic heterocyclic group,
  (g) a 5- to 14-membered aromatic heterocyclic group,
  (h) a C$_{3-10}$ cycloalkyl group,
  (i) a hydroxy group,
  (j) an oxo group,
  (k) a carboxy group,
  (l) a C$_{1-6}$ alkoxy-carbonyl group,
  (m) a carbamoyl group, and
  (n) a mono- or di-C$_{1-6}$ alkyl-carbamoyl group optionally substituted by 1 to 3 hydroxy groups.

3. The compound or salt of claim 1, wherein
Ring A is
(1) a benzene ring optionally further substituted by 1 to 3 substituents selected from
  (a) a halogen atom, and
  (b) a C$_{1-6}$ alkyl group, or
(2) a 5- or 6-membered monocyclic aromatic heterocycle;
X is —CONR$^1$— or —NR$^1$CO—, and R$^1$ is a hydrogen atom or a C$_{1-6}$ alkyl group;
R$^2$ and R$^3$ are hydrogen atoms;
Ring B is a 4- to 10-membered nitrogen-containing heterocycle optionally further substituted by 1 to 3 C$_{6-14}$ aryl-carbonyl groups;
Z$^1$ is a bond, —NR$^a$—, —CR$^b_2$—, —CR$^b_2$—CR$^b_2$— or —CR$^b_2$—O—;
wherein
  R$^a$ is a hydrogen atom or a C$_{1-6}$ alkyl group; and
  R$^b$ are each independently a hydrogen atom, a halogen atom, a C$_{1-6}$ alkyl group or a C$_{6-14}$ aryl group; and
Ring C is
(1) a C$_{6-14}$ aromatic hydrocarbon ring optionally further substituted by 1 to 3 substituents selected from
  (a) a halogen atom,
  (b) a C$_{1-6}$ alkyl group optionally substituted by 1 to 3 halogen atoms,
  (c) a C$_{6-14}$ aryl group,
  (d) a cyano group,
  (e) a C$_{1-6}$ alkoxy group optionally substituted by 1 to 3 hydroxy groups,
  (f) a 3- to 8-membered monocyclic non-aromatic heterocyclic group,
  (g) a carboxy group,
  (h) a C$_{1-6}$ alkoxy-carbonyl group, and
  (i) a mono- or di-C$_{1-6}$ alkyl-carbamoyl group optionally substituted by 1 to 3 hydroxy groups,
(2) a C$_{3-10}$ cycloalkane ring optionally further substituted by 1 to 3 substituents selected from
  (a) a C$_{6-14}$ aryl group, and
  (b) a cyano group,
(3) a 5- to 14-membered aromatic heterocycle optionally further substituted by 1 to 3 substituents selected from
  (a) a C$_{1-6}$ alkyl group optionally substituted by 1 to 3 substituents selected from a halogen atom and a hydroxy group,
  (b) a C$_{3-10}$ cycloalkyl group,
  (c) a C$_{1-6}$ alkoxy group optionally substituted by 1 to 3 halogen atoms, and
  (d) a hydroxy group, or
(4) a 3- to 14-membered non-aromatic heterocycle optionally further substituted by 1 to 3 substituents selected from
  (a) a C$_{1-6}$ alkyl group optionally substituted by 1 to 3 substituents selected from a hydroxy group, a halogen atom and a C$_{1-6}$ alkoxy group,
  (b) a C$_{6-14}$ aryl group,
  (c) an oxo group,
  (d) a halogen atom,
  (e) a hydroxy group,
  (f) a cyano group,
  (g) a 5- or 6-membered monocyclic aromatic heterocyclic group, and
  (h) a carbamoyl group.

4. The compound or salt of claim 1, wherein
Ring A is
(1) a benzene ring optionally further substituted by 1 to 3 substituents selected from
  (a) a halogen atom, and
  (b) a C$_{1-6}$ alkyl group,
(2) a pyridine ring, or
(3) a thiophene ring;
X is —CONR$^1$— or —NR$^1$CO—, and R$^1$ is a hydrogen atom or a C$_{1-6}$ alkyl group;
R$^2$ and R$^3$ are hydrogen atoms;
Ring B is
(1) a morpholine ring,
(2) a piperidine ring,
(3) a piperazine ring optionally further substituted by one benzoyl group,
(4) a pyrrolidine ring,
(5) an indoline ring, (6) an isoindoline ring,
(7) a tetrahydroquinoline ring, or
(8) a tetrahydroisoquinoline ring;

$Z^1$ is a bond, —$NR^a$—, —$CR^b{}_2$—, —$CR^b{}_2$—$CR^b{}_2$— or —$CR^b{}_2$—O—,
wherein
$R^a$ is a hydrogen atom or a $C_{1-6}$ alkyl group, and
$R^b$ are each independently a hydrogen atom, a halogen atom, a $C_{1-6}$ alkyl group or a phenyl group; and Ring C is
(1) a benzene ring optionally further substituted by 1 to 3 substituents selected from
  (a) a halogen atom,
  (b) a $C_{1-6}$ alkyl group optionally substituted by 1 to 3 halogen atoms,
  (c) a phenyl group,
  (d) a cyano group,
  (e) a $C_{1-6}$ alkoxy group optionally substituted by 1 to 3 hydroxy groups,
  (f) a morpholinyl group,
  (g) a carboxy group,
  (h) a $C_{1-6}$ alkoxy-carbonyl group, and
  (i) a mono- or di-$C_{1-6}$ alkyl-carbamoyl group optionally substituted by 1 to 3 hydroxy groups,
(2) a $C_{3-10}$ cycloalkane ring optionally further substituted by 1 to 3 substituents selected from
  (a) a phenyl group, and
  (b) a cyano group,
(3) an adamantane ring,
(4) a pyridine ring optionally further substituted by 1 to 3 substituents selected from
  (a) a $C_{1-6}$ alkyl group,
  (b) a $C_{3-10}$ cycloalkyl group,
  (c) a $C_{1-6}$ alkoxy group optionally substituted by 1 to 3 halogen atoms, and
  (d) a hydroxy group,
(5) a thiophene ring optionally further substituted by 1 to 3 $C_{1-6}$ alkyl groups,
(6) a pyrazole ring optionally further substituted by 1 to 3 $C_{1-6}$ alkyl groups optionally substituted by 1 to 3 substituents selected from a halogen atom and a hydroxy group,
(7) an imidazole ring optionally further substituted by 1 to 3 $C_{1-6}$ alkyl groups,
(8) an oxadiazole ring optionally further substituted by 1 to 3 $C_{1-6}$ alkyl groups,
(9) an isoxazole ring optionally further substituted by 1 to 3 $C_{1-6}$ alkyl groups,
(10) a thiadiazole ring optionally further substituted by 1 to 3 $C_{1-6}$ alkyl groups,
(11) a thiazole ring optionally further substituted by 1 to 3 $C_{1-6}$ alkyl groups,
(12) an indazole ring optionally further substituted by 1 to 3 $C_{1-6}$ alkyl groups,
(13) a benzofuran ring optionally further substituted by 1 to 3 $C_{1-6}$ alkyl groups,
(14) an imidazopyridine ring optionally further substituted by 1 to 3 $C_{1-6}$ alkyl groups,
(15) a pyrazolopyrimidine ring,
(16) an imidazothiazole ring optionally further substituted by 1 to 3 $C_{1-6}$ alkyl groups,
(17) an oxetane ring optionally further substituted by 1 to 3 phenyl groups,
(18) a pyrrolidine ring optionally further substituted by 1 to 3 substituents selected from
  (a) a $C_{1-6}$ alkyl group optionally substituted by 1 to 3 substituents selected from a hydroxy group, a halogen atom and a $C_{1-6}$ alkoxy group,
  (b) an oxo group,
  (c) a phenyl group,
  (d) a hydroxy group,
  (e) a cyano group,
  (f) a pyridyl group, and
  (g) a carbamoyl group,
(19) a piperidine ring optionally further substituted by 1 to 3 substituents selected from
  (a) a halogen atom, and
  (b) a $C_{1-6}$ alkyl group optionally substituted by 1 to 3 hydroxy groups,
(20) a morpholine ring optionally further substituted by 1 to 3 $C_{1-6}$ alkyl groups optionally substituted by 1 to 3 hydroxy groups,
(21) a tetrahydropyran ring,
(22) a tetrahydrofuran ring,
(23) a dihydropyrimidine ring optionally further substituted by 1 to 3 oxo groups,
(24) a dihydrobenzofuran ring,
(25) a dihydrochromene ring,
(26) a tetrahydroindazole ring optionally further substituted by 1 to 3 $C_{1-6}$ alkyl groups,
(27) a 8-oxa-3-azabicyclo[3.2.1]octane ring,
(28) a 3-oxa-8-azabicyclo[3.2.1]octane ring,
(29) a 3-azabicyclo[3.1.0]hexane ring optionally further substituted by 1 to 3 halogen atoms,
(30) a 2-oxa-6-azaspiro[3.5]nonane ring,
(31) a 2-oxa-7-azaspiro[3.5]nonane ring, or
(32) an oxazepane ring optionally further substituted by 1 to 3 $C_{1-6}$ alkyl groups optionally substituted by 1 to 3 hydroxy groups.

5. The compound or salt of claim 1, wherein $Z^1$ is a bond.

6. The compound or salt of claim 1, wherein Ring B is a morpholine ring having no additional substituent.

7. The compound or salt of claim 1, wherein
Ring A is a benzene ring;
X is —CONH—;
$R^2$ and $R^3$ are hydrogen atoms;
Ring B is a morpholine ring;
$Z^1$ is a bond; and
Ring C is a benzene ring, a pyrazole ring, an isoxazole ring or an indazole ring, each of which is optionally further substituted by 1 to 3 substituents selected from
  (a) a halogen atom, and
  (b) a $C_{1-6}$ alkyl group.

8. N-(((3S)-4-Benzoylmorpholin-3-yl)methyl)-4-(5-(trifluoromethyl)-1,2,4-oxadiazol-3-yl)benzamide, or a salt thereof.

9. N-(((3S)-4-(3,5-Dichlorobenzoyl)morpholin-3-yl)methyl)-4-(5-(trifluoromethyl)-1,2,4-oxadiazol-3-yl)benzamide, or a salt thereof.

10. N-(((3S)-4-((1-Methyl-1H-pyrazol-5-yl)carbonyl)morpholin-3-yl)methyl)-4-(5-(trifluoromethyl)-1,2,4-oxadiazol-3-yl)benzamide, or a salt thereof.

11. N-(((3S)-4-((2-Methyl-2H-indazol-3-yl)carbonyl)morpholin-3-yl)methyl)-4-(5-(trifluoromethyl)-1,2,4-oxadiazol-3-yl)benzamide, or a salt thereof.

12. A medicament comprising the compound or salt of claim 1.

13. A method of inhibiting histone deacetylase in a mammal, which comprises administering an effective amount of the compound or salt of claim 1 to the mammal.

14. A method of treating an inflammatory disease in a mammal comprising administering to said mammal an effective amount of the compound or salt of claim 1.

\* \* \* \* \*